United States Patent
Hammer

(10) Patent No.: US 11,844,691 B2
(45) Date of Patent: Dec. 19, 2023

(54) PARTIALLY-COVERED PROSTHETIC VALVES

(71) Applicant: CARDIOVALVE LTD., Or Yehuda (IL)

(72) Inventor: Tal Hammer, Ramat Gan (IL)

(73) Assignee: CARDIOVALVE LTD., Or Yehuda (IL)

(*) Notice: Subject to any disclaimer, the term of this patent is extended or adjusted under 35 U.S.C. 154(b) by 111 days.

(21) Appl. No.: 17/466,785

(22) Filed: Sep. 3, 2021

(65) Prior Publication Data
US 2021/0393402 A1    Dec. 23, 2021

Related U.S. Application Data

(63) Continuation of application No. 16/802,353, filed on Feb. 26, 2020, now Pat. No. 11,135,059, which is a
(Continued)

(51) Int. Cl.
*A61F 2/24*    (2006.01)

(52) U.S. Cl.
CPC .......... *A61F 2/2427* (2013.01); *A61F 2/2409* (2013.01); *A61F 2/2418* (2013.01);
(Continued)

(58) Field of Classification Search
CPC .................................................... A61F 2/2418
See application file for complete search history.

(56) References Cited

U.S. PATENT DOCUMENTS

| | | |
|---|---|---|
| 3,604,488 A | 9/1971 | Wishart et al. |
| 3,656,185 A | 4/1972 | Carpentier |

(Continued)

FOREIGN PATENT DOCUMENTS

| | | |
|---|---|---|
| AI | 2005/107650 | 11/2005 |
| CA | 2822801 | 8/2006 |

(Continued)

OTHER PUBLICATIONS

IPR2021-01051 Preliminary Guidance Patent Owner's Motion to Amend dated Jun. 24, 2022.
(Continued)

*Primary Examiner* — Jacqueline Woznicki
(74) *Attorney, Agent, or Firm* — Sughrue Mion, PLLC

(57) ABSTRACT

An implant includes an expandable frame having a continuous lumen and has (a) an upstream row of upstream cells and (b) at least two downstream rows of downstream cells. An upstream portion of each cell is shaped by ascending and descending struts that form a respective peak that points in an upstream direction. A valve member is disposed within the lumen and facilitates unidirectional flow of blood from an upstream end of the frame to a downstream end of the frame. A covering has (i) a first portion entirely covering an outer surface of a downstream row of downstream cells, and (ii) a second portion partially covering an outer surface of an upstream row of downstream cells. Outer surfaces of the peaks of the upstream row of downstream cells are disposed upstream of an upstream end of the covering at the outer surface. Other embodiments are also described.

21 Claims, 31 Drawing Sheets

Related U.S. Application Data continuation of application No. 15/872,501, filed on Jan. 16, 2018, now Pat. No. 10,631,982, which is a continuation of application No. 14/763,004, filed as application No. PCT/IL2014/050087 on Jan. 23, 2014, now abandoned.

(60) Provisional application No. 61/756,034, filed on Jan. 24, 2013, provisional application No. 61/756,049, filed on Jan. 24, 2013.

(52) U.S. Cl.
CPC .... *A61F 2/2436* (2013.01); *A61F 2210/0076* (2013.01); *A61F 2220/0016* (2013.01); *A61F 2220/0025* (2013.01); *A61F 2220/0075* (2013.01); *A61F 2250/0098* (2013.01)

(56) References Cited

U.S. PATENT DOCUMENTS

| | | |
|---|---|---|
| 3,840,018 A | 10/1974 | Heifetz |
| 3,874,388 A | 4/1975 | King et al. |
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,222,126 A | 9/1980 | Boretos et al. |
| 4,261,342 A | 4/1981 | Aranguren |
| 4,275,469 A | 6/1981 | Gabbay |
| 4,340,091 A | 7/1982 | Skelton et al. |
| 4,423,525 A | 1/1984 | Vallana et al. |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,853,986 A | 8/1989 | Allen |
| 4,892,541 A | 1/1990 | Alonso |
| 4,917,698 A | 4/1990 | Carpenter et al. |
| 4,961,738 A | 10/1990 | Mackin |
| 4,972,494 A | 11/1990 | White et al. |
| 4,994,077 A | 2/1991 | Dobben |
| 5,061,277 A | 10/1991 | Carpentier et al. |
| 5,078,739 A | 1/1992 | Martin |
| 5,104,407 A | 4/1992 | Lam et al. |
| 5,108,420 A | 4/1992 | Marks |
| 5,201,757 A | 4/1993 | Heyn et al. |
| 5,201,880 A | 4/1993 | Wright |
| 5,258,008 A | 11/1993 | Wilk |
| 5,300,034 A | 4/1994 | Behnke |
| 5,306,296 A | 4/1994 | Wright et al. |
| 5,314,473 A | 5/1994 | Godin |
| 5,325,845 A | 7/1994 | Adair |
| 5,332,402 A | 7/1994 | Teitelbaum |
| 5,397,351 A | 3/1995 | Pavcnik et al. |
| 5,405,378 A | 4/1995 | Strecker |
| 5,443,500 A | 8/1995 | Sigwart |
| 5,450,860 A | 9/1995 | O'Connor |
| 5,473,812 A | 12/1995 | Morris et al. |
| 5,477,856 A | 12/1995 | Lundquist |
| 5,593,424 A | 1/1997 | Northrup, III |
| 5,601,572 A | 2/1997 | Middleman et al. |
| 5,607,444 A | 3/1997 | Lam |
| 5,607,470 A | 3/1997 | Milo |
| 5,626,609 A | 5/1997 | Zvenyatsky et al. |
| 5,647,857 A | 7/1997 | Anderson et al. |
| 5,669,919 A | 9/1997 | Sanders et al. |
| 5,674,279 A | 10/1997 | Wright et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,713,948 A | 2/1998 | Uflacker |
| 5,716,370 A | 2/1998 | Williamson et al. |
| 5,716,397 A | 2/1998 | Myers |
| 5,716,417 A | 2/1998 | Girard et al. |
| 5,728,116 A | 3/1998 | Rosenman |
| 5,730,150 A | 3/1998 | Peppel et al. |
| 5,741,297 A | 4/1998 | Simon |
| 5,749,371 A | 5/1998 | Zadini et al. |
| 5,765,682 A | 6/1998 | Bley et al. |
| 5,776,140 A | 7/1998 | Cottone |
| 5,810,882 A | 9/1998 | Bolduc |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,868,777 A | 2/1999 | Lam |
| 5,873,906 A | 2/1999 | Lau et al. |
| 5,876,373 A | 3/1999 | Giba et al. |
| 5,935,098 A | 8/1999 | Blaisdell et al. |
| 5,954,766 A | 9/1999 | Zadno-Azizi et al. |
| 5,957,949 A | 9/1999 | Leonhardt et al. |
| 5,957,953 A | 9/1999 | DiPoto et al. |
| 5,961,440 A | 10/1999 | Schweich et al. |
| 5,961,539 A | 10/1999 | Northrup, III et al. |
| 5,980,565 A | 11/1999 | Jayaraman |
| 5,984,959 A | 11/1999 | Robertson |
| 6,010,530 A | 1/2000 | Goicoechea |
| 6,019,787 A | 2/2000 | Richard et al. |
| 6,042,554 A | 3/2000 | Rosenman |
| 6,042,607 A | 3/2000 | Williamson, IV |
| 6,045,497 A | 4/2000 | Schweich et al. |
| 6,050,936 A | 4/2000 | Schweich et al. |
| 6,059,715 A | 5/2000 | Schweich et al. |
| 6,059,827 A | 5/2000 | Fenton |
| 6,074,401 A | 6/2000 | Gardiner et al. |
| 6,074,417 A | 6/2000 | Peredo |
| 6,102,945 A | 8/2000 | Campbell |
| 6,106,550 A | 8/2000 | Magovern |
| 6,110,200 A | 8/2000 | Hinnenkamp |
| 6,113,612 A | 9/2000 | Swanson et al. |
| 6,120,534 A | 9/2000 | Ruiz |
| 6,126,686 A | 10/2000 | Badylak et al. |
| 6,143,024 A | 11/2000 | Campbell et al. |
| 6,152,937 A | 11/2000 | Peterson et al. |
| 6,159,240 A | 12/2000 | Sparer |
| 6,165,119 A | 12/2000 | Schweich et al. |
| 6,165,183 A | 12/2000 | Kuehn et al. |
| 6,165,210 A | 12/2000 | Lau et al. |
| 6,174,332 B1 | 1/2001 | Loch |
| 6,183,411 B1 | 2/2001 | Mortier et al. |
| 6,187,020 B1 | 2/2001 | Zegdi et al. |
| 6,187,040 B1 | 2/2001 | Wright |
| 6,193,686 B1 | 2/2001 | Estrada et al. |
| 6,193,745 B1 | 2/2001 | Fogarty et al. |
| 6,315,784 B1 | 2/2001 | Djurovic |
| 6,217,610 B1 | 4/2001 | Carpentier et al. |
| 6,231,602 B1 | 5/2001 | Carpentier et al. |
| 6,251,092 B1 | 6/2001 | Qin et al. |
| 6,254,609 B1 | 7/2001 | Vrba et al. |
| 6,264,700 B1 | 7/2001 | Kilcoyne et al. |
| 6,287,339 B1 | 9/2001 | Vasquez et al. |
| 6,296,656 B1 | 10/2001 | Bolduc et al. |
| 6,312,465 B1 | 11/2001 | Griffin et al. |
| 6,319,281 B1 | 11/2001 | Patel |
| 6,332,893 B1 | 12/2001 | Mortier et al. |
| 6,334,873 B1 | 1/2002 | Lane et al. |
| 6,346,074 B1 | 2/2002 | Roth |
| 6,350,278 B1 | 2/2002 | Lenker et al. |
| 6,352,561 B1 | 3/2002 | Leopold et al. |
| 6,391,036 B1 | 5/2002 | Berg et al. |
| 6,402,780 B2 | 6/2002 | Williamson, IV |
| 6,406,420 B1 | 6/2002 | McCarthy et al. |
| 6,406,493 B1 | 6/2002 | Tu et al. |
| 6,409,755 B1 | 6/2002 | Vrba |
| 6,419,696 B1 | 7/2002 | Ortiz et al. |
| 6,428,550 B1 | 8/2002 | Vargas et al. |
| 6,440,164 B1 | 8/2002 | Dimatteo et al. |
| 6,451,054 B1 | 9/2002 | Stevens |
| 6,454,799 B1 | 9/2002 | Schreck |
| 6,458,153 B1 | 10/2002 | Bailey et al. |

(56) References Cited

U.S. PATENT DOCUMENTS

| | | |
|---|---|---|
| 6,461,366 B1 | 10/2002 | Seguin |
| 6,470,892 B1 | 10/2002 | Forsell |
| 6,478,807 B1 | 11/2002 | Foreman et al. |
| 6,482,228 B1 | 11/2002 | Norred |
| 6,491,711 B1 | 12/2002 | Durcan |
| 6,503,274 B1 | 1/2003 | Howanec et al. |
| 6,511,491 B2 | 1/2003 | Grudem et al. |
| 6,524,338 B1 | 2/2003 | Gundry |
| 6,530,952 B2 | 3/2003 | Vesely |
| 6,533,772 B1 | 3/2003 | Sherts et al. |
| 6,537,314 B2 | 3/2003 | Langberg et al. |
| 6,540,782 B1 | 4/2003 | Snyders |
| 6,547,801 B1 | 4/2003 | Dargent et al. |
| 6,551,350 B1 | 4/2003 | Thornton et al. |
| 6,554,845 B1 | 4/2003 | Fleenor et al. |
| 6,558,396 B1 | 5/2003 | Inoue |
| 6,558,418 B2 | 5/2003 | Carpentier et al. |
| 6,564,805 B2 | 5/2003 | Garrison et al. |
| 6,565,603 B2 | 5/2003 | Cox |
| 6,569,196 B1 | 5/2003 | Vesely |
| 6,569,198 B1 | 5/2003 | Wilson et al. |
| 6,579,297 B2 | 6/2003 | Bicek et al. |
| 6,582,464 B2 | 6/2003 | Gabbay |
| 6,589,160 B2 | 7/2003 | Schweich et al. |
| 6,602,263 B1 | 8/2003 | Swanson et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,616,675 B1 | 9/2003 | Evard et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich et al. |
| 6,651,671 B1 | 11/2003 | Donlon et al. |
| 6,652,556 B1 | 11/2003 | VanTassel et al. |
| 6,669,724 B2 | 12/2003 | Park et al. |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,699,256 B1 | 3/2004 | Logan et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,456 B2 | 3/2004 | Langberg et al. |
| 6,711,444 B2 | 3/2004 | Koblish |
| 6,716,244 B2 | 4/2004 | Klaco |
| 6,718,985 B2 | 4/2004 | Hlavka et al. |
| 6,719,781 B1 | 4/2004 | Kim |
| 6,719,786 B2 | 4/2004 | Ryan et al. |
| 6,719,788 B2 | 4/2004 | Cox |
| 6,723,038 B1 | 4/2004 | Schroeder et al. |
| 6,726,716 B2 | 4/2004 | Marquez |
| 6,726,717 B2 | 4/2004 | Alfieri et al. |
| 6,730,118 B2 | 5/2004 | Spenser et al. |
| 6,730,121 B2 | 5/2004 | Ortiz et al. |
| 6,733,525 B2 | 5/2004 | Yang et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,514 B1 | 7/2004 | Li et al. |
| 6,764,518 B2 | 7/2004 | Godin |
| 6,767,362 B2 | 7/2004 | Schreck |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,821,297 B2 | 11/2004 | Snyders |
| 6,830,585 B1 | 12/2004 | Artof et al. |
| 6,830,638 B2 | 12/2004 | Boylan et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,884,257 B1 | 4/2005 | Cox |
| 6,893,459 B1 | 5/2005 | Macoviak |
| 6,893,460 B2 | 5/2005 | Spenser et al. |
| 6,908,482 B2 | 6/2005 | McCarthy et al. |
| 6,918,917 B1 | 7/2005 | Nguyen et al. |
| 6,926,715 B1 | 8/2005 | Hauck et al. |
| 6,926,730 B1 | 8/2005 | Nguyen et al. |
| 6,951,571 B1 | 10/2005 | Srivastava |
| 6,960,217 B2 | 11/2005 | Bolduc |
| 6,964,684 B2 | 11/2005 | Ortiz et al. |
| 6,964,686 B2 | 11/2005 | Gordon |
| 6,974,476 B2 | 12/2005 | McGuckin et al. |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,011,669 B2 | 3/2006 | Kimblad |
| 7,011,681 B2 | 3/2006 | Vesely |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,041,132 B2 | 5/2006 | Quijano et al. |
| 7,074,236 B2 | 7/2006 | Rabkin et al. |
| 7,077,850 B2 | 7/2006 | Kortenbach |
| 7,077,861 B2 | 7/2006 | Spence |
| 7,077,862 B2 | 7/2006 | Vidlund et al. |
| 7,087,064 B1 | 8/2006 | Hyde |
| 7,101,336 B2 | 9/2006 | Miller |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,137,184 B2 | 11/2006 | Schreck |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,656 B2 | 2/2007 | Khairkhahan |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,198,646 B2 | 4/2007 | Figulla et al. |
| 7,201,772 B2 | 4/2007 | Schwammenthal |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,261,686 B2 | 8/2007 | Couvillon, Jr. |
| 7,288,097 B2 | 10/2007 | Seguin |
| 7,288,111 B1 | 10/2007 | Holloway et al. |
| 7,294,148 B2 | 11/2007 | McCarthy |
| 7,297,150 B2 | 11/2007 | Cartledge et al. |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,316,716 B2 | 1/2008 | Egan |
| 7,329,279 B2 | 2/2008 | Haug et al. |
| 7,329,280 B2 | 2/2008 | Bolling et al. |
| 7,335,213 B1 | 2/2008 | Hyde et al. |
| 7,351,256 B2 | 4/2008 | Hojeibane et al. |
| 7,361,190 B2 | 4/2008 | Shoulian et al. |
| 7,364,588 B2 | 4/2008 | Mathis et al. |
| 7,374,571 B2 | 5/2008 | Pease et al. |
| 7,374,573 B2 | 5/2008 | Gabbay |

(56) References Cited

U.S. PATENT DOCUMENTS

| | | |
|---|---|---|
| 7,377,938 B2 | 5/2008 | Sarac et al. |
| 7,377,941 B2 | 5/2008 | Rhee et al. |
| 7,381,218 B2 | 6/2008 | Schreck |
| 7,381,219 B2 | 6/2008 | Salahieh et al. |
| 7,390,329 B2 | 6/2008 | Westra et al. |
| 7,404,824 B1 | 7/2008 | Webler et al. |
| 7,422,603 B2 | 9/2008 | Lane |
| 7,429,269 B2 | 9/2008 | Schwammenthal |
| 7,431,692 B2 | 10/2008 | Zollinger et al. |
| 7,442,204 B2 | 10/2008 | Schwammenthal |
| 7,442,207 B2 | 10/2008 | Rafiee |
| 7,445,630 B2 | 11/2008 | Lashinski et al. |
| 7,452,376 B2 | 11/2008 | Lim et al. |
| 7,455,677 B2 | 11/2008 | Vargas et al. |
| 7,455,688 B2 | 11/2008 | Furst et al. |
| 7,455,690 B2 | 11/2008 | Cartledge et al. |
| 7,462,162 B2 | 12/2008 | Phan et al. |
| 7,481,838 B2 | 1/2009 | Carpentier et al. |
| 7,485,142 B2 | 2/2009 | Milo |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,513,909 B2 | 4/2009 | Lane et al. |
| 7,524,331 B2 | 4/2009 | Birdsall |
| 7,527,646 B2 | 5/2009 | Rahdert et al. |
| 7,527,647 B2 | 5/2009 | Spence |
| 7,530,995 B2 | 5/2009 | Quijano et al. |
| 7,549,983 B2 | 6/2009 | Roue et al. |
| 7,556,632 B2 | 7/2009 | Zadno |
| 7,556,646 B2 | 7/2009 | Yang et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,582,111 B2 | 9/2009 | Krolik et al. |
| 7,585,321 B2 | 9/2009 | Cribier |
| 7,588,582 B2 | 9/2009 | Starksen et al. |
| 7,591,826 B2 | 9/2009 | Alferness et al. |
| 7,597,711 B2 | 10/2009 | Drews et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,611,534 B2 | 11/2009 | Kapadia et al. |
| 7,618,449 B2 | 11/2009 | Tremulis et al. |
| 7,621,948 B2 | 11/2009 | Hermann et al. |
| 7,625,403 B2 | 12/2009 | Krivoruchko |
| 7,632,302 B2 | 12/2009 | Vreeman et al. |
| 7,632,303 B1 | 12/2009 | Stalker et al. |
| 7,635,329 B2 | 12/2009 | Goldfarb et al. |
| 7,635,386 B1 | 12/2009 | Gammie |
| 7,648,528 B2 | 1/2010 | Styrc |
| 7,655,015 B2 | 2/2010 | Goldfarb et al. |
| 7,666,204 B2 | 2/2010 | Thornton et al. |
| 7,682,319 B2 | 3/2010 | Martin |
| 7,682,369 B2 | 3/2010 | Seguin |
| 7,682,380 B2 | 3/2010 | Thornton et al. |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,708,775 B2 | 5/2010 | Rowe et al. |
| 7,717,952 B2 | 5/2010 | Case et al. |
| 7,717,955 B2 | 5/2010 | Lane et al. |
| 7,722,666 B2 | 5/2010 | Lafontaine |
| 7,731,741 B2 | 6/2010 | Eidenschink |
| 7,731,742 B2 | 6/2010 | Schlick et al. |
| 7,736,388 B2 | 6/2010 | Goldfarb et al. |
| 7,748,389 B2 | 7/2010 | Salahieh et al. |
| 7,753,922 B2 | 7/2010 | Starksen |
| 7,753,924 B2 | 7/2010 | Starksen et al. |
| 7,753,949 B2 | 7/2010 | Lamphere et al. |
| 7,758,595 B2 | 7/2010 | Allen et al. |
| 7,758,632 B2 | 7/2010 | Hojeibane et al. |
| 7,758,640 B2 | 7/2010 | Vesely |
| 7,771,467 B2 | 8/2010 | Svensson |
| 7,771,469 B2 | 8/2010 | Liddicoat |
| 7,776,080 B2 | 8/2010 | Bei et al. |
| 7,776,083 B2 | 8/2010 | Vesely |
| 7,780,726 B2 | 8/2010 | Seguin |
| 7,785,341 B2 | 8/2010 | Forster et al. |
| 7,799,069 B2 | 9/2010 | Bailey et al. |
| 7,803,181 B2 | 9/2010 | Furst et al. |
| 7,811,296 B2 | 10/2010 | Goldfarb et al. |
| 7,811,316 B2 | 10/2010 | Kalmann et al. |
| 7,824,442 B2 | 11/2010 | Salahieh et al. |
| 7,837,645 B2 | 11/2010 | Bessler et al. |
| 7,837,727 B2 | 11/2010 | Goetz et al. |
| 7,842,081 B2 | 11/2010 | Yadin |
| 7,850,725 B2 | 12/2010 | Vardi et al. |
| 7,871,368 B2 | 1/2011 | Zollinger et al. |
| 7,871,432 B2 | 1/2011 | Bergin |
| 7,871,433 B2 | 1/2011 | Lattouf |
| 7,871,436 B2 | 1/2011 | Ryan et al. |
| 7,887,583 B2 | 2/2011 | Macoviak |
| 7,892,281 B2 | 2/2011 | Seguin et al. |
| 7,896,915 B2 | 3/2011 | Guyenot et al. |
| 7,914,544 B2 | 3/2011 | Nguyen et al. |
| 7,914,569 B2 | 3/2011 | Nguyen et al. |
| 7,927,370 B2 | 4/2011 | Webler et al. |
| 7,927,371 B2 | 4/2011 | Navia et al. |
| 7,942,927 B2 | 5/2011 | Kaye et al. |
| 7,947,072 B2 | 5/2011 | Yang et al. |
| 7,947,075 B2 | 5/2011 | Goetz et al. |
| 7,951,195 B2 | 5/2011 | Antonsson et al. |
| 7,955,375 B2 | 6/2011 | Agnew |
| 7,955,377 B2 | 6/2011 | Melsheimer |
| 7,955,384 B2 | 6/2011 | Rafiee et al. |
| 7,959,666 B2 | 6/2011 | Salahieh et al. |
| 7,959,672 B2 | 6/2011 | Salahieh et al. |
| 7,967,833 B2 | 6/2011 | Sterman et al. |
| 7,967,857 B2 | 6/2011 | Lane |
| 7,981,151 B2 | 7/2011 | Rowe |
| 7,981,153 B2 | 7/2011 | Fogarty et al. |
| 7,988,725 B2 | 8/2011 | Gross et al. |
| 7,992,567 B2 | 8/2011 | Hirotsuka et al. |
| 7,993,368 B2 | 8/2011 | Gambale et al. |
| 7,993,393 B2 | 8/2011 | Carpentier et al. |
| 7,993,397 B2 | 8/2011 | Lashinski |
| 8,002,825 B2 | 8/2011 | Letac et al. |
| 8,002,826 B2 | 8/2011 | Seguin |
| 8,012,201 B2 | 9/2011 | Lashinski et al. |
| 8,016,877 B2 | 9/2011 | Seguin et al. |
| 8,016,882 B2 | 9/2011 | Macoviak |
| 8,021,420 B2 | 9/2011 | Dolan |
| 8,021,421 B2 | 9/2011 | Fogarty et al. |
| 8,025,695 B2 | 9/2011 | Fogarty et al. |
| 8,029,518 B2 | 10/2011 | Goldfarb et al. |
| 8,029,557 B2 | 10/2011 | Sobrino-Serrano et al. |
| 8,029,564 B2 | 10/2011 | Johnson et al. |
| 8,034,103 B2 | 10/2011 | Burriesci |
| 8,034,104 B2 | 10/2011 | Carpentier et al. |
| 8,038,720 B2 | 10/2011 | Wallace et al. |
| 8,043,360 B2 | 10/2011 | McNamara et al. |
| 8,048,138 B2 | 11/2011 | Sulivan et al. |
| 8,048,140 B2 | 11/2011 | Purdy |
| 8,048,153 B2 | 11/2011 | Salahieh et al. |
| 8,052,592 B2 | 11/2011 | Goldfarb et al. |
| 8,052,741 B2 | 11/2011 | Bruszewski et al. |
| 8,052,749 B2 | 11/2011 | Salahieh et al. |
| 8,057,493 B2 | 11/2011 | Goldfarb et al. |
| 8,057,532 B2 | 11/2011 | Hoffman |
| 8,057,540 B2 | 11/2011 | Letac et al. |
| 8,062,355 B2 | 11/2011 | Figulla et al. |
| 8,062,359 B2 | 11/2011 | Marquez et al. |
| 8,070,708 B2 | 12/2011 | Rottenberg et al. |
| 8,070,800 B2 | 12/2011 | Lock et al. |
| 8,070,802 B2 | 12/2011 | Lamphere et al. |
| 8,070,804 B2 | 12/2011 | Hyde |
| 8,070,805 B2 | 12/2011 | Vidlund |
| 8,075,611 B2 | 12/2011 | Milwee et al. |
| 8,075,616 B2 | 12/2011 | Solem |
| 8,080,054 B2 | 12/2011 | Rowe |

(56) References Cited

U.S. PATENT DOCUMENTS

| | | |
|---|---|---|
| 8,083,793 B2 | 12/2011 | Lane et al. |
| D652,927 S | 1/2012 | Braido et al. |
| D653,341 S | 1/2012 | Braido et al. |
| 8,092,518 B2 | 1/2012 | Schreck |
| 8,092,520 B2 | 1/2012 | Quadri |
| 8,092,521 B2 | 1/2012 | Figulla et al. |
| 8,100,964 B2 | 1/2012 | Spence |
| 8,105,377 B2 | 1/2012 | Liddicoat |
| 8,109,996 B2 | 2/2012 | Stacchino et al. |
| 8,118,866 B2 | 2/2012 | Herrmann et al. |
| 8,123,800 B2 | 2/2012 | McCarthy |
| 8,123,801 B2 | 2/2012 | Milo |
| 8,323,334 B2 | 2/2012 | Deem et al. |
| 8,133,270 B2 | 3/2012 | Kheradvar et al. |
| 8,136,218 B2 | 3/2012 | Millwee et al. |
| 8,137,398 B2 | 3/2012 | Tuval et al. |
| 8,142,492 B2 | 3/2012 | Forster et al. |
| 8,142,493 B2 | 3/2012 | Spence et al. |
| 8,142,494 B2 | 3/2012 | Rahdert et al. |
| 8,142,495 B2 | 3/2012 | Hasenkam et al. |
| 8,142,496 B2 | 3/2012 | Berreklouw |
| 8,142,497 B2 | 3/2012 | Friedman |
| 8,147,504 B2 | 4/2012 | Ino et al. |
| 8,147,542 B2 | 4/2012 | Maisano et al. |
| 8,152,844 B2 | 4/2012 | Rao |
| 8,157,852 B2 | 4/2012 | Bloom et al. |
| 8,157,853 B2 | 4/2012 | Laske et al. |
| 8,157,860 B2 | 4/2012 | McNamara et al. |
| 8,163,008 B2 | 4/2012 | Wilson et al. |
| 8,163,013 B2 | 4/2012 | Machold et al. |
| 8,163,014 B2 | 4/2012 | Lane et al. |
| D660,433 S | 5/2012 | Braido et al. |
| D660,967 S | 5/2012 | Braido et al. |
| 8,167,894 B2 | 5/2012 | Miles et al. |
| 8,167,932 B2 | 5/2012 | Bourang et al. |
| 8,167,935 B2 | 5/2012 | McGuckin, Jr. et al. |
| 8,172,896 B2 | 5/2012 | McNamara et al. |
| 8,172,898 B2 | 5/2012 | Alferness et al. |
| 8,177,836 B2 | 5/2012 | Lee et al. |
| 8,182,528 B2 | 5/2012 | Salahieh et al. |
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,439 B2 | 6/2012 | Gomez-Duran |
| 8,211,169 B2 | 7/2012 | Lane et al. |
| 8,216,256 B2 | 7/2012 | Raschdorf, Jr. et al. |
| 8,216,301 B2 | 7/2012 | Bonhoeffer et al. |
| 8,221,492 B2 | 7/2012 | Case et al. |
| 8,221,493 B2 | 7/2012 | Boyle et al. |
| 8,226,710 B2 | 7/2012 | Nguyen et al. |
| 8,226,711 B2 | 7/2012 | Mortier et al. |
| 8,231,670 B2 | 7/2012 | Salahieh et al. |
| 8,231,671 B2 | 7/2012 | Kim |
| 8,236,045 B2 | 8/2012 | Benichou et al. |
| 8,236,049 B2 | 8/2012 | Rowe et al. |
| 8,241,351 B2 | 8/2012 | Cabiri |
| 8,252,042 B2 | 8/2012 | McNamara et al. |
| 8,252,050 B2 | 8/2012 | Maisano et al. |
| 8,252,051 B2 | 8/2012 | Chau et al. |
| 8,252,052 B2 | 8/2012 | Salahieh et al. |
| 8,257,390 B2 | 9/2012 | Carley et al. |
| 8,262,725 B2 | 9/2012 | Subramanian |
| 8,267,988 B2 | 9/2012 | Hamer et al. |
| 8,277,501 B2 | 10/2012 | Chalekian et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,298,280 B2 | 10/2012 | Yadin et al. |
| 8,303,608 B2 | 11/2012 | Goldfarb et al. |
| 8,303,653 B2 | 11/2012 | Bonhoeffer et al. |
| 8,308,798 B2 | 11/2012 | Pintor et al. |
| 8,317,853 B2 | 11/2012 | Agnew |
| 8,317,855 B2 | 11/2012 | Gregorich et al. |
| 8,323,335 B2 | 12/2012 | Rowe et al. |
| 8,328,868 B2 | 12/2012 | Paul et al. |
| 8,333,777 B2 | 12/2012 | Schaller et al. |
| 8,337,541 B2 | 12/2012 | Quadri et al. |
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,348,999 B2 | 1/2013 | Kheradvar et al. |
| 8,349,002 B2 | 1/2013 | Milo |
| 8,353,956 B2 | 1/2013 | Miller et al. |
| 8,357,195 B2 | 1/2013 | Kuehn |
| 8,361,144 B2 | 1/2013 | Fish et al. |
| 8,366,767 B2 | 2/2013 | Zhang |
| 8,372,140 B2 | 2/2013 | Hoffman et al. |
| 8,377,119 B2 | 2/2013 | Drews et al. |
| 8,382,829 B1 | 2/2013 | Call et al. |
| 8,388,680 B2 | 3/2013 | Starksen et al. |
| 8,393,517 B2 | 3/2013 | Milo |
| 8,398,708 B2 | 3/2013 | Meiri et al. |
| 8,403,981 B2 | 3/2013 | Forster et al. |
| 8,403,983 B2 | 3/2013 | Quadri et al. |
| 8,408,214 B2 | 4/2013 | Spenser |
| 8,414,644 B2 | 4/2013 | Quadri et al. |
| 8,425,593 B2 | 4/2013 | Braido et al. |
| 8,430,926 B2 | 4/2013 | Kirson |
| 8,430,934 B2 | 4/2013 | Das |
| 8,444,689 B2 | 5/2013 | Zhang |
| 8,449,599 B2 | 5/2013 | Chau et al. |
| 8,449,625 B2 | 5/2013 | Campbell et al. |
| 8,454,686 B2 | 6/2013 | Alkhatib |
| 8,460,365 B2 | 6/2013 | Haverkost et al. |
| 8,460,370 B2 | 6/2013 | Zakay et al. |
| 8,460,371 B2 | 6/2013 | Hlavka et al. |
| 8,474,460 B2 | 7/2013 | Barrett et al. |
| 8,475,491 B2 | 7/2013 | Milo |
| 8,480,732 B2 | 7/2013 | Subramanian |
| 8,500,800 B2 | 8/2013 | Maisano et al. |
| 8,500,821 B2 | 8/2013 | Sobrino-Serrano et al. |
| 8,512,400 B2 | 8/2013 | Tran et al. |
| 8,518,107 B2 | 8/2013 | Tsukashima et al. |
| 8,523,881 B2 | 9/2013 | Cabiri et al. |
| 8,523,940 B2 | 9/2013 | Richardson et al. |
| 8,529,431 B2 | 9/2013 | Baker et al. |
| 8,539,662 B2 | 9/2013 | Stacchino et al. |
| 8,540,767 B2 | 9/2013 | Zhang |
| 8,545,544 B2 | 10/2013 | Spenser et al. |
| 8,545,553 B2 | 10/2013 | Zipory et al. |
| 8,551,160 B2 | 10/2013 | Figulla et al. |
| 8,551,161 B2 | 10/2013 | Dolan |
| 8,562,672 B2 | 10/2013 | Bonhoeffer et al. |
| 8,568,475 B2 | 10/2013 | Nguyen et al. |
| 8,579,964 B2 | 11/2013 | Lane et al. |
| 8,579,965 B2 | 11/2013 | Bonhoeffer et al. |
| 8,585,755 B2 | 11/2013 | Chau et al. |
| 8,585,756 B2 | 11/2013 | Bonhoeffer et al. |
| 8,591,460 B2 | 11/2013 | Wilson et al. |
| 8,591,570 B2 | 11/2013 | Revuelta et al. |
| 8,591,576 B2 | 11/2013 | Hasenkam et al. |
| 8,608,797 B2 | 12/2013 | Gross et al. |
| 8,623,075 B2 | 1/2014 | Murray et al. |
| 8,623,080 B2 | 1/2014 | Fogarty et al. |
| 8,628,569 B2 | 1/2014 | Benichou et al. |
| 8,628,570 B2 | 1/2014 | Seguin |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,652,204 B2 | 2/2014 | Quill et al. |
| 8,657,872 B2 | 2/2014 | Seguin |
| 8,663,322 B2 | 3/2014 | Keranen |
| 8,673,020 B2 | 3/2014 | Sobrino-Serrano et al. |
| 8,679,174 B2 | 3/2014 | Ottma et al. |
| 8,685,086 B2 | 4/2014 | Navia et al. |
| 8,690,939 B2 | 4/2014 | Miller et al. |
| 8,696,742 B2 | 4/2014 | Pintor et al. |
| 8,715,342 B2 | 5/2014 | Zipory et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,507 B2 | 5/2014 | Keranen |
| 8,740,920 B2 | 6/2014 | Goldfarb et al. |

(56) References Cited

U.S. PATENT DOCUMENTS

| | | |
|---|---|---|
| 8,747,460 B2 | 6/2014 | Tuval et al. |
| 8,771,345 B2 | 7/2014 | Tuval et al. |
| 8,778,021 B2 | 7/2014 | Cartledge |
| 8,784,472 B2 | 7/2014 | Eidenschink |
| 8,784,479 B2 | 7/2014 | Antonsson et al. |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,801,776 B2 | 8/2014 | House et al. |
| 8,808,366 B2 | 8/2014 | Braido et al. |
| 8,808,368 B2 | 8/2014 | Maisano et al. |
| 8,808,371 B2 | 8/2014 | Cartledge |
| 8,840,663 B2 | 9/2014 | Salahieh et al. |
| 8,840,664 B2 | 9/2014 | Karapetian et al. |
| 8,845,717 B2 | 9/2014 | Khairkhahan et al. |
| 8,845,722 B2 | 9/2014 | Gabbay |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,870,950 B2 | 10/2014 | Hacohen |
| 8,876,800 B2 | 11/2014 | Behan |
| 8,888,843 B2 | 11/2014 | Khairkhahan et al. |
| 8,894,702 B2 | 11/2014 | Quadri et al. |
| 8,900,294 B2 | 12/2014 | Paniagua et al. |
| 8,900,295 B2 | 12/2014 | Migliazza et al. |
| 8,906,083 B2 | 12/2014 | Obermiller et al. |
| 8,911,455 B2 | 12/2014 | Quadri et al. |
| 8,911,461 B2 | 12/2014 | Traynor et al. |
| 8,911,489 B2 | 12/2014 | Ben-Muvhar |
| 8,911,493 B2 | 12/2014 | Rowe et al. |
| 8,911,494 B2 | 12/2014 | Hammer et al. |
| 8,926,695 B2 | 1/2015 | Gross et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,042 B2 | 1/2015 | Miller et al. |
| 8,940,044 B2 | 1/2015 | Hammer et al. |
| 8,945,177 B2 | 2/2015 | Dell et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,979,922 B2 | 3/2015 | Jayasinghe et al. |
| 8,986,370 B2 | 3/2015 | Annest |
| 8,986,373 B2 | 3/2015 | Chau et al. |
| 8,986,375 B2 | 3/2015 | Garde et al. |
| 8,992,599 B2 | 3/2015 | Thubrikar et al. |
| 8,992,604 B2 | 3/2015 | Gross et al. |
| 8,992,608 B2 | 3/2015 | Haug et al. |
| 8,998,982 B2 | 4/2015 | Richter et al. |
| 9,005,273 B2 | 4/2015 | Salahieh et al. |
| 9,011,468 B2 | 4/2015 | Ketai et al. |
| 9,011,520 B2 | 4/2015 | Miller et al. |
| 9,011,527 B2 | 4/2015 | Li et al. |
| 9,011,530 B2 | 4/2015 | Reich et al. |
| 9,017,399 B2 | 4/2015 | Gross et al. |
| D730,520 S | 5/2015 | Braido et al. |
| D730,521 S | 5/2015 | Braido et al. |
| 9,023,100 B2 | 5/2015 | Quadri et al. |
| 9,034,032 B2 | 5/2015 | McLean et al. |
| 9,034,033 B2 | 5/2015 | McLean et al. |
| 9,039,757 B2 | 5/2015 | McLean et al. |
| D732,666 S | 6/2015 | Nguyen et al. |
| 9,050,188 B2 | 6/2015 | Schweich et al. |
| 9,060,858 B2 | 6/2015 | Thornton et al. |
| 9,072,603 B2 | 7/2015 | Tuval et al. |
| 9,084,676 B2 | 7/2015 | Chau et al. |
| 9,095,434 B2 | 8/2015 | Rowe |
| 9,119,719 B2 | 9/2015 | Zipory et al. |
| 9,125,632 B2 | 9/2015 | Loulmet et al. |
| 9,125,738 B2 | 9/2015 | Figulla et al. |
| 9,125,740 B2 | 9/2015 | Morriss et al. |
| 9,132,006 B2 | 9/2015 | Spenser et al. |
| 9,132,009 B2 | 9/2015 | Hacohen et al. |
| 9,138,312 B2 | 9/2015 | Tuval et al. |
| 9,155,619 B2 | 10/2015 | Liu et al. |
| 9,173,646 B2 | 11/2015 | Fabro |
| 9,173,659 B2 | 11/2015 | Bodewadt et al. |
| 9,173,738 B2 | 11/2015 | Murray et al. |
| 9,180,005 B1 | 11/2015 | Lashinski et al. |
| 9,192,472 B2 | 11/2015 | Gross et al. |
| 9,220,594 B2 | 12/2015 | Braido et al. |
| 9,226,820 B2 | 1/2016 | Braido et al. |
| 9,226,825 B2 | 1/2016 | Starksen et al. |
| 9,226,839 B1 | 1/2016 | Kariniemi et al. |
| 9,232,995 B2 | 1/2016 | Kovalsky et al. |
| 9,241,790 B2 | 1/2016 | Lane et al. |
| 9,241,791 B2 | 1/2016 | Braido et al. |
| 9,241,792 B2 | 1/2016 | Benichou et al. |
| 9,241,794 B2 | 1/2016 | Braido et al. |
| 9,248,014 B2 | 2/2016 | Lane et al. |
| 9,265,608 B2 | 2/2016 | Miller et al. |
| 9,277,994 B2 | 3/2016 | Miller et al. |
| 9,289,290 B2 | 3/2016 | Alkhatib et al. |
| 9,289,291 B2 | 3/2016 | Gorman et al. |
| 9,295,550 B2 | 3/2016 | Nguyen et al. |
| 9,295,551 B2 | 3/2016 | Straubinger et al. |
| 9,295,552 B2 | 3/2016 | McLean et al. |
| 9,301,836 B2 | 4/2016 | Buchbinder et al. |
| 9,308,087 B2 | 4/2016 | Lane et al. |
| 9,320,591 B2 | 4/2016 | Bolduc |
| D755,384 S | 5/2016 | Pesce et al. |
| 9,326,852 B2 | 5/2016 | Spenser |
| 9,326,876 B2 | 5/2016 | Acosta et al. |
| 9,345,573 B2 | 5/2016 | Nyuli et al. |
| 9,351,830 B2 | 5/2016 | Gross et al. |
| 9,387,078 B2 | 7/2016 | Gross et al. |
| 9,393,110 B2 | 7/2016 | Levi et al. |
| 9,421,098 B2 | 8/2016 | Gifford et al. |
| 9,427,303 B2 | 8/2016 | Liddy et al. |
| 9,427,316 B2 | 8/2016 | Schweich, Jr. et al. |
| 9,439,757 B2 | 9/2016 | Wallace et al. |
| 9,463,102 B2 | 10/2016 | Kelly |
| 9,474,599 B2 | 10/2016 | Keränen |
| 9,474,638 B2 | 10/2016 | Robinson et al. |
| 9,480,559 B2 | 11/2016 | Vidlund et al. |
| 9,492,273 B2 | 11/2016 | Wallace et al. |
| 9,498,314 B2 | 11/2016 | Behan |
| 9,498,332 B2 | 11/2016 | Hacohen et al. |
| 9,510,947 B2 | 12/2016 | Straubinger et al. |
| 9,532,870 B2 | 1/2017 | Cooper et al. |
| 9,554,897 B2 | 1/2017 | Lane et al. |
| 9,554,899 B2 | 1/2017 | Granada et al. |
| 9,561,103 B2 | 2/2017 | Granada et al. |
| 9,566,152 B2 | 2/2017 | Schweich et al. |
| 9,597,182 B2 | 3/2017 | Straubinger et al. |
| 9,629,716 B2 | 4/2017 | Seguin |
| 9,662,203 B2 | 5/2017 | Sheahan et al. |
| 9,681,952 B2 | 6/2017 | Hacohen et al. |
| 9,717,591 B2 | 8/2017 | Chau et al. |
| 9,743,932 B2 | 8/2017 | Amplatz et al. |
| 9,763,657 B2 | 9/2017 | Hacohen et al. |
| 9,763,817 B2 | 9/2017 | Roeder |
| 9,770,256 B2 | 9/2017 | Cohen et al. |
| D800,908 S | 10/2017 | Hariton et al. |
| 9,788,941 B2 | 10/2017 | Hacohen |
| 9,895,226 B1 | 2/2018 | Harari et al. |
| 9,974,651 B2 | 5/2018 | Hariton et al. |
| 9,987,132 B1 | 6/2018 | Hariton et al. |
| 9,993,360 B2 | 6/2018 | Shalev et al. |
| 10,010,414 B2 | 7/2018 | Cooper et al. |
| 10,045,845 B2 | 8/2018 | Hacohen et al. |
| 10,076,415 B1 | 9/2018 | Metchik et al. |
| 10,098,732 B1 | 10/2018 | Hariton et al. |
| 10,105,222 B1 | 10/2018 | Metchik et al. |

(56) References Cited

U.S. PATENT DOCUMENTS

| | | | |
|---|---|---|---|
| 10,111,751 B1 | 10/2018 | Metchik et al. |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,143,552 B2 | 12/2018 | Wallace et al. |
| 10,149,761 B2 | 12/2018 | Granada et al. |
| 10,154,903 B2 | 12/2018 | Albitov et al. |
| 10,154,906 B2 | 12/2018 | Granada et al. |
| 10,159,570 B1 | 12/2018 | Metchik et al. |
| 10,182,908 B2 | 1/2019 | Tubishevitz et al. |
| 10,206,668 B2 | 2/2019 | Mcgoldrick et al. |
| 10,226,341 B2 | 3/2019 | Gross et al. |
| 10,231,831 B2 | 3/2019 | Hacohen |
| 10,231,837 B1 | 3/2019 | Metchik et al. |
| 10,238,493 B1 | 3/2019 | Metchik et al. |
| 10,245,143 B2 | 4/2019 | Gross et al. |
| 10,245,144 B1 | 4/2019 | Metchik et al. |
| 10,258,471 B2 | 4/2019 | Lutter et al. |
| 10,292,816 B2 | 5/2019 | Raanani et al. |
| 10,299,927 B2 | 5/2019 | McLean et al. |
| 10,321,995 B1 | 6/2019 | Christianson et al. |
| 10,322,020 B2 | 6/2019 | Lam et al. |
| 10,327,895 B2 | 6/2019 | Lozonschi et al. |
| 10,335,278 B2 | 7/2019 | McLean et al. |
| 10,376,361 B2 | 8/2019 | Gross et al. |
| 10,390,952 B2 | 8/2019 | Hariton et al. |
| 10,426,614 B2 | 10/2019 | Hariton et al. |
| 10,449,047 B2 | 10/2019 | Hariton et al. |
| 10,456,256 B2 | 10/2019 | Braido et al. |
| 10,492,908 B2 | 12/2019 | Hammer et al. |
| 10,507,108 B2 | 12/2019 | Delgado et al. |
| 10,507,109 B2 | 12/2019 | Metchik et al. |
| 10,512,456 B2 | 12/2019 | Hacohen et al. |
| 10,517,719 B2 | 12/2019 | Miller et al. |
| 10,524,792 B2 | 1/2020 | Hernandez et al. |
| 10,524,910 B2 | 1/2020 | Hammer et al. |
| 10,531,866 B2 | 1/2020 | Hariton et al. |
| 10,531,872 B2 | 1/2020 | Hacohen et al. |
| 10,537,426 B2 | 1/2020 | Iamberger et al. |
| 10,548,726 B2 | 2/2020 | Hacohen et al. |
| 10,548,731 B2 | 2/2020 | Lashinski et al. |
| 10,575,948 B2 | 3/2020 | Iamberger et al. |
| 10,595,992 B2 | 3/2020 | Chambers |
| 10,595,997 B2 | 3/2020 | Metchik et al. |
| 10,610,358 B2 | 4/2020 | Vidlund et al. |
| 10,610,359 B2 | 4/2020 | Hacohen |
| 10,631,871 B2 | 4/2020 | Goldfarb et al. |
| 10,631,982 B2 | 4/2020 | Hammer et al. |
| 10,646,342 B1 | 5/2020 | Marr et al. |
| 10,660,751 B2 | 5/2020 | Hacohen |
| 10,667,908 B2 | 6/2020 | Hariton et al. |
| 10,667,912 B2 | 6/2020 | Dixon et al. |
| 10,682,227 B2 | 6/2020 | Hariton et al. |
| 10,695,173 B2 | 6/2020 | Gross et al. |
| 10,695,177 B2 | 6/2020 | Hariton et al. |
| 10,702,385 B2 | 7/2020 | Hacohen |
| 10,736,742 B2 | 8/2020 | Hariton et al. |
| 10,758,342 B2 | 9/2020 | Chau et al. |
| 10,779,939 B2 | 9/2020 | Hariton et al. |
| 10,813,760 B2 | 10/2020 | Metchik et al. |
| 10,820,998 B2 | 11/2020 | Marr et al. |
| 10,835,377 B2 | 11/2020 | Hacohen et al. |
| 10,842,627 B2 | 11/2020 | Delgado et al. |
| 10,856,972 B2 | 12/2020 | Hariton et al. |
| 10,856,975 B2 | 12/2020 | Hariton et al. |
| 10,856,978 B2 | 12/2020 | Straubinger et al. |
| 10,874,514 B2 | 12/2020 | Dixon et al. |
| 10,888,422 B2 | 1/2021 | Hariton et al. |
| 10,888,425 B2 | 1/2021 | Delgado et al. |
| 10,888,644 B2 | 1/2021 | Ratz et al. |
| 10,905,552 B2 | 2/2021 | Dixon et al. |
| 10,905,554 B2 | 2/2021 | Cao |
| 10,918,481 B2 | 2/2021 | Hariton et al. |
| 10,918,483 B2 | 2/2021 | Metchik et al. |
| 10,925,732 B2 | 2/2021 | Delgado et al. |
| 10,945,843 B2 | 3/2021 | Delgado et al. |
| 10,945,844 B2 | 3/2021 | McCann et al. |
| 10,952,850 B2 | 3/2021 | Hariton et al. |
| 10,959,846 B2 | 3/2021 | Marr et al. |
| 10,993,809 B2 | 5/2021 | McCann et al. |
| 11,065,114 B2 | 7/2021 | Raanani et al. |
| 11,083,582 B2 | 8/2021 | McCann et al. |
| 11,135,059 B2 | 10/2021 | Hammer et al. |
| 11,147,672 B2 | 10/2021 | McCann et al. |
| 11,179,240 B2 | 11/2021 | Delgado et al. |
| 11,246,704 B2 | 2/2022 | Hariton et al. |
| 11,291,545 B2 | 4/2022 | Hacohen |
| 11,291,546 B2 | 4/2022 | Gross et al. |
| 11,291,547 B2 | 4/2022 | Gross et al. |
| 11,304,806 B2 | 4/2022 | Hariton et al. |
| 11,389,297 B2 | 7/2022 | Franklin et al. |
| 2001/0002445 A1 | 5/2001 | Vesely |
| 2001/0005787 A1 | 6/2001 | Oz et al. |
| 2001/0021872 A1 | 9/2001 | Bailey et al. |
| 2001/0021874 A1 | 9/2001 | Carpentier et al. |
| 2001/0044656 A1 | 11/2001 | Williamson et al. |
| 2001/0056295 A1 | 12/2001 | Solem |
| 2002/0013571 A1 | 1/2002 | Goldfarb et al. |
| 2002/0022862 A1 | 2/2002 | Grafton et al. |
| 2002/0029080 A1 | 3/2002 | Mortier et al. |
| 2002/0032481 A1 | 3/2002 | Gabbay |
| 2002/0042621 A1 | 4/2002 | Liddicoat et al. |
| 2002/0082525 A1 | 6/2002 | Oslund et al. |
| 2002/0087048 A1 | 7/2002 | Brock et al. |
| 2002/0099436 A1 | 7/2002 | Thornton et al. |
| 2002/0103532 A1 | 8/2002 | Langberg et al. |
| 2002/0151916 A1 | 10/2002 | Muramatsu et al. |
| 2002/0151961 A1 | 10/2002 | Lashinski et al. |
| 2002/0151970 A1 | 10/2002 | Garrison et al. |
| 2002/0169358 A1 | 11/2002 | Mortier et al. |
| 2002/0173841 A1 | 11/2002 | Ortiz et al. |
| 2002/0177894 A1 | 11/2002 | Acosta et al. |
| 2002/0177904 A1 | 11/2002 | Huxel et al. |
| 2002/0198586 A1 | 12/2002 | Inoue |
| 2003/0009236 A1 | 1/2003 | Godin |
| 2003/0018358 A1 | 1/2003 | Saadat |
| 2003/0036791 A1 | 2/2003 | Philipp et al. |
| 2003/0050693 A1 | 3/2003 | Quijano et al. |
| 2003/0050694 A1 | 3/2003 | Yang et al. |
| 2003/0060846 A1 | 3/2003 | Egnelov et al. |
| 2003/0060875 A1 | 3/2003 | Wittens |
| 2003/0069635 A1 | 4/2003 | Cartledge |
| 2003/0074052 A1 | 4/2003 | Besselink |
| 2003/0078465 A1 | 4/2003 | Pai et al. |
| 2003/0078653 A1 | 4/2003 | Vesely et al. |
| 2003/0083742 A1 | 5/2003 | Spence et al. |
| 2003/0100943 A1 | 5/2003 | Bolduc |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0130731 A1 | 7/2003 | Vidlund et al. |
| 2003/0158578 A1 | 8/2003 | Pantages et al. |
| 2003/0167062 A1 | 9/2003 | Gambale et al. |
| 2003/0171760 A1 | 9/2003 | Gambale |
| 2003/0191528 A1 | 10/2003 | Quijano et al. |
| 2003/0199974 A1 | 10/2003 | Lee et al. |
| 2003/0204195 A1 | 10/2003 | Keane et al. |
| 2003/0229350 A1 | 12/2003 | Kay |
| 2003/0229395 A1 | 12/2003 | Cox |
| 2003/0233142 A1 | 12/2003 | Morales et al. |
| 2004/0010272 A1 | 1/2004 | Manetakis et al. |
| 2004/0019377 A1 | 1/2004 | Taylor et al. |
| 2004/0024451 A1 | 2/2004 | Johnson et al. |
| 2004/0030382 A1 | 2/2004 | St. Goar et al. |
| 2004/0039414 A1 | 2/2004 | Carley et al. |
| 2004/0039436 A1* | 2/2004 | Spenser ............... A61F 2/2436 623/2.14 |
| 2004/0039442 A1 | 2/2004 | St. Goar et al. |
| 2004/0049207 A1 | 3/2004 | Goldfarb et al. |
| 2004/0059413 A1 | 3/2004 | Argento |
| 2004/0092962 A1 | 5/2004 | Thornton et al. |
| 2004/0093060 A1 | 5/2004 | Seguin et al. |
| 2004/0122448 A1 | 6/2004 | Levine |
| 2004/0122503 A1 | 6/2004 | Campbell et al. |

(56) References Cited

U.S. PATENT DOCUMENTS

| | | |
|---|---|---|
| 2004/0122514 A1 | 6/2004 | Fogarty et al. |
| 2004/0127982 A1 | 7/2004 | Machold et al. |
| 2004/0127983 A1 | 7/2004 | Mortier et al. |
| 2004/0133220 A1 | 7/2004 | Lashinski et al. |
| 2004/0133267 A1 | 7/2004 | Lane |
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0143315 A1 | 7/2004 | Bruun et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0153146 A1 | 8/2004 | Lashinski et al. |
| 2004/0172046 A1 | 9/2004 | Hlavka et al. |
| 2004/0176788 A1 | 9/2004 | Opolski |
| 2004/0176839 A1 | 9/2004 | Huynh et al. |
| 2004/0181287 A1 | 9/2004 | Gellman |
| 2004/0186558 A1 | 9/2004 | Pavcnik et al. |
| 2004/0186565 A1 | 9/2004 | Schreck |
| 2004/0186566 A1 | 9/2004 | Hindrichs et al. |
| 2004/0210244 A1 | 10/2004 | Vargas et al. |
| 2004/0210304 A1 | 10/2004 | Seguin et al. |
| 2004/0220593 A1 | 11/2004 | Greenhalgh |
| 2004/0225354 A1 | 11/2004 | Allen et al. |
| 2004/0236354 A1 | 11/2004 | Seguin |
| 2004/0236419 A1 | 11/2004 | Milo |
| 2004/0249433 A1 | 12/2004 | Freitag |
| 2004/0249453 A1 | 12/2004 | Cartledge et al. |
| 2004/0260317 A1 | 12/2004 | Bloom et al. |
| 2004/0260389 A1 | 12/2004 | Case et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0021056 A1 | 1/2005 | St. Goar et al. |
| 2005/0027305 A1 | 2/2005 | Shiu et al. |
| 2005/0027348 A1 | 2/2005 | Case et al. |
| 2005/0038494 A1 | 2/2005 | Eidenschink |
| 2005/0055038 A1 | 3/2005 | Kelleher et al. |
| 2005/0055086 A1 | 3/2005 | Stobie |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075726 A1* | 4/2005 | Svanidze ............ A61F 2/2439 623/2.14 |
| 2005/0075727 A1 | 4/2005 | Wheatley |
| 2005/0075731 A1 | 4/2005 | Artof et al. |
| 2005/0080430 A1 | 4/2005 | Wright et al. |
| 2005/0080474 A1 | 4/2005 | Andreas et al. |
| 2005/0085900 A1 | 4/2005 | Case et al. |
| 2005/0085903 A1 | 4/2005 | Lau |
| 2005/0090827 A1 | 4/2005 | Gedebou |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137695 A1 | 6/2005 | Salahieh et al. |
| 2005/0137697 A1 | 6/2005 | Salahieh et al. |
| 2005/0137699 A1 | 6/2005 | Salahieh et al. |
| 2005/0143809 A1 | 6/2005 | Salahieh et al. |
| 2005/0149160 A1 | 7/2005 | McFerran |
| 2005/0154443 A1 | 7/2005 | Linder et al. |
| 2005/0159728 A1 | 7/2005 | Armour et al. |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0182483 A1 | 8/2005 | Osborne et al. |
| 2005/0182486 A1 | 8/2005 | Gabbay |
| 2005/0187613 A1 | 8/2005 | Bolduc et al. |
| 2005/0192596 A1 | 9/2005 | Jugenheimer et al. |
| 2005/0197695 A1 | 9/2005 | Stacchino et al. |
| 2005/0197696 A1 | 9/2005 | Gomez Duran |
| 2005/0203549 A1 | 9/2005 | Realyvasquez |
| 2005/0203606 A1 | 9/2005 | VanCamp |
| 2005/0203618 A1 | 9/2005 | Sharkawy et al. |
| 2005/0216039 A1 | 9/2005 | Lederman |
| 2005/0216079 A1 | 9/2005 | MaCoviak |
| 2005/0222665 A1 | 10/2005 | Aranyi |
| 2005/0222678 A1 | 10/2005 | Lashinski et al. |
| 2005/0234508 A1 | 10/2005 | Cummins et al. |
| 2005/0240200 A1 | 10/2005 | Bergheim |
| 2005/0251251 A1 | 11/2005 | Cribier |
| 2005/0256532 A1 | 11/2005 | Nayak et al. |
| 2005/0256566 A1 | 11/2005 | Gabbay |
| 2005/0267478 A1 | 12/2005 | Corradi et al. |
| 2005/0267573 A9 | 12/2005 | Macoviak et al. |
| 2005/0273138 A1 | 12/2005 | To et al. |
| 2005/0288776 A1 | 12/2005 | Shaoulian et al. |
| 2005/0288778 A1 | 12/2005 | Shaoulian et al. |
| 2005/0288781 A1 | 12/2005 | Moaddeb et al. |
| 2006/0004439 A1 | 1/2006 | Spenser et al. |
| 2006/0004442 A1 | 1/2006 | Spenser et al. |
| 2006/0004443 A1 | 1/2006 | Liddicoat et al. |
| 2006/0004469 A1 | 1/2006 | Sokel |
| 2006/0015171 A1 | 1/2006 | Armstrong |
| 2006/0020275 A1 | 1/2006 | Goldfarb et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025855 A1 | 2/2006 | Lashinski et al. |
| 2006/0025858 A1 | 2/2006 | Alameddine |
| 2006/0030885 A1 | 2/2006 | Hyde |
| 2006/0041189 A1 | 2/2006 | Vancaillie |
| 2006/0041319 A1 | 2/2006 | Taylor et al. |
| 2006/0052867 A1 | 3/2006 | Revuelta et al. |
| 2006/0052868 A1 | 3/2006 | Mortier |
| 2006/0058871 A1 | 3/2006 | Zakay et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0089627 A1 | 4/2006 | Burnett et al. |
| 2006/0095009 A1 | 5/2006 | Lampropoulos et al. |
| 2006/0106423 A1 | 5/2006 | Weisel et al. |
| 2006/0111773 A1 | 5/2006 | Rittgers et al. |
| 2006/0116750 A1 | 6/2006 | Herbert et al. |
| 2006/0116757 A1 | 6/2006 | Lashinski et al. |
| 2006/0122692 A1 | 6/2006 | Gilad et al. |
| 2006/0129166 A1 | 6/2006 | Lavelle |
| 2006/0135964 A1 | 6/2006 | Vesley |
| 2006/0149280 A1 | 7/2006 | Harvine et al. |
| 2006/0149368 A1 | 7/2006 | Spence |
| 2006/0155357 A1 | 7/2006 | Melsheimer |
| 2006/0161250 A1 | 7/2006 | Shaw |
| 2006/0161265 A1 | 7/2006 | Levine et al. |
| 2006/0047297 A1 | 8/2006 | Case |
| 2006/0178700 A1 | 8/2006 | Quinn |
| 2006/0178740 A1 | 8/2006 | Stacchino et al. |
| 2006/0184203 A1 | 8/2006 | Martin et al. |
| 2006/0184240 A1 | 8/2006 | Jimenez et al. |
| 2006/0184242 A1 | 8/2006 | Lichtenstein |
| 2006/0190036 A1 | 8/2006 | Wendel et al. |
| 2006/0190038 A1 | 8/2006 | Carley et al. |
| 2006/0195134 A1 | 8/2006 | Crittenden |
| 2006/0195183 A1 | 8/2006 | Navia et al. |
| 2006/0195184 A1 | 8/2006 | Lane et al. |
| 2006/0201519 A1 | 9/2006 | Frazier et al. |
| 2006/0212111 A1 | 9/2006 | Case et al. |
| 2006/0216404 A1 | 9/2006 | Seyler et al. |

(56) References Cited

U.S. PATENT DOCUMENTS

| | | |
|---|---|---|
| 2006/0229708 A1 | 10/2006 | Powell et al. |
| 2006/0241622 A1 | 10/2006 | Zergiebel |
| 2006/0241656 A1 | 10/2006 | Starksen et al. |
| 2006/0241745 A1 | 10/2006 | Solem |
| 2006/0241748 A1 | 10/2006 | Lee et al. |
| 2006/0247680 A1 | 11/2006 | Amplatz et al. |
| 2006/0247763 A1 | 11/2006 | Slater |
| 2006/0253191 A1 | 11/2006 | Salahieh et al. |
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0271166 A1 | 11/2006 | Thill et al. |
| 2006/0271171 A1 | 11/2006 | McQuinn et al. |
| 2006/0271175 A1 | 11/2006 | Woolfson |
| 2006/0282150 A1 | 12/2006 | Olson et al. |
| 2006/0282161 A1 | 12/2006 | Huyn et al. |
| 2006/0287661 A1 | 12/2006 | Bolduc et al. |
| 2006/0287716 A1 | 12/2006 | Banbury et al. |
| 2006/0287719 A1 | 12/2006 | Rowe et al. |
| 2007/0001627 A1 | 1/2007 | Lin et al. |
| 2007/0008018 A1 | 1/2007 | Nagashima et al. |
| 2007/0016286 A1 | 1/2007 | Herrmann et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027528 A1 | 2/2007 | Agnew |
| 2007/0027533 A1 | 2/2007 | Douk |
| 2007/0027536 A1 | 2/2007 | Mihaljevic et al. |
| 2007/0027549 A1 | 2/2007 | Godin |
| 2007/0038221 A1 | 2/2007 | Fine et al. |
| 2007/0038293 A1 | 2/2007 | St. Goar et al. |
| 2007/0038295 A1 | 2/2007 | Case et al. |
| 2007/0043435 A1 | 2/2007 | Seguin et al. |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0055340 A1 | 3/2007 | Pryor |
| 2007/0056346 A1 | 3/2007 | Spenser et al. |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0078510 A1 | 4/2007 | Ryan |
| 2007/0080188 A1 | 4/2007 | Spence et al. |
| 2007/0083168 A1 | 4/2007 | Whiting et al. |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0173932 A1 | 7/2007 | Cali et al. |
| 2007/0197858 A1 | 8/2007 | Goldfarb et al. |
| 2007/0198077 A1 | 8/2007 | Cully et al. |
| 2007/0198082 A1 | 8/2007 | Kapadia et al. |
| 2007/0198097 A1 | 8/2007 | Zegdi |
| 2007/0208550 A1* | 9/2007 | Cao .................. G06F 30/23 703/11 |
| 2007/0213582 A1 | 9/2007 | Zollinger et al. |
| 2007/0213810 A1 | 9/2007 | Newhauser et al. |
| 2007/0213813 A1 | 9/2007 | Von Segesser et al. |
| 2007/0219558 A1 | 9/2007 | Deutsch |
| 2007/0219630 A1 | 9/2007 | Chu |
| 2007/0225759 A1 | 9/2007 | Thommen et al. |
| 2007/0225760 A1 | 9/2007 | Moszner et al. |
| 2007/0233186 A1 | 10/2007 | Meng |
| 2007/0233237 A1 | 10/2007 | Krivoruchko |
| 2007/0233239 A1 | 10/2007 | Navia et al. |
| 2007/0239208 A1 | 10/2007 | Crawford |
| 2007/0239272 A1 | 10/2007 | Navia et al. |
| 2007/0239273 A1 | 10/2007 | Allen |
| 2007/0244546 A1 | 10/2007 | Francis |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255397 A1 | 11/2007 | Ryan et al. |
| 2007/0255400 A1 | 11/2007 | Parravicini et al. |
| 2007/0270755 A1 | 11/2007 | Von Oepen et al. |
| 2007/0270943 A1 | 11/2007 | Solem et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2007/0299424 A1 | 12/2007 | Cumming et al. |
| 2008/0004688 A1 | 1/2008 | Spenser et al. |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0035160 A1 | 2/2008 | Woodson et al. |
| 2008/0039935 A1 | 2/2008 | Buch |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Mackoviak et al. |
| 2008/0071361 A1 | 3/2008 | Tuval et al. |
| 2008/0071363 A1 | 3/2008 | Tuval et al. |
| 2008/0071366 A1 | 3/2008 | Tuval et al. |
| 2008/0071369 A1 | 3/2008 | Tuval et al. |
| 2008/0077235 A1 | 3/2008 | Kirson |
| 2008/0082083 A1 | 4/2008 | Forde et al. |
| 2008/0082159 A1 | 4/2008 | Tseng et al. |
| 2008/0082166 A1 | 4/2008 | Styrc et al. |
| 2008/0086138 A1 | 4/2008 | Stone et al. |
| 2008/0086164 A1 | 4/2008 | Rowe et al. |
| 2008/0086203 A1 | 4/2008 | Roberts |
| 2008/0086204 A1 | 4/2008 | Rankin |
| 2008/0091257 A1 | 4/2008 | Andreas et al. |
| 2008/0091261 A1 | 4/2008 | Long et al. |
| 2008/0097523 A1 | 4/2008 | Bolduc et al. |
| 2008/0097595 A1 | 4/2008 | Gabbay |
| 2008/0132989 A1 | 6/2008 | Snow et al. |
| 2008/0140003 A1 | 6/2008 | Bei et al. |
| 2008/0140116 A1 | 6/2008 | Bonutti |
| 2008/0147182 A1 | 6/2008 | Righini et al. |
| 2008/0161910 A1 | 7/2008 | Revuelta et al. |
| 2008/0167705 A1 | 7/2008 | Agnew |
| 2008/0167714 A1 | 7/2008 | St. Goar et al. |
| 2008/0188929 A1 | 8/2008 | Schreck |
| 2008/0195126 A1 | 8/2008 | Solem |
| 2008/0195200 A1 | 8/2008 | Vidlund et al. |
| 2008/0200980 A1 | 8/2008 | Robin et al. |
| 2008/0208265 A1 | 8/2008 | Frazier et al. |
| 2008/0208328 A1 | 8/2008 | Antocci et al. |
| 2008/0208330 A1 | 8/2008 | Keranen |
| 2008/0208332 A1 | 8/2008 | Lamphere et al. |
| 2008/0221672 A1 | 9/2008 | Lamphere et al. |
| 2008/0234814 A1 | 9/2008 | Salahieh et al. |
| 2008/0243245 A1 | 10/2008 | Thambar et al. |
| 2008/0255580 A1 | 10/2008 | Hoffman et al. |
| 2008/0262609 A1 | 10/2008 | Gross et al. |
| 2008/0269879 A1 | 10/2008 | Sathe et al. |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281411 A1 | 11/2008 | Berreklouw |
| 2008/0288044 A1 | 11/2008 | Osborne |
| 2008/0288062 A1 | 11/2008 | Andrieu et al. |
| 2008/0294234 A1 | 11/2008 | Hartley et al. |
| 2008/0300629 A1 | 12/2008 | Surti |
| 2009/0005863 A1 | 1/2009 | Goetz et al. |
| 2009/0036966 A1 | 2/2009 | O'Connor et al. |
| 2009/0043153 A1 | 2/2009 | Zollinger et al. |
| 2009/0043381 A1 | 2/2009 | Macoviak et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |

(56) References Cited

U.S. PATENT DOCUMENTS

| | | |
|---|---|---|
| 2009/0082844 A1 | 3/2009 | Zacharias et al. |
| 2009/0088836 A1 | 4/2009 | Bishop et al. |
| 2009/0088837 A1 | 4/2009 | Gillinov et al. |
| 2009/0099554 A1 | 4/2009 | Forster et al. |
| 2009/0099650 A1 | 4/2009 | Bolduc et al. |
| 2009/0105794 A1 | 4/2009 | Ziarno et al. |
| 2009/0105816 A1 | 4/2009 | Olsen et al. |
| 2009/0112159 A1 | 4/2009 | Slattery et al. |
| 2009/0125098 A1 | 5/2009 | Chuter |
| 2009/0125102 A1 | 5/2009 | Cartledge |
| 2009/0149872 A1 | 6/2009 | Gross et al. |
| 2009/0157175 A1 | 6/2009 | Benichou |
| 2009/0163934 A1 | 6/2009 | Raschdorf, Jr. et al. |
| 2009/0177274 A1 | 6/2009 | Scorsin et al. |
| 2009/0171363 A1 | 7/2009 | Chocron |
| 2009/0171439 A1 | 7/2009 | Nissl |
| 2009/0177266 A1 | 7/2009 | Powell et al. |
| 2009/0177277 A1 | 7/2009 | Milo |
| 2009/0177278 A1 | 7/2009 | Spence |
| 2009/0210052 A1 | 8/2009 | Forster et al. |
| 2009/0222081 A1 | 9/2009 | Linder et al. |
| 2009/0240320 A1 | 9/2009 | Tuval et al. |
| 2009/0241656 A1 | 10/2009 | Jacquemin |
| 2009/0248143 A1 | 10/2009 | Laham |
| 2009/0248148 A1 | 10/2009 | Shaolian et al. |
| 2009/0254103 A1 | 10/2009 | Deustch |
| 2009/0259306 A1 | 10/2009 | Rowe |
| 2009/0259307 A1 | 10/2009 | Gross et al. |
| 2009/0264859 A1 | 10/2009 | Mas |
| 2009/0264994 A1 | 10/2009 | Saadat |
| 2009/0264995 A1 | 10/2009 | Subramanian |
| 2009/0276040 A1 | 11/2009 | Rowe et al. |
| 2009/0281619 A1 | 11/2009 | Le et al. |
| 2009/0287299 A1* | 11/2009 | Tabor ............... A61F 2/07 623/1.26 |
| 2009/0287304 A1 | 11/2009 | Dahlgren et al. |
| 2009/0299409 A1 | 12/2009 | Coe et al. |
| 2009/0299449 A1 | 12/2009 | Styrc |
| 2009/0306768 A1 | 12/2009 | Quardi |
| 2009/0319037 A1 | 12/2009 | Rowe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0022823 A1 | 1/2010 | Goldfarb et al. |
| 2010/0023117 A1 | 1/2010 | Yoganathan et al. |
| 2010/0023118 A1 | 1/2010 | Medlock et al. |
| 2010/0023120 A1 | 1/2010 | Holecek et al. |
| 2010/0030014 A1 | 2/2010 | Ferrazzi |
| 2010/0036479 A1 | 2/2010 | Hill et al. |
| 2010/0036484 A1* | 2/2010 | Hariton ............... E03C 1/066 623/2.18 |
| 2010/0042147 A1 | 2/2010 | Janovsky et al. |
| 2010/0049313 A1 | 2/2010 | Alon et al. |
| 2010/0063542 A1 | 3/2010 | Van der Burg et al. |
| 2010/0063550 A1 | 3/2010 | Felix et al. |
| 2010/0063586 A1 | 3/2010 | Hasenkam et al. |
| 2010/0069852 A1 | 3/2010 | Kelley |
| 2010/0076499 A1 | 3/2010 | McNamara et al. |
| 2010/0076548 A1 | 3/2010 | Konno |
| 2010/0082094 A1* | 4/2010 | Quadri ............... A61F 2/2409 29/890.132 |
| 2010/0094248 A1 | 4/2010 | Nguyen et al. |
| 2010/0100167 A1 | 4/2010 | Bortlein et al. |
| 2010/0114180 A1 | 5/2010 | Rock |
| 2010/0114299 A1 | 5/2010 | Ben-Muvhar et al. |
| 2010/0121349 A1 | 5/2010 | Meier |
| 2010/0130992 A1 | 5/2010 | Machold et al. |
| 2010/0131054 A1 | 5/2010 | Tuval et al. |
| 2010/0137979 A1 | 6/2010 | Tuval et al. |
| 2010/0152845 A1 | 6/2010 | Bloom et al. |
| 2010/0160958 A1 | 6/2010 | Clark |
| 2010/0161036 A1 | 6/2010 | Pintor et al. |
| 2010/0161041 A1 | 6/2010 | Maisano et al. |
| 2010/0161042 A1 | 6/2010 | Maisano et al. |
| 2010/0161043 A1 | 6/2010 | Maisano et al. |
| 2010/0161047 A1 | 6/2010 | Cabiri |
| 2010/0168845 A1 | 7/2010 | Wright |
| 2010/0174358 A1 | 7/2010 | Rabkin et al. |
| 2010/0174363 A1 | 7/2010 | Castro |
| 2010/0179574 A1 | 7/2010 | Longoria et al. |
| 2010/0179643 A1 | 7/2010 | Shalev |
| 2010/0179648 A1 | 7/2010 | Richter et al. |
| 2010/0179649 A1 | 7/2010 | Richter et al. |
| 2010/0185277 A1* | 7/2010 | Braido ............... A61F 2/2433 623/2.37 |
| 2010/0198347 A1 | 8/2010 | Zakay et al. |
| 2010/0217382 A1 | 8/2010 | Chau et al. |
| 2010/0222810 A1 | 9/2010 | DeBeer et al. |
| 2010/0228285 A1 | 9/2010 | Miles et al. |
| 2010/0234935 A1 | 9/2010 | Bashiri et al. |
| 2010/0234940 A1 | 9/2010 | Dolan |
| 2010/0249908 A1 | 9/2010 | Chau et al. |
| 2010/0249915 A1 | 9/2010 | Zhang |
| 2010/0249917 A1 | 9/2010 | Zhang |
| 2010/0249920 A1 | 9/2010 | Bolling et al. |
| 2010/0256737 A1 | 10/2010 | Pollock et al. |
| 2010/0262232 A1 | 10/2010 | Annest |
| 2010/0262233 A1 | 10/2010 | He |
| 2010/0280603 A1 | 11/2010 | Maisano et al. |
| 2010/0280604 A1 | 11/2010 | Zipory et al. |
| 2010/0280605 A1 | 11/2010 | Hammer et al. |
| 2010/0280606 A1 | 11/2010 | Naor |
| 2010/0286628 A1 | 11/2010 | Gross |
| 2010/0286767 A1 | 11/2010 | Zipory et al. |
| 2010/0305475 A1 | 12/2010 | Hinchliffe et al. |
| 2010/0312333 A1 | 12/2010 | Navia et al. |
| 2010/0324595 A1 | 12/2010 | Linder et al. |
| 2010/0331971 A1 | 12/2010 | Keränen et al. |
| 2011/0004210 A1 | 1/2011 | Johnson et al. |
| 2011/0004227 A1 | 1/2011 | Goldfarb et al. |
| 2011/0004296 A1 | 1/2011 | Lutter et al. |
| 2011/0004298 A1 | 1/2011 | Lee et al. |
| 2011/0004299 A1 | 1/2011 | Navia et al. |
| 2011/0011917 A1 | 1/2011 | Loulmet |
| 2011/0015729 A1 | 1/2011 | Jimenez et al. |
| 2011/0015731 A1 | 1/2011 | Carpentier et al. |
| 2011/0015739 A1 | 1/2011 | Cheung et al. |
| 2011/0021985 A1 | 1/2011 | Spargias |
| 2011/0022165 A1 | 1/2011 | Oba et al. |
| 2011/0178597 A9 | 1/2011 | Navia et al. |
| 2011/0026208 A1 | 2/2011 | Otsuro et al. |
| 2011/0029066 A1 | 2/2011 | Gilad et al. |
| 2011/0029067 A1 | 2/2011 | Mcguckin, Jr. et al. |
| 2011/0029072 A1 | 2/2011 | Gabbay |
| 2011/0035000 A1 | 2/2011 | Nieminen et al. |
| 2011/0040374 A1 | 2/2011 | Goetz et al. |
| 2011/0040375 A1 | 2/2011 | Letac et al. |
| 2011/0046662 A1 | 2/2011 | Moszner et al. |
| 2011/0054466 A1 | 3/2011 | Rothstein et al. |
| 2011/0054596 A1 | 3/2011 | Taylor |
| 2011/0054598 A1 | 3/2011 | Johnson |
| 2011/0066231 A1 | 3/2011 | Cartledge et al. |
| 2011/0066233 A1 | 3/2011 | Thornton et al. |
| 2011/0067770 A1 | 3/2011 | Pederson et al. |
| 2011/0071626 A1 | 3/2011 | Wright et al. |
| 2011/0077730 A1 | 3/2011 | Fentster |
| 2011/0082538 A1 | 4/2011 | Dahlgren et al. |
| 2011/0087146 A1 | 4/2011 | Ryan et al. |
| 2011/0087322 A1 | 4/2011 | Letac et al. |
| 2011/0093002 A1 | 4/2011 | Rucker et al. |
| 2011/0093063 A1 | 4/2011 | Schreck |
| 2011/0098525 A1 | 4/2011 | Kermode et al. |
| 2011/0106245 A1 | 5/2011 | Miller et al. |
| 2011/0106247 A1 | 5/2011 | Miller et al. |
| 2011/0112625 A1 | 5/2011 | Ben-Muvhar et al. |
| 2011/0112632 A1 | 5/2011 | Chau et al. |
| 2011/0113768 A1 | 5/2011 | Bauer et al. |
| 2011/0118830 A1 | 5/2011 | Liddicoat et al. |
| 2011/0118832 A1 | 5/2011 | Punjabi |
| 2011/0125257 A1 | 5/2011 | Seguin et al. |
| 2011/0125258 A1 | 5/2011 | Centola |
| 2011/0137326 A1 | 6/2011 | Bachman |
| 2011/0137397 A1 | 6/2011 | Chau et al. |
| 2011/0137409 A1 | 6/2011 | Yang et al. |

(56) References Cited

U.S. PATENT DOCUMENTS

| | | |
|---|---|---|
| 2011/0137410 A1 | 6/2011 | Hacohen |
| 2011/0144703 A1 | 6/2011 | Krause et al. |
| 2011/0144742 A1 | 6/2011 | Madrid et al. |
| 2011/0166636 A1 | 7/2011 | Rowe |
| 2011/0166649 A1 | 7/2011 | Gross et al. |
| 2011/0172784 A1 | 7/2011 | Richter |
| 2011/0184510 A1 | 7/2011 | Maisano et al. |
| 2011/0190877 A1 | 8/2011 | Lane et al. |
| 2011/0190879 A1 | 8/2011 | Bobo et al. |
| 2011/0202076 A1 | 8/2011 | Richter |
| 2011/0202130 A1 | 8/2011 | Cartledge et al. |
| 2011/0208283 A1 | 8/2011 | Rust |
| 2011/0208293 A1 | 8/2011 | Tabor |
| 2011/0208298 A1 | 8/2011 | Tuval et al. |
| 2011/0213459 A1 | 9/2011 | Garrison et al. |
| 2011/0213461 A1 | 9/2011 | Seguin et al. |
| 2011/0218619 A1 | 9/2011 | Benichou et al. |
| 2011/0218620 A1 | 9/2011 | Meiri et al. |
| 2011/0224785 A1 | 9/2011 | Hacohen |
| 2011/0230941 A1 | 9/2011 | Markus |
| 2011/0230961 A1 | 9/2011 | Langer et al. |
| 2011/0238088 A1 | 9/2011 | Bodluc et al. |
| 2011/0238094 A1 | 9/2011 | Thomas et al. |
| 2011/0238159 A1 | 9/2011 | Guyenot et al. |
| 2011/0245911 A1 | 10/2011 | Quill et al. |
| 2011/0245917 A1 | 10/2011 | Savage et al. |
| 2011/0251675 A1 | 10/2011 | Dwork |
| 2011/0251676 A1 | 10/2011 | Sweeney et al. |
| 2011/0251678 A1 | 10/2011 | Eidenschink et al. |
| 2011/0251679 A1 | 10/2011 | Weimeyer et al. |
| 2011/0251680 A1 | 10/2011 | Tran et al. |
| 2011/0251682 A1 | 10/2011 | Murray, III et al. |
| 2011/0251683 A1 | 10/2011 | Tabor |
| 2011/0257433 A1 | 10/2011 | Walker |
| 2011/0257633 A1 | 10/2011 | Cartledge et al. |
| 2011/0257721 A1 | 10/2011 | Tabor |
| 2011/0257728 A1 | 10/2011 | Kuehn |
| 2011/0257729 A1 | 10/2011 | Spenser et al. |
| 2011/0257736 A1 | 10/2011 | Marquez et al. |
| 2011/0257737 A1 | 10/2011 | Fogarty et al. |
| 2011/0264191 A1 | 10/2011 | Rothstein |
| 2011/0264196 A1 | 10/2011 | Savage et al. |
| 2011/0264198 A1 | 10/2011 | Murray, III et al. |
| 2011/0264199 A1 | 10/2011 | Tran et al. |
| 2011/0264200 A1 | 10/2011 | Tran et al. |
| 2011/0264201 A1 | 10/2011 | Yeung |
| 2011/0264202 A1 | 10/2011 | Murray, III et al. |
| 2011/0264203 A1 | 10/2011 | Dwork et al. |
| 2011/0264206 A1 | 10/2011 | Tabor |
| 2011/0264208 A1 | 10/2011 | Duffy |
| 2011/0270276 A1 | 11/2011 | Rothstein et al. |
| 2011/0271967 A1 | 11/2011 | Mortier et al. |
| 2011/0276062 A1 | 11/2011 | Bolduc |
| 2011/0282361 A1 | 11/2011 | Miller et al. |
| 2011/0282438 A1 | 11/2011 | Drews et al. |
| 2011/0282439 A1 | 11/2011 | Thill et al. |
| 2011/0282440 A1 | 11/2011 | Cao |
| 2011/0283514 A1 | 11/2011 | Fogarty et al. |
| 2011/0288435 A1 | 11/2011 | Christy et al. |
| 2011/0288632 A1 | 11/2011 | White |
| 2011/0288634 A1 | 11/2011 | Tuval et al. |
| 2011/0288635 A1 | 11/2011 | Miller et al. |
| 2011/0295354 A1 | 12/2011 | Bueche et al. |
| 2011/0295363 A1 | 12/2011 | Girard et al. |
| 2011/0301498 A1 | 12/2011 | Maenhout et al. |
| 2011/0301688 A1 | 12/2011 | Dolan |
| 2011/0301698 A1 | 12/2011 | Miller et al. |
| 2011/0301701 A1 | 12/2011 | Padala et al. |
| 2011/0301702 A1 | 12/2011 | Rust et al. |
| 2011/0306916 A1 | 12/2011 | Nitzan et al. |
| 2011/0307049 A1 | 12/2011 | Kao |
| 2011/0313452 A1 | 12/2011 | Carley et al. |
| 2011/0313515 A1 | 12/2011 | Quadri et al. |
| 2011/0319989 A1 | 12/2011 | Lane et al. |
| 2011/0319991 A1 | 12/2011 | Hariton et al. |
| 2012/0010694 A1 | 1/2012 | Lutter et al. |
| 2012/0016468 A1 | 1/2012 | Robin et al. |
| 2012/0022557 A1 | 1/2012 | Cabiri et al. |
| 2012/0022629 A1 | 1/2012 | Perera et al. |
| 2012/0022633 A1 | 1/2012 | Olson et al. |
| 2012/0022637 A1 | 1/2012 | Ben-Movhar et al. |
| 2012/0022639 A1 | 1/2012 | Hacohen et al. |
| 2012/0022640 A1 | 1/2012 | Gross et al. |
| 2012/0022644 A1 | 1/2012 | Reich et al. |
| 2012/0035703 A1 | 2/2012 | Lutter et al. |
| 2012/0035712 A1 | 2/2012 | Maisano et al. |
| 2012/0035713 A1 | 2/2012 | Lutter et al. |
| 2012/0035722 A1 | 2/2012 | Tuval et al. |
| 2012/0041547 A1 | 2/2012 | Duffy et al. |
| 2012/0041551 A1 | 2/2012 | Spenser et al. |
| 2012/0046738 A1 | 2/2012 | Lau et al. |
| 2012/0046742 A1 | 2/2012 | Tuval et al. |
| 2012/0053676 A1 | 3/2012 | Ku et al. |
| 2012/0053680 A1 | 3/2012 | Bolling et al. |
| 2012/0053682 A1 | 3/2012 | Kovalsky et al. |
| 2012/0053688 A1 | 3/2012 | Fogarty et al. |
| 2012/0059337 A1 | 3/2012 | Eilat |
| 2012/0059454 A1 | 3/2012 | Millwee et al. |
| 2012/0059458 A1 | 3/2012 | Buchbinder et al. |
| 2012/0065464 A1 | 3/2012 | Ellis et al. |
| 2012/0078237 A1 | 3/2012 | Wang et al. |
| 2012/0078353 A1 | 3/2012 | Quadri et al. |
| 2012/0078355 A1 | 3/2012 | Zipory et al. |
| 2012/0078357 A1 | 3/2012 | Conklin |
| 2012/0078359 A1 | 3/2012 | Li et al. |
| 2012/0083832 A1 | 4/2012 | Delaloye et al. |
| 2012/0083839 A1 | 4/2012 | Letac et al. |
| 2012/0083879 A1 | 4/2012 | Eberhardt et al. |
| 2012/0089022 A1 | 4/2012 | House et al. |
| 2012/0089223 A1 | 4/2012 | Nguyen et al. |
| 2012/0095552 A1 | 4/2012 | Spence et al. |
| 2012/0101570 A1 | 4/2012 | Tuval et al. |
| 2012/0101571 A1 | 4/2012 | Thambar et al. |
| 2012/0101572 A1 | 4/2012 | Kovalsky et al. |
| 2012/0109155 A1 | 5/2012 | Robinson et al. |
| 2012/0123511 A1 | 5/2012 | Brown |
| 2012/0123529 A1* | 5/2012 | Levi ................... A61F 2/2433 623/2.11 |
| 2012/0123530 A1 | 5/2012 | Carpentier et al. |
| 2012/0130473 A1 | 5/2012 | Norris et al. |
| 2012/0130474 A1 | 5/2012 | Buckley |
| 2012/0130475 A1 | 5/2012 | Shaw |
| 2012/0136434 A1 | 5/2012 | Carpentier et al. |
| 2012/0136436 A1 | 5/2012 | Cabiri et al. |
| 2012/0143323 A1 | 6/2012 | Hasenkam et al. |
| 2012/0150218 A1 | 6/2012 | Sandgren et al. |
| 2012/0150290 A1 | 6/2012 | Gabbay |
| 2012/0158021 A1 | 6/2012 | Morrill |
| 2012/0165915 A1 | 6/2012 | Melsheimer et al. |
| 2012/0165930 A1 | 6/2012 | Gifford, III et al. |
| 2012/0179086 A1 | 7/2012 | Shank et al. |
| 2012/0179244 A1 | 7/2012 | Schankereli et al. |
| 2012/0191182 A1 | 7/2012 | Hauser et al. |
| 2012/0197292 A1 | 8/2012 | Chin-Chen et al. |
| 2012/0197388 A1 | 8/2012 | Khairkhahan et al. |
| 2012/0215303 A1 | 8/2012 | Quadri et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0277845 A1 | 11/2012 | Bowe |
| 2012/0283757 A1 | 11/2012 | Miller et al. |
| 2012/0283824 A1 | 11/2012 | Lutter et al. |
| 2012/0290062 A1 | 11/2012 | McNamara et al. |
| 2012/0296349 A1 | 11/2012 | Smith et al. |
| 2012/0296360 A1 | 11/2012 | Norris et al. |
| 2012/0296417 A1 | 11/2012 | Hill et al. |
| 2012/0296418 A1 | 11/2012 | Bonyuet et al. |
| 2012/0296419 A1 | 11/2012 | Richardson |
| 2012/0300063 A1 | 11/2012 | Majkrzak et al. |
| 2012/0123531 A1 | 12/2012 | Tsukashima et al. |
| 2012/0310328 A1 | 12/2012 | Olson et al. |
| 2012/0310330 A1 | 12/2012 | Buchbinder et al. |
| 2012/0323313 A1 | 12/2012 | Seguin |
| 2012/0323316 A1 | 12/2012 | Chau et al. |

(56) References Cited

U.S. PATENT DOCUMENTS

| | | |
|---|---|---|
| 2012/0330408 A1 | 12/2012 | Hillukka et al. |
| 2012/0330410 A1 | 12/2012 | Hammer et al. |
| 2012/0330411 A1 | 12/2012 | Gross et al. |
| 2013/0006347 A1 | 1/2013 | McHugo |
| 2013/0018450 A1 | 1/2013 | Hunt |
| 2013/0018458 A1* | 1/2013 | Yohanan .............. A61F 2/2418 623/2.38 |
| 2013/0023758 A1 | 1/2013 | Fabro |
| 2013/0030519 A1 | 1/2013 | Tran et al. |
| 2013/0030522 A1 | 1/2013 | Rowe et al. |
| 2013/0035759 A1 | 2/2013 | Gross et al. |
| 2013/0041204 A1 | 2/2013 | Heilman et al. |
| 2013/0041451 A1 | 2/2013 | Patterson et al. |
| 2013/0046373 A1 | 2/2013 | Cartledge et al. |
| 2013/0066341 A1 | 3/2013 | Ketai et al. |
| 2013/0066342 A1 | 3/2013 | Dell et al. |
| 2013/0079872 A1 | 3/2013 | Gallagher |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0116776 A1 | 5/2013 | Gross et al. |
| 2013/0116779 A1 | 5/2013 | Weber |
| 2013/0116780 A1 | 5/2013 | Miller et al. |
| 2013/0123896 A1 | 5/2013 | Bloss et al. |
| 2013/0123900 A1 | 5/2013 | Eblacas et al. |
| 2013/0123910 A1 | 5/2013 | Cartledge et al. |
| 2013/0131791 A1 | 5/2013 | Hlavka et al. |
| 2013/0131792 A1 | 5/2013 | Miller et al. |
| 2013/0150945 A1 | 6/2013 | Crawford et al. |
| 2013/0150956 A1 | 6/2013 | Yohanan et al. |
| 2013/0158647 A1 | 6/2013 | Norris et al. |
| 2013/0166017 A1 | 6/2013 | Cartledge et al. |
| 2013/0166022 A1 | 6/2013 | Conklin |
| 2013/0172978 A1 | 7/2013 | Vidlund et al. |
| 2013/0172992 A1 | 7/2013 | Gross et al. |
| 2013/0178930 A1 | 7/2013 | Straubinger et al. |
| 2013/0190857 A1* | 7/2013 | Mitra .................. A61L 31/06 623/1.36 |
| 2013/0190861 A1 | 7/2013 | Chau et al. |
| 2013/0190863 A1 | 7/2013 | Call et al. |
| 2013/0190866 A1 | 7/2013 | Zipory et al. |
| 2013/0197632 A1 | 8/2013 | Kovach et al. |
| 2013/0204361 A1 | 8/2013 | Adams et al. |
| 2013/0211501 A1 | 8/2013 | Buckley et al. |
| 2013/0211508 A1 | 8/2013 | Lane et al. |
| 2013/0226289 A1 | 8/2013 | Shaolian et al. |
| 2013/0226290 A1 | 8/2013 | Yellin et al. |
| 2013/0231735 A1 | 9/2013 | Deem et al. |
| 2013/0245742 A1 | 9/2013 | Norris |
| 2013/0253643 A1 | 9/2013 | Rolando et al. |
| 2013/0261737 A1 | 10/2013 | Costello |
| 2013/0261738 A1 | 10/2013 | Clague et al. |
| 2013/0268069 A1 | 10/2013 | Zakai et al. |
| 2013/0274870 A1 | 10/2013 | Lombardi et al. |
| 2013/0282059 A1 | 10/2013 | Ketai et al. |
| 2013/0289711 A1 | 10/2013 | Liddy et al. |
| 2013/0289718 A1 | 10/2013 | Tsukashima et al. |
| 2013/0289740 A1 | 10/2013 | Liddy et al. |
| 2013/0297013 A1 | 11/2013 | Klima et al. |
| 2013/0304093 A1 | 11/2013 | Serina et al. |
| 2013/0304197 A1 | 11/2013 | Buchbinder et al. |
| 2013/0304200 A1* | 11/2013 | McLean .............. A61F 2/2412 623/2.18 |
| 2013/0310928 A1 | 11/2013 | Morriss et al. |
| 2013/0325114 A1 | 12/2013 | McLean et al. |
| 2013/0325118 A1 | 12/2013 | Cartledge |
| 2013/0331929 A1 | 12/2013 | Mitra et al. |
| 2014/0000112 A1 | 1/2014 | Braido et al. |
| 2014/0005767 A1 | 1/2014 | Glazier et al. |
| 2014/0005778 A1 | 1/2014 | Buchbinder et al. |
| 2014/0018911 A1 | 1/2014 | Zhou et al. |
| 2014/0018914 A1 | 1/2014 | Zipory et al. |
| 2014/0018915 A1 | 1/2014 | Biadillah et al. |
| 2014/0031928 A1 | 1/2014 | Murphy et al. |
| 2014/0046430 A1 | 2/2014 | Shaw |
| 2014/0052237 A1 | 2/2014 | Lane et al. |
| 2014/0067050 A1 | 3/2014 | Costello et al. |
| 2014/0067054 A1 | 3/2014 | Chau et al. |
| 2014/0081376 A1 | 3/2014 | Burkart et al. |
| 2014/0088368 A1 | 3/2014 | Park |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0099726 A1 | 4/2014 | Heller |
| 2014/0106951 A1 | 4/2014 | Brandon |
| 2014/0120287 A1 | 5/2014 | Jacoby et al. |
| 2014/0121749 A1 | 5/2014 | Roeder |
| 2014/0121763 A1 | 5/2014 | Duffy et al. |
| 2014/0135799 A1 | 5/2014 | Henderson |
| 2014/0135894 A1 | 5/2014 | Norris et al. |
| 2014/0135895 A1 | 5/2014 | Andress et al. |
| 2014/0142619 A1 | 5/2014 | Serina et al. |
| 2014/0142681 A1 | 5/2014 | Norris |
| 2014/0142688 A1 | 5/2014 | Duffy et al. |
| 2014/0142695 A1 | 5/2014 | Gross et al. |
| 2014/0148849 A1 | 5/2014 | Serina et al. |
| 2014/0148891 A1 | 5/2014 | Johnson |
| 2014/0148898 A1 | 5/2014 | Gross et al. |
| 2014/0155783 A1 | 6/2014 | Starksen et al. |
| 2014/0163670 A1 | 6/2014 | Alon et al. |
| 2014/0163690 A1 | 6/2014 | White |
| 2014/0172069 A1 | 6/2014 | Roeder et al. |
| 2014/0172077 A1 | 6/2014 | Bruchman et al. |
| 2014/0172082 A1 | 6/2014 | Bruchman et al. |
| 2014/0188108 A1 | 7/2014 | Goodine et al. |
| 2014/0188140 A1 | 7/2014 | Meier et al. |
| 2014/0188210 A1 | 7/2014 | Beard et al. |
| 2014/0188215 A1 | 7/2014 | Hlavka et al. |
| 2014/0188221 A1 | 7/2014 | Chung et al. |
| 2014/0194970 A1 | 7/2014 | Chobotov |
| 2014/0194976 A1 | 7/2014 | Starksen et al. |
| 2014/0194981 A1 | 7/2014 | Menk et al. |
| 2014/0194983 A1 | 7/2014 | Kovalsky et al. |
| 2014/0207231 A1 | 7/2014 | Hacohen et al. |
| 2014/0214157 A1 | 7/2014 | Börtlein et al. |
| 2014/0214159 A1 | 7/2014 | Vidlund et al. |
| 2014/0222136 A1 | 8/2014 | Geist et al. |
| 2014/0222137 A1 | 8/2014 | Miller et al. |
| 2014/0222142 A1 | 8/2014 | Kovalsky et al. |
| 2014/0236287 A1 | 8/2014 | Clague et al. |
| 2014/0236289 A1 | 8/2014 | Alkhatib |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0249622 A1 | 9/2014 | Carmi et al. |
| 2014/0257461 A1 | 9/2014 | Robinson et al. |
| 2014/0257467 A1 | 9/2014 | Lane et al. |
| 2014/0257475 A1 | 9/2014 | Gross et al. |
| 2014/0257476 A1 | 9/2014 | Montorfano et al. |
| 2014/0275757 A1 | 9/2014 | Goodwin et al. |
| 2014/0276648 A1 | 9/2014 | Hammer et al. |
| 2014/0277358 A1 | 9/2014 | Slazas |
| 2014/0277409 A1 | 9/2014 | Börtlein et al. |
| 2014/0277411 A1 | 9/2014 | Börtlein et al. |
| 2014/0277412 A1 | 9/2014 | Börtlein et al. |
| 2014/0277418 A1 | 9/2014 | Miller |
| 2014/0277422 A1 | 9/2014 | Ratz et al. |
| 2014/0277427 A1 | 9/2014 | Ratz et al. |
| 2014/0296962 A1 | 10/2014 | Cartledge et al. |
| 2014/0296969 A1 | 10/2014 | Tegels et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0324164 A1 | 10/2014 | Gross et al. |
| 2014/0329225 A1 | 11/2014 | Morin |
| 2014/0331475 A1 | 11/2014 | Duffy et al. |
| 2014/0336744 A1 | 11/2014 | Tani et al. |
| 2014/0343668 A1 | 11/2014 | Zipory et al. |
| 2014/0343670 A1 | 11/2014 | Bakis et al. |
| 2014/0350662 A1 | 11/2014 | Vaturi |
| 2014/0350670 A1 | 11/2014 | Keränen |
| 2014/0358222 A1 | 12/2014 | Gorman, III et al. |

(56) References Cited

U.S. PATENT DOCUMENTS

| | | |
|---|---|---|
| 2014/0358224 A1 | 12/2014 | Tegels et al. |
| 2014/0378331 A1 | 12/2014 | Morin |
| 2014/0379006 A1 | 12/2014 | Sutherland et al. |
| 2014/0379065 A1 | 12/2014 | Johnson et al. |
| 2014/0379074 A1 | 12/2014 | Spence et al. |
| 2014/0379076 A1 | 12/2014 | Vidlund et al. |
| 2015/0012087 A1 | 1/2015 | Miller et al. |
| 2015/0018940 A1 | 1/2015 | Quill et al. |
| 2015/0018944 A1 | 1/2015 | O'Connor et al. |
| 2015/0032205 A1 | 1/2015 | Matheny |
| 2015/0045880 A1 | 2/2015 | Hacohen |
| 2015/0045881 A1 | 2/2015 | Lim |
| 2015/0051697 A1 | 2/2015 | Spence et al. |
| 2015/0081014 A1 | 3/2015 | Gross et al. |
| 2015/0094802 A1 | 4/2015 | Buchbinder et al. |
| 2015/0105855 A1 | 4/2015 | Cabiri et al. |
| 2015/0119970 A1 | 4/2015 | Nakayama et al. |
| 2015/0127097 A1 | 5/2015 | Neumann et al. |
| 2015/0142100 A1 | 5/2015 | Morriss et al. |
| 2015/0142103 A1 | 5/2015 | Vidlund |
| 2015/0148894 A1 | 5/2015 | Damm et al. |
| 2015/0157457 A1 | 6/2015 | Hacohen |
| 2015/0157458 A1 | 6/2015 | Thambar et al. |
| 2015/0164640 A1 | 6/2015 | McLean et al. |
| 2015/0173896 A1 | 6/2015 | Richter et al. |
| 2015/0173897 A1 | 6/2015 | Raanani et al. |
| 2015/0182336 A1 | 7/2015 | Zipory et al. |
| 2015/0196390 A1 | 7/2015 | Ma et al. |
| 2015/0196393 A1 | 7/2015 | Vidlund et al. |
| 2015/0216661 A1 | 8/2015 | Hacohen et al. |
| 2015/0230924 A1 | 8/2015 | Miller et al. |
| 2015/0238313 A1 | 8/2015 | Spence et al. |
| 2015/0245934 A1 | 9/2015 | Lombardi et al. |
| 2015/0250588 A1 | 9/2015 | Yang et al. |
| 2015/0272730 A1 | 10/2015 | Melnick et al. |
| 2015/0272731 A1 | 10/2015 | Racchini et al. |
| 2015/0272734 A1 | 10/2015 | Sheps et al. |
| 2015/0282964 A1 | 10/2015 | Beard et al. |
| 2015/0305903 A1 | 10/2015 | Kitaoka |
| 2015/0320556 A1 | 11/2015 | Levi et al. |
| 2015/0327994 A1 | 11/2015 | Morriss et al. |
| 2015/0328000 A1 | 11/2015 | Ratz et al. |
| 2015/0335429 A1 | 11/2015 | Morriss et al. |
| 2015/0342736 A1 | 12/2015 | Rabito et al. |
| 2015/0351903 A1 | 12/2015 | Morriss et al. |
| 2015/0351904 A1 | 12/2015 | Cooper et al. |
| 2015/0351906 A1 | 12/2015 | Hammer et al. |
| 2015/0359629 A1 | 12/2015 | Ganesan et al. |
| 2016/0030169 A1 | 2/2016 | Shahriari |
| 2016/0030171 A1 | 2/2016 | Quijano et al. |
| 2016/0089482 A1 | 3/2016 | Siegenthaler |
| 2016/0095700 A1 | 4/2016 | Righini |
| 2016/0100939 A1 | 4/2016 | Armstrong et al. |
| 2016/0106539 A1 | 4/2016 | Buchbinder et al. |
| 2016/0113766 A1 | 4/2016 | Ganesan et al. |
| 2016/0113768 A1 | 4/2016 | Ganesan et al. |
| 2016/0125160 A1 | 5/2016 | Heneghan et al. |
| 2016/0157862 A1 | 6/2016 | Hernandez et al. |
| 2016/0175095 A1 | 6/2016 | Dienno et al. |
| 2016/0200773 A1 | 7/2016 | Morin |
| 2016/0213473 A1 | 7/2016 | Hacohen et al. |
| 2016/0220367 A1 | 8/2016 | Barrett |
| 2016/0228247 A1 | 8/2016 | Maimon et al. |
| 2016/0242902 A1 | 8/2016 | Morriss et al. |
| 2016/0245802 A1 | 8/2016 | Morin et al. |
| 2016/0258939 A1 | 9/2016 | Morin et al. |
| 2016/0266089 A1 | 9/2016 | Morin et al. |
| 2016/0270911 A1 | 9/2016 | Ganesan et al. |
| 2016/0296330 A1 | 10/2016 | Hacohen |
| 2016/0310268 A1 | 10/2016 | Oba et al. |
| 2016/0310274 A1 | 10/2016 | Gross et al. |
| 2016/0317301 A1 | 11/2016 | Quadri et al. |
| 2016/0317305 A1 | 11/2016 | Pelled et al. |
| 2016/0324633 A1 | 11/2016 | Gross et al. |
| 2016/0324635 A1 | 11/2016 | Vidlund et al. |
| 2016/0324640 A1 | 11/2016 | Gifford et al. |
| 2016/0331526 A1 | 11/2016 | Schweich et al. |
| 2016/0331527 A1 | 11/2016 | Vidlund et al. |
| 2016/0338706 A1 | 11/2016 | Rowe |
| 2016/0367360 A1 | 12/2016 | Cartledge et al. |
| 2016/0367368 A1 | 12/2016 | Vidlund et al. |
| 2016/0374801 A1 | 12/2016 | Jimenez et al. |
| 2016/0374802 A1 | 12/2016 | Levi et al. |
| 2017/0042678 A1 | 2/2017 | Ganesan et al. |
| 2017/0049435 A1 | 2/2017 | Sauer et al. |
| 2017/0056166 A1 | 3/2017 | Ratz et al. |
| 2017/0056171 A1 | 3/2017 | Cooper et al. |
| 2017/0065407 A1 | 3/2017 | Hacohen et al. |
| 2017/0065411 A1 | 3/2017 | Grundeman et al. |
| 2017/0074855 A1 | 3/2017 | Morin et al. |
| 2017/0100236 A1 | 4/2017 | Robertson et al. |
| 2017/0128205 A1 | 5/2017 | Tamir et al. |
| 2017/0135816 A1 | 5/2017 | Lashinski et al. |
| 2017/0189174 A1 | 7/2017 | Braido et al. |
| 2017/0196688 A1 | 7/2017 | Christianson et al. |
| 2017/0196692 A1 | 7/2017 | Kirk et al. |
| 2017/0209264 A1 | 7/2017 | Chau et al. |
| 2017/0216026 A1 | 8/2017 | Quill et al. |
| 2017/0224323 A1 | 8/2017 | Rowe et al. |
| 2017/0231757 A1 | 8/2017 | Gassler |
| 2017/0231759 A1 | 8/2017 | Geist et al. |
| 2017/0231760 A1 | 8/2017 | Lane et al. |
| 2017/0231766 A1 | 8/2017 | Hariton et al. |
| 2017/0234850 A1 | 8/2017 | Morin |
| 2017/0239048 A1 | 8/2017 | Goldfarb et al. |
| 2017/0252159 A1 | 9/2017 | Hacohen et al. |
| 2017/0266003 A1 | 9/2017 | Hammer et al. |
| 2017/0333183 A1 | 11/2017 | Backus |
| 2017/0333187 A1 | 11/2017 | Hariton et al. |
| 2017/0349940 A1 | 12/2017 | Morin et al. |
| 2017/0360426 A1 | 12/2017 | Hacohen et al. |
| 2017/0367823 A1 | 12/2017 | Hariton et al. |
| 2018/0000580 A1 | 1/2018 | Wallace et al. |
| 2018/0014930 A1 | 1/2018 | Hariton et al. |
| 2018/0014932 A1 | 1/2018 | Hammer et al. |
| 2018/0021129 A1 | 1/2018 | Peterson et al. |
| 2018/0023114 A1 | 1/2018 | Morin et al. |
| 2018/0023115 A1 | 1/2018 | Morin et al. |
| 2018/0028215 A1 | 2/2018 | Cohen |
| 2018/0028311 A1 | 2/2018 | Hacohen |
| 2018/0049873 A1 | 2/2018 | Manash et al. |
| 2018/0055628 A1 | 3/2018 | Patel et al. |
| 2018/0055630 A1 | 3/2018 | Patel et al. |
| 2018/0098850 A1 | 4/2018 | Rafiee et al. |
| 2018/0116790 A1 | 5/2018 | Ratz et al. |
| 2018/0116843 A1 | 5/2018 | Schreck et al. |
| 2018/0125644 A1 | 5/2018 | Conklin |
| 2018/0132999 A1 | 5/2018 | Perouse |
| 2018/0147059 A1 | 5/2018 | Hammer et al. |
| 2018/0153687 A1 | 6/2018 | Hariton et al. |
| 2018/0153689 A1 | 6/2018 | Maimon et al. |
| 2018/0153696 A1 | 6/2018 | Albitov et al. |
| 2018/0161159 A1 | 6/2018 | Lee et al. |
| 2018/0177593 A1 | 6/2018 | Hariton et al. |
| 2018/0177594 A1 | 6/2018 | Patel et al. |
| 2018/0185148 A1 | 7/2018 | Hariton et al. |
| 2018/0206983 A1 | 7/2018 | Noe et al. |
| 2018/0214263 A1 | 8/2018 | Rolando et al. |
| 2018/0243086 A1 | 8/2018 | Barbarino et al. |
| 2018/0250126 A1 | 9/2018 | O'Connor et al. |
| 2018/0250147 A1 | 9/2018 | Syed |
| 2018/0271654 A1 | 9/2018 | Hariton et al. |
| 2018/0280136 A1 | 10/2018 | Hariton et al. |
| 2018/0296333 A1 | 10/2018 | Dixon et al. |
| 2018/0296336 A1 | 10/2018 | Cooper et al. |
| 2018/0296341 A1 | 10/2018 | Noe et al. |
| 2018/0325671 A1 | 11/2018 | Abunassar et al. |
| 2018/0344457 A1 | 12/2018 | Gross et al. |
| 2018/0344490 A1 | 12/2018 | Fox et al. |
| 2018/0353294 A1 | 12/2018 | Calomeni et al. |
| 2018/0360457 A1 | 12/2018 | Ellis et al. |
| 2019/0000613 A1 | 1/2019 | Delgado et al. |
| 2019/0015200 A1 | 1/2019 | Delgado et al. |
| 2019/0021852 A1 | 1/2019 | Delgado et al. |

(56) References Cited

U.S. PATENT DOCUMENTS

| | | |
|---|---|---|
| 2019/0021857 A1 | 1/2019 | Hacohen et al. |
| 2019/0038404 A1 | 2/2019 | Iamberger et al. |
| 2019/0038405 A1 | 2/2019 | Iamberger et al. |
| 2019/0053896 A1 | 2/2019 | Adamek-bowers et al. |
| 2019/0060060 A1 | 2/2019 | Chau et al. |
| 2019/0060068 A1 | 2/2019 | Cope et al. |
| 2019/0060070 A1 | 2/2019 | Groothuis et al. |
| 2019/0069997 A1 | 3/2019 | Ratz et al. |
| 2019/0069998 A1 | 3/2019 | Hacohen |
| 2019/0083248 A1 | 3/2019 | Hariton et al. |
| 2019/0083249 A1 | 3/2019 | Hariton et al. |
| 2019/0083261 A1 | 3/2019 | Perszyk et al. |
| 2019/0105153 A1 | 4/2019 | Barash et al. |
| 2019/0117391 A1 | 4/2019 | Humair |
| 2019/0167423 A1 | 6/2019 | Hariton et al. |
| 2019/0175339 A1 | 6/2019 | Vidlund |
| 2019/0175342 A1 | 6/2019 | Hariton et al. |
| 2019/0183639 A1 | 6/2019 | Moore |
| 2019/0183644 A1 | 6/2019 | Hacohen |
| 2019/0192295 A1 | 6/2019 | Spence et al. |
| 2019/0216602 A1 | 7/2019 | Lozonschi |
| 2019/0231525 A1 | 8/2019 | Hariton et al. |
| 2019/0240010 A1 | 8/2019 | Hacohen |
| 2019/0321172 A1 | 10/2019 | Gross et al. |
| 2019/0336280 A1 | 11/2019 | Naor |
| 2019/0350701 A1 | 11/2019 | Adamek-bowers et al. |
| 2019/0365530 A1 | 12/2019 | Hoang et al. |
| 2019/0388218 A1 | 12/2019 | Vidlund et al. |
| 2019/0388220 A1 | 12/2019 | Vidlund et al. |
| 2020/0000449 A1 | 1/2020 | Goldfarb et al. |
| 2020/0000579 A1 | 1/2020 | Manash et al. |
| 2020/0000580 A1 | 1/2020 | Hacohen |
| 2020/0015964 A1 | 1/2020 | Noe et al. |
| 2020/0030098 A1 | 1/2020 | Delgado et al. |
| 2020/0038181 A1 | 2/2020 | Hariton et al. |
| 2020/0046496 A1 | 2/2020 | Hammer et al. |
| 2020/0054335 A1 | 2/2020 | Hernandez et al. |
| 2020/0060818 A1 | 2/2020 | Geist et al. |
| 2020/0078002 A1 | 3/2020 | Hacohen et al. |
| 2020/0113677 A1 | 4/2020 | McCann et al. |
| 2020/0113689 A1 | 4/2020 | McCann et al. |
| 2020/0113692 A1 | 4/2020 | McCann et al. |
| 2020/0138567 A1 | 5/2020 | Marr et al. |
| 2020/0146824 A1 | 5/2020 | Hammer et al. |
| 2020/0163760 A1 | 5/2020 | Hariton et al. |
| 2020/0163761 A1 | 5/2020 | Hariton et al. |
| 2020/0205969 A1 | 7/2020 | Hacohen |
| 2020/0214832 A1 | 7/2020 | Metchik et al. |
| 2020/0237512 A1 | 7/2020 | McCann et al. |
| 2020/0246136 A1 | 8/2020 | Marr et al. |
| 2020/0246140 A1 | 8/2020 | Hariton et al. |
| 2020/0253600 A1 | 8/2020 | Darabian |
| 2020/0261094 A1 | 8/2020 | Goldfarb et al. |
| 2020/0306037 A1* | 10/2020 | Siegel ............... A61M 25/0662 264/269 |
| 2020/0315786 A1 | 10/2020 | Metchik et al. |
| 2020/0330221 A1 | 10/2020 | Hacohen |
| 2020/0330227 A1 | 10/2020 | Hacohen |
| 2020/0337842 A1 | 10/2020 | Metchik et al. |
| 2020/0360139 A1 | 11/2020 | Hammer et al. |
| 2020/0390548 A1 | 12/2020 | Hariton et al. |
| 2021/0093449 A1 | 4/2021 | Hariton et al. |
| 2021/0106419 A1 | 4/2021 | Abunassar |
| 2021/0113331 A1 | 4/2021 | Quadri et al. |
| 2021/0137680 A1 | 5/2021 | Kizuka et al. |
| 2021/0145578 A1 | 5/2021 | Hariton et al. |
| 2021/0196461 A1 | 7/2021 | Hariton et al. |
| 2021/0259835 A1 | 8/2021 | Tyler, II et al. |
| 2021/0330456 A1 | 10/2021 | Hacohen et al. |
| 2021/0361422 A1 | 11/2021 | Gross et al. |
| 2021/0361426 A1 | 11/2021 | Hacohen |
| 2021/0401573 A1 | 12/2021 | Gross et al. |
| 2022/0000612 A1 | 1/2022 | Hacohen |

FOREIGN PATENT DOCUMENTS

| | | |
|---|---|---|
| CA | 2671966 | 6/2008 |
| CN | 101653365 | 2/2010 |
| CN | 103974674 | 8/2014 |
| CN | 103997990 | 8/2014 |
| CN | 105324091 | 2/2016 |
| EP | 0170262 | 2/1986 |
| EP | 06/14342 | 9/1994 |
| EP | 10/06905 | 6/2000 |
| EP | 0954257 | 8/2000 |
| EP | 1258437 | 11/2002 |
| EP | 1264582 | 12/2002 |
| EP | 0871417 | 10/2003 |
| EP | 1266641 | 10/2004 |
| EP | 1034753 | 2/2005 |
| EP | 1258232 | 1/2006 |
| EP | 1637092 | 3/2006 |
| EP | 1990014 | 11/2008 |
| EP | 1562522 | 12/2008 |
| EP | 1420723 | 1/2009 |
| EP | 1903991 | 9/2009 |
| EP | 1418865 | 10/2009 |
| EP | 2119399 | 11/2009 |
| EP | 1531762 | 4/2010 |
| EP | 1450733 | 2/2011 |
| EP | 2 446 915 A1 | 5/2012 |
| EP | 2088965 | 11/2012 |
| EP | 1768630 | 1/2015 |
| EP | 1861045 | 3/2015 |
| EP | 1465555 | 5/2015 |
| EP | 2349124 | 10/2018 |
| EP | 2739214 | 10/2018 |
| EP | 3417813 | 12/2018 |
| EP | 3583922 | 12/2019 |
| EP | 3270825 | 4/2020 |
| EP | 2485795 | 9/2020 |
| IL | 223448 | 12/2012 |
| JP | S53152790 | 12/1978 |
| KR | 20010046894 | 6/2001 |
| WO | 92/05093 | 4/1992 |
| WO | 93/10714 | 6/1993 |
| WO | 96/39963 | 12/1996 |
| WO | 96/40344 | 12/1996 |
| WO | 97/01369 | 1/1997 |
| WO | 98/46149 | 10/1998 |
| WO | 1998/043557 | 10/1998 |
| WO | 1999/030647 | 6/1999 |
| WO | 00/22981 | 4/2000 |
| WO | 2000-047139 | 8/2000 |
| WO | 01/26586 | 4/2001 |
| WO | 01/56457 | 8/2001 |
| WO | 2001-062189 | 8/2001 |
| WO | 01/82832 | 11/2001 |
| WO | 02/085250 | 10/2002 |
| WO | 02/085251 | 10/2002 |
| WO | 02/085252 | 10/2002 |
| WO | 2003/020179 | 3/2003 |
| WO | 2003/028558 | 4/2003 |
| WO | 03/047467 | 6/2003 |
| WO | 2003/049647 | 6/2003 |
| WO | 2003/105667 | 12/2003 |
| WO | 2004/028399 | 4/2004 |
| WO | 04/103434 | 12/2004 |
| WO | 2004/108191 | 12/2004 |
| WO | 05/021063 | 3/2005 |
| WO | 05/046488 | 5/2005 |
| WO | 2005/062931 | 7/2005 |
| WO | 2006/007389 | 1/2006 |
| WO | 2006/007401 | 1/2006 |
| WO | 06/012013 | 2/2006 |
| WO | 06/012038 | 2/2006 |
| WO | 06/054930 | 5/2006 |
| WO | 2006/065212 | 6/2006 |
| WO | 2006/070372 | 7/2006 |
| WO | 06/086434 | 8/2006 |
| WO | 2006/089236 | 8/2006 |
| WO | 2006/091163 | 8/2006 |
| WO | 06/097931 | 9/2006 |

(56) References Cited

FOREIGN PATENT DOCUMENTS

| | | |
|---|---|---|
| WO | 06/105084 | 10/2006 |
| WO | 06/116558 | 11/2006 |
| WO | 2006/128193 | 11/2006 |
| WO | 07/011799 | 1/2007 |
| WO | 2007/030063 | 3/2007 |
| WO | 2007/047488 | 4/2007 |
| WO | 2007/059252 | 5/2007 |
| WO | 07/121314 | 10/2007 |
| WO | 07/136783 | 11/2007 |
| WO | 07/136981 | 11/2007 |
| WO | 08/013915 | 1/2008 |
| WO | 2008/014144 | 1/2008 |
| WO | 2008/029296 | 3/2008 |
| WO | 2008/031103 | 3/2008 |
| WO | 2008/058940 | 5/2008 |
| WO | 08/068756 | 6/2008 |
| WO | 2008/070797 | 6/2008 |
| WO | 2008/103722 | 8/2008 |
| WO | 2009/026563 | 2/2009 |
| WO | 09/033469 | 3/2009 |
| WO | 09/053497 | 4/2009 |
| WO | 2009/080801 | 7/2009 |
| WO | 2009/091509 | 7/2009 |
| WO | 2009/160631 | 10/2009 |
| WO | 10/004546 | 1/2010 |
| WO | 2010/000454 | 1/2010 |
| WO | 2010/005827 | 1/2010 |
| WO | 2010/006627 | 1/2010 |
| WO | 2010/006905 | 1/2010 |
| WO | 2010/027485 | 3/2010 |
| WO | 2010/037141 | 4/2010 |
| WO | 2010/044851 | 4/2010 |
| WO | 2010/045297 | 4/2010 |
| WO | 2010/057262 | 5/2010 |
| WO | 2010/073246 | 7/2010 |
| WO | 2010/081033 | 7/2010 |
| WO | 2010/085649 | 7/2010 |
| WO | 2010/121076 | 10/2010 |
| WO | 2010/128502 | 11/2010 |
| WO | 2010/128503 | 11/2010 |
| WO | 2010/150178 | 12/2010 |
| WO | 2011/025972 | 3/2011 |
| WO | 2011/051942 | 5/2011 |
| WO | 2011/067770 | 6/2011 |
| WO | 2011/069048 | 6/2011 |
| WO | 2011/089401 | 7/2011 |
| WO | 2011/089601 | 7/2011 |
| WO | 2011/106137 | 9/2011 |
| WO | 2011/111047 | 9/2011 |
| WO | 01/87190 | 11/2011 |
| WO | 2011/137531 | 11/2011 |
| WO | 2011-143263 | 11/2011 |
| WO | 2011/144351 | 11/2011 |
| WO | 2011/148374 | 12/2011 |
| WO | 2011/154942 | 12/2011 |
| WO | 2012/011108 | 1/2012 |
| WO | 2012/014201 | 2/2012 |
| WO | 2012/024428 | 2/2012 |
| WO | 2012/036740 | 3/2012 |
| WO | 2012/048035 | 4/2012 |
| WO | 2012/068541 | 5/2012 |
| WO | 2012/127309 | 9/2012 |
| WO | 2012/176195 | 12/2012 |
| WO | 2012/177942 | 12/2012 |
| WO | 2013/021374 | 2/2013 |
| WO | 2013/021375 | 2/2013 |
| WO | 2013/021384 | 2/2013 |
| WO | 2013/059747 | 4/2013 |
| WO | 2013/069019 | 5/2013 |
| WO | 2013/072496 | 5/2013 |
| WO | 2013/078497 | 6/2013 |
| WO | 2013/088327 | 6/2013 |
| WO | 2013/114214 | 8/2013 |
| WO | 2013/128436 | 9/2013 |
| WO | 2013/175468 | 11/2013 |
| WO | 2014/022124 | 2/2014 |
| WO | 2014/064694 | 5/2014 |
| WO | 2014/064695 | 5/2014 |
| WO | 2014/076696 | 5/2014 |
| WO | 2014/087402 | 6/2014 |
| WO | 2014/115149 | 7/2014 |
| WO | 2014/121280 A2 | 8/2014 |
| WO | 2014/144937 | 9/2014 |
| WO | 2014/145338 | 9/2014 |
| WO | 2014/164364 | 10/2014 |
| WO | 2014/194178 | 12/2014 |
| WO | 2014/195786 | 12/2014 |
| WO | 2015/059699 | 4/2015 |
| WO | 2015/173794 | 11/2015 |
| WO | 2015/191923 | 12/2015 |
| WO | 2016/016899 | 2/2016 |
| WO | 2016/093877 | 6/2016 |
| WO | 2016/125160 | 8/2016 |
| WO | 2017/223486 | 12/2017 |
| WO | 2018/025260 | 2/2018 |
| WO | 2018/025263 | 2/2018 |
| WO | 2018/029680 | 2/2018 |
| WO | 2018/039631 | 3/2018 |
| WO | 2018/106837 | 6/2018 |
| WO | 2018/112429 | 6/2018 |
| WO | 2018/118717 | 6/2018 |
| WO | 2018/131042 | 7/2018 |
| WO | 2018/131043 | 7/2018 |
| WO | 2019/026059 | 2/2019 |
| WO | 2019/027507 | 2/2019 |
| WO | 2019/030753 | 2/2019 |
| WO | 2019/077595 | 4/2019 |
| WO | 2019/116369 | 6/2019 |
| WO | 2019/138400 | 7/2019 |
| WO | 2019/195860 | 10/2019 |
| WO | 2019/202579 | 10/2019 |
| WO | 2020/058972 | 3/2020 |
| WO | 2020/167677 | 8/2020 |
| WO | 2021/156866 A1 | 8/2021 |
| WO | 2021/186424 A1 | 9/2021 |

OTHER PUBLICATIONS

Ex Parte Quayle dated May 2, 2022, which issued during the prosecution of U.S. Appl. No. 16/879,952.
An International Search Report and a Written Opinion both dated May 3, 2022, which issued during the prosecution of Applicant's PCT/IL2021/051433.
An Office Action together with an English Summary dated May 7, 2022 which issued during the prosecution of Chinese Patent Application No. 201880058940.2.
Notice of Allowance dated May 4, 2022, which issued during the prosecution of U.S. Appl. No. 16/680,739.
An Office Action dated Jun. 28, 2022, which issued during the prosecution of U.S. Appl. No. 16/135,969.
An Office Action dated Jul. 8, 2022, which issued during the prosecution of U.S. Appl. No. 16/144,054.
IPR2021-00383 Final Written Decision dated Jul. 18, 2022.
An Office Action dated Apr. 11, 2022, which issued during the prosecution of U.S. Appl. No. 17/473,472.
IPR2021-00383 Preliminary Guidance dated Jan. 31, 2022.
An Office Action dated Mar. 18, 2022, which issued during the prosecution of U.S. Appl. No. 16/746,489.
Notice of Allowance dated Mar. 22, 2022, which issued during the prosecution of U.S. Appl. No. 17/366,711.
Notice of Allowance dated Mar. 4, 2022, which issued during the prosecution of U.S. Appl. No. 16/768,909.
An Office Action dated Dec. 9, 2021, which issued during the prosecution of U.S. Appl. No. 16/135,969.
An Office Action dated Jan. 24, 2022, which issued during the prosecution of U.S. Appl. No. 16/135,466.
An Office Action dated Sep. 29, 2022, which issued during the prosecution of U.S. Appl. No. 17/010,886.
An Office Action dated Sep. 29, 2022, which issued during the prosecution of U.S. Appl. No. 16/656,790.

(56) References Cited

OTHER PUBLICATIONS

An Office Action dated Nov. 2, 2022, which issued during the prosecution of U.S. Appl. No. 17/004,693.
An Office Action dated Nov. 28, 2022, which issued during the prosecution of U.S. Appl. No. 17/141,853.
An Office Action dated Oct. 19, 2022, which issued during the prosecution of U.S. Appl. No. 17/875,589.
An Office Action dated Oct. 26, 2022, which issued during the prosecution of U.S. Appl. No. 16/746,489.
An Office Action dated Nov. 23. 2012, which issued during the prosecution of U.S. Appl. No. 13/033,852.
An Office Action dated Dec. 31, 2012, which issued during the prosecution of U.S. Appl. No. 13/044,694.
An Office Action dated Feb. 6, 2013, which issued during the prosecution of U.S. Appl. No. 13/412,814.
Langer F et al., "RING plus STRING: Papillary muscle repositioning as an adjunctive repair technique for ischemic mitral regurgitation," J Thorac Cardiovasc Surg 133:247-9, Jan. 2007.
Langer F et al., "RING+STRING: Successful repair technique for ischemic mitral regurgitation with severe leaflet tethering," Circulation 120[suppl 1]: S85-S91, Sep. 2009.
"Transcatheter Valve-in-Valve Implantation for Failed Bioprosthetic Heart Valves", J Webb et al., Circulation. Apr. 2010; 121: 1848-1857.
Jansen, J., Willeke, S., Reul, H. and Rum, G. (1992), Detachable Shape-Memory Sewing Ring for Heart Valves. Artificial Organs, 16:294-297. 1992 (an abstract).
Alexander S. Geha, et al., Replacement of degenerated mitral and aortic bioprostheses without explanation Ann Thorac Surg. Jun. 2001; 72:1509-1514.
An International Search Report and a Written Opinion both dated Oct. 13, 2011 which issued during the prosecution of Applicant's PCT/IL11/00231.
An Office Action dated Jul. 1, 2016, which issued during the prosecution of U.S. Appl. No. 14/161,921.
An International Search Report and a Written Opinion both dated Dec. 5, 2011, which issued during the prosecution of Applicant's PCT/IL11/00582.
An Office Action dated May 29, 2012, which issued during the prosecution of U.S. Appl. No. 12/840,463.
U.S. Appl. No. 61/555,160, filed Nov. 3, 2011.
U.S. Appl. No. 61/525,281, filed Aug. 19, 2011.
U.S. Appl. No. 61/537,276, filed Sep. 21, 2011.
U.S. Appl. No. 61/515,372, filed Aug. 5, 2011.
U.S. Appl. No. 61/492,449, filed Jun. 2, 2011.
U.S. Appl. No. 61/588,892, filed Jan. 20, 2012.
An International Search Report and a Written Opinion both dated Feb. 6, 2013, which issued during the prosecution of Applicant's PCT/IL12/00292.
An International Search Report and a Written Opinion both dated Feb. 6, 2013, which issued during the prosecution of Applicant's PCT/IL12/00293.
An Office Action dated Nov. 28, 2012, which issued during the prosecution of U.S. Appl. No. 12/961,721.
An Office Action dated Feb. 15, 2013, which issued during the prosecution of U.S. Appl. No. 12/840,463.
An Office Action dated Feb. 10, 2014, which issued during the prosecution of U.S. Appl. No. 13/031,852.
An Office Action dated Sep. 19, 2014, which issued during the prosecution of U.S. Appl. No. 13/044,694.
An International Search Report and a Written Opinion both dated Sep. 4, 2014 which issued during the prosecution of Applicant's PCT/IL2014/050087.
Invitation to Pay Additional Fees dated Jun. 12, 2014 PCT/IL2014/050087.
An Office Action dated Jun. 17, 2014, which issued during the prosecution of U.S. Appl. No. 12/961,721.
An Office Action dated Jul. 3, 2014, which issued during the prosecution of U.S. Appl. No. 13/033,852.
An Office Action dated May 23, 2014, which issued during the prosecution of U.S. Appl. No. 13/411,814.
Dominique Himbert; Mitral Regurgitation and Stenosis from Bioprosthesis and Annuloplasty Failure: Transcatheter approaches and outcomes 24 pages Oct. 28, 2013.
An International Search Report and a Written Opinion both dated Mar. 17, 2014 which issued during the prosecution of Applicant's PCT/IL2013/050937.
An International Preliminary Report on patentabilty dated Dec. 2, 2013, which issued during the prosecution of Applicant's PCT/IL11/00582.
An Office Action dated Sep. 12, 2013, which issued during the prosecution of U.S. Appl. No. 13/411,814.
An Office Action dated Aug. 2, 2013, which issued during the prosecution of U.S. Appl. No. 13/033,852.
An International Preliminary Report on patentabilty dated Sep. 11, 2012, which issued during the prosecution of Applicant's PCT/IL2011/000231.
An Office Action dated Jul. 2, 2014, which issued during the prosecution of U.S. Appl. No. 13/811,308.
An Office Action dated Jan. 20, 2016, which issued during the prosecution of U.S. Appl. No. 14/161,921.
An Office Action dated Jul. 23, 2013, which issued during the prosecution of U.S. Appl. No. 12/961,721.
An Office Action dated Jul. 18, 2013, which issued during the prosecution of U.S. Appl. No. 13/044,694.
An Office Action dated Nov. 8, 2013, which issued during the prosecution of U.S. Appl. No. 12/840,463.
An Office Action dated Jun. 4, 2014, which issued during the prosecution of U.S. Appl. No. 12/840,463.
An Office Action dated Aug. 13, 2012, which issued during the prosecution of U.S. Appl. No. 13/044,694.
An Office Action dated Jul. 2, 2012, which issued during the prosecution of U.S. Appl. No. 13/033,852.
An Office Action dated Feb. 3, 2014, which issued during the prosecution of U.S. Appl. No. 13/811,308.
An International Preliminary Report on patentabilty dated Feb. 11, 2014, which issued during the prosecution of Applicant's PCT/IL12/00292.
An International Preliminary Report on patentabilty dated Feb. 11, 2014, which issued during the prosecution of Applicant's PCT/IL12/00293.
A Notice of Allowance dated Aug. 15, 2014, which issued during the prosecution of U.S. Appl. No. 13/411,814.
An Office Action dated Aug. 14. 2012, which issued during the prosecution of U.S. Appl. No. 12/961,721.
U.S. Appl. No. 61/283,819, filed Dec. 8, 2009.
Notice of Allowance dated Apr. 8, 2016, which issued during the prosecution of U.S. Appl. No. 14/237,258.
U.S. Appl. No. 61/756,034, filed Jan. 24, 2013.
U.S. Appl. No. 61/756,049, filed Jan. 24, 2013.
An International Preliminary Report on Patentability dated Jan. 31, 2017, which issued during the prosecution of Applicant's PCT/IL2015/050792.
U.S. Appl. No. 62/372,861, filed Aug. 10, 2016.
Notice of Allowance dated Aug. 13, 2018, which issued during the prosecution of U.S. Appl. No. 15/995,597.
Notice of Allowance dated Apr. 20, 2018, which issued during the prosecution of U.S. Appl. No. 15/878,206.
An Office Action dated Dec. 10, 2015, which issued during the prosecution of U.S. Appl. No. 14/237,258.
An International Preliminary Report on Patentability dated Jul. 28, 2015, which issued during the prosecution of Applicant's PCT/IL2014/050087.
An Office Action dated Nov. 27, 2015, which issued during the prosecution of U.S. Appl. No. 14/626,267.
An Office Action dated Jan. 21, 2016, which issued during the prosecution of U.S. Appl. No. 14/237,264.
An Office Action dated Jan. 30, 2015, which issued during the prosecution of UK Patent Application No. 1413474.6.
An International Search Report and a Written Opinion both dated May 30, 2016, which issued during the prosecution of Applicant's PCT/IL2016/050125.

(56) References Cited

OTHER PUBLICATIONS

An Office Action dated Sep. 26, 2016, which issued during the prosecution of U.S. Appl. No. 14/761,004.
An Office Action dated Jan. 18, 2017, which issued during the prosecution of U.S. Appl. No. 14/626,267.
An Office Action dated Feb. 7, 2017, which issued during the prosecution of U.S. Appl. No. 14/689,608.
An Office Action dated Feb. 8, 2017, which issued during the prosecution of UK Patent Application No. 1613219.3.
An Office Action together dated Feb. 10, 2017: which issued during the prosecution of European Patent Application No. 12821522.5.
An International Search Report and a Written Opinion both dated Oct. 27, 2015, which issued during the prosecution of Applicant's PCT/IL2015/050792.
European Search Report dated Feb. 18. 2015, which issued during the prosecution of Applicant's European App No. 12821522.5.
Saturn Project—a novel solution for transcatheter heart valve replacement specifically designed to address clinical therapeutic needs on mitral valve: Dec. 2016.
Righini presentation EuroPCR May 2015 (Saturn)—(downloaded from: https://www.pcronline.com/Cases-resourcesimages/Resources/Course-videos-slides/2015/Cardiovascularinnovation-pipeline-Mitral-and-tricuspid-valve-interventions).
An Advisory Action dated Apr. 2, 2018, which issued during the prosecution of U.S. Appl. No. 14/761,004.
An Office Action dated Jul. 26, 2018, which issued during the prosecution of U.S. Appl. No. 15/872.501.
An Office Action dated May 4, 2018, which issued during the prosecution of U.S. Appl. No. 15/872.501.
An Office Action dated Apr. 20, 2018, which issued during the prosecution of U.S. Appl. No. 15/886,517.
An Office Action dated Aug. 9, 2018, which issued during the prosecution of U.S. Appl. No. 15/899,858.
An Office Action dated Aug. 9, 2018, which issued during the prosecution of U.S. Appl. No. 15/902,403.
An Office Action dated Jun. 28, 2018, which issued during the prosecution of U.S. Appl. No. 29/635,658.
An Office Action dated Jun. 28, 2018, which issued during the prosecution of U.S. Appl. No. 29/635,661.
Georg Lutter, MD, et al; "Percutaneous Valve Replacement: Current State and Future Prospects", The Annals of Thoracic Surgery ; vol. 78, pp. 2199-2206, Dec. 2004.
An Office Action dated Jun. 6, 2018, which issued during the prosecution of UK Patent Application No. 1720803.4.
An International Search Report and a Written Opinion both dated Jun. 20, 2018, which issued during the prosecution of Applicant's PCT/IL2018/050024.
An Office Action dated Jun. 18, 2018, which issued during the prosecution of UK Patent Application No. 1800399.6.
An Office Action dated Oct. 23, 2017, which issued during the prosecution of U.S. Appl. No. 14/761,004.
An Office Action dated Dec. 7, 2017, which issued during the prosecution of U.S. Appl. No. 15/211,791.
Interview Summary dated Feb. 8, 2018, which issued during the prosecution of U.S. Appl. No. 15/213,791.
An Office Action dated Feb. 7, 2018, which issued during the prosecution of U.S. Appl. No. 15/197,069.
An International Search Report and a Written Opinion both dated Nov. 24, 2017, which issued during the prosecution of Applicant's PCT/IL2017/050873.
An Office Action dated Jan. 5, 2018, which issued during the prosecution of U.S. Appl. No. 15/541,783.
An Office Action dated Feb. 2, 2018, which issued during the prosecution of U.S. Appl. No. 15/329,920.
An Invitation to pay additional fees dated Jan. 2, 2018, which issued during the prosecution of Applicant's PCT/IL2017/050849.
An Invitation to pay additional fees dated Sep. 29, 2017, which issued during the prosecution of Applicant's PCT/IL2017/050873.
European Search Report dated Jun. 29, 2017, which issued during the prosecution of Applicant's European App No. 11809374.9.

An Invitation to pay additional fees dated Oct. 11, 2018, which issued during the prosecution of Applicant's PCT/IL2018/050725.
An Office Action dated Dec. 4, 2018, which issued during the prosecution of U.S. Appl. No. 16/041,059.
An Office Action together with the English translation dated Nov. 5, 2018 which issued during the prosecution of Chinese Patent Application No. 201680008328.5.
Notice of Allowance dated Sep. 25, 2018, which issued during the prosecution of U.S. Appl. No. 15/188,507.
European Search Report dated Sep. 26, 2018 which issued during the prosecution of Applicant's European App No. 18186784.7.
An Office Action dated Jun. 30, 2015, which issued during the prosecution of U.S. Appl. No. 14/522,987.
Notice of Allowance dated Dec. 13. 2013, which issued during the prosecution of U.S. Appl. No. 13/675,119.
An International Preliminary Report on Patentability dated Aug. 8, 2017, which issued during the prosecution of Applicant's PCT/IL2016/050125.
An Office Action dated Jan. 17, 2018, which issued during the prosecution of U.S. Appl. No. 14/763,004.
An Office Action dated Mar. 25, 2015, which issued during the prosecution of U.S. Appl. No. 12/840,463.
An Office Action dated Feb. 25, 2016, which issued during the prosecution of U.S. Appl. No. 14/522,987.
An Office Action dated Apr. 13, 2016, which issued during the prosecution of U.S. Appl. No. 14/626,267.
An Office Action dated Aug. 28, 2015, which issued during the prosecution of U.S. Appl. No. 14/237,264.
Maisano (2015) TCR presentation re Cardiovalve.
Notice of Allowance dated Sep. 29, 2016, which issued during the prosecution of U.S. Appl. No. 14/442,541.
Notice of Allowance dated May 10, 2016, which issued during the prosecution of U.S. Appl. No. 14/237,258.
Notice of Allowance dated May 20, 2016, which issued during the prosecution of U.S. Appl. No. 14/237,258.
An International Preliminary Report on Patentability dated May 19, 2015, which issued during the prosecution of Applicant's PCT/IL2013/050937.
Dusan Pavcnik, MD, PhD2, et al.; "Development and Initial Experimental Evaluation of a Prosthetic Aortic Valve for Transcatheter Placement", Cardiovascular Radiology. Radiology Apr. 1992, vol. 183, pp. 151-154.
Notice of Allowance dated Oct. 16, 2013, which issued during the prosecution of U.S. Appl. No. 13/675,119.
Notice of Allowance dated Feb. 11. 2015, which issued during the prosecution of U.S. Appl. No. 13/033,852.
Notice of Allowance dated May 5, 2015, which issued during the prosecution of U.S. Appl. No. 12/840,463.
Notice of Allowance dated Mar. 10, 2015, which issued during the prosecution of U.S. Appl. No. 13/811,308.
Notice of Allowance dated Jul 1, 2016, which issued during the prosecution of U.S. Appl. No. 14/442,541.
An Office Action dated Mar. 25, 2019, which issued during the prosecution of European Patent Application No. 14710060.6.
An International Search Report and a Written Opinion both dated Nov. 9, 2018, which issued during the prosecution of Applicant's PCT/IL2018/050869.
An International Search Report and a Written Opinion both dated Dec. 5, 2018, which issued during the prosecution of Applicant's PCT/IL2018/050725.
An International Search Report and a Written Opinion both dated Apr. 25, 2019, which issued during the prosecution of Applicant's PCT/IL2019/050142.
An International Preliminary Report on Patentability dated Feb. 12, 2019, which issued during the prosecution of Applicant's PCT/IL2017/050873.
An Office Action dated Sep. 13, 2019, which issued during the prosecution of U.S. Appl. No. 16/460,313.
An Office Action dated Nov. 26, 2019, which issued during the prosecution of U.S. Appl. No. 16/532,945.
An Office Action dated Aug. 16, 2019, which issued during the prosecution of U.S. Appl. No. 15/668,659.

(56) References Cited

OTHER PUBLICATIONS

An Office Action dated Nov. 1, 2019, which issued during the prosecution of U.S. Appl. No. 15/872,501.
An Office Action dated Jun. 14, 2019, which issued during the prosecution of U.S. Appl. No. 15/703,385.
An Office Action dated Oct. 4, 2019, which issued during the prosecution of U.S. Appl. No. 16/183,140.
An Office Action dated Jun. 13, 2019, which issued during the prosecution of U.S. Appl. No. 16/388,038.
An International Preliminary Report on Patentability dated Feb. 4, 2020, which issued during the prosecution of Applicant's PCT/IL2018/050725.
An International Search Report and a Written Opinion both dated Jan. 25, 2019, which issued during the prosecution of Applicant's PCT/IL2018/051122.
An International Search Report and a Written Opinion both dated May 13, 2019, which issued during the prosecution of Applicant's PCT/IL2018/051350.
An International Preliminary Report on Patentability dated Feb. 5, 2019, which issued during the prosecution of Applicant's PCT/IL2017/050849.
An Office Action dated Oct. 25, 2018, which issued during the prosecution of U.S. Appl. No. 14/761,004.
An Office Action dated Mar. 4, 2019, which issued during the prosecution of U.S. Appl. No. 14/763,004.
An Office Action dated Jan. 9, 2019, which issued during the prosecution of U.S. Appl. No. 15/329,920.
An Office Action dated Jan. 30, 2019, which issued during the prosecution of U.S. Appl. No. 15/872,501.
An Office Action dated Feb. 5, 2019, which issued during the prosecution of U.S. Appl. No. 15/899,858.
An Office Action dated May 23, 2019, which issued during the prosecution of U.S. Appl. No. 15/668,659.
An Office Action dated May 1, 2019, which issued during the prosecution of U.S. Appl. No. 15/691,032.
An Office Action dated Aug. 1, 2019, which issued during the prosecution of U.S. Appl. No. 15/668,559.
An Office Action dated Jun. 19, 2019, which issued during the prosecution of U.S. Appl. No. 15/682,789.
Notice of Allowance dated Jan. 13, 2020, which issued during the prosecution of U.S. Appl. No. 15/956,956.
An Office Action dated Jun. 25, 2019, which issued during the prosecution of U.S. Appl. No. 15/329,920.
An Office Action dated May 16, 2019, which issued during the prosecution of U.S. Appl. No. 15/433,547.
U.S. Appl. No. 62/560,384, filed Sep. 19, 2017.
U.S. Appl. No. 62/112,343, filed Feb. 5, 2015.
An International Preliminary Report on Patentability dated Feb. 11, 2020, which issued during the prosecution of Applicant's PCT/IL2018/050869.
An International Preliminary Report on Patentability dated Oct. 20, 2020, which issued during the prosecution of Applicant's PCT/IL2019/050142.
An Office Action dated Jan. 6, 2020, which issued during the prosecution of U.S. Appl. No. 16/660,231.
An Office Action dated Dec. 31, 2019, which issued during the prosecution of U.S. Appl. No. 16/183,140.
Notice of Allowance dated Apr. 24, 2019, which issued during the prosecution of U.S. Appl. No. 16/045,059.
An Office Action dated Jan. 14, 2020, which issued during the prosecution of U.S. Appl. No. 16/284,331.
European Search Report dated Mar. 5, 2020 which issued during the prosecution of Applicant's European App No. 17752184.6.
European Search Report dated Mar. 4, 2020 which issued during the prosecution of Applicant's European App No. 16706913.7.
Notice of Allowance dated Mar. 12, 2020, which issued during the prosecution of U.S. Appl. No. 16/460,313.
An Office Action dated Jan. 9, 2020, which issued during the prosecution of U.S. Appl. No. 15/600,190.
An Office Action dated Jan. 3, 2020, which issued during the prosecution of U.S. Appl. No. 16/678,355.
An Office Action dated Feb. 6, 2020, which issued during the prosecution of U.S. Appl. No. 15/668,659.
Notice of Allowance dated Jan. 16, 2020, which issued during the prosecution of U.S. Appl. No. 16/532,945.
Notice of Allowance dated Aug. 19, 2020, which issued during the prosecution of U.S. Appl. No. 16/637,166.
Notice of Allowance dated Jul. 27, 2020, which issued during the prosecution of U.S. Appl. No. 16/637,166.
Notice of Allowance dated Jun. 23, 2020, which issued during the prosecution of U.S. Appl. No. 16/637,166.
Notice of Allowance dated May 7, 2020, which issued during the prosecution of U.S. Appl. No. 16/637,166.
Sündermann, Simon H., et al. "Feasibility of the Engager™ aortic transcatheter valve system using a flexible over-the-wire design." European Journal of Cardio-Thoracic Surgery 42.4 (2012): e48-e52.
An Office Action summarized English translation and Search Report dated Jul. 3, 2020, which issued during the prosecution of Chinese Patent Application No. 201780061210.3.
Serruys, P. W., Piazza, N., Cribier, A., Webb, J., Laborde, J. C., & de Jaegere, P. (Eds.). (2009). Transcatheter aortic valve implantation: tips and tricks to avoid failure. CRC Press.—Screenshots from Google Books downloaded from: https://books.google.co.il/books?id=FLzLBQAAQBAJ&lpg=PA198&ots=soqWrDH-y_&dq=%20%22Edwards%20SAPIEN%22&lr&pg=PA20#v=onepage&q=%22Edwards%20SAPIEN%22&f=false ; Downloaded on Jun. 18, 2020.
An International Search Report and a Written Opinion both dated Jun. 24, 2020, which issued during the prosecution of Applicant's PCT/IL2019/051398.
An Office Action dated Jul. 14, 2020, which issued during the prosecution of U.S. Appl. No. 16/324,339.
Notice of Allowance dated Aug. 28, 2020, which issued during the prosecution of U.S. Appl. No. 16/324,339.
Notice of Allowance dated Jul. 29, 2020, which issued during the prosecution of U.S. Appl. No. 16/132,937.
An Office Action dated Jul. 29, 2020, which issued during the prosecution of U.S. Appl. No. 16/269,328.
Notice of Allowance dated Aug. 26, 2020, which issued during the prosecution of U.S. Appl. No. 16/269,328.
An Office Action dated Aug. 7, 2020, which issued during the prosecution of U.S. Appl. No. 15/668,659.
Tchetche, D. and Nicolas M. Van Mieghem: "New-generation TAVI devices: description and specifications" EuroIntervention, 2014, No. 10:U90-U100.
An Office Action dated Aug. 23, 2019, which issued during the prosecution of U.S. Appl. No. 15/600,190.
Symetis S.A.: "ACURATE neo ™ Aortic Bioprosthesis for Implantation using the ACURATE neo ™ TA Transapical Delivery System in Patients with Severe Aortic Stenosis," Clinical Investigation Plan, Protocol No. 2015-01, Vs. No. 2, 2015:1-76.
Notice of Allowance dated Sep. 10, 2020, which issued during the prosecution of U.S. Appl. No. 15/600,190.
Notice of Allowance dated Sep. 10, 2020, which issued during the prosecution of U.S. Appl. No. 16/324,339.
Notice of Allowance dated Oct. 19, 2020, which issued during the prosecution of U.S. Appl. No. 16/324,339.
Notice of Allowance dated Sep. 21, 2020, which issued during the prosecution of U.S. Appl. No. 16/269,328.
Notice of Allowance dated Oct. 28, 2020, which issued during the prosecution of U.S. Appl. No. 16/269,328.
Notice of Allowance dated Jan. 16, 2020, which issued during the prosecution of U.S. Appl. No. 15/872,501.
An Office Action dated May 11, 2020, which issued during the prosecution of U.S. Appl. No. 16/811,732.
An Office Action dated Sep. 24, 2020, which issued during the prosecution of U.S. Appl. No. 16/811,732.
Notice of Allowance dated Mar. 29, 2017, which issued during the prosecution of U.S. Appl. No. 14/161,921.
Agarwal et al. International Cardiology Perspective Functional Tricuspid Regurgitation, Circ Cardiovasc Interv 2009;2;2;565-573 (2009).

(56) References Cited

OTHER PUBLICATIONS

Alfieri et al., "An effective technique to correct anterior mitral leaflet prolapse," J Card 14(6):468-470 (1999).
Alfieri et al., "The double orifice technique in mitral valve repair: a simple solution for complex problems," Journal of Thoracic Cardiovascular Surgery 122:674-681 (2001).
Alfieri, "The edge-to-edge repair of the mitral valve," [Abstract] 6th Annual NewEra Cardiac Care: Innovation & Technology, Heart Surgery Forum pp. 103. (2000).
Alfieri et al. "Novel Suture Device for Beating-Heart Mitral Leaflet Approximation", Ann Thorac Surg. 2002, 74:1488-1493.
Alfieri et al., "The edge to edge technique," The European Association for Cardio-Thoracic Surgery 14th Annual Meeting Oct. 7-11, Book of Procees. (2000).
Amplatzer Cardiac Plug brochure (English pages), AGA Medical Corporation (Plymouth, MN) (copyright 2008-2010, downloaded Jan. 11, 2011).
AMPLATZER® Cribriform Occluder. A patient guide to Percutaneous, Transcatheter, Atrial Septal Defect Closuer, AGA Medical Corporation, Apr. 2008.
AMPLATZER® Septal Occluder. A patient guide to the Non-Surgical Closuer of the Atrial Septal Defect Using the AMPLATZER Septal Occluder System, AGA Medical Corporation, Apr. 2008.
Brennan, Jennifer, 510(k) Summary of safety and effectiveness, Jan. 2008.
Dictionary.com definition of "lock", Jul. 29, 2013.
Dang NC et al. "Simplified Placement of Multiple Artificial Mitral Valve Chords," The Heart Surgery Forum #2005-1005, 8 (3) (2005).
Maisano, The double-orifice technique as a standardized approach to treat mitral . . . , European Journal of Cardio-thoracic Surgery 17 (2000) 201-205.
"Two dimensional real-time ultrasonic imaging of the heart and great vessels", Mayo Clin Proc. vol. 53:271-303, 1978.
Odell JA et al, "Early Results o4yf a Simplified Method of Mitral Valve Annuloplasty," Circulation 92: 150-154 (1995).
O'Reilly S et al., "Heart valve surgery pushes the envelope," Medtech Insight 8(3): 73, 99-108 (2006).
Swain CP et al., "An endoscopically deliverable tissue-transfixing device for securing biosensors in the gastrointestinal tract," Gastrointestinal Endoscopy 40(6): 730-734 (1994).
An Invitation to pay additional fees dated Jan. 31, 2014, which issued during the prosecution of Applicant's PCT/IL2013/050860.
U.S. Appl. No. 62/030,715, filed Jul. 30, 2014.
U.S. Appl. No. 62/139,854, filed Mar. 30, 2015.
U.S. Appl. No. 61/312,412, filed Mar. 10, 2010.
An Invitation to pay additional fees dated Jan. 31, 2014, which issued during the prosecution of Applicant's PCT/IL2013/050861.
An International Preliminary Report on Patentability dated Dec. 23, 2013, which issued during the prosecution of Applicant's PCT/IL2012/000250.
An International Preliminary Report on Patentability dated Sep. 18, 2007, which issued during the prosecution of Applicant's PCT/IL2006/000342.
An International Preliminary Report on Patentability dated Jun. 5, 2012, which issued during the prosecution of Applicant's PCT/IL2010/001024.
An International Preliminary Report on Patentability dated Apr. 28, 2015, which issued during the prosecution of Applicant's PCT/IL2013/050861.
An International Preliminary Report on Patentability dated Apr. 26, 2016, which issued during the prosecution of Applicant's PCT/IL2014/050914.
An International Preliminary Report on Patentability dated Jun. 10, 2009, which issued during the prosecution of Applicant's PCT/IL07/01503.
An International Preliminary Report on Patentability dated Dec. 18, 2010, which issued during the prosecution of Applicant's PCT/IL09/00593.
An International Preliminary Report on Patentability dated Jun. 29, 2011, which issued during the prosecution of Applicant's PCT/IL2009/001209.
Notice of Allowance dated Aug. 18, 2017, which issued during the prosecution of U.S. Appl. No. 14/682,608.
Notice of Allowance dated Jul. 6, 2017, which issued during the prosecution of U.S. Appl. No. 14/682,608.
Notice of Allowance dated May 22, 2017, which issued during the prosecution of U.S. Appl. No. 14/682,608.
An Office Action dated Apr. 21, 2017, which issued during the prosecution of U.S. Appl. No. 15/213,791.
An Office Action dated Sep. 29, 2017, which issued during the prosecution of U.S. Appl. No. 15/191,069.
An International Preliminary Report on Patentability dated Nov. 9, 2011, which issued during the prosecution of Applicant's PCT/IL2010/000357.
An International Preliminary Report on Patentability dated Nov. 9, 2011 which issued during the prosecution of Applicant's PCT/IL2010/000358.
An International Preliminary Report on Patentability dated Nov. 27, 2012, which issued during the prosecution of Applicant's PCT/IL2011/000404.
An International Preliminary Report on Patentability dated Feb. 4, 2014, which issued during the prosecution of Applicant's PCT/IL2011/000446.
An International Preliminary Report on Patentability dated Jan. 29, 2013, which issued during the prosecution of Applicant's PCT/IL2011/000600.
An International Preliminary Report on Patentability dated Dec. 23, 2014, which issued during the prosecution of Applicant's PCT/IL2012/050451.
A Notice of Allowance dated Jul. 30, 2015, which issued during the prosecution of U.S. Appl. No. 13/319,007.
An Office Action dated Sep. 29, 2014, which issued during the prosecution of U.S. Appl. No. 13/504,870.
An Office Action dated Jan. 13, 2015, which issued during the prosecution of U.S. Appl. No. 13/707,013.
An Office Action dated Mar. 23, 2015, which issued during the prosecution of U.S. Appl. No. 13/707,013.
Notice of Allowance dated Mar. 25, 2015, which issued during the prosecution of U.S. Appl. No. 13/749,153.
An Office Action dated Oct. 3, 2014, which issued during the prosecution of U.S. Appl. No. 13/749,153.
Notice of Allowance dated May 22, 2015, which issued during the prosecution of U.S. Appl. No. 13/749,153.
Notice of Allowance dated Aug. 3, 2015, which issued during the prosecution of U.S. Appl. No. 13/749,153.
An Office Action dated Dec. 19, 2013, which issued during the prosecution of U.S. Appl. No. 14/027,934.
An Office Action dated Jun. 11, 2014, which issued during the prosecution of U.S. Appl. No. 14/027,934.
An Office Action dated Aug. 22, 2014, which issued during the prosecution of U.S. Appl. No. 14/027,934.
An Office Action dated Apr. 2, 2015, which issued during the prosecution of U.S. Appl. No. 14/027,934.
An Office Action dated Jan. 5, 2016, which issued during the prosecution of U.S. Appl. No. 14/027,934.
An Office Action dated Jan. 5, 2016, which issued during the prosecution of U.S. Appl. No. 14/084,426.
An Office Action dated Mar. 16, 2015, which issued during the prosecution of U.S. Appl. No. 14/084,426.
An Office Action dated Jan. 6, 2016, which issued during the prosecution of U.S. Appl. No. 14/128,756.
An Office Action dated May 11, 2016, which issued during the prosecution of U.S. Appl. No. 14/128,756.
Notice of Allowance dated Oct. 20, 2015, which issued during the prosecution of U.S. Appl. No. 12/996,954.
Notice of Allowance dated Feb. 19, 2014, which issued during the prosecution of U.S. Appl. No. 12/795,192.
An Office Action dated Jul. 20, 2012, which issued during the prosecution of U.S. Appl. No. 12/843,412.
An Office Action dated Mar. 27, 2013, which issued during the prosecution of U.S. Appl. No. 12/843,412.

(56) References Cited

OTHER PUBLICATIONS

A Restriction Requirement dated May 1, 2012, which issued during the prosecution of U.S. Appl. No. 12/843,412.
A Notice of Allowance dated May 2, 2013, which issued during the prosecution of U.S. Appl. No. 12/843,412.
A Restriction Requirement dated Nov. 19, 2012, which issued during the prosecution of U.S. Appl. No. 12/926,673.
An Office Action dated Feb. 12, 2013, which issued during the prosecution of U.S. Appl. No. 12/926,673.
An Office Action dated Oct. 22, 2013, which issued during the prosecution of U.S. Appl. No. 12/926,673.
A Notice of Allowance dated Jan. 7, 2014, which issued during the prosecution of U.S. Appl. No. 12/926,673.
An Office Action dated Oct. 9, 2013, which issued during the prosecution of U.S. Appl. No. 12/996,954.
An Office Action dated Mar. 24, 2015, which issued during the prosecution of U.S. Appl. No. 12/996,954.
An Office Action dated Oct. 5, 2012, which issued during the prosecution of U.S. Appl. No. 12/996,954.
Notice of Allowance dated Jul. 7, 2015, which issued during the prosecution of U.S. Appl. No. 12/996,954.
An Office Action dated Nov. 16, 2018, which issued during the prosecution of U.S. Appl. No. 16/042,028.
An International Search Report with Written Opinion both dated Feb. 2, 2012, which issued during the prosecution of Applicant's PCT/IL2011/000600.
An International Search Report together with Written Opinion both dated Mar. 30, 2011, which issued during the prosecution of Applicant's PCT/IL2010/001024.
An International Search Report and a Written Opinion both dated Feb. 10, 2011, which issued during the prosecution of Applicant's PCT/IL10/00890.
An Office Action dated May 28, 2015, which issued during the prosecution of U.S. Appl. No. 14/128,756.
An Office Action dated Sep. 6, 2018, which issued during the prosecution of U.S. Appl. No. 15/994,022.
An Office Action dated Sep. 7, 2018, which issued during the prosecution of U.S. Appl. No. 15/991,725.
An Office Action dated Nov. 26, 2018, which issued during the prosecution of U.S. Appl. No. 16/040,831.
An Office Action dated Jul. 11, 2018, which issued during the prosecution of U.S. Appl. No. 15/978,494.
An Office Action dated Nov. 23, 2018, which issued during the prosecution of U.S. Appl. No. 16/041,208.
An Office Action dated Jun. 15, 2018, which issued during the prosecution of U.S. Appl. No. 15/970,314.
An Office Action dated Oct. 12, 2018, which issued during the prosecution of U.S. Appl. No. 15/970,314.
An Office Action dated Jul. 26, 2018, which issued during the prosecution of U.S. Appl. No. 15/979,686.
An Office Action dated Sep. 10, 2018, which issued during the prosecution of U.S. Appl. No. 16/008,618.
An International Preliminary Report on Patentability dated Apr. 28, 2015, which issued during the prosecution of Applicant's PCT/IL2013/050860.
An Office Action dated Apr. 22, 2019, which issued during the prosecution of U.S. Appl. No. 15/668,559.
Notice of Allowance dated Aug. 30, 2019, which issued during the prosecution of U.S. Appl. No. 15/682,789.
Notice of Allowance dated Mar. 29, 2019, which issued during the prosecution of U.S. Appl. No. 15/541,783.
Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).
An Advisory Action dated Dec. 13, 2013, which issued during the prosecution of U.S. Appl. No. 12/961,721.
An Office Action dated Aug. 7, 2015, which issued during the prosecution of U.S. Appl. No. 14/128,756.
An Office Action dated May 19, 2011, which issued during the prosecution of U.S. Appl. No. 12/706,868.
An Office Action dated Sep. 1, 2011, which issued during the prosecution of U.S. Appl. No. 12/706,868.
An Office Action dated May 30, 2012, which issued during the prosecution of U.S. Appl. No. 12/706,868.
A Notice of Allowance dated Sep. 18, 2012, which issued during the prosecution of U.S. Appl. No. 12/706,868.
Restriction Requirement dated May 5, 2011, which issued during the prosecution of U.S. Appl. No. 12/706,868.
A Restriction Requirement dated Mar. 30, 2012, which issued during the prosecution of U.S. Appl. No. 12/785,717.
An Office Action dated Oct. 5, 2020, which issued during the prosecution of Canadian Patent Application No. 2,973,940.
An Office Action dated Nov. 30, 2020, which issued during the prosecution of U.S. Appl. No. 16/138,129.
An Office Action summarized English translation and Search Report dated Nov. 25, 2020, which issued during the prosecution of Chinese Patent Application No. 201910449820.1.
Notice of Allowance dated Nov. 19, 2020, which issued during the prosecution of U.S. Appl. No. 16/318,025.
An Office Action dated Aug. 2, 2011, which issued during the prosecution of U.S. Appl. No. 12/435,291.
Notice of Allowance dated Dec. 7, 2011, which issued during the prosecution of U.S. Appl. No. 12/435,291.
An Office Action dated Apr. 6, 2010, which issued during the prosecution of Applicant's U.S. Appl. No. 12/484,512.
An Office Action dated Oct. 6, 2010, which issued during the prosecution of Applicant's U.S. Appl. No. 12/484,512.
Notice of Allowance dated Apr. 20, 2011, which issued during the prosecution of U.S. Appl. No. 12/484,512.
Notice of Allowance dated Mar. 23, 2011, which issued during the prosecution of U.S. Appl. No. 12/484,512.
An Office Action dated Jan. 27, 2012, which issued during the prosecution of U.S. Appl. No. 12/548,991.
An Office Action dated Aug. 6, 2012, which issued during the prosecution of U.S. Appl. No. 12/548,991.
An Advisory Action dated Sep. 6, 2012 which issued during the prosecution of U.S. Appl. No. 12/548,991.
Notice of Allowance dated Jun. 23, 2014, which issued during the prosecution of U.S. Appl. No. 12/548,991.
A Restriction Requirement dated Nov. 14, 2011 which issued during the prosecution of U.S. Appl. No. 12/548,991.
Amendment, Terminal Disclaimer and Extension dated Jun. 27, 2012, which issued during the prosecution of U.S. Appl. No. 12/548,991.
A Restriction Requirement dated Jul. 5, 2012, which issued during the prosecution of U.S. Appl. No. 12/563,930.
An Office Action dated Apr. 2, 2013, which issued during the prosecution of U.S. Appl. No. 12/785,717.
An Office Action dated Dec. 27, 2013, which issued during the prosecution of U.S. Appl. No. 12/781,717.
An Office Action dated Nov. 5, 2012, which issued during the prosecution of U.S. Appl. No. 12/791,026.
An Office Action dated May 10, 2012, which issued during the prosecution of U.S. Appl. No. 12/795,026.
Notice of Allowance dated Nov. 13, 2014, which issued during the prosecution of U.S. Appl. No. 12/791,026.
Notice of Allowance dated Dec. 24, 2014, which issued during the prosecution of U.S. Appl. No. 12/791,026.
A Restriction Requirement dated Jan. 6, 2012, which issued during the prosecution of U.S. Appl. No. 12/791,026.
A Restriction Requirement dated Sep. 14, 2012, which issued during the prosecution of U.S. Appl. No. 12/795,192.
An Office Action dated Aug. 15, 2013, which issued during the prosecution of U.S. Appl. No. 12/795,192.
An Office Action dated Jan. 17, 2013, which issued during the prosecution of U.S. Appl. No. 12/795,192.
Notice of Allowance dated Nov. 19, 2013, which issued during the prosecution of U.S. Appl. No. 12/795,192.
A Notice of Allowance dated Jun. 26, 2012, which issued during the prosecution of U.S. Appl. No. 12/608,316.

(56) References Cited

OTHER PUBLICATIONS

An Office Action dated Nov. 14, 2011, which issued during the prosecution of U.S. Appl. No. 12/608,316.
A Restriction Requirement dated Apr. 1, 2011, which issued during the prosecution of U.S. Appl. No. 12/608,316.
An Office Action dated Jul. 6, 2012, which issued during the prosecution of U.S. Appl. No. 12/692,061.
An Office Action dated Jan. 23, 2012, which issued during the prosecution of U.S. Appl. No. 12/692,061.
An Office Action dated Mar. 9, 2012, which issued during the prosecution of U.S. Appl. No. 12/689,635.
An Office Action dated Nov. 30, 2012, which issued during the prosecution of U.S. Appl. No. 12/689,635.
A Notice of Allowance dated May 22, 2013, which issued during the prosecution of U.S. Appl. No. 12/689,635.
Restriction Requirement dated Nov. 14, 2011, which issued during the prosecution of U.S. Appl. No. 12/689,635.
An Office Action dated May 6, 2013, which issued during the prosecution of U.S. Appl. No. 12/689,693.
An Office Action dated Feb. 3, 2014, which issued during the prosecution of U.S. Appl. No. 12/689,693.
Notice of Allowance dated Jun. 11, 2014, which issued during the prosecution of U.S. Appl. No. 12/689,693.
A Restriction Requirement dated Sep. 17, 2012, which issued during the prosecution of U.S. Appl. No. 12/689,693.
A Notice of Allowance dated Sep. 3, 2014, which issued during the prosecution of U.S. Appl. No. 12/689,693.
European Search Report dated Jul. 8, 2016, which issued during the prosecution of Applicant's European App No. 13849843.1.
A Supplementary European Search Report dated Dec. 4, 2012, which issued during the prosecution of European Patent Application No. EP 09834225.6.
A Supplementary European Search Report dated Mar. 28, 2013, which issued during the prosecution of European Patent Application No. EP 1077 2091.4.
Search Report in European Patent Application 10772090.6 dated Jan. 17, 2014.
Supplementary European Search Report dated Oct. 23, 2014 which issued during the prosecution of Applicant's European App No. 10826224.7.
Notice of Allowance dated May 6, 2016, which issued during the prosecution of U.S. Appl. No. 14/667,090.
Notice of Allowance dated Apr. 12, 2016, which issued during the prosecution of U.S. Appl. No. 14/667,090.
An Office Action dated Jun. 7, 2013 which issued during the prosecution of U.S. Appl. No. 13/141,606.
An Office Action dated Jun. 13, 2014, which issued during the prosecution of U.S. Appl. No. 13/141,606.
Notice of Allowance dated Sep. 29, 2014, which issued during the prosecution of U.S. Appl. No. 13/141,606.
An Office Action dated Feb. 4, 2013 which issued during the prosecution of U.S. Appl. No. 13/141,606.
An English translation of an Office Action dated Apr. 23, 2014 which issued during the prosecution of Chinese Patent Application No. 201080059948.4.
Communication dated Jul. 25, 2014, issued by the State Intellectual Property Office of the P.R. of China in counterpart Application No. 200980157331.3.
An International Search Report and a Written Opinion both dated Jan. 25, 2016, which issued during the prosecution of Applicant's PCT/IL2015/051027.
An International Search Report dated May 19, 2011, which issued during the prosecution of Applicant's PCT/IL2011/00064.
An International Search Report and a Written Opinion both dated Feb. 22, 2013, which issued during the prosecution of Applicant's PCT/IL201/050451.
An International Search Report & Written Opinion both dated Mar. 21, 2014, which issued during the prosecution of Applicant's PCT/IL13/50992.
An International Search Report and Written Opinion both dated Apr. 9, 2014, which issued during the prosecution of Applicant's PCT/IL13/50860.
An International Search Report and a Written Opinion both dated Apr. 15, 2014, which issued during the prosecution of Applicant's PCT/IL2013/050861.
An International Search Report & Written Opinion both dated May 12, 2015, which issued during the prosecution of Applicant's PCT/IL2014/050914.
An International Search Report and a Written Opinion both dated May 30, 2007, which issued during the prosecution of Applicant's PCT/IL2006/000342.
An International Search Report and a Written Opinion both dated Jun. 10, 2010, which issued during the prosecution of Applicant's PCT/IL09/01209.
An International Search Report and a Written Opinion both dated Aug. 17, 2010. which issued during the prosecution of Applicant's PCT/IL10/00357.
An International Search Report & Written Opinion both dated Sep. 8, 2009, which issued during the prosecution of Applicant's PCT/IL09/00593.
An International Search Report and a Written Opinion both dated Sep. 12, 2008, which issued during the prosecution of Applicant's PCT/IL07/01503.
An International Search Report and Written Opinion dated Nov. 8, 2010, which issued during the prosecution of Applicant's PCT/IL2010/000358.
An International Search Report and a Written Opinion both dated Nov. 23, 2011, which issued during the prosecution of Applicant's PCT/IL2011/000446.
Supplementary European Search Report dated Sep. 25, 2015, which issued during the prosecution of Applicant's European App No. 09794095.1.
A Supplementary European Search Report dated Feb. 1, 2011, which issued during the prosecution of European Patent Application No. EP 07849540.
An English translation of an Office Action dated Dec. 12, 2013 which issued during the prosecution of Chinese Patent Application No. 200980157331.3.
Communication regarding amended claims filed dated Dec. 27, 2012, regarding European App No. 11792047.0.
An Office Action dated Mar. 23, 2015, which issued during the prosecution of European Patent Application No. EP 09834225.6.
An English translation of an Office Action dated Jul. 17, 2015 which issued during the prosecution of Chinese Patent Application No. 201080059948.4.
An English translation of an Office Action dated Dec. 16, 2015 which issued during the prosecution of Chinese Patent Application No. 201080059948.4.
Communication from the European Patent Office dated Jun. 11, 2015, which issued during the prosecution of European U.S. Appl. No. 11/811,934.
A communication from the European Patent Office dated Sep. 28, 2011 which issued during the prosecution of European Application No. 09834225.6.
A communication from the European Patent Office dated Oct. 19, 2012 which issued during the prosecution of European Application No. 11792047.0.
An Office Action dated Oct. 23, 2012, which issued during the prosecution of Japanese Patent Application No. 2009-539871.
An English Translation of an Office Action dated Nov. 24, 2015, which issued during the prosecution of Israel Patent Application No. 223448. (the relevant part only).
Notice of Allowance dated Nov. 17, 2015, which issued during the prosecution of U.S. Appl. No. 14/486,226.
Notice of Allowance dated Jan. 29, 2016, which issued during the prosecution of U.S. Appl. No. 14/551,951.
An Office Action dated Jun. 18, 2015, which issued during the prosecution of U.S. Appl. No. 14/551,951.
An Office Action dated Jan. 4, 2016, which issued during the prosecution of U.S. Appl. No. 14/589,100.
An Office Action dated May 4, 2016, which issued during the prosecution of U.S. Appl. No. 14/589,100.

(56) References Cited

OTHER PUBLICATIONS

An International Search Report and a Written Opinion both dated Nov. 14, 2011, which issued during the prosecution of Applicant's PCT/IL2011/000404.
An International Search Report and a Written Opinion both dated Dec. 6, 2012 which issued during the prosecution of Applicant's PCT/IL2012/000250.
A Notice of Allowance dated Apr. 3, 2013, which issued during the prosecution of U.S. Appl. No. 12/563,930.
An Office Action dated Aug. 24, 2012, which issued during the prosecution of U.S. Appl. No. 12/563,930.
An Office Action dated Dec. 29, 2011, which issued during the prosecution of U.S. Appl. No. 12/563,952.
A Restriction Requirement dated Oct. 27, 2011, which issued during the prosecution of U.S. Appl. No. 12/563,952.
A Notice of Allowance dated May 24, 2012, which issued during the prosecution of U.S. Appl. No. 12/563,952.
An Office Action dated Apr. 1, 2013 which issued during the prosecution of U.S. Appl. No. 13/161,476.
An Office Action dated Nov. 21, 2013, which issued during the prosecution of U.S. Appl. No. 13/161,476.
An Advisory Action dated Feb. 4, 2014, which issued during the prosecution of U.S. Appl. No. 13/167,476.
A Restriction Requirement dated Oct. 25, 2012 which issued during the prosecution of U.S. Appl. No. 13/167,444.
An Office Action dated Jan. 17, 2013, which issued during the prosecution of U.S. Appl. No. 13/167,444.
An Office Action dated Aug. 26, 2014 which issued during the prosecution of U.S. Appl. No. 13/167,444.
An Office Action dated Aug. 23, 2013 which issued during the prosecution of U.S. Appl. No. 13/167,444.
Notice of Allowance dated Nov. 12, 2015, which issued during the prosecution of U.S. Appl. No. 13/319,007.
Notice of Allowance dated Jan. 7, 2016, which issued during the prosecution of U.S. Appl. No. 13/319,007.
An Office Action dated Oct. 2, 2013, which issued during the prosecution of U.S. Appl. No. 13/167,492.
A Restriction Requirement dated Nov. 2, 2012, which issued during the prosecution of U.S. Appl. No. 13/167,492.
An Office Action dated Feb. 14, 2013 which issued during the prosecution of U.S. Appl. No. 13/167,492.
Notice of Allowance dated Nov. 7, 2014, which issued during the prosecution of U.S. Appl. No. 13/167,492.
An Office Action dated Jun. 10, 2014, which issued during the prosecution of U.S. Appl. No. 13/167,492.
Notice of Allowance dated Dec. 9, 2014, which issued during the prosecution of U.S. Appl. No. 13/167,476.
Notice of Allowance dated Jan. 22, 2015, which issued during the prosecution of U.S. Appl. No. 13/167,444.
An International Preliminary Report on Patentability dated May 1, 2012, which issued during the prosecution of Applicant's PCT/IL2010/000890.
An International Preliminary Report on Patentability dated Jun. 9, 2015, which issued during the prosecution of Applicant's PCT/IL2013/050992.
U.S. Appl. No. 60/873,075, filed Dec. 5, 2006.
U.S. Appl. No. 60/902,146, filed Feb. 16, 2007.
An Office Action dated Mar. 29, 2018, which issued during the prosecution of U.S. Appl. No. 15/188,507.
Notice of Allowance dated Sep. 17, 2014, which issued during the prosecution of U.S. Appl. No. 12/961,721.
An Office Action dated Oct. 1, 2015, which issued during the prosecution of U.S. Appl. No. 14/141,228.
A Restriction Requirement dated Jun. 2, 2014, which issued during the prosecution of U.S. Appl. No. 13/319,030.
An Office Action dated Oct. 14, 2014, which issued during the prosecution of US Appl. No. 13/319,030.
An Office Action dated Jun. 18, 2015, which issued during the prosecution of U.S. Appl. No. 13/319,030.
An Office Action dated May 3, 2016, which issued during the prosecution of U.S. Appl. No. 13/319,030.
Notice of Allowance dated Dec. 30, 2016, which issued during the prosecution of U.S. Appl. No. 13/319,030.
An Office Action dated Apr. 7, 2015, which issued during the prosecution of U.S. Appl. No. 13/319,007.
An Office Action dated Apr. 8, 2016, which issued during the prosecution of U.S. Appl. No. 14/141,228.
An Office Action dated Oct. 5, 2015, which issued during the prosecution of U.S. Appl. No. 14/246,417.
An Office Action dated Apr. 7, 2016, which issued during the prosecution of U.S. Appl. No. 14/242,151.
An Office Action dated May 23, 2016, which issued during the prosecution of U.S. Appl. No. 14/209,171.
An Office Action dated Jul. 20, 2016, which issued during the prosecution of U.S. Appl. No. 14/246,417.
An Office Action dated Jun. 14, 2016, which issued during the prosecution of U.S. Appl. No. 14/273,155.
An Office Action dated Jun. 17, 2016, which issued during the prosecution of U.S. Appl. No. 14/357,040.
An Office Action dated Mar. 24, 2015, which issued during the prosecution of U.S. Appl. No. 14/486,226.
U.S. Appl. No. 61/001,013, filed Oct. 29, 2007.
U.S. Appl. No. 61/132,295, filed Jun. 16, 2008.
U.S. Appl. No. 61/265,936, filed Dec. 2, 2009.
U.S. Appl. No. 61/283,445, filed Dec. 2, 2009.
U.S. Appl. No. 61/207,908, filed Feb. 17, 2009.
U.S. Appl. No. 61/733,979, filed Dec. 6, 2012.
U.S. Appl. No. 61/717,303, filed Oct. 23, 2012.
U.S. Appl. No. 61/820,979, filed May 8, 2013.
U.S. Appl. No. 61/745,848, filed Dec. 6, 2012.
U.S. Appl. No. 61/555,570, filed Nov. 4, 2011.
U.S. Appl. No. 61/557,082, filed Nov. 8, 2011.
U.S. Appl. No. 60/662,616, filed Mar. 17, 2005.
U.S. Appl. No. 60/700,542, filed Jul. 18, 2005.
U.S. Appl. No. 61/782,121, filed Mar. 14, 2013.
European Search Report dated Jul. 15, 2016, which issued during the prosecution of Applicant's European App No. 13849947.0.
European Search Report dated Nov. 4, 2015, which issued during the prosecution of European Patent Application No. EP 1077 2091.4.
Search Report in European Patent Application 10826224.7 dated Nov. 16, 2015.
Supplementary European Search Report dated Dec. 23, 2014 which issued during the prosecution of Applicant's European App No. 10834311.
Supplementary European Search Report dated Jan. 21, 2014 which issued during the prosecution of Applicant's European App No. 11 78 6226.
A Supplementary European Search Report dated Jan. 20, 2015, which issued during the prosecution of European Patent Application No. 12803037.6.
Supplementary European Search Report dated Aug. 4, 2014 which issued during the prosecution of Applicant's European App No. 11 81 1934.6.
European Search Report dated Jun. 24, 2016, which issued during the prosecution of European Patent Application No. EP 12847363.
Supplementary European Search Report dated Apr. 29, 2015, which issued during the prosecution of Applicant's European App No. 14200202.
An Office Action dated Dec. 16, 2013, which issued during the prosecution of U.S. Appl. No. 13/666,262.
An Office Action dated Dec. 18, 2013, which issued during the prosecution of U.S. Appl. No. 13/666,141.
Notice of Allowance dated Jun. 25, 2014, which issued during the prosecution of U.S. Appl. No. 13/666,262.
A Notice of Allowance dated Feb. 2, 2015, which issued during the prosecution of U.S. Appl. No. 13/504,870.
Notice of Allowance dated Aug. 19, 2013, which issued during the prosecution of U.S. Appl. No. 11/908,906.
An Office Action dated Jun. 8, 2012, which issued during the prosecution of U.S. Appl. No. 11/908,906.

(56) References Cited

OTHER PUBLICATIONS

An Office Action dated Dec. 21, 2013, which issued during the prosecution of U.S. Appl. No. 11/908,906.
A Restriction Requirement dated Aug. 5, 2011, which issued during the prosecution of U.S. Appl. No. 11/908,906.
An Office Action dated Sep. 16, 2009 which issued during the prosecution of U.S. Appl. No. 11/950,930.
Notice of Allowance dated Sep. 12, 2014, which issued during the prosecution of U.S. Appl. No. 11/950,930.
An Office Action dated Aug. 5, 2010 which issued during the prosecution of U.S. Appl. No. 11/950,930.
An Office Action dated Feb. 17, 2010 which issued during the prosecution of U.S. Appl. No. 11/950,930.
A Restriction Requirement dated Apr. 19, 2010 which issued during the prosecution of U.S. Appl. No. 12/341,960.
An Office Action dated Sep. 28, 2011, which issued during the prosecution of U.S. Appl. No. 12/437,103.
An Office Action dated Jun. 13, 2012, which issued during the prosecution of U.S. Appl. No. 12/437,103.
A Restriction Requirement dated Jul. 12, 2011, which issued during the prosecution of U.S. Appl. No. 12/437,103.
Notice of Allowance dated Mar. 6, 2014, which issued during the prosecution of U.S. Appl. No. 12/437,103.
Notice of Allowance dated Dec. 20, 2013, which issued during the prosecution of U.S. Appl. No. 12/437,103.
Notice of Allowance dated Apr. 27, 2012, which issued during the prosecution of U.S. Appl. No. 12/341,960.
An Office Action dated Mar. 29, 2011, which issued during the prosecution of U.S. Appl. No. 12/341,960.
An Office Action dated Aug. 4, 2010, which issued during the prosecution of U.S. Appl. No. 12/341,960.
An Interview Summary dated Jul. 27, 2011, which issued during the prosecution of U.S. Appl. No. 12/341,960.
Notice of Allowance dated Aug. 21, 2019, which issued during the prosecution of U.S. Appl. No. 15/703,385.
Notice of Allowance dated Oct. 16, 2019, which issued during the prosecution of U.S. Appl. No. 15/703,385.
Notice of Allowance dated Dec. 24, 2020, which issued during the prosecution of U.S. Appl. No. 15/668,559.
Notice of Allowance dated Oct. 21, 2020, which issued during the prosecution of U.S. Appl. No. 15/668,659.
Declaration of Ivan Vesely, Ph.D., in Support of Petition for Inter Partesreview of U.S. Pat. No. 7,563,267—dated May 29, 2019.
U.S. Appl. No. 60/128,690, filed Apr. 9, 1999.
U.S. Appl. No. 60/613,867, filed Sep. 27, 2004.
An Office Action dated Dec. 24, 2020, which issued during the prosecution of U.S. Appl. No. 16/144,054.
An Office Action dated Feb. 2, 2021, which issued during the prosecution of U.S. Appl. No. 16/811,732.
An Office Action dated Jan. 13, 2021, which issued during the prosecution of European Patent Application No. 15751089.2.
An Office Action together with an English summary dated Mar. 3, 2021, which issued during the prosecution of Chinese Patent Application No. 201780047391.4.
Declaration of Dr. Ivan Vesely, Ph.D. in Support of Petition for *Inter Partes* Review of U.S. Pat. No. 10,226,341—dated Dec. 17, 2020.
Petition for Inter Partes Review of U.S. Pat. No. 10,226,341 and EXHIBITS 1001-1013—dated Dec. 29, 2020.
Batista, Randas JV, et al. "Partial left ventriculectomy to treat end-stage heart disease." The Annals of thoracic surgery 64.3 (1997): 634-638.
Beall Jr, Arthur C., et al. "Clinical experience with a dacron velour-covered teflon-disc mitral-valve prosthesis." The Annals of thoracic surgery 5.5 (1968): 402-410.
Kalbacher, D., et al. "1000 MitraClip™ procedures: Lessons learnt from the largest single-centre experience worldwide." (2019): 3137-3139.
Maisano, F., et al. "The edge-to-edge technique: a simplified method to correct mitral insufficiency." European journal of cardio-thoracic surgery 13.3 (1998): 240-246.
Fucci, C., et al. "Improved results with mitral valve repair using new surgical techniques." European journal of cardio-thoracic surgery 9.11 (1995): 621-627.
Notice of Allowance dated Nov. 19, 2019, which issued during the prosecution of U.S. Appl. No. 15/668,559.
Mitral Valve Academic Research Consortium. "Clinical Trial Design Principles and Endpoint Definitions for Transcatheter Mitral Valve Repair and Replacement: Part 1: Clinical Trial Design Principles a Consensus Document from the Mitral Valve Academic Research Consortium." Journal of the American College of Cardiology 66.3 (2015): 278-307.
An Office Action dated Aug. 29, 2018, which issued during the prosecution of U.S. Appl. No. 15/329,920.
An Office Action dated May 8, 2018, which issued during the prosecution of U.S. Appl. No. 15/902,403.
An Office Action dated May 11, 2018, which issued during the prosecution of U.S. Appl. No. 15/899,858.
Notice of Allowance dated Oct. 5, 2018, which issued during the prosecution of U.S. Appl. No. 15/886,517.
Notice of Allowance dated Jul. 19, 2019, which issued during the prosecution of U.S. Appl. No. 15/899,858.
Notice of Allowance dated Nov. 16, 2020, which issued during the prosecution of U.S. Appl. No. 16/324,339.
Notice of Allowance dated Apr. 27, 2020, which issued during the prosecution of U.S. Appl. No. 16/591,330.
An Advisory Action dated Jan. 2, 2020, which issued during the prosecution of U.S. Appl. No. 15/668,659.
Notice of Allowance dated Oct. 17, 2019, which issued during the prosecution of U.S. Appl. No. 15/329,920.
An Office Action dated Dec. 31, 2019, which issued during the prosecution of U.S. Appl. No. 16/591,330.
Notice of Allowance dated Feb. 9, 2021, which issued during the prosecution of U.S. Appl. No. 16/937,216.
An Advisory Action dated Nov. 18, 2020, which issued during the prosecution of U.S. Appl. No. 16/811,732.
An International Search Report and a Written Opinion both dated Mar. 27, 2018, which issued during the prosecution of Applicant's PCT/IL2017/050849.
Notice of Allowance dated Jun. 11, 2021, which issued during the prosecution of U.S. Appl. No. 16/811,732.
Notice of Allowance dated Jul. 16, 2021, which issued during the prosecution of U.S. Appl. No. 16/811,732.
Patent Trial and Appeal Board Decision Granting Institution in U.S. Pat. No. 10,226,341—Dated Jul. 20, 2021.
European Search Report dated Jun. 10, 2021 which issued during the prosecution of Applicant's European App No. 21157988.3.
Notice of Allowance dated Nov. 19, 2018, which issued during the prosecution of U.S. Appl. No. 15/197,069.
Poirier, Nancy C., et al. "A novel repair for patients with atrioventricular septal defect requiring reoperation for left atrioventricular valve regurgitation." European journal of cardio-thoracic surgery 18.1 (2000): 54-61.
An Office Action dated Mar. 29, 2021, which issued during the prosecution of U.S. Appl. No. 16/738,516.
Ando, Tomo, et al. "Iatrogenic ventricular septal defect following transcatheter aortic valve replacement: a systematic review." Heart, Lung and Circulation 25.10 (2016): 968-974.
Urena, Marina, et al. "Transseptal transcatheter mitral valve replacement using balloon-expandable transcatheter heart valves: a step-by-step approach." JACC: Cardiovascular Interventions 10.19 (2017): 1905-1919.
An English summary of an Official Action dated Mar. 29, 2021, which issued during the prosecution of Chinese Patent Application No. 201780061210.3.
An International Search Report and a Written Opinion both dated Jan. 28, 2020, which issued during the prosecution of Applicant's PCT/IL2019/051031.
An International Preliminary Report on Patentability dated Mar. 9, 2021, which issued during the prosecution of Applicant's PCT/IL2019/051031.
An Office Action dated May 4, 2021, which issued during the prosecution of U.S. Appl. No. 16/636,204.

(56) References Cited

OTHER PUBLICATIONS

Notice of Allowance dated May 17, 2021, which issued during the prosecution of U.S. Appl. No. 16/138,129.
Notice of Allowance dated Jun. 4, 2021, which issued during the prosecution of U.S. Appl. No. 16/802,353.
An Office Action dated May 12, 2021, which issued during the prosecution of Canadian Patent Application No. 2,973,940.
Petition for Inter Partes Review of U.S. Pat. No. 10,702,385—dated Jun. 4, 2021.
Declaration of Ivan Vesely, Ph.D. In Support of Petition for Inter Partes Review of U.S. Pat. No. 10,702,385—dated Jun. 4, 2021.
Notice of Allowance dated Oct. 30, 2018, which issued during the prosecution of U.S. Appl. No. 15/197,069.
An International Search Report and a Written Opinion both dated Jul. 12, 2021, which issued during the prosecution of Applicant's PCT/IL2021/050132.
Notice of Allowance dated Oct. 3, 2019, which issued during the prosecution of U.S. Appl. No. 15/691,032.
An Office Action dated Sep. 6, 2018, which issued during the prosecution of U.S. Appl. No. 15/213,791.
Condado, José Antonio, et al. "Percutaneous edge-to-edge mitral valve repair: 2-year follow-up in the first human case." Catheterization and cardiovascular interventions 67.2 (2006): 323-325.
Notice of Allowance dated Mar. 18, 2020, which issued during the prosecution of U.S. Appl. No. 16/284,331.
Feldman, Ted, et al. "Percutaneous mitral repair with the MitraClip system: safety and midterm durability in the initial EVEREST (Endovascular Valve Edge-to-Edge REpair Study) cohort." Journal of the American College of Cardiology 54.8 (2009): 686-694.
Notice of Allowance dated Nov. 21, 2018, which issued during the prosecution of U.S. Appl. No. 15/213,791.
Notice of Allowance dated Jul. 3, 2019, which issued during the prosecution of U.S. Appl. No. 15/691,032.
IPR2021-00383 Petitioners' Authorized Reply to Patent Owner's Preliminary Response dated May 27, 2021.
Exhibit 1014—Transcript of proceedings held May 20, 2021 (Edwards Lifesciences vs. Cardiovalve).
Exhibit 1015—Facilitate, Meriam-Webster.com, https://www.merriamwebster.com/dictionary/facilitate (visited May 26, 2021).
Patent Owner's Authorized Surreply to Petitioner's Reply to Patent Owner's Preliminary Response dated Jun. 4, 2021(Edwards Lifesciences vs. Cardiovalve).
An Invitation to pay additional fees dated May 19, 2021, which issued during the prosecution of Applicant's PCT/IL2021/050132.
An Office Action dated Aug. 18, 2021, which issued during the prosecution of U.S. Appl. No. 17/210,183.
An Office Action dated Sep. 9, 2021, which issued during the prosecution of U.S. Appl. No. 16/768,909.
An Office Action dated Sep. 15, 2021, which issued during the prosecution of U.S. Appl. No. 16/135,599.
Notice of Allowance dated Oct. 14, 2021, which issued during the prosecution of U.S. Appl. No. 16/680,739.
An Office Action dated Oct. 21, 2021, which issued during the prosecution of U.S. Appl. No. 17/331,845.
European Search Report dated Oct. 11, 2021 which issued during the prosecution of Applicant's European App No. 21176010.3.
Fann, James I., et al. "Beating heart catheter-based edge-to-edge mitral valve procedure in a porcine model: efficacy and healing response." Circulation 110.8 (2004): 988-993.
IPR2021-00383 Patent Owner'S Contingent Motion to Amend Under 37 C.F.R. §42.121 dated Oct. 13, 2021.
IPR2021-00383 Patent Owner's Response Pursuant to 37 C.F.R. §42.120 dated Oct. 13, 2021.
IPR2021-00383 Second Declaration of Dr. Michael Sacks dated Oct. 13, 2021.
An Office Action dated Oct. 21, 2021, which issued during the prosecution of U.S. Appl. No. 17/306,231.
Maisano, Francesco, et al. "The evolution from surgery to percutaneous mitral valve interventions: the role of the edge-to-edge technique." Journal of the American College of Cardiology 58.21 (2011): 2174-2182.
An Office Action dated Nov. 6, 2015, which issued during the prosecution of U.S. Appl. No. 14/626,267.
An Office Action dated Jan. 26, 2022, which issued during the prosecution of U.S. Appl. No. 16/888,210.
IPR2021-00383 Deposition of Dr. Ivan Vesely, dated Sep. 22, 2021.
Cardiovalve Exhibit 2009—Percutaneous Mitral Leaflet Repair: MitraClip® Therapy for Mitral Regurgitation (2012).
Feldman, Ted, et al. "Percutaneous mitral valve repair using the edge-to-edge technique: six-month results of the EVEREST Phase I Clinical Trial." Journal of the American College of Cardiology 46.11 (2005): 2134-2140.
An Office Action summarized English translation and Search Report dated Oct. 8, 2021, which issued during the prosecution of Chinese Patent Application No. 201780061210.3.
An Office Action dated Nov. 4, 2021, which issued during the prosecution of U.S. Appl. No. 17/366,711.
An Office Action summarized English translation and Search Report dated Aug. 12, 2021, which issued during the prosecution of Chinese Patent Application No. 201880058940.2.
An Office Action dated Nov. 25, 2021, which issued during the prosecution of European Patent Application No. 18826823.9.
IPR2021-01051 Institution decision dated Dec. 10, 2021
Notice of Allowance dated Dec. 7, 2021, which issued during the prosecution of U.S. Appl. No. 17/394,307.
Notice of Allowance dated Dec. 6, 2021, which issued during the prosecution of U.S. Appl. No. 16/738,516.
Notice of Allowance dated Dec. 29: 2021, which issued during the prosecution of U.S. Appl. No. 17/210,183.
IPR2021-00383 Petitioners' Reply to Patent Owner's Response dated Jan. 5, 2022.
IPR2021-00383 Petitioners' Opposition to Patent Owner's Contingent Motion to Amend dated Jan. 5, 2022.
An Office Action dated Sep. 22, 2021, which issued during the prosecution of European Patent Application No. 20714289.4.
Summary of Examination Notice dated Jan. 6, 2022, which issued during the prosecution of Chinese Patent Application No. 201880064313.X.
An Office Action dated Jan. 12, 2022, which issued during the prosecution of U.S. Appl. No. 17/101,787.
Notice of Allowance dated Jun. 20, 2017, which issued during the prosecution of U.S. Appl. No. 14/626,267.
Notice of Allowance dated Oct. 20, 2021, which issued during the prosecution of U.S. Appl. No. 16/636,204.
Notice of Allowance dated Jan. 31, 2022, which issued during the prosecution of U.S. Appl. No. 17/479,418.
An Office Action dated Jan. 13, 2022, which issued during the prosecution of U.S. Appl. No. 17/473,472.
An Office Action dated Jul. 27, 2022, which issued during the prosecution of U.S. Appl. No. 16/881,350.
An Office Action dated Sep. 21, 2022, which issued during the prosecution of U.S. Appl. No. 16/776,581.
An Office Action dated Jul. 20, 2022, which issued during the prosecution of U.S. Appl. No. 17/101,787.
An Office Action dated Sep. 16, 2022, which issued during the prosecution of U.S. Appl. No. 16/135,466.
An Office Action dated Aug. 1, 2022, which issued during the prosecution of European Patent Application No. 18826823.9.
European Search Report dated Sep. 6, 2022 which issued during the prosecution of Applicant's European App No. 22161862.2.
IPR2021-01051 Petitioners' Reply to Preliminary Guidance dated Aug. 2, 2022.
IPR2021-01051 Patent Owner's Sur-Reply To Petitioners' Reply to Preliminary Guidance dated Aug. 23, 2022.
An Office Action dated Aug. 5, 2022, which issued during the prosecution of U.S. Appl. No. 16/760,147.
An Office Action dated Sep. 8, 2022, which issued during the prosecution of U.S. Appl. No. 16/896,858.
European Search Report dated Mar. 20, 2023 which issued during the prosecution of Applicant's European App No. 22204764.9.

(56) References Cited

OTHER PUBLICATIONS

An Office Action dated Apr. 14, 2023, which issued during the prosecution of U.S. Appl. No. 16/144,054.
An Office Action dated May 15, 2023, which issued during the prosecution of U.S. Appl. No. 16/656,790.
An Office Action dated May 16, 2023, which issued during the prosecution of U.S. Appl. No. 17/114,771.
An Office Action dated May 25, 2023, which issued during the prosecution of U.S. Appl. No. 17/397,235.
An Office Action dated Mar. 3, 2023, which issued during the prosecution of European Patent Application No. 17 751 143.3.
An Office Action dated Mar. 20, 2023, which issued during the prosecution of U.S. Appl. No. 17/181,722.

\* cited by examiner

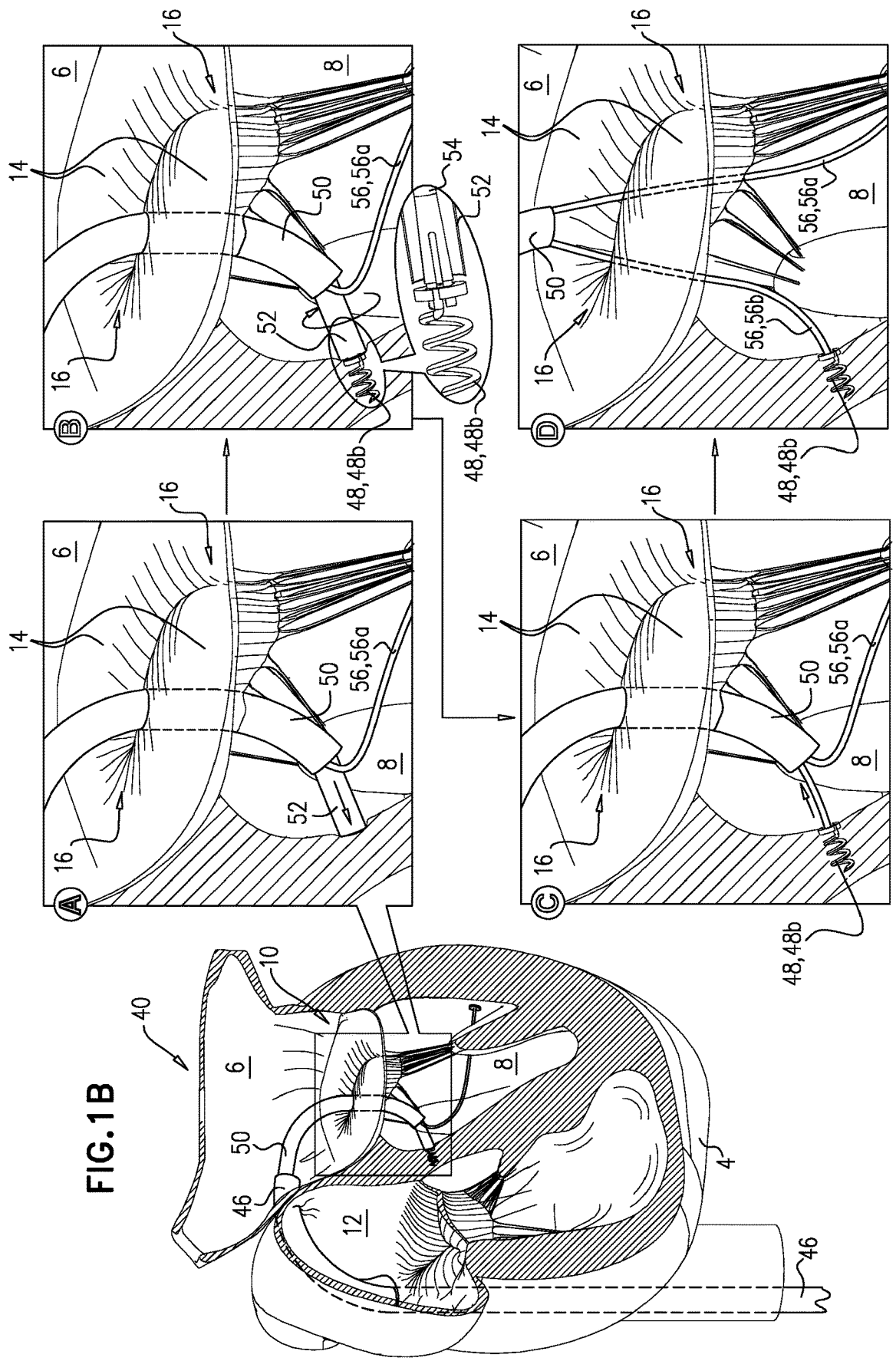

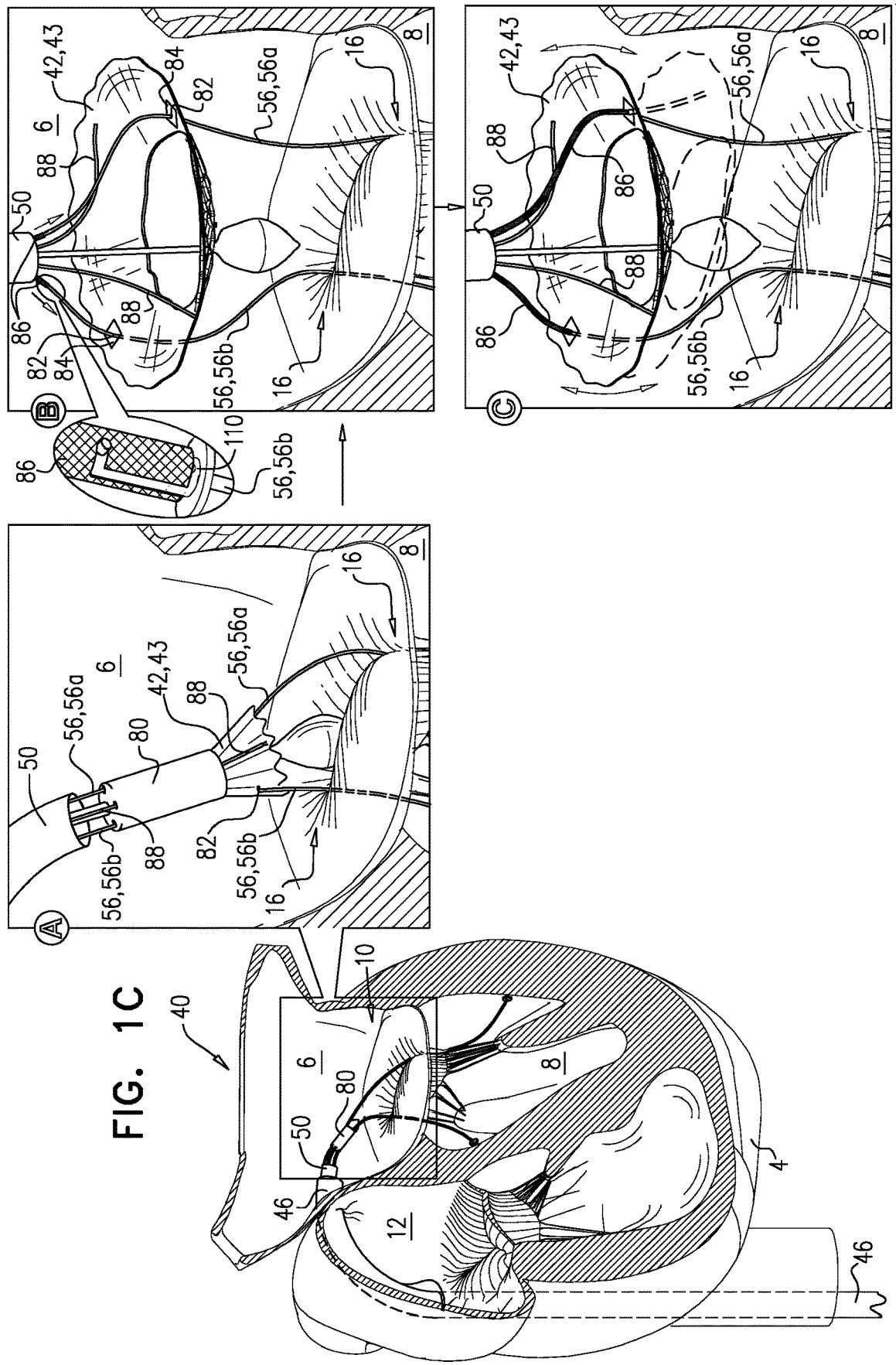

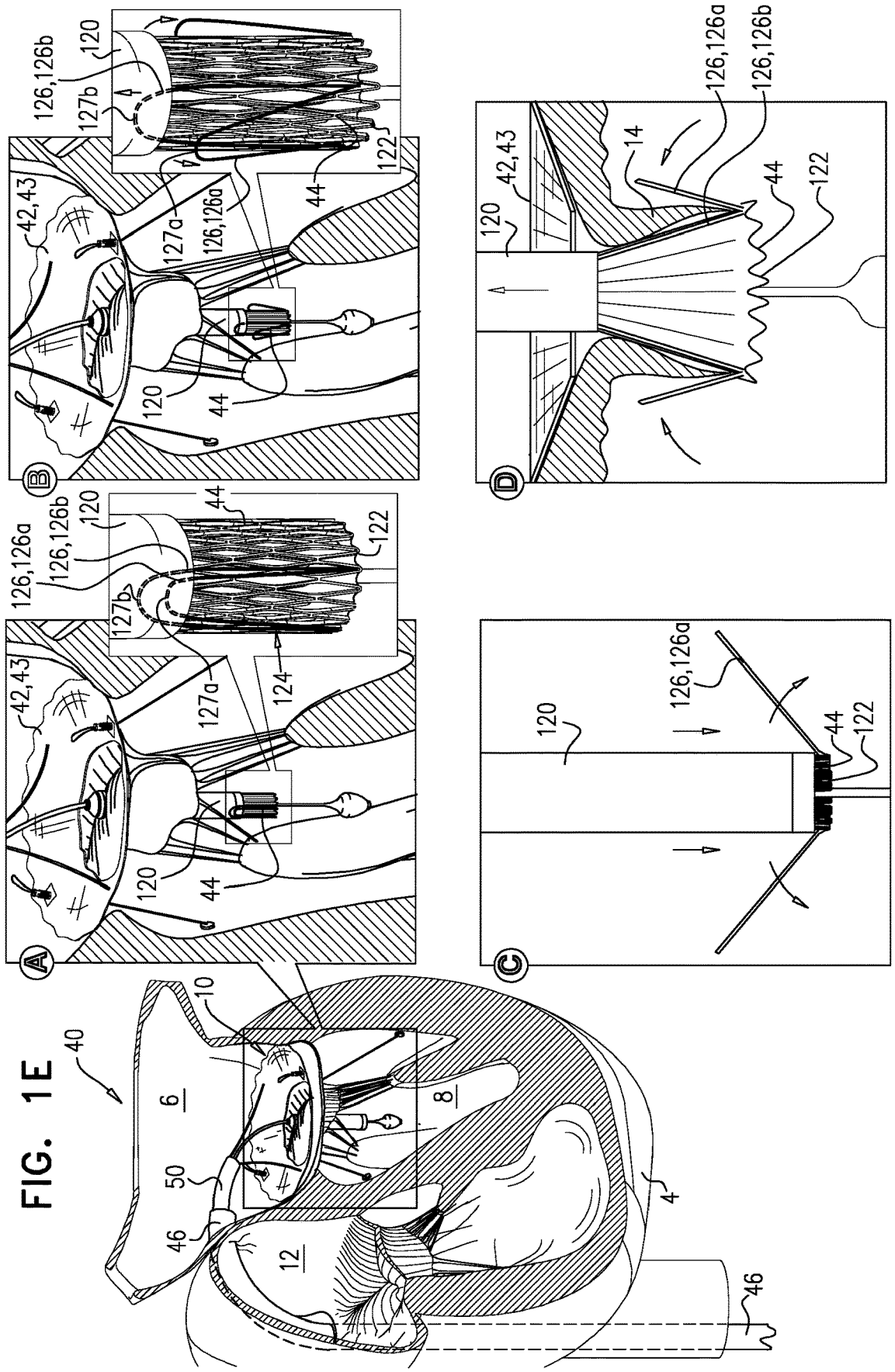

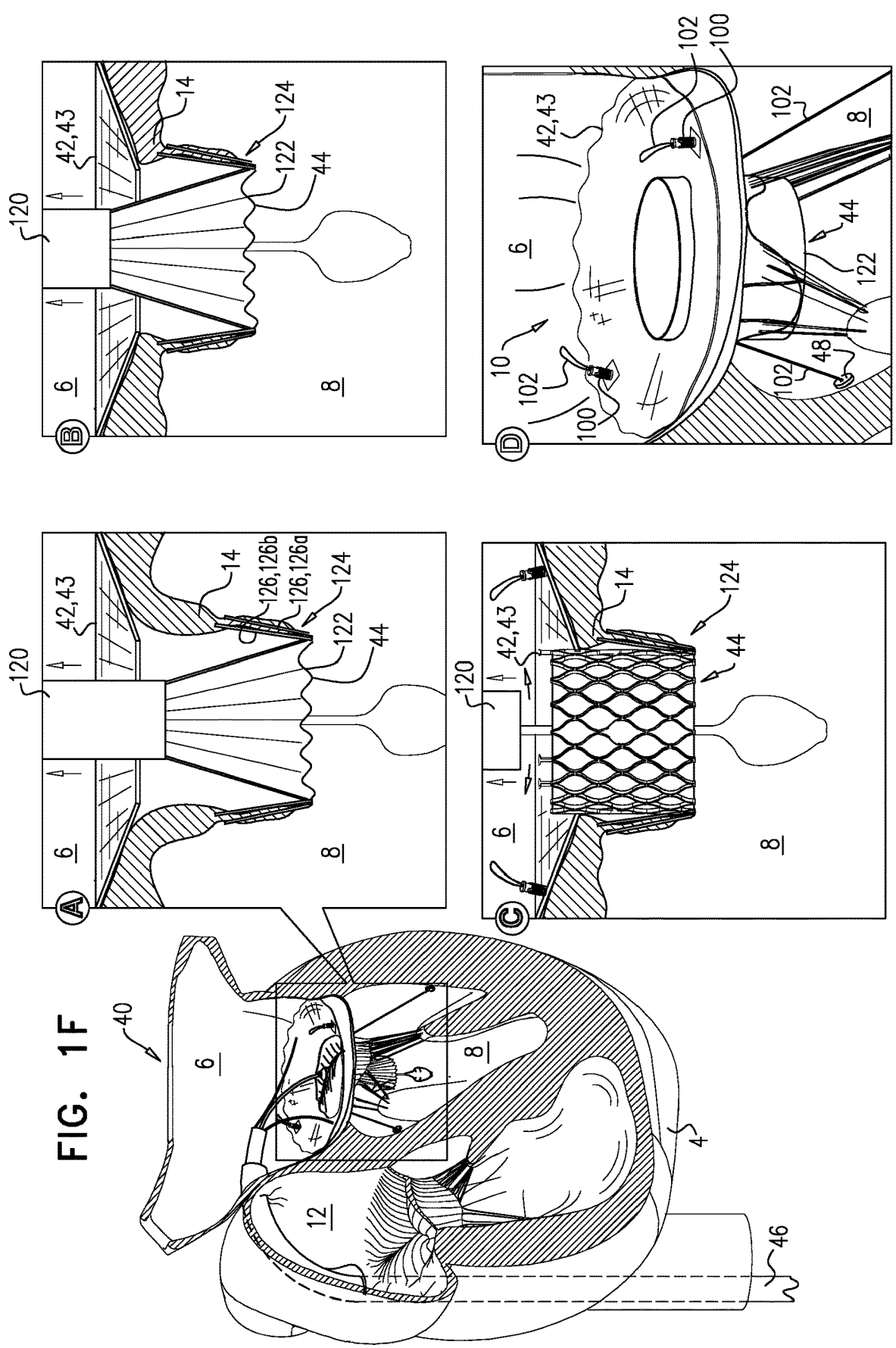

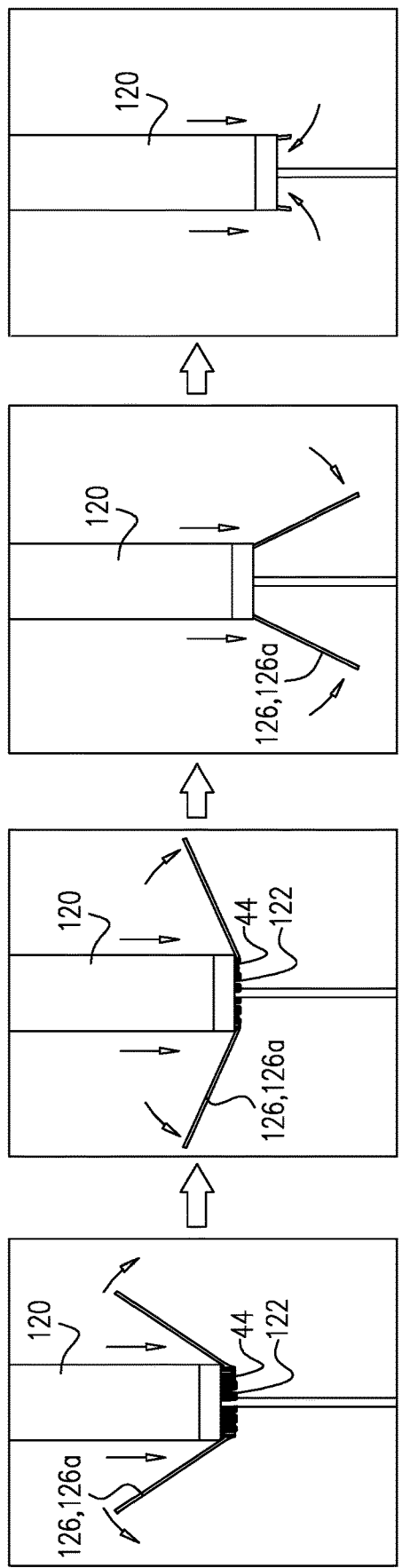

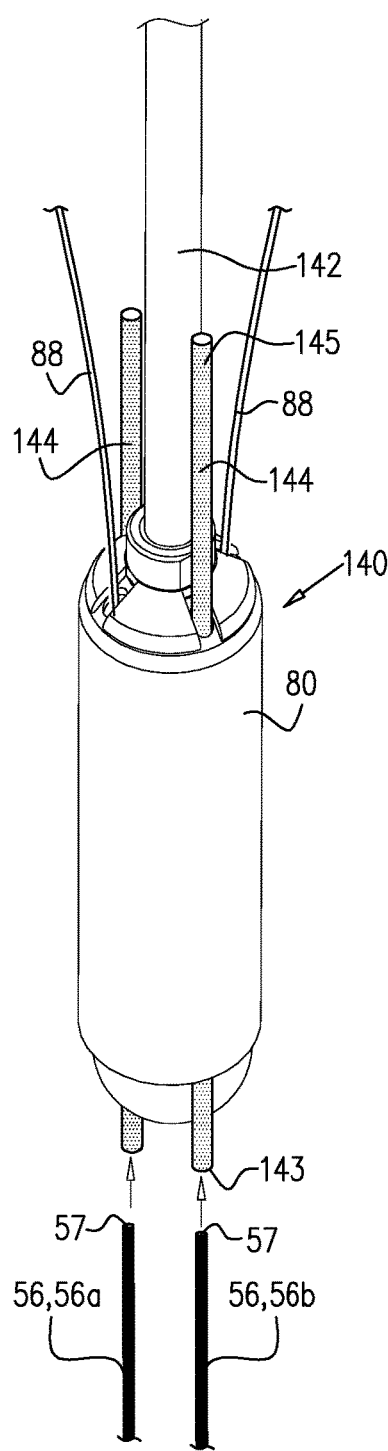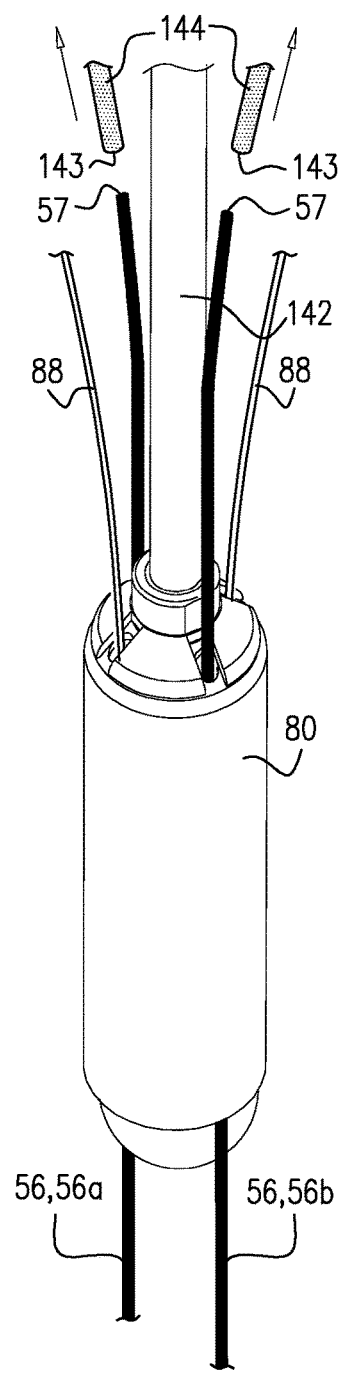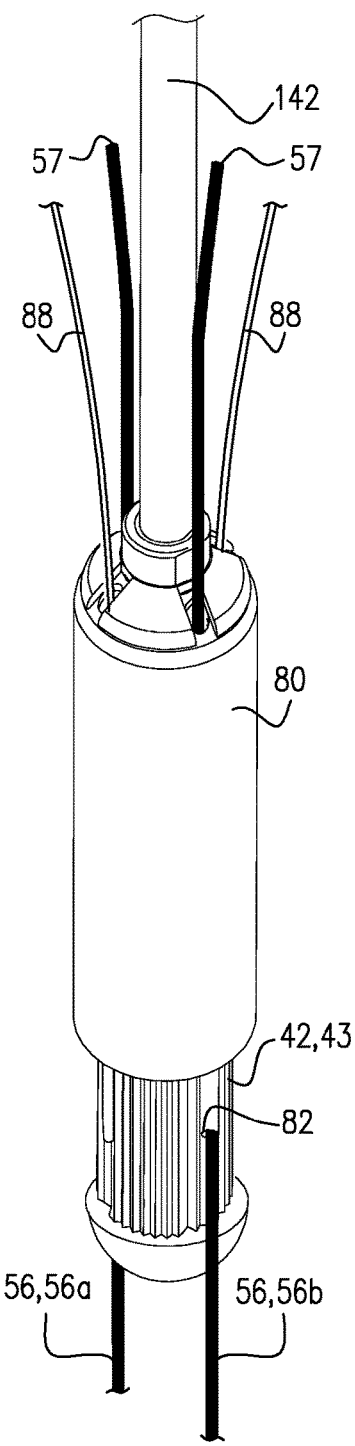

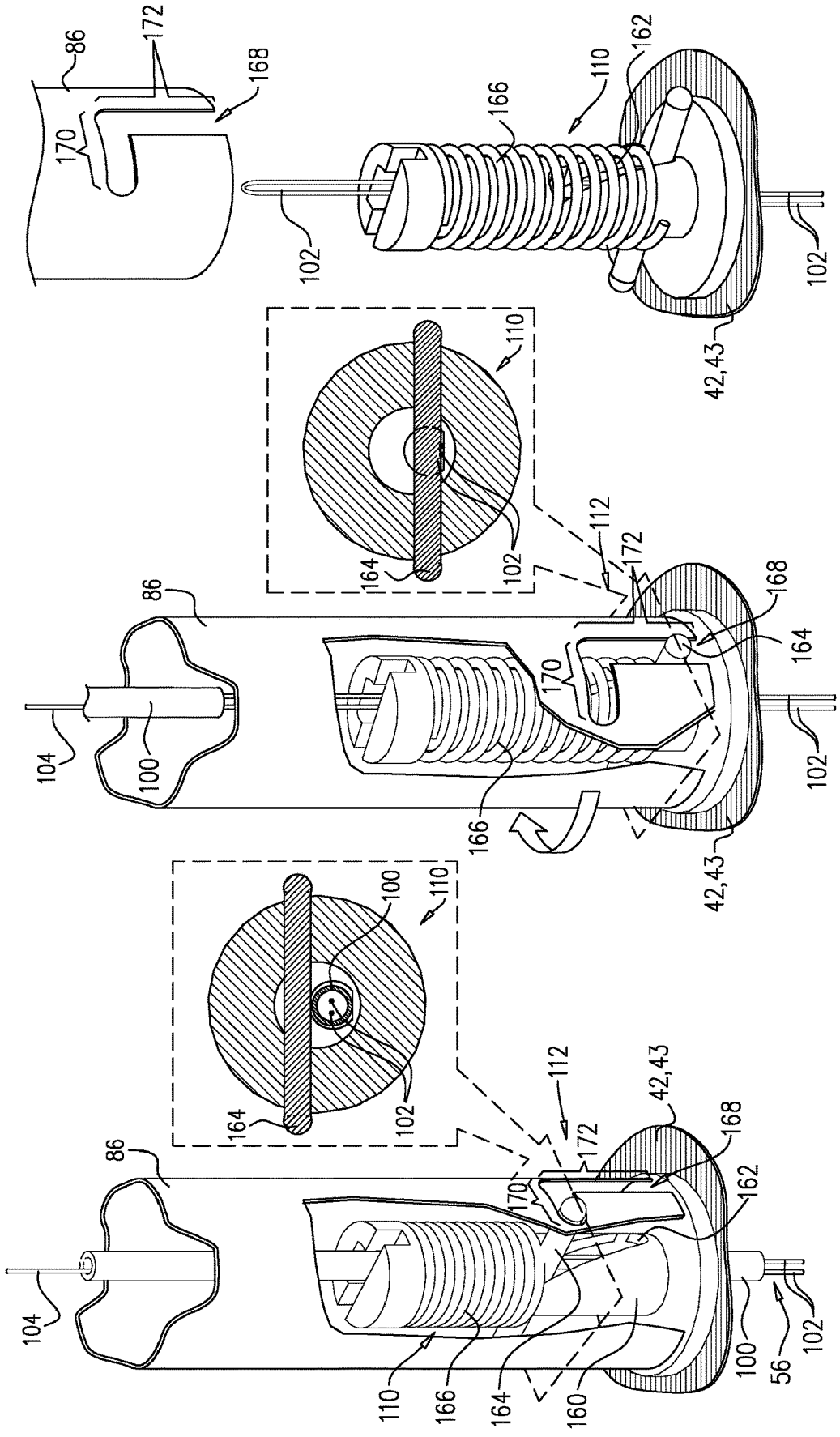

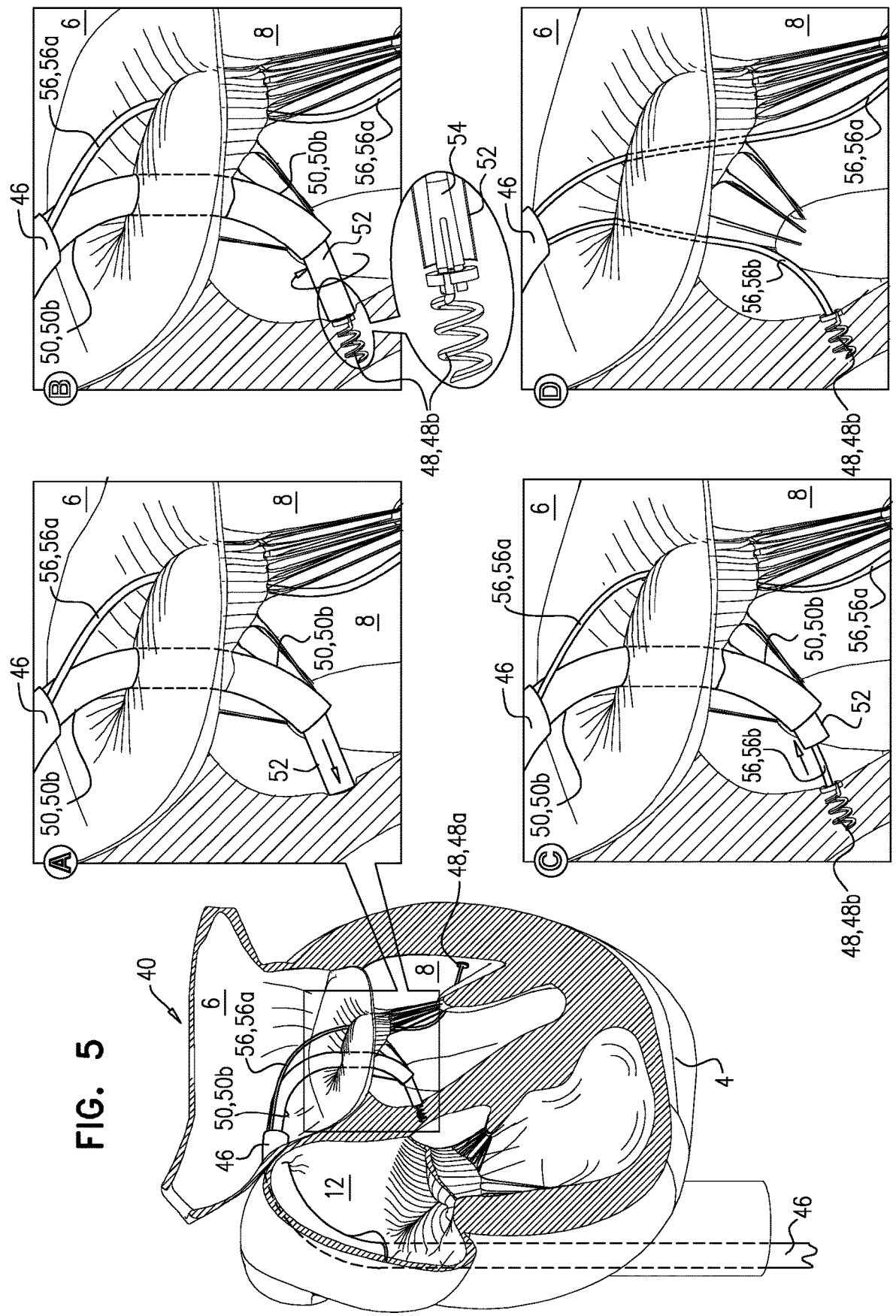

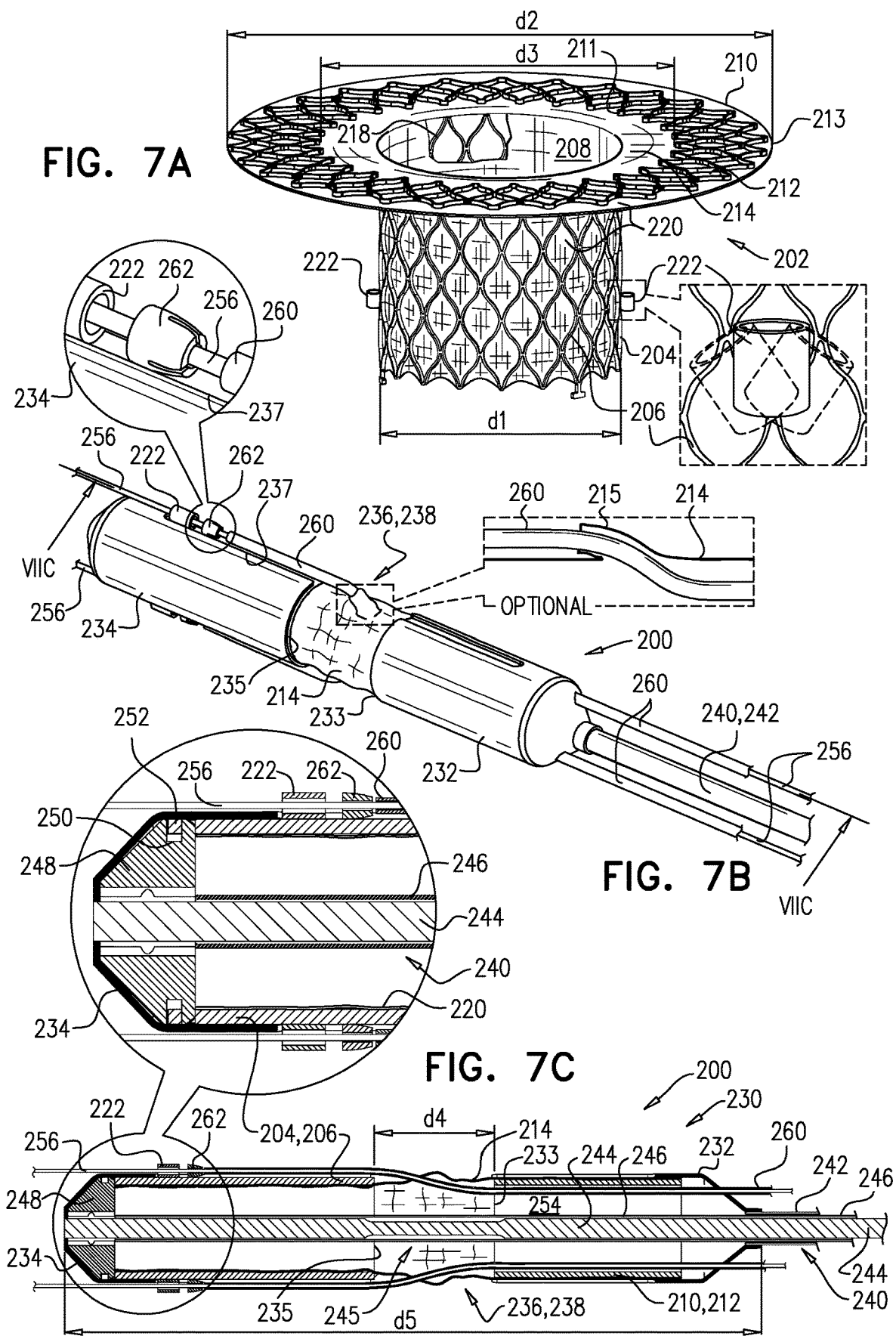

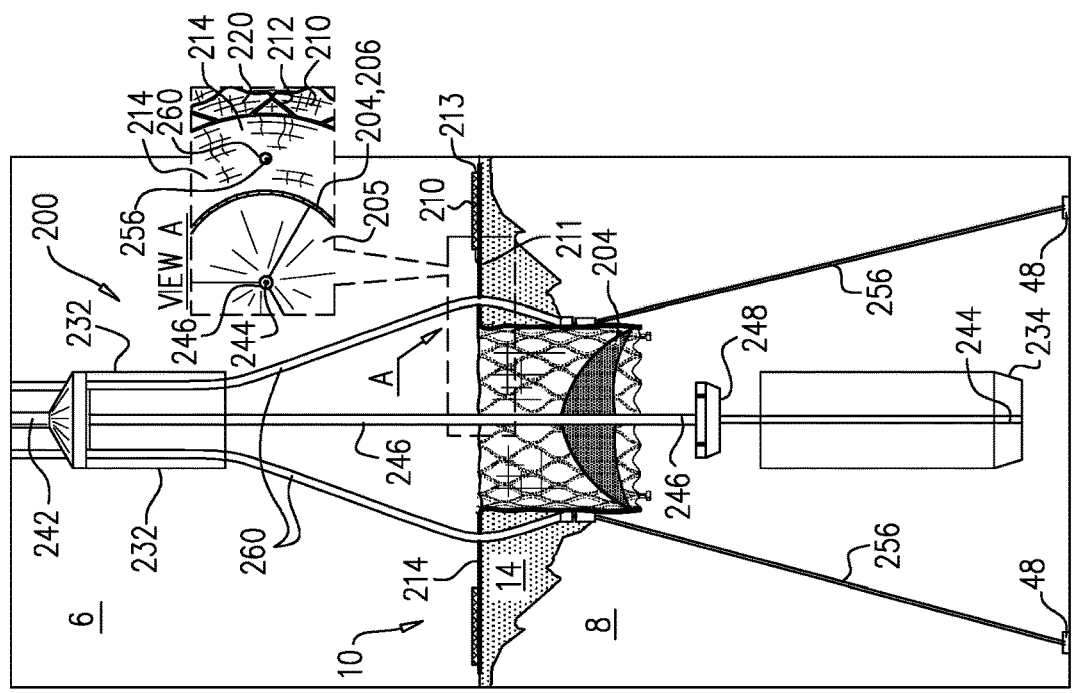
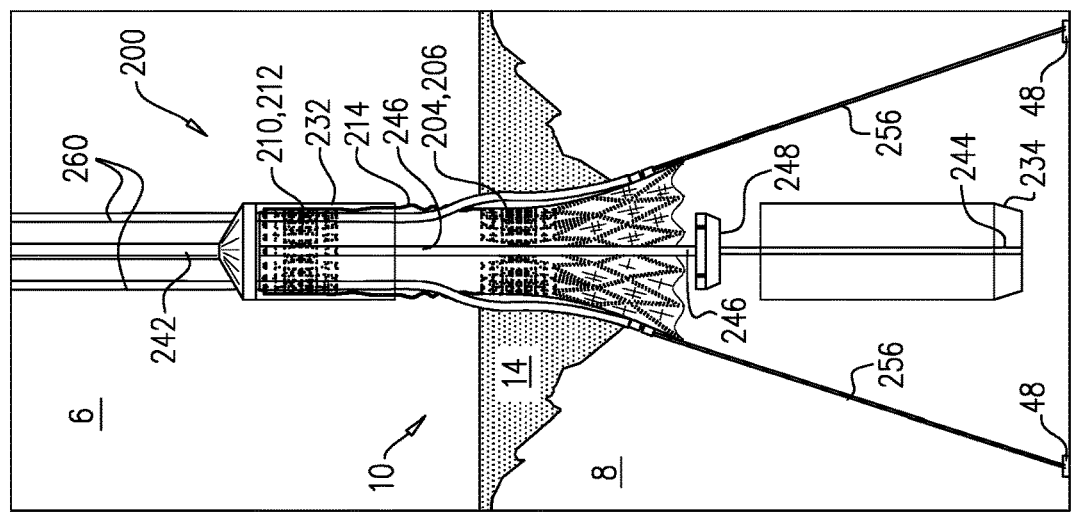
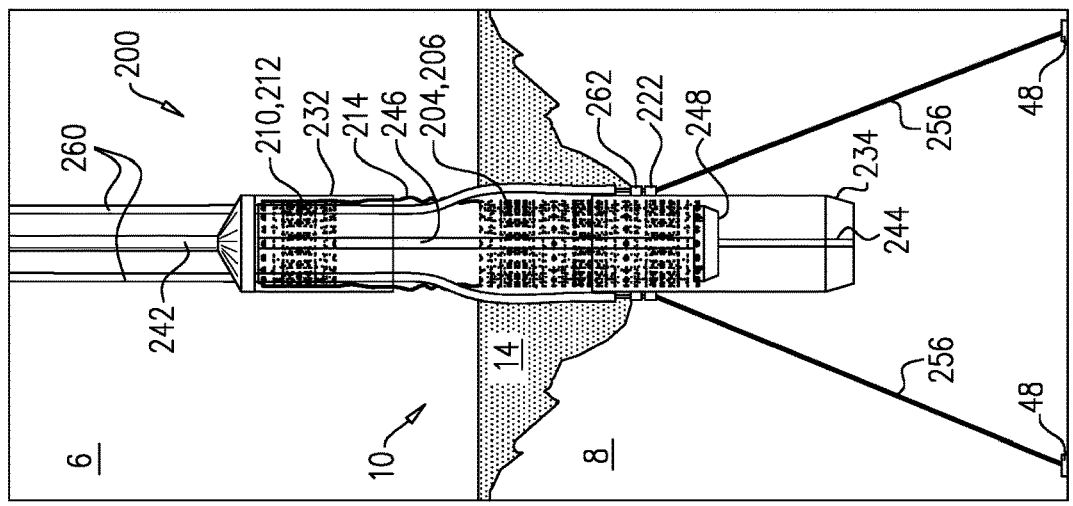

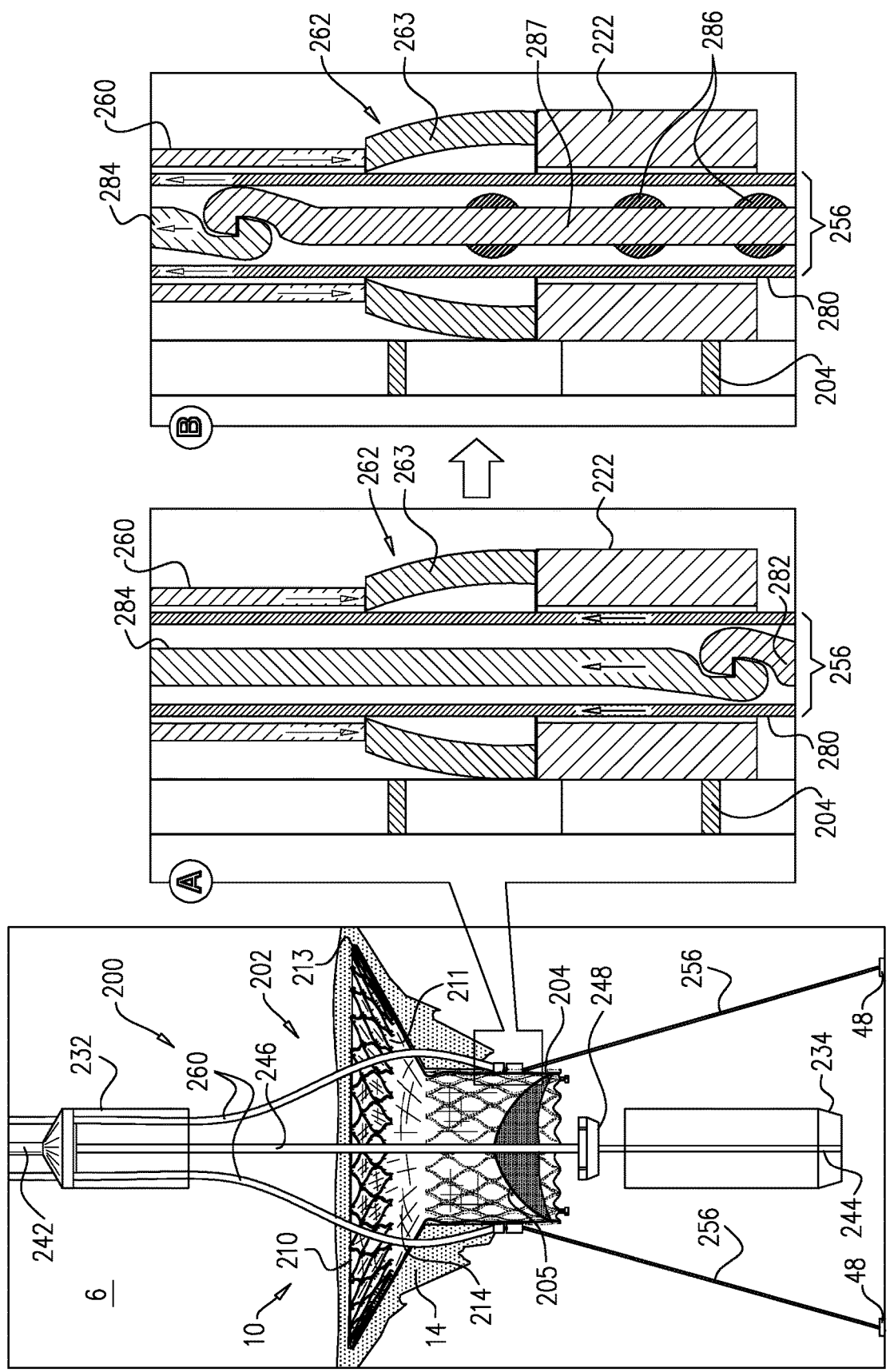

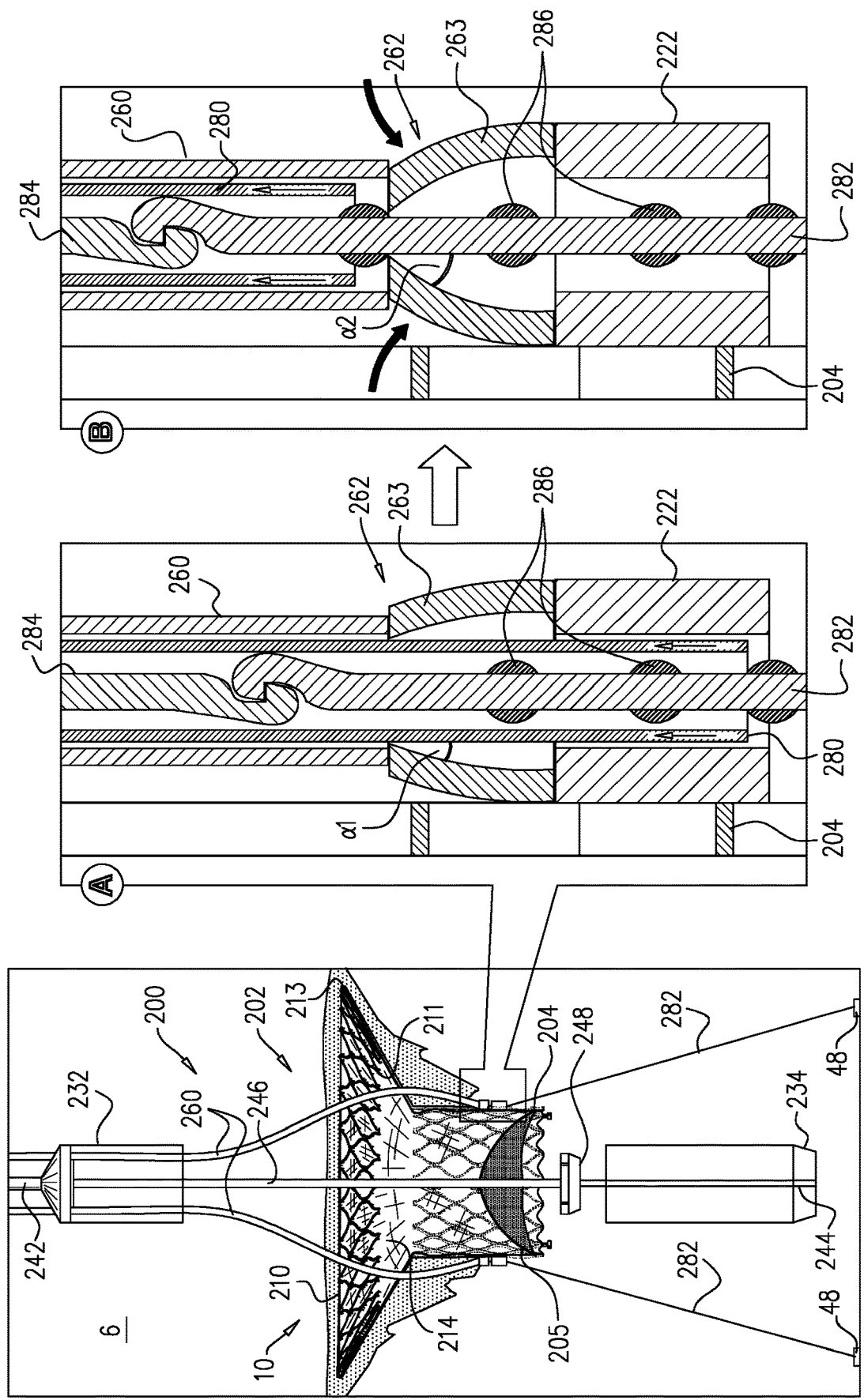

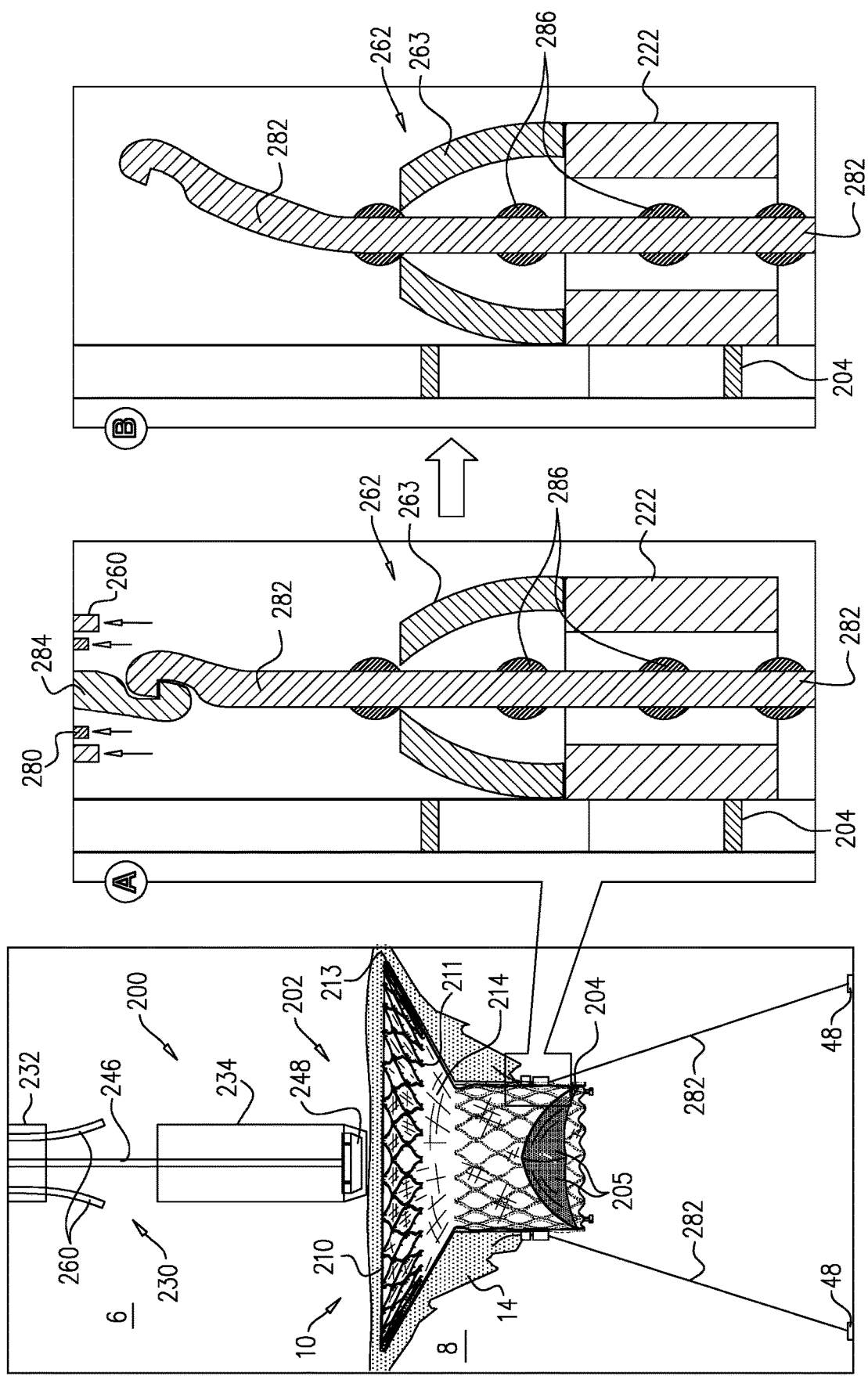

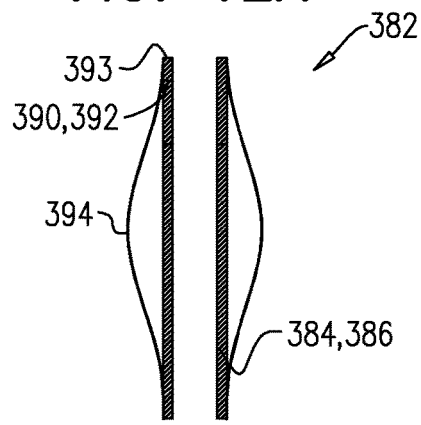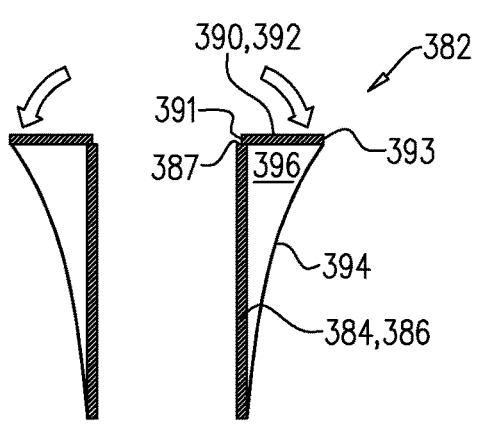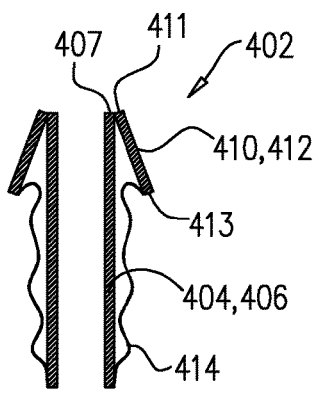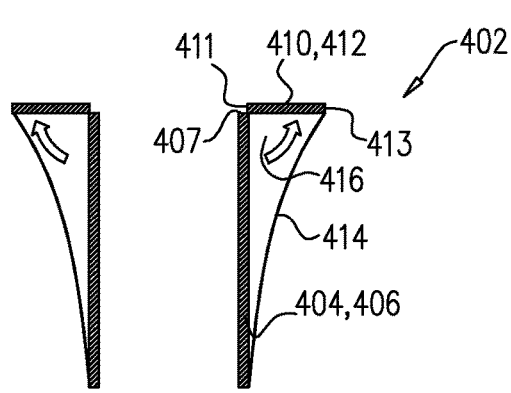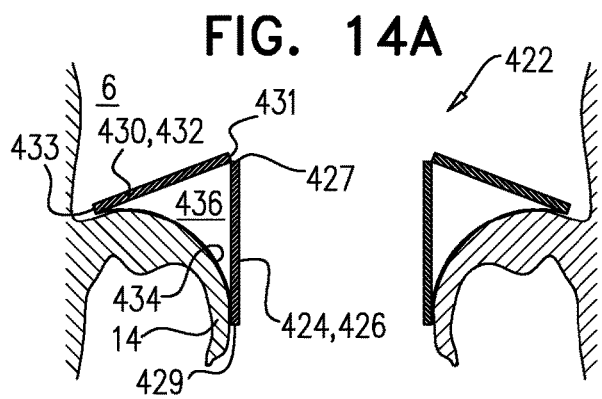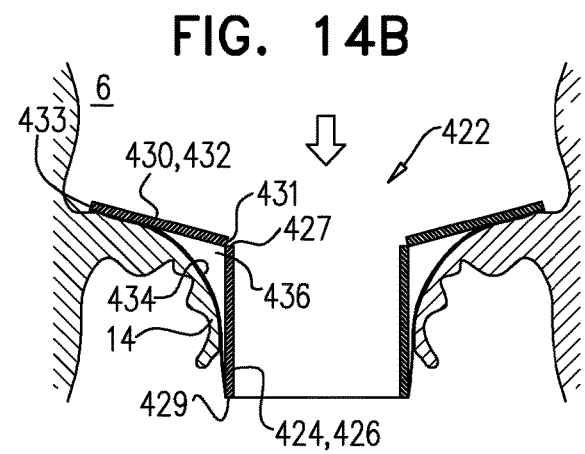

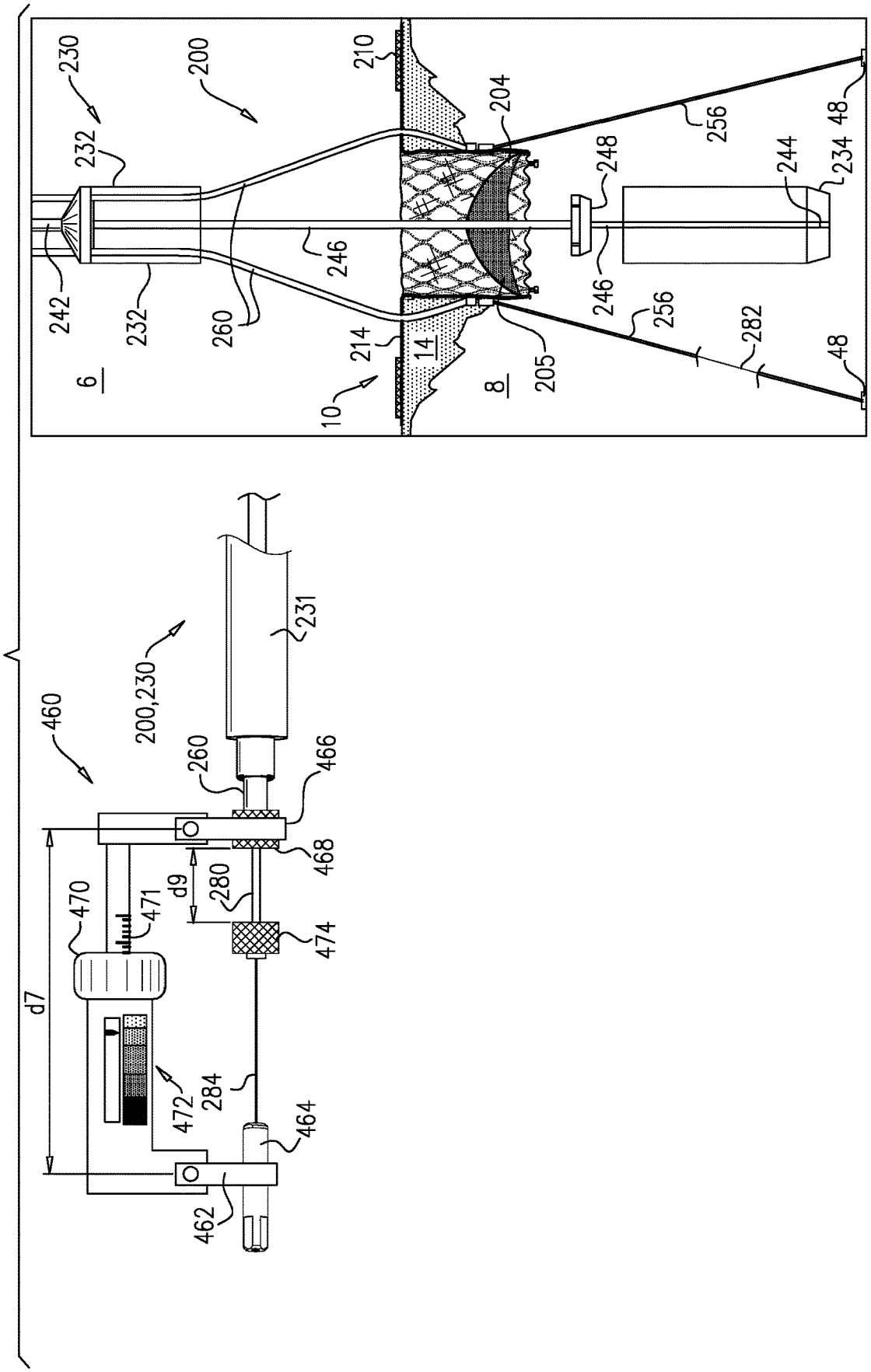

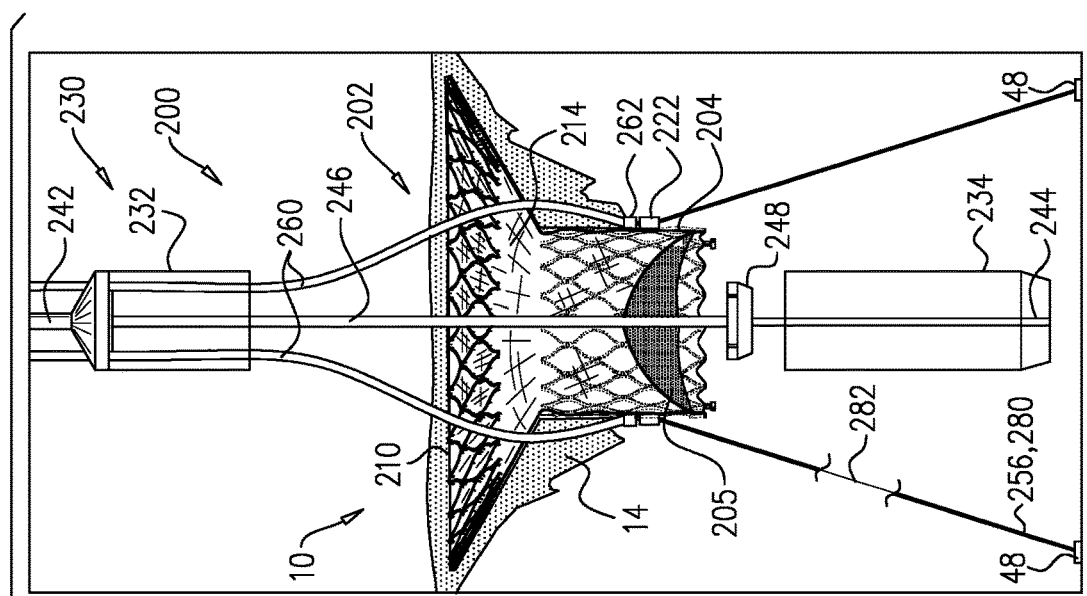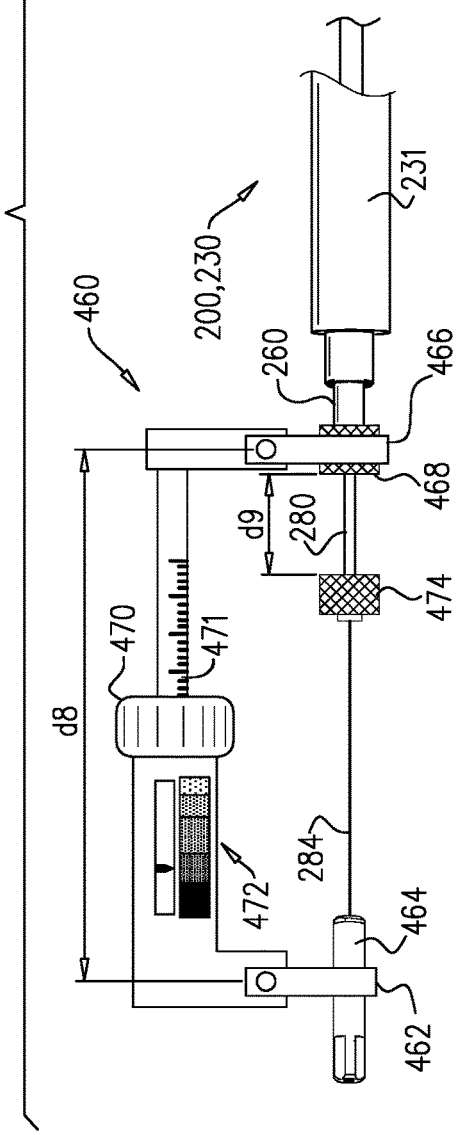
FIG. 15B

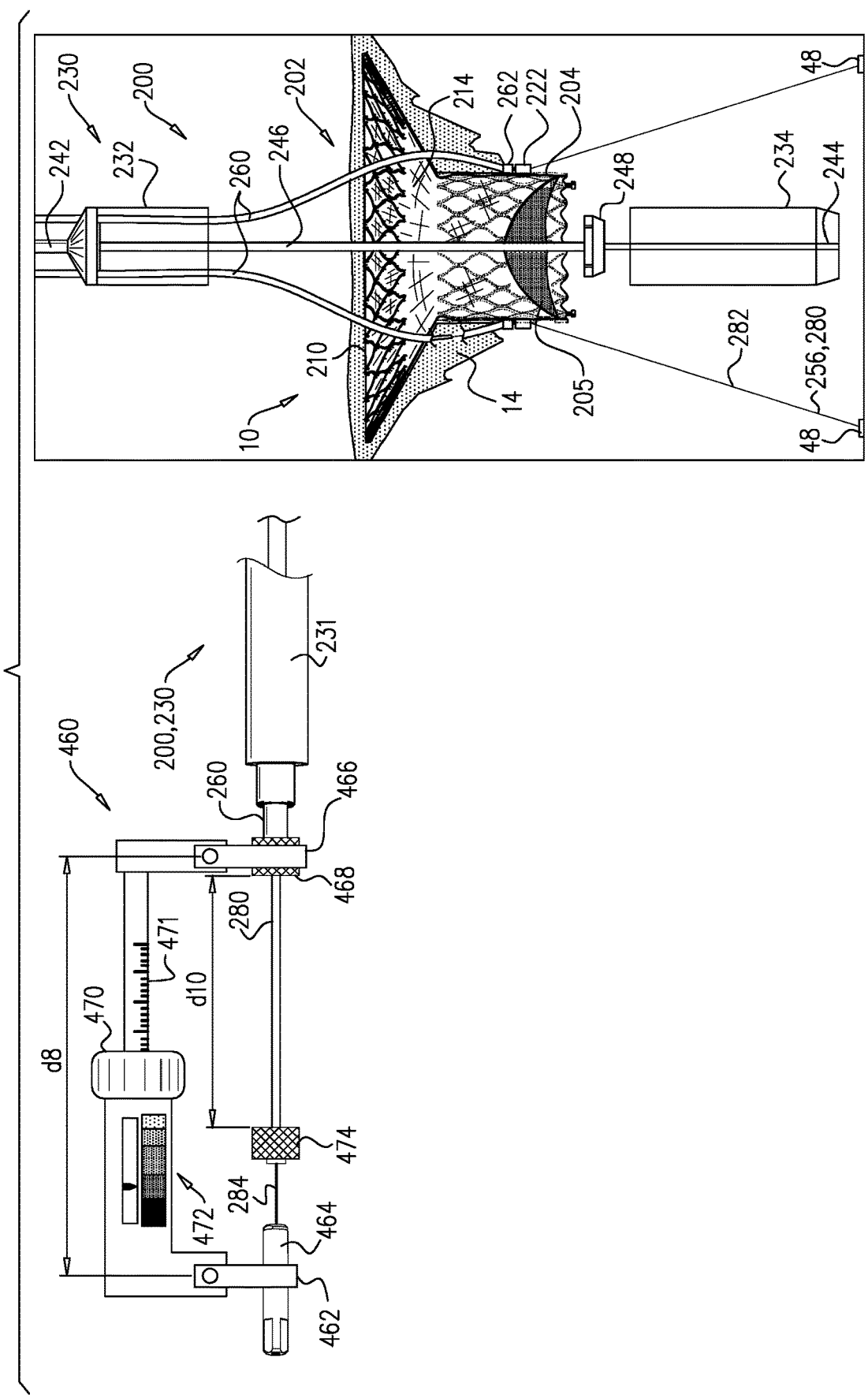

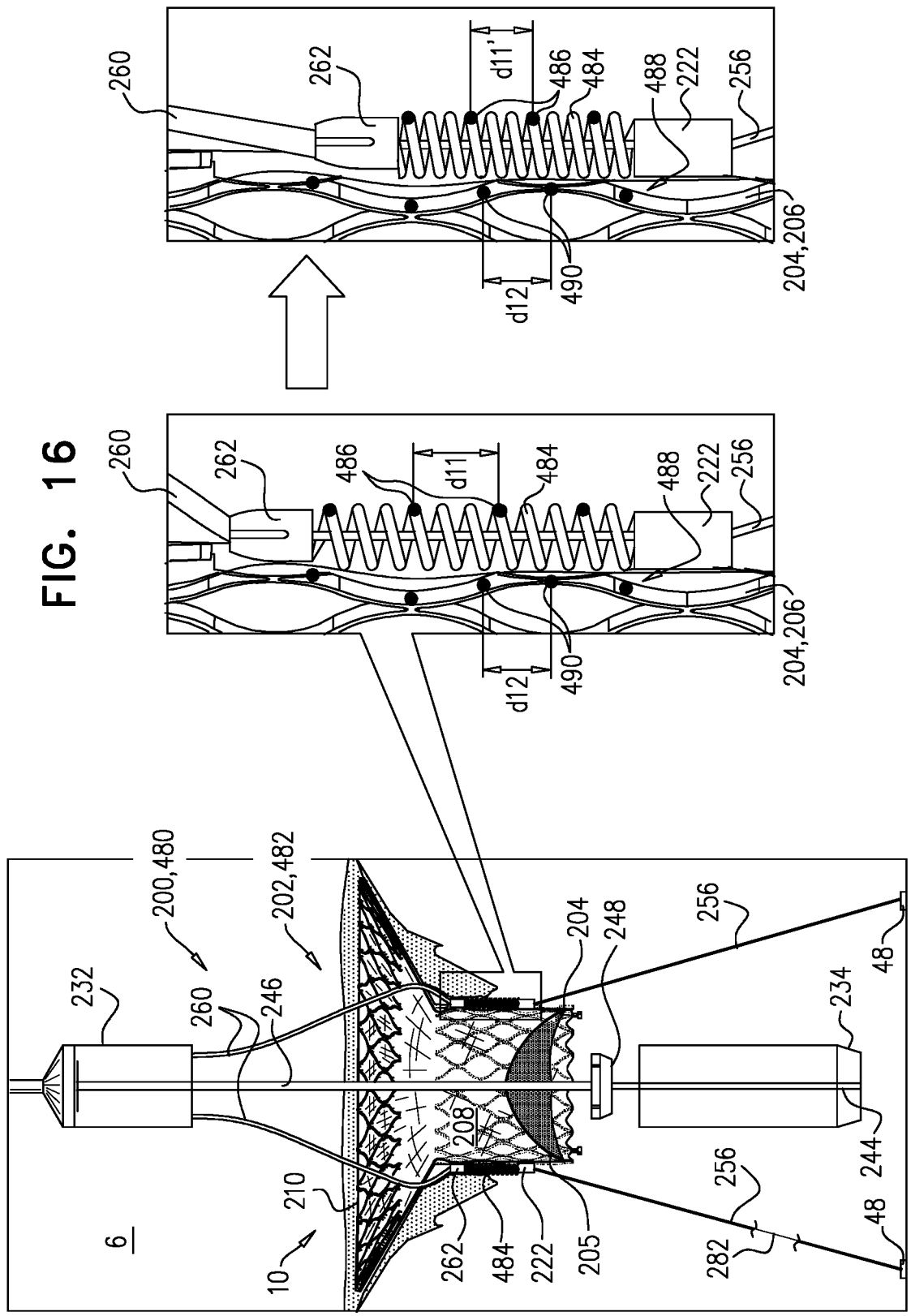

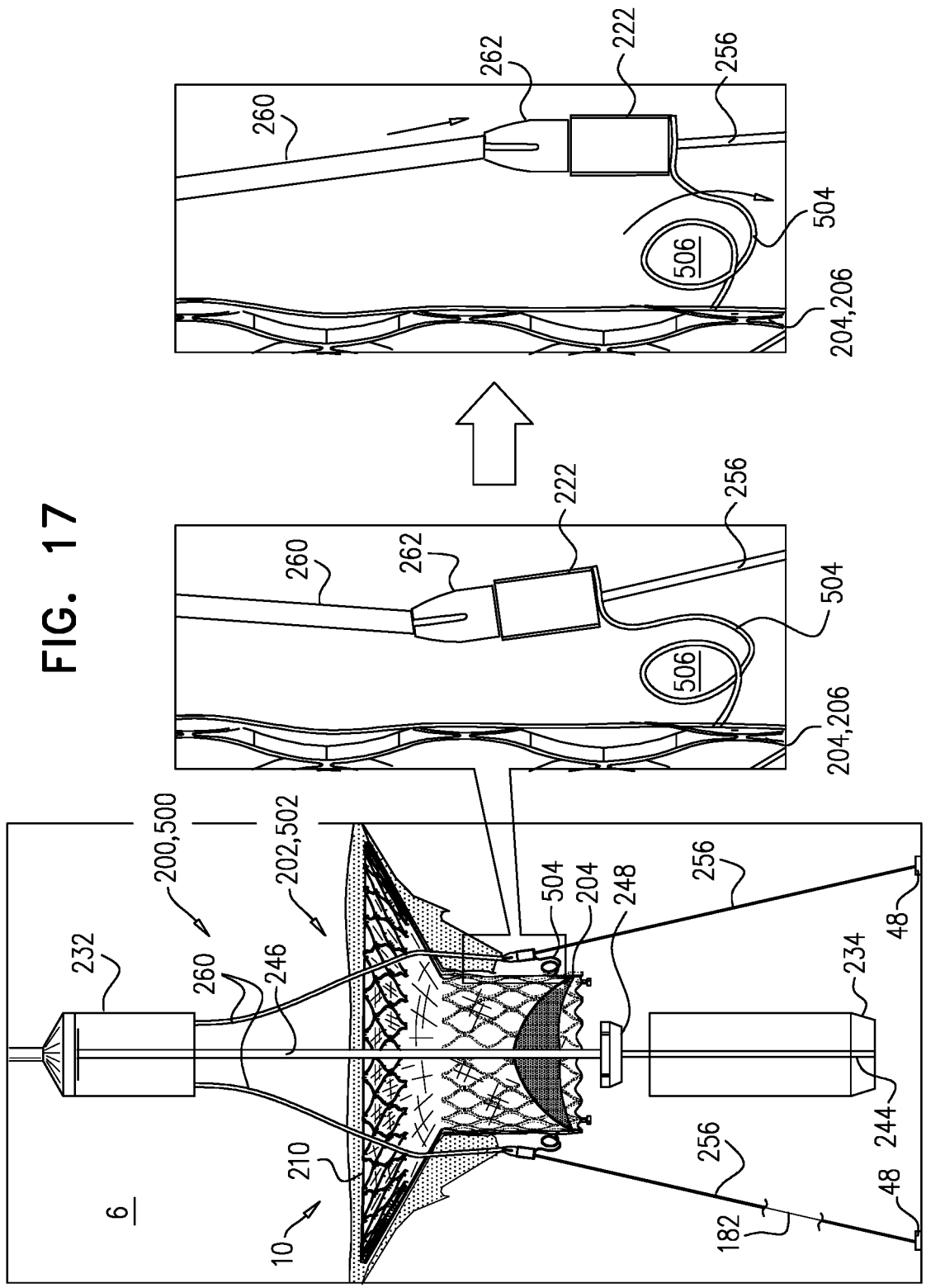

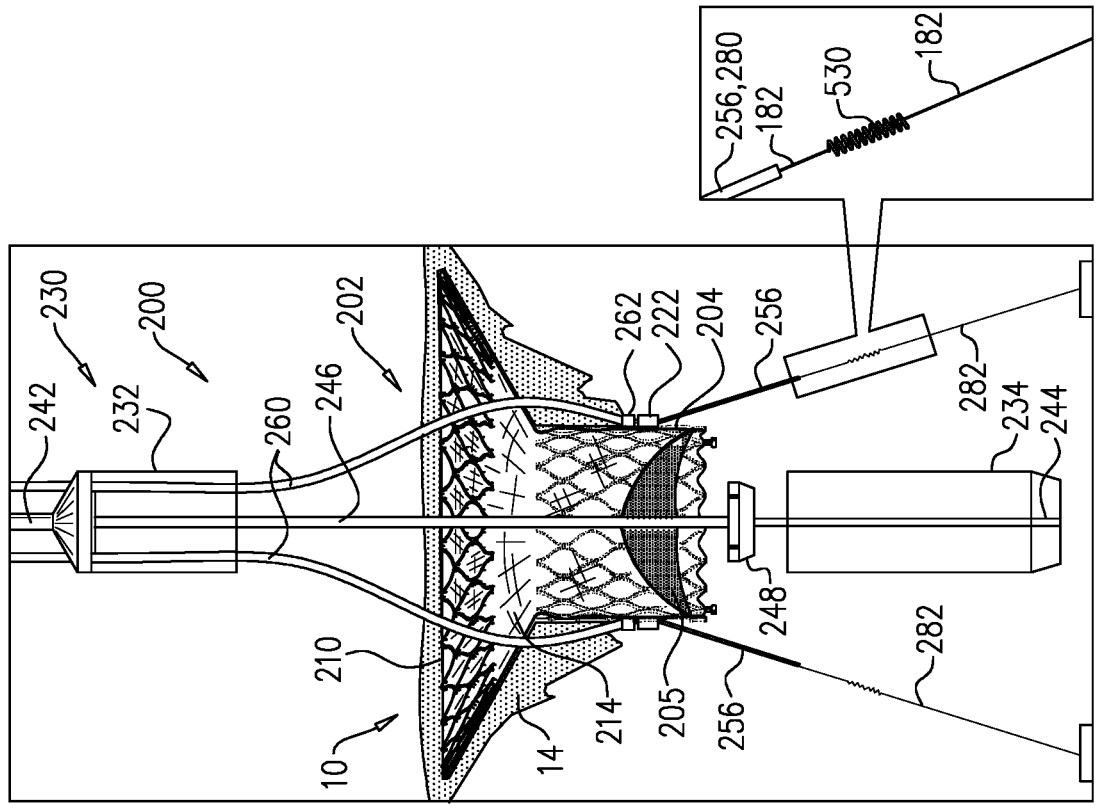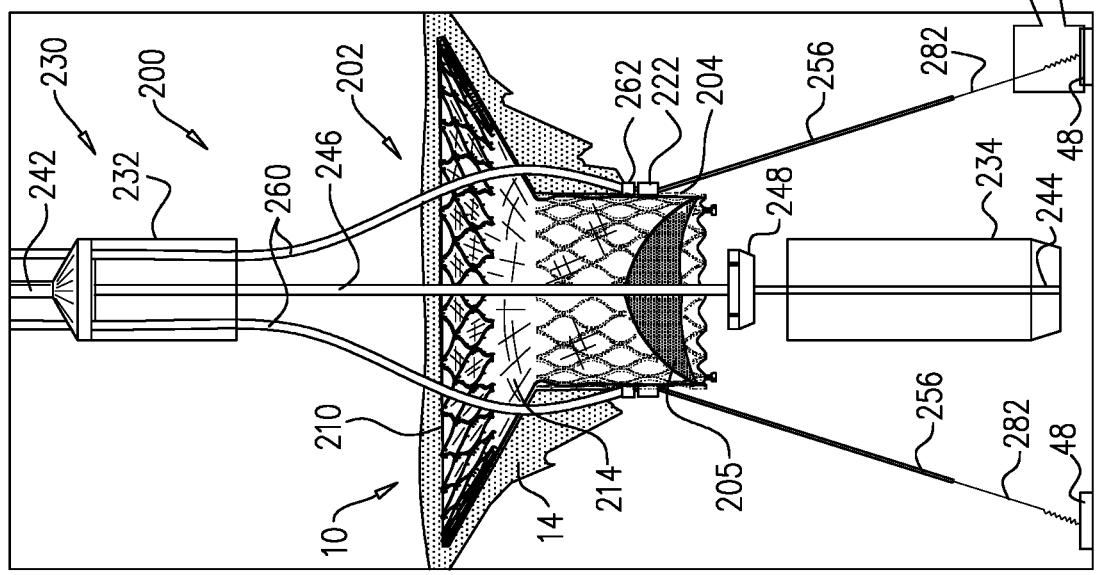

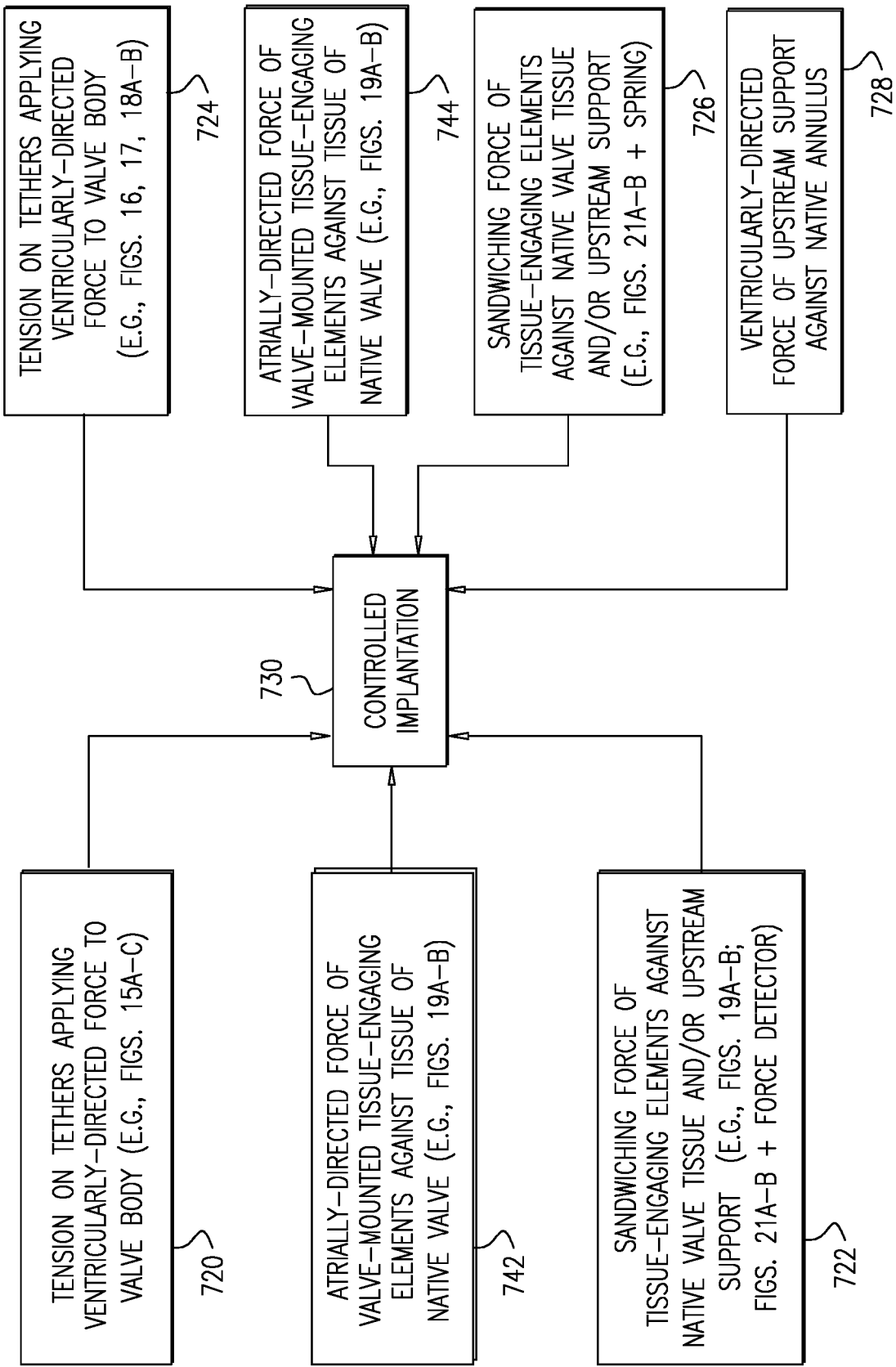

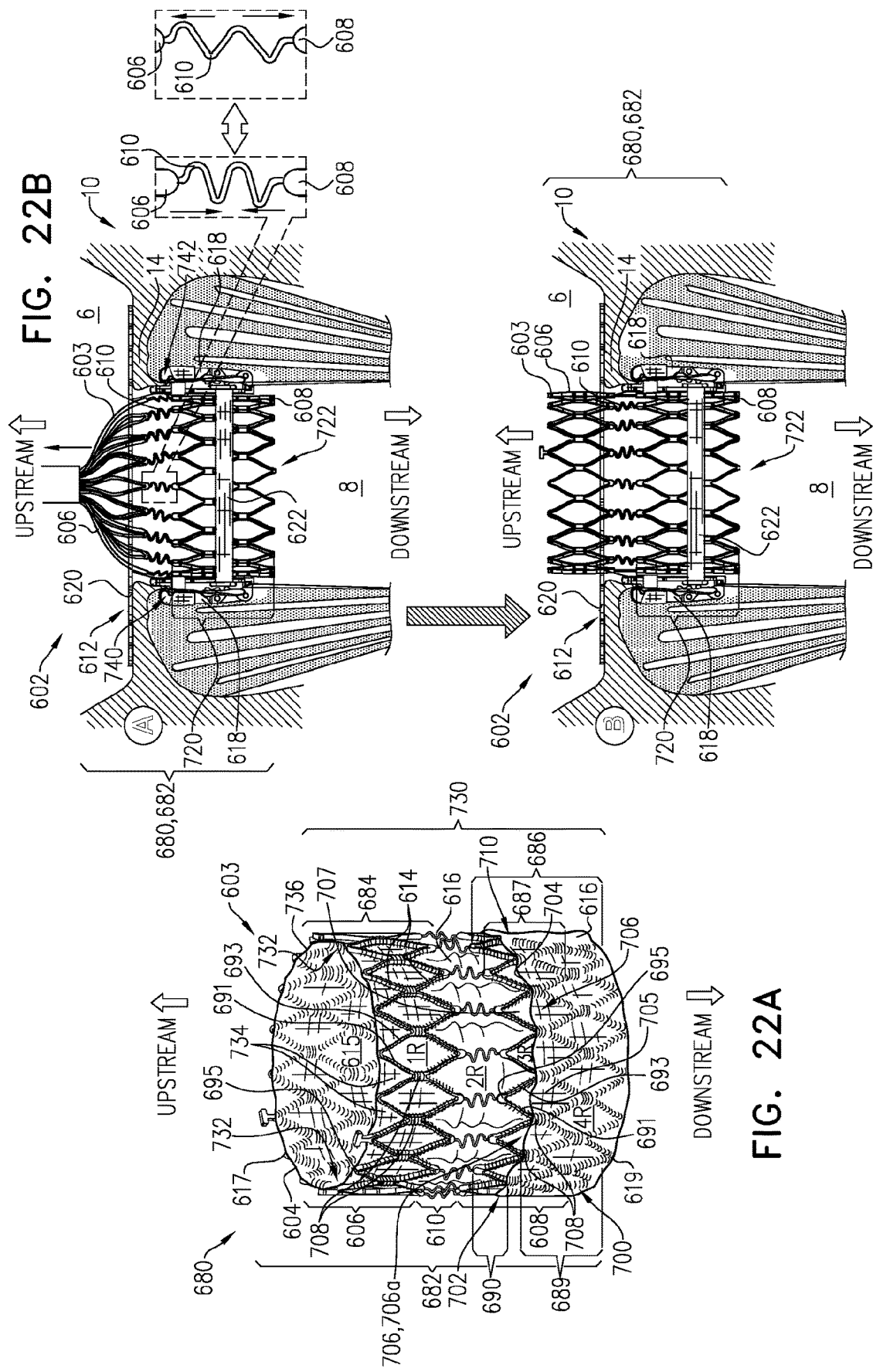

PARTIALLY-COVERED PROSTHETIC VALVES

CROSS-REFERENCES TO RELATED APPLICATIONS

The present application is a continuation of U.S. patent application Ser. No. 16/802,353 to Hammer et al., filed Feb. 26, 2020, and entitled "Prosthetic valve and upstream support therefor" (now U.S. Pat. No. 11,135,059), which is a continuation of U.S. patent application Ser. No. 15/872,501 to Hammer et al., filed Jan. 16, 2018, and entitled "Prosthetic valve and upstream support therefor" (now U.S. Pat. No. 10,631,982), which is a continuation of U.S. patent application Ser. No. 14/763,004 to Hammer et al., filed Jul. 23, 2015, and entitled "Ventricularly-anchored prosthetic valves," which published as US 2015/0351906, which is a national phase of PCT/IL2014/050087 to Hammer et al., filed Jan. 23, 2014, and entitled "Ventricularly-anchored prosthetic valves," which published as WO 2014/115149, and which claims priority from U.S. provisional patent application 61/756,049 to HaCohen et al., filed Jan. 24, 2013, and entitled "Ventricularly-anchored prosthetic valve support"; and U.S. provisional patent application 61/756,034 to HaCohen et al., filed Jan. 24, 2013, and entitled "Tissue-engaging elements", and is related to:

US patent application publication 2012/0022639 to Hacohen et al., filed Jul. 21, 2010 (now U.S. Pat. No. 9,132,009);

US patent application publication 2012/0022640 to Gross et al., filed Feb. 24, 2011 (now U.S. Pat. No. 8,992,604);

U.S. patent application Ser. No. 13/811,308 to Gross et al., filed Jan. 21, 2013, which published as US 2013/0172992 (now U.S. Pat. No. 9,017,399);

U.S. patent application Ser. No. 13/412,814 to Gross et al., filed Mar. 6, 2012, which published as US 2013/0035759 (now U.S. Pat. No. 8,852,272);

PCT patent application IL2012/000292 to Gross et al., filed Aug. 5, 2012, which published as WO/2013/021374;

PCT patent application IL2012/000293 to Gross et al., filed Aug. 5, 2012, which published as WO/2013/021375; and U.S. patent application Ser. No. 14/161,921 to HaCohen et al., entitled "Anchoring of prosthetic valve supports", filed on Jan. 23, 2014 (now U.S. Pat. No. 9,681,952), all of which are incorporated herein by reference.

FIELD OF THE INVENTION

Some applications of the present invention relate in general to valve replacement. More specifically, some applications of the present invention relate to prosthetic cardiac valves and techniques for implantation thereof.

BACKGROUND

Ischemic heart disease causes regurgitation of a heart valve by the combination of ischemic dysfunction of the papillary muscles, and the dilatation of the ventricle that is present in ischemic heart disease, with the subsequent displacement of the papillary muscles and the dilatation of the valve annulus.

Dilation of the annulus of the valve prevents the valve leaflets from fully coapting when the valve is closed. Regurgitation of blood from the ventricle into the atrium results in increased total stroke volume and decreased cardiac output, and ultimate weakening of the ventricle secondary to a volume overload and a pressure overload of the atrium.

SUMMARY OF THE INVENTION

For some applications of the invention, tissue anchors coupled to tethers are transluminally anchored to ventricular tissue of a native valve. A prosthetic valve component, such as a prosthetic valve assembly, a prosthetic valve body, or a support, is transluminally slid along a guide member coupled to the tethers, and is anchored to the tethers.

For some applications, a prosthetic valve assembly comprises (1) a valve body shaped to define a lumen therethrough, and a valve member disposed within the lumen, (2) an upstream support configured to be placed against an upstream surface of a native heart valve, and (2) a flexible sheet that couples the upstream support to the valve body.

For some applications, the prosthetic valve assembly comprises eyelets to facilitate sliding along the guide member.

For some applications, the prosthetic valve assembly has a compressed delivery state in which the valve body and the upstream support are articulatably coupled to each other by the sheet. For such applications, a delivery tool houses the prosthetic valve assembly such that the valve body and upstream support are articulatable with respect to each other during transluminal delivery.

For some applications, the prosthetic valve assembly comprises tethers that, when tensioned, move the valve body closer to the support. For such applications, the assembly typically comprises tissue-engaging elements that protrude from the valve body, and the tethers are tensioned to sandwich tissue of the native valve between the tissue-engaging elements and the support.

For some applications, one or more forces is measured during implantation, and distributed among various anchoring elements. For some such applications, an intracorporeal spring is used that is extracorporeally observable using imaging techniques. For some such applications, the spring facilitates force distribution.

For some applications, a prosthetic valve assembly comprises a flexible sheet forms a pocket between the sheet and a frame of the assembly, and facilitates sealing between the assembly and tissue of the native valve.

For some applications of the invention, tissue anchors coupled to longitudinal members that are reversibly couplable to wires are transluminally advanced to the ventricle downstream of a native heart valve, and are anchored there. A prosthetic valve support comprising an upstream support portion is slid, in a compressed delivery configuration, over the wires and part of each longitudinal member, and into an atrium upstream of the native valve where it is deployed (e.g., expanded) and placed against an upstream surface (e.g., an atrial surface) of the native valve. A locking member is also slid over the wires and part of each longitudinal member, and locks to the longitudinal member, thereby securing the prosthetic valve support against the upstream surface of the native valve. A prosthetic valve is subsequently transluminally advanced to the native valve, and is implanted by coupling the prosthetic valve to leaflets of the native valve and to the prosthetic valve support.

For some applications of the invention, a tubular member is slidable over the wire and the longitudinal member, and when disposed over the wire and the long member, inhibits decoupling of the wire from the longitudinal member. For such applications, the prosthetic valve support and the locking member are typically slidable over the tubular member.

For some applications of the invention, a control rod, reversibly coupled to the locking member, is slid over the tubular member so as to push the locking member and the prosthetic valve support over the tubular member. For some such applications, the control rod is used to lock the locking member to the longitudinal member.

There is therefore provided, in accordance with an application of the present invention, apparatus for use with a native valve of a heart of a subject, the apparatus including:
a valve body:
including (1) a first frame shaped to define a lumen therethrough, and (2) a valve member disposed within the lumen,
having a compressed state in which the first frame has a first diameter, and
having an expanded state in which the first frame has a second diameter that is greater than the first diameter;
an upstream support:
configured to be placed against an upstream surface of the native valve,
including a second frame,
having a compressed state, and
having an expanded state in which the second frame is annular, has an inner perimeter that defines an opening through the second frame, and has an outer perimeter; and
a flexible sheet that couples the upstream support to the valve body.

In an application, the upstream support is coupled to the valve body only via the sheet.

In an application:
the valve body has an upstream end, a downstream end, and a longitudinal axis therebetween along which the lumen is defined, and
when the valve body is in the expanded state thereof and the upstream support is in the expanded state thereof:
the first frame is attached to the second frame at the inner perimeter of the second frame, and
the sheet is attached to the valve body and to the upstream support in a manner that defines a pocket region between the sheet and at least the inner perimeter of the second frame, the sheet not being attached to the first frame or the second frame in the pocket region.

In an application, the sheet provides fluid communication between the opening and the lumen.

In an application, the sheet is not attached to the inner perimeter of the second frame.

In an application, the sheet is not attached to an upstream end of the valve body.

In an application, the sheet is generally annular when the valve body is in the expanded state thereof and the upstream support is in the expanded state thereof.

In an application, the sheet is generally frustoconical when the valve body is in the expanded state thereof and the upstream support is in the expanded state thereof.

In an application, the sheet is attached to the inner perimeter of the second frame.

In an application, the sheet is circumferentially attached to the second frame at a radius that is greater than a radius of the inner perimeter.

In an application, the sheet is circumferentially attached to the second frame at the outer perimeter of the second frame.

In an application, the sheet is attached to an upstream end of the valve body.

In an application, the first frame is generally cylindrical in both the compressed state thereof and the expanded state thereof.

In an application, the second frame is generally cylindrical in the compressed state thereof.

In an application, the valve body includes at least one downstream anchor, configured such that, in the expanded configuration of the valve body, the anchor protrudes radially outward from the first frame.

In an application, the apparatus further includes at least one tensioning element, coupled to the valve body and to the upstream support, a length of the tensioning element between the valve body and the upstream portion being adjustable such that a distance between the first frame and the second frame is adjustable.

In an application, the at least one tensioning element includes a tether.

In an application, the at least one tensioning element is coupled to the first frame, and slidably coupled to the second frame.

In an application, the valve body, the upstream support and the sheet together define a prosthetic valve assembly, the prosthetic valve assembly:
having an expanded state in which the valve body is in the expanded state thereof and the second frame of the upstream support is in the expanded state thereof,
having a compressed state in which:
the prosthetic valve assembly has a longitudinal axis,
the valve body is in the compressed state thereof at a first zone of the longitudinal axis,
the upstream support is in the compressed state thereof at a second zone of the longitudinal axis, and
the prosthetic valve assembly defines an articulation zone, between the first zone and the second zone, in which at least part of the sheet is disposed, in which neither the first frame nor the second frame is disposed, and about which the valve body and the upstream support are articulatable with respect to each other.

In an application, the apparatus further includes a delivery tool:
including a first housing configured to house and maintain at least part of the upstream support in the compressed state thereof, and defining a first housing orifice through which the at least part of the upstream support is removable from the first housing,
including a second housing configured to house and maintain at least part of the valve body in the compressed state thereof, and defining a second housing orifice through which the at least part of the valve body is removable from the second housing,
having a contracted state in which the second housing is disposed at a first distance from the first housing, and in which the delivery tool is configured to transluminally advance the prosthetic valve assembly in the compressed state thereof, to the native valve, and
having an extended state in which the second housing is disposed at a second distance from the first housing, the second distance being greater than the first distance, and the apparatus is configured such that, when the at least part of the upstream support is housed by the first housing and the at least part of the valve body is housed by the second housing, transitioning of the delivery tool from the contracted state into the extended state exposes at least part of at least one component selected from the group consisting of: the valve body and the upstream support, from the housing that houses the selected component.

In an application:
the apparatus is configured to be used with at least two guide members,
the prosthetic valve assembly includes at least two eyelets, each eyelet being slidable over a respective one of the guide members, and
the apparatus is configured such that the eyelets of the prosthetic valve assembly protrude radially outward and radially beyond an outer surface of the second housing while: (1) the at least part of the valve body, in the compressed state thereof, is housed by the second housing, and (2) the at least part of the upstream support, in the compressed state thereof, is housed by the first housing.

In an application, the eyelets are pivotably coupled to the valve body.

In an application, the delivery tool further includes at least two reference-force tubes, each reference-force tube configured (1) to be slidable over a respective one of the guide members, and (2) to apply a distally-directed force to the prosthetic valve assembly.

In an application, in the compressed state of the prosthetic valve assembly, each reference-force tube extends distally (1) through a lumen defined by the second frame of the upstream support, (2) through the sheet, and (3) along an outside of at least part of the valve body.

In an application, the apparatus further includes at least two locking members, each locking member:
having an unlocked state in which the locking member is slidable along a respective one of the guide members,
being transitionable into a locked state in which (1) the locking member is locked to the respective one of the guide members, and (2) the sliding of the eyelet over the guide member is inhibited.

In an application, the apparatus further includes the at least two guide members:
each guide member includes:
a tubular member, shaped to define a lumen therethrough,
a tether, coupled at a distal end thereof to a tissue anchor configured to be anchored to ventricular tissue of the heart, at least a proximal portion of the tether being disposed within the lumen of the tubular member, and
a pull-wire, coupled at a distal portion thereof to the proximal portion of the tether, at least the distal portion of the pull-wire being disposed within the lumen of the tubular member,
the tubular member inhibits decoupling of the pull-wire from the tether while the distal portion of the pull-wire and the proximal portion of the tether are disposed within the lumen of the tubular member, and
while the tubular member of each guide member is disposed within the respective locking member, the tubular member inhibits transitioning of the locking member into the locked state.

In an application, the apparatus is configured such that, for each respective guide member and locking member, while (1) the tubular member is disposed within the locking member, (2) the distal portion of the pull-wire and the proximal portion of the tether are disposed within the lumen of the tubular member, and (3) the tissue anchor is coupled to the ventricular tissue:
proximal sliding of the tubular member with respect to the tether facilitates automatic transitioning of the locking member into the locked state, and
further proximal sliding of the tubular member with respect to the tether facilitates decoupling of the pull-wire from the tether.

In an application, at least one housing selected from the group consisting of: the first housing and the second housing has a lateral wall that is shaped to define at least two slits, the eyelets being configured to protrude radially outward from the delivery tool via the slits.

In an application, each slit of the at least one selected housing is continuous with the orifice of the at least one selected housing.

In an application, the eyelets are coupled to and protrude radially outward from the valve body.

In an application, the eyelets are pivotably coupled to the valve body.

In an application:
the articulation zone defined by the prosthetic valve assembly includes a first articulation zone, and
while (1) the at least part of the valve body, in the compressed state thereof, is housed by the second housing, (2) the at least part of the upstream support, in the compressed state thereof, is housed by the first housing, and (3) the delivery tool is in the contracted state thereof, the apparatus defines a second articulation zone at a longitudinal zone of the apparatus (a) between the second housing and the first housing, and (b) in which is disposed at least part of the first articulation zone.

In an application, the delivery tool further includes a housing-control rod that extends through the first housing and is coupled to the second housing such that a first portion of the housing-control rod is disposed within the first housing, a second portion of the housing-control rod is disposed within the second housing, and a third portion of the housing-control rod (1) is disposed within the second articulation zone, and (2) is more flexible than at least one portion of the housing-control rod selected from the group consisting of: the first portion and the second portion.

In an application:
the delivery tool further includes (1) a control rod assembly including at least a first housing-control rod coupled to the first housing, and (2) a second housing-control rod, more flexible than the first housing-control rod, extending through the first housing-control rod, extending through the second articulation zone, and coupled to the second housing.

In an application, the second housing orifice faces the first housing orifice.

In an application:
the delivery tool further includes a flexible control rod assembly including (1) a first housing-control rod coupled to the first housing, (2) a second housing-control rod coupled to the second housing, and (3) a prosthesis-control rod reversibly couplable to the prosthetic valve assembly,
longitudinal movement of the second housing-control rod with respect to the first housing-control rod transitions the delivery tool between the contracted state and the extended state thereof, and
the valve body is removable from the second housing by moving the second housing-control rod with respect to the prosthesis-control rod.

In an application, the prosthesis-control rod is reversibly couplable to the prosthetic valve assembly by being reversibly couplable to the valve body.

In an application, at least part of the second housing-control rod is disposed within and slidable through the prosthesis-control rod, and at least part of the prosthesis-control rod is disposed within and slidable through the first housing-control rod.

In an application, the outer perimeter of the second frame has a third diameter that is greater than the second diameter.

In an application, the inner perimeter has a fourth diameter that is greater than the second diameter.

In an application, when the valve body is in the expanded state thereof and the upstream support is in the expanded state thereof, a gap is defined between the first frame and the second frame, the sheet spanning the gap.

In an application, no metallic structure is disposed within the gap.

In an application, the sheet is configured to inhibit expansion of the second frame.

In an application, the apparatus is configured such that when the second frame expands from the compressed state thereof toward the expanded state thereof, the sheet retains the second frame in a generally frustoconical shape by inhibiting expansion of at least the outer perimeter of the second frame.

In an application, the sheet extends over at least part of the second frame to serve as a covering of the upstream support.

In an application, the covering defines a tissue-contacting surface of the upstream support.

In an application, the sheet extends over at least part of the first frame to serve as a covering of the valve body.

In an application, the covering is disposed on an inner surface of the first frame.

There is further provided, in accordance with an application of the present invention, apparatus for use with a native valve of a heart of a subject, the apparatus including:
a prosthetic valve, configured to be percutaneously delivered to the native valve;
an annular upstream support, configured to be placed against an upstream surface of the native valve, and to support the prosthetic valve at the native valve;
a tissue anchor, including a tissue-engaging element configured to be anchored to ventricular muscle tissue of the heart;
a tether, coupled to the tissue anchor; and
a spring, couplable to the tether so as to elastically couple the tissue-engaging element to the prosthetic valve.

In an application, the spring is shaped to define a repeating pattern.

In an application, the spring is pre-loaded.

In an application, the spring is a constant-force spring.

In an application, the spring is configured to facilitate extracorporeal fluoroscopic observation of a state of the spring.

In an application, the spring is coupled to a plurality of radiopaque markers such that a juxtaposition of the markers changes as the state of the spring changes, the juxtaposition of the markers being extracorporeally fluoroscopically observable.

In an application, the spring is coupled to at least one radiopaque marker, and the apparatus further includes an intracorporeal reference, a juxtaposition between the radiopaque marker and the intracorporeal reference being extracorporeally fluoroscopically observable.

In an application, the intracorporeal reference includes a scale including a plurality of radiopaque markers.

In an application, the plurality of radiopaque markers includes a first plurality of radiopaque markers, and the at least one radiopaque marker includes a second plurality of radiopaque markers.

In an application, the spring is configured to provide distinct indication that is observable using fluoroscopy, when the spring is experiencing a force that is within a margin force from a target force.

In an application, the spring is configured to provide the distinct indication when the spring experiences a force that is above 300 g force.

In an application, the spring is configured to provide the distinct indication when the spring experiences a force that is above 400 g force.

In an application, the spring is configured to provide the distinct indication when the spring experiences a force that is about 500 g force.

In an application, the spring is coupled to the prosthetic valve, and is intracorporeally lockable to the tether subsequently to anchoring of the tissue anchor to the ventricular muscle tissue.

In an application, the spring is slidable along at least part of the tether, and is intracorporeally couplable to the tether by inhibiting the sliding.

In an application, the prosthetic valve includes a generally cylindrical valve body having an upstream end, and the spring includes an elastically-deformable appendage that protrudes laterally from the valve body.

In an application:
the prosthetic valve includes a generally cylindrical valve body having an upstream end, a downstream end, and a longitudinal lumen therebetween, and
the spring (1) includes a compression spring having a longitudinal axis, and (2) is disposed laterally from, the valve body such that the longitudinal axis of the spring is generally parallel with the longitudinal lumen.

In an application, the prosthetic valve includes:
a generally cylindrical valve body having an upstream end, a downstream end, and a longitudinal lumen therebetween; and
one or more tissue-engaging legs, protruding laterally outward from the valve body, and configured to be placed against a ventricular surface of the native valve.

In an application, the prosthetic valve is couplable to the upstream support intracorporeally by being expanded within an opening defined by the upstream support while the upstream support is disposed against the upstream surface.

In an application, the apparatus is configured such that the coupling of the prosthetic valve to the upstream support couples the tether to the prosthetic valve.

In an application, the apparatus is configured to sandwich a portion of the native valve between the tissue-engaging legs and the upstream support by providing a space having a height between the tissue-engaging legs and the upstream support.

In an application, the apparatus is configured to facilitate altering the height without altering a force on the spring.

In an application, the apparatus is configured such that altering the height automatically alters a force on the spring.

In an application, the apparatus is configured to facilitate altering the height by moving the valve body through the opening defined by the upstream support.

There is further provided, in accordance with an application of the present invention, apparatus for use with a native heart valve of a subject, the apparatus including:
a valve body:

having an upstream end, a downstream end, and a longitudinal axis therebetween,
including a lateral wall that circumscribes the longitudinal axis and defines a longitudinal lumen, and
including a valve member disposed within the lumen;
an upstream support having an inner perimeter couplable to the valve body at a first longitudinal position of the valve body, the upstream support being configured to extend radially outward from the valve body and the inner perimeter; and
a flexible sheet defining a first aperture, a second aperture and a lateral wall therebetween, a first portion of the sheet that defines the first aperture being circumferentially attached to the upstream support portion at a radius that is greater than a radius of the inner perimeter, and a second portion of the sheet that defines the second aperture being circumferentially attached to the valve body at a second longitudinal position of the valve body, such that a pocket region is defined between the sheet and at least the first longitudinal position.

In an application, the second longitudinal position is closer to the downstream end of the valve body than is the first longitudinal position.

In an application, the first aperture is larger than the second aperture.

In an application, the sheet is attached to the upstream support at an outer perimeter of the upstream support.

In an application, the sheet assumes a frustoconical shape.

In an application, the sheet assumes a funnel shape.

In an application, the apparatus is provided with the inner perimeter of the upstream support pre-coupled to the valve body at the first longitudinal position of the valve body.

In an application, the apparatus is configured such that the inner perimeter of the upstream support is intracorporeally couplable to the valve body at the first longitudinal position of the valve body.

There is further provided, in accordance with an application of the present invention, apparatus for use with a native heart valve disposed between an atrium and a ventricle of a heart of a subject, the apparatus including:
an annular upstream support defining an opening therethrough, and configured to be placed against an upstream surface of the native heart valve;
a tubular valve body having an upstream end, a downstream end and a lumen therebetween, the lumen having a first diameter, and the valve body being separated from the upstream element by a gap between the upstream end of the valve body and the upstream element;
one or more tissue-engaging elements that protrude radially outward from the valve body so as to define a second diameter that is greater than the first diameter; and
a flexible sheet shaped to define a conduit, a downstream portion of the sheet being coupled to the valve body, an upstream portion of the sheet being coupled to the upstream element, and the sheet spanning the gap.

In an application, the apparatus further includes at least one tether, a first portion of the tether being coupled to the valve body and a second portion of the tether being coupled to the upstream support, such that tensioning of at least a portion of the tether reduces the gap.

In an application, the apparatus is configured such that tensioning of at least the portion of the tether rumples the sheet.

There is further provided, in accordance with an application of the present invention, apparatus for use with a native heart valve disposed between an atrium and a ventricle of a heart of a subject, the apparatus including:
an annular upstream element defining an opening therethrough, and configured to be placed against an upstream surface of the native heart valve;
a flexible sheet, shaped to define a conduit, and coupled to the upstream element such that the conduit is in fluid communication with the opening; and
a valve body, coupled to the flexible sheet such that the conduit provides fluid communication between the prosthetic valve and the upstream element.

In an application, the valve body includes:
a generally cylindrical frame shaped to define a lumen therethrough, and
a valve member coupled to the frame and disposed within the lumen.

In an application, the frame is separated from the upstream element by a gap, and the conduit spans the gap.

There is further provided, in accordance with an application of the present invention, apparatus, for use with a guide member that extends into a subject, the apparatus including:
a delivery tool, including a housing, the housing:
being transluminally advanceable into the subject,
shaped to define an orifice at an end of the housing, and
having a lateral wall shaped to define a slit that is continuous with the orifice;
an implant:
configured to be housed by the housing, and
including an eyelet that (1) is slidable over the guide member, and (2) when the implant is housed by the housing, extends through the slit and radially beyond the lateral wall such that the eyelet facilitates transluminal sliding of the implant and the housing along the guide member and into the subject,
the apparatus being configured such that, while (1) the implant remains within the subject, and (2) the guide member remains disposed through the eyelet, (1) the implant is removable from the housing via the orifice, and (2) the housing is removable from the subject.

In an application, the implant is configured to be implanted by being intracorporeally locked to the guide member.

In an application, the implant has a compressed state and an expanded state, is configured to be housed by the housing while in the compressed state, and is configured to automatically expand toward the expanded state when removed from the housing.

There is further provided, in accordance with an application of the present invention, a method for use with a native valve of a heart of a subject, the method including:
transluminally anchoring a tissue anchor to ventricular tissue of a subject using an anchor-manipulation tool, the tissue anchor being coupled to a first portion of a tether;
transluminally delivering an annular upstream support and a prosthetic valve to the heart, the prosthetic valve including (1) a valve body shaped to define a lumen therethrough, and (2) one or more tissue-engaging legs configured to protrude laterally outward from the valve body;
pressing the tissue-engaging legs in an upstream direction against a ventricular surface of the native valve by applying a force to the prosthetic valve while measuring the force;

applying, to the tether, a tension that changes a shape of a spring coupled to the tether, while observing the shape of the spring using imaging; and at least in part responsively to the observed shape of the spring, facilitating holding of the upstream support against an upstream surface of the native valve by locking a second portion of the tether to at least one component selected from the group consisting of: the prosthetic valve and the upstream support.

In an application, measuring the force includes measuring the force using an extracorporeal force meter.

In an application, measuring the force includes observing a shape of the tissue-engaging legs using imaging.

In an application, applying the tension includes applying the tension while applying the force.

In an application, locking the second portion to the selected component includes locking the second portion to the prosthetic valve.

In an application, locking the second portion to the selected component includes locking the second portion to the upstream support.

In an application, locking the second portion includes locking the second portion when the observed shape indicates that the spring is experiencing between 400 g force and 600 g force.

In an application, locking the second portion includes locking the second portion subsequently to applying the tension, and applying the force includes applying the force subsequently to locking the second portion.

In an application:
anchoring the tissue anchor coupled to the tether includes anchoring a first tissue anchor coupled to a first tether, and applying the tension includes applying a first tension that changes a shape of a first spring coupled to the first tether,
the method further includes:
anchoring a second tissue anchor to the ventricular tissue, the second tissue anchor being coupled to a first portion of a second tether; and
applying, to the second tether, a second tension that changes a shape of a second spring coupled to the second tether, while observing the shape of the second spring using imaging, and
facilitating holding of the prosthetic valve against the upstream surface includes, at least in part responsively to the observed shape of the second spring, facilitating holding of the prosthetic valve against the upstream surface by locking a second portion of the second tether to the selected at least one component.

In an application, facilitating holding includes locking the second portion of the first tether and the second portion of the second tether to the selected at least one component, at least in part responsively to a ratio between tension in the first tether and tension in the second tether, the ratio being derived from the observed shape of the first spring and the observed shape of the second spring.

In an application, locking includes locking the second portion to the at least one component at least in part responsively to the observed shape.

In an application, locking includes locking the second portion to the at least one component at least in part responsively to the measured force.

In an application, applying the force includes moving the valve body in an upstream direction through an opening defined by the upstream support, and the method further includes coupling the prosthetic valve to the upstream support by expanding the valve body within the opening.

In an application, coupling the prosthetic valve to the upstream support includes coupling the prosthetic valve to the upstream support at least in part responsively to the measured force.

There is further provided, in accordance with an application of the present invention, a method, including:
transluminally advancing a plurality of tissue anchors, coupled to a respective plurality of springs, into a body of a subject;
anchoring the plurality of tissue anchors to tissue of the subject;
tensioning at least one of the springs;
using imaging, while the tension is applied to the at least one spring, observing a state of the at least one spring; and
at least in part responsively to the observed state of at least one spring, adjusting a tension on at least one of the springs.

There is further provided, in accordance with an application of the present invention, a method, for use with a native valve of a heart of a subject, the method including:
applying a first tension to a tether that couples (a) a tissue anchor anchored to ventricular tissue of a subject, to (b) a prosthetic valve body, the tether having a length between the tissue anchor and the valve body;
by applying an atrially-directed force to the prosthetic valve body, pressing, against tissue of the native valve, a tissue-engaging element that protrudes radially from the valve body
transluminally advancing a prosthetic valve body to a native valve of the subject;
while applying the atrially-directed force, measuring:
a pressing force of the tissue-engaging element against the tissue of the native valve, and
a second tension on the tether, the second tension differing from the first tension at least in part due to the atrially-directed force; and
at least in part responsively to the measured pressing force and the measured second tension, performing an action selected from the group consisting of: adjusting the length of the tether between the tissue anchor and the valve body, and locking the valve body to the tether.

There is further provided, in accordance with an application of the present invention, a method for use with a native valve of a heart of a subject, the method including:
transluminally delivering a tissue anchor to a ventricle of the heart, and anchoring the tissue anchor to ventricular muscle tissue of the subject;
transluminally delivering an upstream support to an atrium of the heart, and placing the upstream support against an upstream surface of an annulus of the native valve; and
changing a shape of the upstream support by tensioning a tether coupled to upstream support and to the tissue anchor; and
extracorporeally fluoroscopically observing the shape change of the upstream support.

In an application, tensioning the tether coupled to the upstream support includes tensioning a tether that is coupled to a valve body coupled to the upstream support.

In an application, before the tensioning, the upstream support is generally flat annular, and changing the shape includes making the support assume a frustoconical shape.

In an application, before the tensioning, the upstream support is frustoconical, and changing the shape includes changing a slant of the frustoconical shape.

There is further provided, in accordance with an application of the present invention, apparatus for use with a valve of a heart of a subject, the apparatus including:
- a transluminally-deliverable tissue anchor;
- a tether, a first end thereof coupled to the tissue anchor; and
- a delivery tool, including:
  - a steerable catheter having a longitudinal axis, and being transluminally deliverable to the valve, and
  - an obstructing element:
    - disposed at a longitudinal site of the catheter,
    - configured to extend laterally outward from the catheter, and
    - dimensioned, when extending laterally outward from the catheter, to inhibit movement of at least the longitudinal site through the valve by abutting tissue of the valve, and
  - an anchor manipulator:
    - reversibly couplable to the tissue anchor,
    - slidable through the catheter, and
    - configured to drive the anchor into ventricular tissue of the heart of the subject.

In an application, the anchor manipulator is slidably coupled to the catheter such that a distal end of the anchor manipulator is slidable distally no more than a pre-determined distance from the longitudinal site.

In an application, the apparatus further includes an implant, intracorporeally lockable to the tether.

In an application, the apparatus further includes a guide member, reversibly couplable to the tether, and the implant is intracorporeally slidable along the guide member toward the tether and the implant.

In an application, the tether has exactly one locking site at which the implant is lockable to the tether.

In an application, the exactly one locking site is disposed at a pre-determined distance from the anchor that is pre-determined at least in part dependently on a distance between the longitudinal site and a distal end of the catheter.

There is further provided, in accordance with an application of the present invention, a method, including:
- transluminally anchoring a tissue anchor to tissue of a subject using an anchor-manipulation tool;
- subsequently applying to the anchor a pulling force having a given magnitude;
- using imaging, observing a movement of the tissue anchor in response to the pulling force; and
- at least in part responsively to the observed movement, performing an action selected from the group consisting of: de-anchoring the tissue anchor from the tissue, and decoupling the anchor-manipulation tool from the tissue anchor.

There is further provided, in accordance with an application of the present invention, apparatus, for implantation at a native valve of a heart of a subject, the native valve being disposed between an atrium and a ventricle of the heart, the apparatus including:
- a tubular valve body:
  - having an upstream portion, configured to be disposed in the atrium of the heart of the subject,
  - having a downstream portion, configured to be disposed in the ventricle of the subject,
  - having an elastic portion, disposed between the upstream portion and the downstream portion, and elastically coupling the upstream portion to the downstream portion, and
  - shaped to define a continuous lumen through the upstream portion, the elastic portion, and the downstream portion; and
- at least one valve member, disposed in the lumen of the valve body, and configured to facilitate flow of blood of the subject from the upstream portion of the valve body to the downstream portion of the valve body, and to inhibit flow of the blood from the downstream portion of the valve body to the upstream portion of the valve body.

In an application, the at least one valve member is coupled to the downstream portion of the valve body.

In an application, the native valve includes a plurality of native leaflets, and the downstream portion of the valve body is configured to be coupled to the native leaflets.

In an application, the apparatus further includes a plurality of clips, configured to facilitate the coupling of the downstream portion of the valve body to the native leaflets.

In an application, each clip:
- includes at least two clip arms, articulatably coupled to each other, and
- is reversibly closeable.

In an application, the clips are coupled to the downstream portion of the valve body, and the downstream portion of the valve body is configured to be coupled to the native leaflets by the clips being coupled to the native leaflets.

In an application, each clip of the plurality of clips is articulatably coupled to the downstream portion of the valve body.

In an application, the native valve includes an annulus having an upstream surface, and the apparatus further includes a prosthetic valve support:
- including (1) an upstream support portion, configured to be placed against the upstream surface of the annulus of the native valve, and (2) the plurality of clips, coupled to the upstream support portion,
- shaped to define an opening therethrough that is configured to receive the prosthetic valve,
- and the clips are configured to facilitate the coupling of the downstream portion of the valve body to the native leaflets by coupling the prosthetic valve support to the native leaflets.

There is further provided, in accordance with an application of the present invention, apparatus for use with a native valve of a heart of a subject, the native valve having a plurality of leaflets that meet at a plurality of commissures, the apparatus including:
- at least one tissue anchor, configured to be anchored to a first site within a ventricle of the heart of the subject;
- at least one longitudinal member, coupled at a distal end thereof to a respective one of the at least one tissue anchors;
- an upstream support, including an upstream support portion configured to be slidable over the longitudinal member and placed against an upstream surface of the native valve; and
- at least one locking member, configured to be slidable over a respective one of the at least one longitudinal members, and to be lockable to the respective longitudinal member such that a portion of the respective longitudinal member that is disposed between the respective anchor and the upstream support portion is longer than 1 cm.

In an application, the longitudinal member is flexible.

In an application, the longitudinal member includes a suture.

There is further provided, in accordance with an application of the present invention, a method for use with a native valve of a heart of a subject, the native valve having a plurality of leaflets that meet at a first commissure and at a second commissure, the method including:
- anchoring a first tissue anchor to a first site within a ventricle of the heart of the subject, the first tissue anchor being coupled to a distal end of a first longitudinal member;
- anchoring a second tissue anchor to a second site within the ventricle of the heart of the subject, the second tissue anchor being coupled to a distal end of a second longitudinal member;
- subsequently, placing at least an upstream support portion of a prosthetic valve support against an upstream surface of the native valve, the valve being disposed between the ventricle and an atrium of the heart of the subject; and
- securing the upstream support portion against the upstream surface of the valve by:
  - coupling the upstream support portion to the first longitudinal member such that at least part of a portion of the first longitudinal member that is disposed between the upstream support portion and the first tissue anchor, is disposed between the first and second leaflets at the first commissure, and
  - coupling the upstream support portion to the second longitudinal member such that at least part of a portion of the second longitudinal member that is disposed between the upstream support portion and the first tissue anchor, is disposed between the first and second leaflets at the second commissure.

In an application, anchoring, placing, and securing include anchoring, securing, and placing without the use of cardiopulmonary bypass.

In an application, anchoring to the first site and anchoring to the second site include anchoring to myocardium.

In an application, placing the upstream support portion against the upstream surface includes sliding the upstream support portion over at least part of the first longitudinal member.

In an application, coupling the upstream support portion to the first longitudinal member and to the second longitudinal member includes coupling the upstream support portion to the first longitudinal member in the atrium of the heart of the subject, and coupling the upstream support portion to the second longitudinal member includes coupling the upstream support portion to the second longitudinal member in the atrium of the heart of the subject.

In an application, the leaflets move in response to beating of the heart of the subject, and securing the upstream support portion includes securing the upstream support portion without eliminating the movement of the native leaflets.

In an application, coupling the upstream support portion to the first longitudinal member includes coupling the upstream support portion to the first longitudinal member such that a length of the portion of the first longitudinal member is greater than 1 cm.

In an application, the method further includes:
- transluminally advancing at least the first tissue anchor to the first site while the respective longitudinal member coupled thereto is disposed within a respective tubular member; and
- subsequently to anchoring the at least first tissue anchor, and before coupling the upstream support portion to the respective longitudinal member, sliding the at least first tubular member off of at least part of the respective longitudinal member.

In an application, sliding the at least first tubular member includes sliding at least part of the at least first tubular member through a channel defined by a locking member, and coupling the upstream support portion to the respective longitudinal member includes locking the locking member to the respective longitudinal member by narrowing at least a portion of the channel.

In an application:
- advancing the at least first tissue anchor includes advancing the at least first tissue anchor while (1) the respective longitudinal member is reversibly coupled to a portion of a wire, and (2) the respective tubular member inhibits the portion of the wire from decoupling from the portion of the wire, and
- the method further includes facilitating decoupling of the wire from the respective longitudinal member by sliding the at least first tubular member off of the portion of the wire.

In an application:
- advancing the at least first tissue anchor includes advancing the at least first tissue anchor while (1) the respective longitudinal member is shaped to define a loop, and is coupled to the portion of the wire by the portion of the wire being threaded through the loop, and (2) the respective tubular member inhibits the portion of the wire from unthreading from the loop, and
- facilitating decoupling of the wire from the respective longitudinal member includes facilitating unthreading of the wire from the loop by sliding the at least first tubular member off of the portion of the wire.

In an application, sliding the at least first tubular member off of the portion of the wire includes sliding the at least first tubular member off of the portion of the wire by applying less than 500 g of pulling force to the at least first tubular member.

In an application, applying less than 500 g of pulling force to the at least first tubular member includes applying less than 300 g of pulling force to the at least first tubular member.

In an application, the method further includes, subsequently to securing the upstream support portion, coupling a prosthetic valve to the prosthetic valve support.

In an application, the upstream support portion has an inner edge that defines an opening through the upstream support portion, and coupling the prosthetic valve to the prosthetic valve support includes placing at least a portion of the prosthetic valve within the opening, and expanding at least the portion of the prosthetic valve such that at least the portion of the prosthetic valve applies a radially-expansive force against the inner edge of the upstream support portion.

In an application, the prosthetic valve includes one or more tissue-engaging elements, each of the one or more tissue-engaging elements including at least two arms, and the method further includes, subsequent to securing the upstream support portion, coupling the prosthetic valve to at least one of the leaflets by sandwiching the at least one of the leaflets between the at least clip arms of the one or more tissue-engaging elements.

In an application, coupling the prosthetic valve to the at least one of the leaflets includes coupling the prosthetic valve to the at least one of the leaflets before coupling the prosthetic valve to the prosthetic valve support.

In an application:

the prosthetic valve includes a valve body, having an outer surface, the at least two arms include a first arm and a second arm, the first arm being longer than the second arm, and the method further includes:

delivering, within a delivery tube, the prosthetic valve in a delivery configuration thereof, in which the first arm and the second arm are constrained against the outer surface of the valve body;

facilitating deflection of the first arm away from the outer surface of the prosthetic valve, by advancing a first portion of the prosthetic valve out of the delivery tube such that the first arm automatically deflects away from the outer surface of the prosthetic valve; and facilitating deflection of the second arm away from the outer surface of the prosthetic valve, by advancing a second portion of the prosthetic valve out of the delivery tube such that the second arm automatically deflects away from the outer surface of the prosthetic valve.

In an application:

facilitating deflection of the first arm includes facilitating deflection of the first arm a first angle from the outer surface of the prosthetic valve, and the method further includes facilitating deflection of the first arm away from the outer surface of the prosthetic valve a second angle that is greater than the first angle, by applying a force to the first arm using the delivery tube:

subsequently to facilitating deflection of the first arm the first angle, and prior to facilitating deflection of the second arm.

In an application, applying the force to the first arm using the delivery tube includes pushing on the first arm by sliding the delivery tube over at least part of the prosthetic valve.

There is further provided, in accordance with an application of the present invention, apparatus for use with a body of a subject, the apparatus including:

at least a first implantable member;

a first longitudinal member, coupled at a distal end thereof to the first implantable member;

a second longitudinal member, at least a portion of the second longitudinal member being reversibly couplable to the first longitudinal member; and a tubular member:

slidable over the first and second longitudinal members, shaped to define a lumen therethrough, and configured, when the portion of the second longitudinal member is (1) coupled to the first longitudinal member, and (2) disposed within the lumen of the tubular member, to inhibit decoupling of the portion of the second longitudinal member from the first longitudinal member.

In an application, the portion of the second longitudinal member is configured, when (1) the portion of the second longitudinal member is coupled to the first longitudinal member, and (2) the portion of the second longitudinal member is disposed outside of the lumen of the tubular member, to be decouplable from the first longitudinal member by the second longitudinal member being pulled away from the first longitudinal member.

In an application, at least one longitudinal member selected from the group consisting of: the first longitudinal member and the second longitudinal member, is flexible.

In an application, the tubular member is more rigid than the first longitudinal member.

In an application, the tubular member fits snugly over at least the portion of the second longitudinal member.

In an application, the first implantable member includes a tissue anchor, configured to be anchored to a tissue of the subject.

In an application, the apparatus further includes a second implantable member, slidable over the tubular member, and couplable to the first longitudinal member while the portion of the second longitudinal member is coupled to the first longitudinal member.

In an application, the portion of the second longitudinal member is reversibly couplable to the first longitudinal member at a first site of the first longitudinal member, and the second implantable member is couplable to the first longitudinal member at a second site of the first longitudinal member that is distal to the first site of the longitudinal member.

In an application, the apparatus further includes a locking member having an unlocked state and a locked state, and configured to be slid over the tubular member in the unlocked state and to be locked to the first longitudinal member by being transitioned to the locked state.

In an application, the locking member is configured to facilitate coupling of the second implantable member to the first longitudinal member.

In an application, the locking member is configured to be coupled to the first longitudinal member at least 1 cm away from the first implantable member.

There is further provided, in accordance with an application of the present invention, apparatus for use at a native valve of a heart of a subject, the apparatus including:

a tissue anchor, configured to be transluminally, transcatheterally advanced to a ventricle of the heart of the subject, and to be coupled to tissue of the ventricle;

a longitudinal member, coupled at a distal end thereof to the tissue anchor;

a wire, a portion of the wire being reversibly couplable to the longitudinal member;

a tubular member:

slidable over the longitudinal member and the wire, shaped to define a lumen therethrough, and configured, when the portion of the wire is (1) coupled to the longitudinal member, and (2) disposed within the lumen of the tubular member, to inhibit decoupling of the portion of the wire from the longitudinal member;

a prosthetic valve support including an upstream support portion slidable over the tubular member, and to be placed against an upstream surface of an annulus of the native valve by sliding over the tubular member; and a locking member, slidable over the tubular element and lockable to the longitudinal member.

In an application, the locking member is configured to be locked to the longitudinal member at a site of the longitudinal member that is distal to a site of the longitudinal member to which the portion of the wire is reversibly couplable.

In an application, the tubular member is configured to be slid out of the locking member before the locking member is locked to the longitudinal member.

In an application, the apparatus further includes a control rod, slidable over the tubular member, the locking member being reversibly coupled to a control rod, the control rod being configured to restrain the locking member in an unlocked configuration thereof, and to facilitate locking of the locking member by ceasing to restrain the locking member in the unlocked configuration.

In an application, the control rod is configured to decouple from the locking member when the control rod ceases to restrain the locking member in the unlocked configuration thereof.

In an application, the control rod is configured to cease to restrain the locking member in the unlocked configuration thereof by the control rod being rotated with respect to the locking member.

In an application:
the prosthetic valve support is shaped to define a hole through which the tubular member is slidable,
at least while the control rod is coupled to the locking member, the control rod is not slidable through the hole defined by the prosthetic valve support, and the control rod is configured to facilitate the sliding of the prosthetic valve support over the tubular member by pushing the prosthetic valve support over the tubular member.

The present invention will be more fully understood from the following detailed description of applications thereof, taken together with the drawings, in which:

BRIEF DESCRIPTION OF THE DRAWINGS

FIGS. 1A-F are schematic illustrations of a system for implanting a prosthetic valve support and a prosthetic valve at a native valve of a heart of a subject, in accordance with some applications of the invention;

FIG. 2 is a schematic illustration of the prosthetic valve being retrieved into a delivery tube, in accordance with some applications of the invention;

FIGS. 3A-C are schematic illustrations of the introduction of guide members through the prosthetic valve support and a delivery tube, in accordance with some applications of the invention;

FIGS. 4A-C are schematic illustrations of a locking member, and control thereof, in accordance with some applications of the invention;

FIG. 5 is a schematic illustration of steps in the delivery and anchoring of tissue anchors, in accordance with some applications of the invention;

FIGS. 7A-C are schematic illustrations of a system for facilitating transluminal delivery of a prosthetic valve assembly, in accordance with some applications of the invention;

FIGS. 8A-H are schematic illustrations of a technique for use with the system of FIGS. 7A-C, to transluminally implant a prosthetic valve assembly, in accordance with some applications of the invention;

FIGS. 9A-B, 10A-B, 11A-B, 12A-B, 13A-B, and 14A-B are schematic illustrations of prosthetic valve assemblies, in accordance with some applications of the invention;

FIGS. 15A-C are schematic illustrations of a tool for facilitating application of force between a prosthetic valve assembly and tethers, in accordance with some applications of the invention;

FIG. 16 is a schematic illustration of a system comprising a prosthetic valve assembly and one or more springs, via which the prosthetic valve assembly is elastically coupled to one or more tissue anchors, in accordance with some applications of the invention;

FIG. 17 is a schematic illustration of a system comprising a prosthetic valve assembly and one or more springs, via which the prosthetic valve assembly is elastically coupled to one or more tissue anchors, in accordance with some applications of the invention;

FIGS. 18A-B are schematic illustrations of springs coupled to respective tethers so as to elastically couple a tissue anchor to a prosthetic valve assembly, in accordance with some applications of the invention;

FIG. 20 is a schematic illustration showing examples in which force measurements described herein may be combined to facilitate implantation of a prosthetic valve, in accordance with some applications of the invention;

FIGS. 22A-B are schematic illustrations of a prosthetic valve assembly comprising a prosthetic valve having a tubular valve body that comprises an upstream portion, a downstream portion, and an elastic portion disposed between the upstream portion and the downstream portion, in accordance with some applications of the invention.

DETAILED DESCRIPTION OF EMBODIMENTS

Figure 1A:
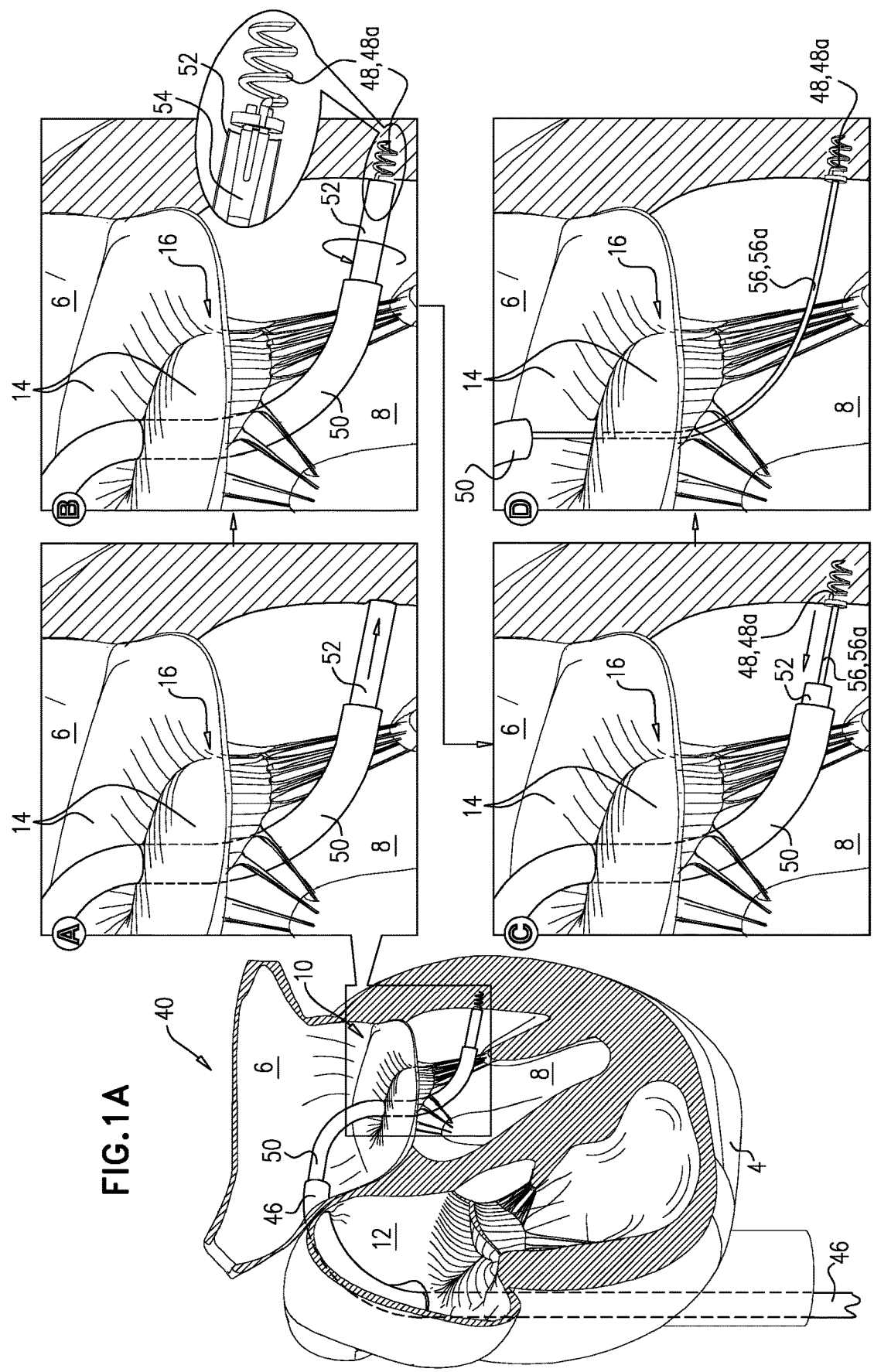

Reference is made to FIGS. 1A-F, which are schematic illustrations of a system 40 for implanting an upstream prosthetic valve support 42 and a prosthetic valve 44 at a native valve 10 of a heart 4 of a subject, in accordance with some applications of the invention. Typically, applications of the invention are for use with the mitral valve of the subject (that is, native valve 10 comprises the mitral valve of the subject), but it is to be noted that applications of the invention may be used at other heart valves of the subject, such as the tricuspid valve, the aortic valve, or the pulmonary valve, mutatis mutandis.

Reference is now made to FIGS. 1A-B. A sheath 46 is advanced transluminally (e.g., transfemorally) to right atrium 12 of the heart, and is typically advanced through the fossa ovalis into left atrium 6 of the heart using standard transseptal techniques. For some applications, sheath 46 is steerable. For some such applications, sheath 46 is steerable in two axes. One or more (typically two) tissue anchors 48 are advanced through sheath 46, between leaflets 14 of the native valve, and into left ventricle 8 of the heart, and are there anchored to tissue (e.g., ventricular muscle tissue) of the heart. FIG. 1A shows a first tissue anchor 48a being anchored at a first ventricular site, and FIG. 1B shows a second tissue anchor 48b being anchored at a second ventricular site. Typically, anchors 48 are anchored to muscle of the heart, such as to the walls of ventricle 8 and/or to papillary muscles. Typically, and as shown, anchors 48 comprise helical anchors that are anchored by being rotated. However, other types of anchors may be used, such as barbed or harpoon-like anchors, e.g., that are anchored by being pushed into the tissue.

State A of FIGS. 1A and 1B show a catheter 50 having been advanced through sheath 46 and into ventricle 8, and an anchor-delivery tube 52 having been advanced through catheter 50 to the respective ventricular site. Typically, and as shown, the distal end of delivery tube 52 is placed against the tissue at the ventricular site. Typically, at least a distal portion of catheter 50 is steerable (e.g., independently of sheath 46).

State B of FIGS. 1A and 1B each show a respective anchor 48 being anchored to a respective ventricular site. Typically, anchor 48 is reversibly coupled to an anchor manipulator 54 (e.g., an anchor driver), which is slidable through at least part of tube 52, and which is configured to apply a force (e.g., a rotational force) to the anchor so as to anchor the anchor at the ventricular site. For some applications, anchor manipulator 54 and anchor 48 are advanced from outside the subject to the ventricular site only once the distal end of tube 52 is disposed against the ventricular site. For some applications, the manipulator and anchor are disposed within, and advanced with, tube 52. For some applications, anchor 48 is anchored by rotating anchor manipulator 54 and tube 52 together. For some applications, a separate anchor manipulator 54 is used to deliver and anchor each anchor 48 (e.g., each anchor 48 may be provided pre-coupled to a respective anchor manipulator). For some applications, one anchor manipulator 54 may be used to deliver and anchor all (e.g., both) anchors 48 (e.g., each anchor 48 may be configured to be sequentially coupled to the anchor manipulator outside the body of the subject by the operating physician). It is to be noted that typically anchor 48 is not exposed from tube 52 other than when being anchored. It is hypothesized that for some applications this reduces a likelihood of inadvertently engaging and/or damaging tissue of the heart (e.g., chordae tendineae).

For some applications, subsequent to anchoring each tissue anchor 48 to the tissue, a testing pulling force of known magnitude is applied to the anchor (e.g., by applying the pulling force to anchor manipulator 54), and movement of the tissue anchor in response to the pulling force is observed using imaging (e.g., fluoroscopy). The observed movement may be used to confirm successful and/or stable anchoring (e.g., relatively little movement may indicate firm anchoring in firm tissue) or to determine sub-optimal anchoring (e.g., relatively large movement may indicate weak anchoring and/or anchoring in weak tissue). Thus, at least in part responsively to the observed movement, the operating physician may decouple manipulator 54 from anchor 48, or may de-anchor the anchor from the tissue using the manipulator.

State C of FIGS. 1A and 1B show anchor manipulator 54 having been decoupled from anchor 48, and the manipulator and tube 52 being withdrawn proximally into catheter 50. Each anchor 48 is provided pre-coupled to a guide member 56 (e.g., a first guide member 56*a*, and a second guide member 56*b*), described in more detail hereinbelow (e.g., with reference to FIGS. 1D and 4A-C). As manipulator 54 and tube 52 are withdrawn, guide member 56 is exposed from tube 52.

Typically, and as shown in FIGS. 1A-B, the same catheter 50 is used to deliver both anchors 48. For such applications, and as shown in states B and C of FIG. 1B, when delivering second tissue anchor 48*b*, anchor-delivery tube 52 fits alongside first guide member 56*a* within catheter 50. Alternatively, and as described hereinbelow with reference to FIG. 5, a separate catheter is used for each anchor, in which case the second catheter fits alongside first guide member 56*a* within sheath 46.

State D of FIGS. 1A and 1B show catheter 50 having been withdrawn proximally, into atrium 6. For some applications, catheter 50 is withdrawn completely from the body of the subject. For some applications, catheter 50 is used for delivery of components during later steps in the procedure. Guide members 56 extend from atrium 6, between leaflets 14, and to respective ventricular sites. Typically, guide members 56 do not eliminate functioning of leaflets 14 and/or valve 10. For some applications, guide members 56 are configured to automatically move toward respective commissures 16 (e.g., into the joining corners at the commissures of leaflets 14). For some applications, and as shown in FIG. 1C, prosthetic valve support 42 (e.g., deployment thereof) pushes guide members 56 toward the respective commissures.

Reference is now made to FIG. 1C, which shows prosthetic valve support being delivered to, and deployed at, native valve 10. Prosthetic valve support 42 is advanced through sheath 46 and into atrium 6. Typically, support 42 is delivered in a compressed configuration thereof, within a housing, such as a delivery tube 80. For some applications, catheter 50 is used to facilitate delivery of prosthetic valve support 42 and delivery tube 80 (e.g., the support and delivery tube are advanced through catheter 50). For some applications, a different catheter is used to facilitate delivery of prosthetic valve support 42 and delivery tube 80. For some applications, prosthetic valve support 42 and delivery tube 80 are advanced directly through sheath 46.

Prosthetic valve support 42 comprises an annular upstream support portion 43 which, in the delivery configuration of the prosthetic valve support, is generally cylindrical, and which, once the prosthetic valve is deployed and expands to an uncompressed configuration thereof, is generally annular. For some applications, upstream support portion 43 is generally frustoconical in the uncompressed configuration thereof. Typically, a distal end of upstream support portion 43 in the compressed, cylindrical configuration, defines an inner perimeter of the upstream support portion in the uncompressed configuration, the inner perimeter defining an opening through the upstream support portion.

State A of FIG. 1C shows delivery tube 80, containing support 42, having been delivered to atrium 6 over guide members 56, and support 42 starting to be subsequently exposed from the delivery tube, and automatically expanding. Upstream support portion 43 of prosthetic valve support 42 is shaped to define holes 82 through which guide members 56 are slidable, thereby facilitating sliding of the prosthetic valve support over guide members 56. Typically, holes 82 are disposed opposite each other around the generally annular shape of upstream support portion 43. For some applications, holes 82 are defined and/or reinforced by an eyelet 84 or pledget (visible in states B and C of FIG. 1C). Guide members 56 extend proximally from delivery tube 80, e.g., via holes in a proximal end of the delivery tube, such that the delivery tube, and prosthetic valve support 42, in the compressed state within the delivery tube, are slidable over the guide members, the guide members thereby facilitating delivery of the prosthetic valve support within the delivery tube. Introduction of guide members 56 through the prosthetic valve support and delivery tube are described hereinbelow with reference to FIGS. 3A-C.

State B of FIG. 1C shows prosthetic valve support 42 (e.g., upstream support portion 43 thereof) having been completely deployed from delivery tube 80, and having automatically expanded to the uncompressed configuration thereof. Guide members 56 are typically pushed toward commissures 16 by the expansion of support 42. For some applications, delivery tube 80 is subsequently removed from the body of the subject. A tubular control rod 86 is advanced over each guide member 56 toward prosthetic valve support 42, and is used to push prosthetic valve support 42 (e.g., upstream support portion 43 thereof) toward the annulus of valve 10. Control rods 86 have a cross-sectional diameter that is larger than that of holes 82, and may thereby be used to push against upstream support portion 43 without passing through the holes.

Typically, prosthetic valve support 42 (e.g., upstream support portion 43 thereof) is provided with one or more (e.g., two) control filaments 88 reversibly coupled thereto. Typically, filaments 88 are coupled to upstream support portion 43 at sites that are disposed opposite each other around the generally annular shape of the upstream support portion, and disposed evenly between holes 82. That is, in the expanded configuration of upstream support portion 43, a straight line between holes 82 is typically perpendicular to a straight line between the sites at which filaments 88 are coupled to the upstream support portion. It should be noted that other numbers and arrangements of control filaments may also be used. Typically, each control filament 88 (1) comprises two portions of a loop of filament that passes through upstream support portion 43, loops around a downstream surface of the upstream support portion (i.e., the surface that is placed in contact with the annulus of the native valve), and passes back through the upstream support portion, and (2) is decouplable from the upstream support portion by releasing a first end of the filament and pulling a second end, thereby unthreading and/or unlooping the control filament from the upstream support portion.

Control filaments 88 facilitate some manipulation of prosthetic valve support 42 following deployment from delivery tube 80. Typically, control rods 86 further facilitate such manipulation. State C of FIG. 1C shows such manipulation of prosthetic valve support 42. For example, it may be desirable to rotate the prosthetic valve support (e.g., to position and/or orient the upstream support portion correctly with respect to native valve 10, to control the order in which different regions of upstream support portion 43 contact the native valve, and/or to uncoil control rods 86 and/or control filaments 88 from each other).

Figure 1D:
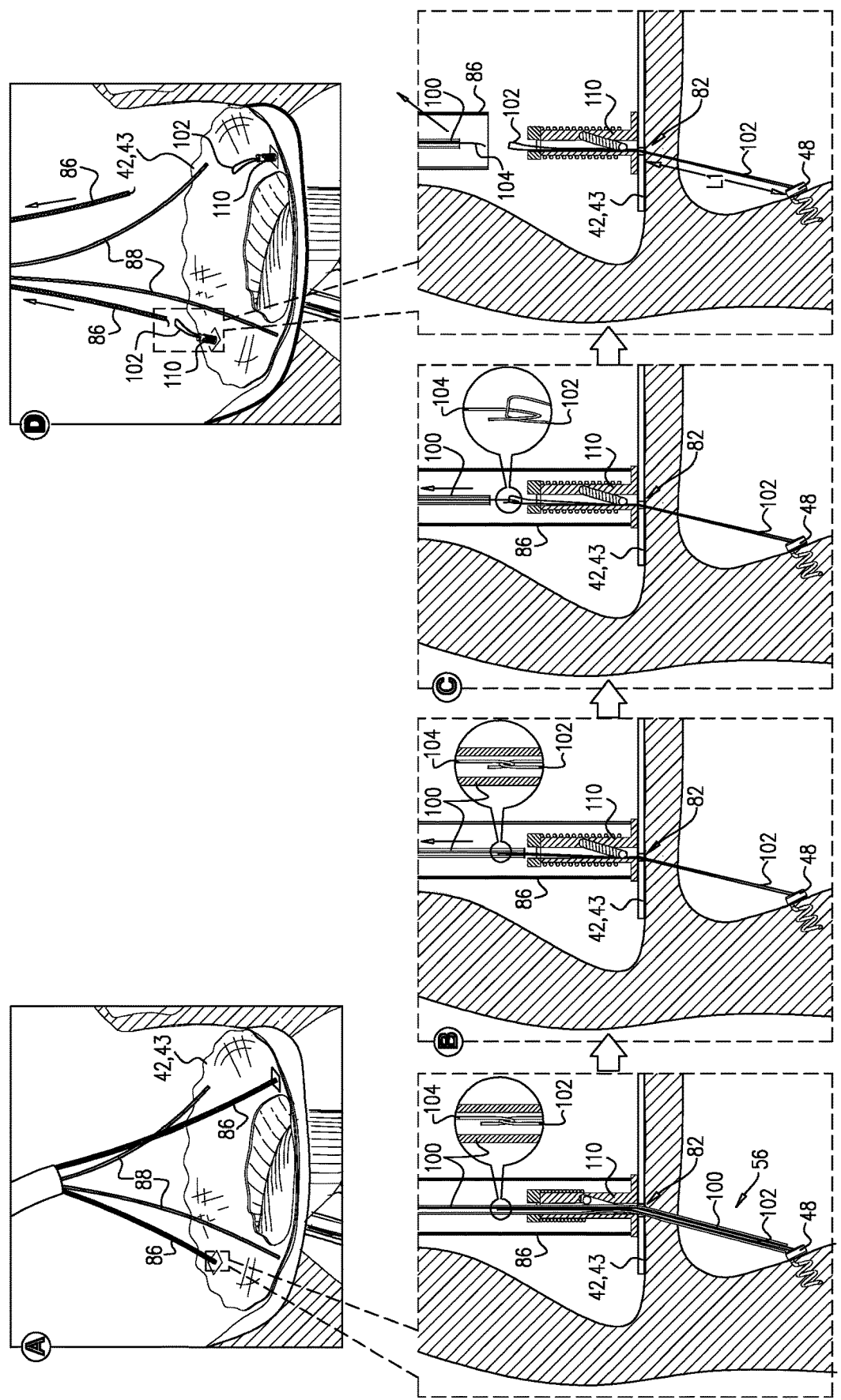

Reference is now made to FIG. 1D, which show steps in securing prosthetic valve support 42 against the upstream surface (e.g., the atrial surface) of native valve 10. Each guide member 56 typically comprises a tether (e.g., a longitudinal member 102), a pull-wire 104 reversibly coupled to the longitudinal member, and a tubular member 100 in which the longitudinal member and the pull-wire are disposed, the tubular member fitting snugly over the longitudinal member and the pull-wire so as to inhibit the pull-wire from becoming decoupled from the longitudinal member (e.g., to maintain a state of coupling therebetween). Pull-wire 104 may or may not be metallic and may have various cross-sectional shapes (e.g., circular or rectangular). Typically, (1) longitudinal member 102 defines a loop (e.g., a closed loop) (2) a portion (e.g., a distal portion) of pull-wire 104 is threaded through the loop defined by member 102 (e.g., is looped through the loop), and (3) the snug fitting of tubular member 100 over member 102 and pull-wire 104 inhibits the portion of the pull-wire from unthreading from the loop. It is to be noted that, although longitudinal member 102 is shown as defining a loop that extends most (e.g., all) of the length of the longitudinal member, the loop may alternatively be defined only at a proximal end of the longitudinal member.

For some applications, longitudinal member 102 and pull-wire 104 are coupled via complementary screw threads. For example, longitudinal member 102 may comprise, or be coupled to, a screw at a proximal end thereof, and pull-wire 104 may comprise, or be coupled to, a socket at a distal end thereof. For some applications, tubular member 100 is used to decouple (e.g., unscrew) pull-wire 104 from longitudinal member 102.

Tubular member 100 is typically more rigid than pull-wire 104 and/or longitudinal member 102 (although it is still sufficiently flexible to be transluminally delivered). This rigidity reduces a likelihood of twisting, kinking, snagging, and/or other undesirable phenomenon or interactions within the transluminal delivery system (e.g., within sheath 46, catheter 50, and/or anchor-delivery tube 52). For some applications tubular member 100 has a smoother surface than does pull-wire 104 or longitudinal member 102. For some applications, tubular member 100, which is necessarily wider than pull-wire 104 and/or longitudinal member 102, is also more visible using imaging techniques such as fluoroscopy. This advantageously allows an operating physician to monitor the intracorporeal juxtaposition of the tubular members and, if necessary, to intervene, such as by revolving the tubular members (e.g., proximal ends thereof) around each other.

As described hereinabove, control rods 86 are used to push prosthetic valve support 42 toward the annulus of valve 10 by sliding the control rod over a respective guide member 56 (i.e., over the tubular member 100 of the respective guide member). Each control rod 86 is reversibly coupled at a distal end thereof to a respective locking member 110 that, in an unlocked state thereof, is slidable over guide member 56. Thereby, the pushing of prosthetic valve support 42 is typically performed by pushing with both control rod 86 and locking member 110. State A of FIG. 1D shows control rods 86 and respective locking members 110 having been slid over respective tubular members 100 of respective guide members 56, such that prosthetic valve support 42 has been pushed against the annulus of valve 10. Typically, a counter force (e.g., a proximal pulling force) is applied to guide member 56 (e.g., to tubular member 100, longitudinal member 102, and pull-wire 104) so as to facilitate such sliding.

State B of FIG. 1D shows tubular member 110 having been pulled proximally such that the distal end of the tubular member is disposed proximal to locking member 110, thereby exposing, from the tubular member, progressive portions of longitudinal member 102, at least until the tubular member is not disposed between the longitudinal member and the locking member (e.g., such that the locking member can directly contact the longitudinal member). Typically, and as shown in state B of FIG. 1D, tubular member 100 is pulled proximally such that the distal end thereof is disposed distal to the point at which longitudinal member 102 and pull-wire 104 are coupled, thereby retaining the coupling therebetween. While in this state, locking member 110 is locked to longitudinal member 102 (e.g., to a portion of the longitudinal member that is disposed within a channel of the locking member). For some applications, locking member 110 locks automatically in response to withdrawal of tubular member 100. For some applications, locking of locking member 110 is independent of the withdrawal of the tubular member. An embodiment of locking member 110 and control thereof is described in more detail hereinbelow with respect to FIGS. 4A-C. It is to be noted that the scope of the invention also comprises the use of other locking members such as crimp-based locking members, and also comprises other locking techniques such as tying.

Subsequently, and as shown in state C of FIG. 1D, tubular member 100 is pulled further proximally, such that the distal end of the tubular member is disposed proximal to the point at which longitudinal member 102 and pull-wire 104 are coupled, such that the pull-wire is decouplable from the longitudinal member (e.g., unthreadable from the loop defined by the longitudinal member).

Typically, anchors 48 and longitudinal members 102 are configured to withstand a pulling force of at least 500 g, so as to withstand forces within the beating heart. The apparatus is typically configured such that a pulling force required to pull tubular member 100 proximally, is less than 500 g, such as less than 300 g. For some applications, such a configuration is achieved at least in part by reducing friction between tubular member 100 and pull-wire 104, such as by thermally treating the pull-wire 104.

Subsequently, control rod 86, tubular member 100, and pull-wire 104 are pulled proximally, as shown in state D of FIG. 1D, thereby separating the control rod from locking member 110, and the pull-wire from longitudinal member 102. In order for control rod 86 to be pulled proximally, the control rod is decoupled from locking member 110 prior to said pulling. For some applications, the decoupling of control rod 86 from locking member 110 is synchronous with the locking of the locking member (e.g., the same action locks the locking member and decouples the control rod from the locking member, such as described hereinbelow with respect to FIGS. 4A-C). For some applications, the decoupling of the control rod from the locking member is independent of the locking of the locking member.

It is to be noted that, as shown in FIG. 1D, for some applications, prosthetic valve support 42 (e.g., upstream support portion 43 thereof) is secured to the upstream surface of the annulus of native valve 10, only by anchors 48 that are anchored to tissue in ventricle 8 of the subject. It is also to be noted that prosthetic valve support 42 is coupled to longitudinal members 102 in atrium 6 of the subject. Typically, a distance L1 between each anchor 48 and the point of upstream support portion 43 to which it is coupled (e.g., to a respective hole 82 and/or locking member 110) is greater than 0.5 cm, e.g., greater than 1 cm, such as greater than 2 cm. That is, the length of each longitudinal member 102 that is disposed between a respective anchor and upstream support portion 43 is typically greater than 0.5 cm, e.g., greater than 1 cm, such as greater than 2 cm. The length of each longitudinal member 102 that is disposed between the respective anchor and the upstream support portion is typically less than 10 cm (e.g., less than 7 cm, such as less than 5 cm). Thereby, the ventricular sites at which anchors 48 are anchored are typically more than 0.5 cm (e.g., more than 1 cm, such as more than 2 cm) away from prosthetic valve support 42.

Reference is now made to FIG. 1E-F, which show steps in the delivery and implantation of prosthetic valve 44 at native valve 10, facilitated by prosthetic valve support 42. Prosthetic valve 44 is advanced in a delivery configuration (e.g., in a compressed state), through sheath 44, typically within a delivery tube 120. Prosthetic valve 44 comprises a stent-like valve body 122, typically comprising an expandable frame that typically contains a shape-memory material such as nitinol. Valve body 122 is shaped to define a lumen therethrough, and an inner surface of the valve body is typically lined with a covering, such as a fabric. One or more prosthetic valve members (not shown for clarity), such as prosthetic leaflets, are coupled to valve body 122 and disposed within the lumen thereof.

Prosthetic valve 44 further comprises one or more tissue-engaging elements 124. Typically, and as shown, valve 44 comprises two tissue-engaging elements 124 coupled to valve body 122 at sites that are on opposite sides of the circumference of the valve body. Each tissue-engaging element 124 typically comprises two arms 126 (e.g., a first clip arm 126a and a second clip arm 126b). For some applications, and as shown, each arm 126 defines an arc that is coupled to valve body 122 at the base of the arc. For example, and as shown, each arm 126 may comprise a single arc of the same shape-memory material as the frame of valve body 122. For some applications, one or both arms 126 of each tissue-engaging element 124 may be covered in a covering, such as a fabric.

When valve 44 is in the compressed state thereof within delivery tube 120, arms 126 are held against valve body 122 with a tip 127 of each arm disposed proximally to a site at which that arm is coupled to the valve body. Each tissue-engaging element 124 is configured such that a tip 127a of arm 126a is disposed distal to a tip 127b of arm 126b. For example, arm 126a may be shorter than arm 126b. Alternatively or additionally, arm 126a may be coupled to valve body 122 at a site that is distal to a site at which arm 126b is coupled to the valve body.

Prosthetic valve 44, within delivery tube 120, is advanced distally between leaflets 14 of native valve 10, and the prosthetic valve is progressively advanced distally out of a distal end of the delivery tube, as shown in states A-B of FIG. 1E. It is to be noted that leaflets 14 typically continue to function following implantation of prosthetic valve support 42, and may further continue to function while delivery tube 120 is disposed therebetween; the leaflets typically coapt around the delivery tube. At a given degree of advancement of prosthetic valve 44 out of delivery tube 120, first arm 126a is deployed: tip 127a of each first arm 126a becomes exposed from the delivery tube and each arm 126a responsively deflects radially outward from valve body 122, toward a pre-set position (state B of FIG. 1E). Tip 127b of each arm 126b remains within delivery tube 120. Throughout the procedure, as distal portions of valve body 122 are progressively exposed from delivery tube 120, they typically automatically expand toward an expanded state Subsequently, and as shown in state D of FIG. 1E, prosthetic valve 44 and delivery tube 120 are moved proximally (e.g., atrially) such that arm 126a of each tissue-engaging element 124 engages (e.g., captures) a leaflet 14 of native valve 10, e.g., such that a portion of each leaflet is disposed between (1) each arm 126a and (2) a respective second arm 126b and valve body 122. Optionally, subsequently to deployment of first arm 126a and prior to moving prosthetic valve 44 proximally, the first arm is deflected further from valve body 122 than its pre-set position by applying a force to the first arm using the delivery tube. That is, an angle between the first arm and an outer surface of the valve body is increased by applying the force to the first arm using the delivery tube.

Typically, the force is applied by moving delivery tube 120 distally with respect to the prosthetic valve (e.g., sliding the delivery tube over at least part of the prosthetic valve), so as to push the arm, as shown in state C of FIG. 1E. It is hypothesized that such "opening" of tissue-engaging element 124 facilitates engagement of leaflets 14 (e.g., engagement of a larger portion of leaflets 14). Subsequently, delivery tube 120 is returned proximally with respect to prosthetic valve 44, such that arm 126a returns toward its pre-set position (state D of FIG. 1E). For some applications, until at least the step shown in state D of FIG. 1E, prosthetic valve 44 is retrievable into delivery tube 120 and removable from the body of the subject, e.g., as described hereinbelow with respect to FIG. 2.

Subsequently, delivery tube 120 is pulled further proximally with respect to prosthetic valve 44, such that tip 127*b* of second arm 126*b* of each tissue-engaging element 124 becomes exposed from the delivery tube, and each arm 126*b* responsively deflects radially outward from valve body 122, toward a pres-set position (state A of FIG. 1F), thereby coupling the tissue-engaging element to the leaflet by sandwiching a portion of a leaflet 14 between the first and second arms of each tissue-engaging element. Second arm 126*b* is typically configured, when completely unrestricted (e.g., in the absence of leaflet 14) to have a pre-set position that is close to that of first arm 126*a*, planar with that of first arm 126*a*, and/or further from valve body 122 than is arm 126*a*. For some applications, the difference in size and/or position of the arc of second arm 126*b* to that of first arm 126*a* facilitates the second arm to move into plane with, and/or beyond the plane of, the first arm.

Subsequently, prosthetic valve 44 is fully deployed by a proximal end of the prosthetic valve (e.g., valve body 122 thereof) being exposed from delivery tube 120 (e.g., by further withdrawing the delivery tube proximally with respect to the prosthetic valve)(state C of FIG. 1F). The proximal end of prosthetic valve 44 responsively (e.g., automatically) expands toward the expanded state thereof. Expansion of the prosthetic valve (e.g., of valve body 122 thereof) applies a radially-expansive force against prosthetic valve support 42 (e.g., against an inner perimeter of upstream support portion 43 thereof), thereby coupling the prosthetic valve to the prosthetic valve support. Typically, prosthetic valve support 42 (e.g., the inner perimeter of upstream support portion 43) restricts expansion of prosthetic valve 44, at least in part.

For some applications, and as shown in state B of FIG. 1F, subsequently to the coupling of tissue-engaging elements 124 to leaflets 14, and prior to coupling of prosthetic valve 44 to prosthetic valve support 42, the prosthetic valve is pulled proximally, e.g., so as to align a portion of valve body 122 with upstream support portion 43 and/or to drawn leaflets 14 toward the upstream support portion.

It is to be noted that, for some applications, each tissue-engaging element 124 comprises only one arm 126. For some such applications, the one arm 126 comprises and/or functions like first arm 126*a* described herein. For some such applications, the one arm 126 is configured to couple to the leaflet by sandwiching a portion of the leaflet between the one arm and valve body 122. For some such applications, the one arm 126 is configured, when the prosthetic valve is pulled proximally as shown in state B of FIG. 1F, to sandwich a portion of the leaflet between the one arm and prosthetic valve support 42 (e.g., upstream support portion 43 thereof).

State D of FIG. 1F shows the implanted (e.g., final) state of prosthetic valve support 42 and prosthetic valve 44, following implantation thereof at native valve 10. For some applications, in this implanted state, prosthetic valve support 42 and prosthetic valve 44 are inhibited from moving upstream (e.g., atrially) both by tissue anchors 48 and by tissue-engaging elements 124. That is, for some applications, resistance to forces on support 42 and valve 44 from the functioning of the heart of the subject, is provided in part by anchors 48 and in part by elements 124. For some applications, in this implanted state, prosthetic valve support 42 and prosthetic valve 44 are inhibited from moving upstream mostly (e.g., solely) by tissue-engaging elements 124. That is, for some applications, resistance to forces on support 42 and valve 44 from the functioning of the heart of the subject, is provided mostly (e.g., solely) by elements 124. For some such applications, anchors 48 and longitudinal members 102 are thereby only required until prosthetic valve 44 has been implanted. It is to be noted that in both cases, prosthetic valve support 42 (e.g., upstream support portion 43 thereof) inhibits movement ventricularly of prosthetic valve 44, and of the prosthetic valve support itself.

Reference is again made to FIGS. 1D-F. For some applications, locking of locking members 110 to longitudinal members 102 and/or decoupling of pull-wires 104 from longitudinal members 102 (FIG. 1D) is not performed until after implantation of prosthetic valve 44 (FIGS. 1E-F). For such applications, it is thereby possible to adjust the length of the portion of longitudinal members 102 (e.g., tension on the longitudinal members) after implantation of prosthetic valve 44. For some applications, a similar advantage is conferred by locking members being reversibly lockable, being locked before implantation of prosthetic valve 44, and subsequently to implantation of the prosthetic valve, being unlocked to allow re-adjustment of longitudinal members 102.

Reference is again made to FIGS. 1A-F. For some applications, anatomical dimensions of native valve 10 and/or surrounding tissues are determined (e.g., measured), and prosthetic valve support 42 and/or prosthetic valve 44 are selected accordingly (e.g., from a selection of prosthetic valve supports and/or prosthetic valves of different sizes). For example, an optimal lumen size (e.g., transverse cross-sectional area) for a prosthetic valve may be determined according to an area of the lumen defined by the annulus of the native valve of the subject. Responsively, a prosthetic valve having a lumen of that particular size may be selected. Similarly, a prosthetic valve support having an inner perimeter that defines an opening having a particular cross-sectional area may be selected, so as to restrict the expansion of a prosthetic valve to have a lumen of that particular size. Alternatively or additionally, a prosthetic valve support having an outer perimeter of a particular size may be selected according to determined dimensions of the annulus of the valve and/or walls of the atrium. It is to be noted that selecting a size according to determined anatomical dimensions may only in some cases comprise selecting a size that matches the anatomical dimensions. For example, an optimal size for the transverse cross-sectional area of a prosthetic valve is typically less than 90% of the area defined by the annulus of the native valve, so as to allow the leaflets of the native valve to coapt around the prosthetic valve and facilitate sealing.

Because prosthetic valve support 42 is typically implantable without eliminating functioning of the native leaflets, for some applications, the prosthetic valve support is implantable without the use of cardiopulmonary bypass. For some applications, prosthetic valve 44 is also implantable without the use of cardiopulmonary bypass.

Reference is made to FIG. 2, which is a schematic illustration of prosthetic valve 44 being retrieved into delivery tube 120, in accordance with some applications of the invention. As described hereinabove, for some applications, until at least the step shown in state D of FIG. 1E, prosthetic valve 44 is retrievable into delivery tube 120 and removable from the body of the subject. Delivery tube 120 is moved distally with respect to prosthetic valve 44, in a manner similar to that used to push arms 127*a*, described with reference to FIG. 1E (state C), but such that delivery tube 120 is slid over the site at which arms 127*a* are coupled to valve body 122, thereby pushing arms 127*a* to deflect distally. Prosthetic valve 44, including at least part of arms 127*a*, is drawn into delivery tube 120 (e.g., by sliding the prosthetic valve distally and/or the delivery tube proximally), and is typically subsequently removed from the body of the subject.

Reference is made to FIGS. 3A-C, which are schematic illustrations of the introduction of guide members 56 through prosthetic valve support 42 and delivery tube 80, in accordance with some applications of the invention. As described hereinabove (e.g., with reference to FIG. 1C), prosthetic valve support 42 is slidable toward native valve 10, over guide members 56, including while the prosthetic valve support is compressed within delivery tube 80. Following coupling of anchors 48 to the ventricular sites, guide members 56 extend from the anchors to outside of the body of the subject, and have respective free proximal ends 57. Before introduction of support 42 within tube 80 into the body of the subject (e.g., into sheath 46), guide members 56 are threaded through holes 82 in upstream support portion 43 of prosthetic valve 42, and through delivery tube 80, e.g., by the operating physician.

Typically, prosthetic valve support 42 is provided in the compressed state thereof, within delivery tube 80, e.g., as a unit 140, coupled to a distal end of a controller 142 that is used to move the unit transluminally (e.g., within sheath 46). Unit 140 comprises (e.g., is provided having) one or more introducer tubes 144, each introducer tube being shaped to define a lumen therethrough, and having an open distal end 143 and an open proximal end 145. Distal end 143 of each tube is disposed outside a distal end of support 42 and/or tube 80, and proximal end 145 of each tube is disposed outside a proximal end of the support and/or tube 80. Each introducer tube 144 passes (1) from the distal end thereof, (2) through a respective hole 82 in upstream support portion 43 from the downstream surface of the support portion (which defines an outer surface of the support portion in the compressed state thereof) to an upstream surface of the support portion (which defines an inner surface of the support portion in the compressed state thereof), and (3) to the proximal end thereof.

As shown in FIG. 3A, free proximal end 57 of each guide member 56 is advanced through a respective introducer tube 144, thereby threading the guide member through upstream support portion 43 of prosthetic valve support 42. Typically, and as shown in FIG. 3B, introducer tubes 144 are subsequently removed, prior to introduction of unit 140 into the body of the subject. That is, introducer tubes 144 are typically temporary. FIG. 3C shows upstream support portion 43 of prosthetic valve support 42 having been partially exposed from delivery tube 80, in order to illustrate the resulting threading of guide members 56 through upstream support portion 43.

Reference is made to FIGS. 4A-C, which are schematic illustrations of locking member 110, and control thereof, in accordance with some applications of the invention. As described hereinabove, locking member 110 is slidable over guide member 56 (e.g., over tubular member 100 thereof). As also described hereinabove, locking member 110 is configured to lock to longitudinal member 102.

FIG. 4A shows locking member 110 in the unlocked state thereof, in which the locking member typically defines a channel therethrough through which tubular member 100 and longitudinal member 102, either within the tubular member or outside of the tubular member, are slidable. The channel of locking member 110 is defined by a generally tubular portion 160 of the locking member. Tubular portion 160 defines one or more, such as two, oblique slits 162 in the lateral walls thereof. Locking member 110 comprises locking element, such as a locking bar 164, that is disposed generally orthogonally to the channel of the locking member, and passes through the slits (e.g., through both slits) of the tubular member. When locking bar 164 is slid distally and/or proximally, the locking bar thereby moves across at least part of the channel defined by tubular portion 160. Locking member 110 further comprises a spring 166 that is configured to push locking bar 164 in a given direction (e.g., distally), thereby transitioning the locking member into the locked configuration thereof (i.e., locking the locking member)(FIG. 4B).

Locking member 110 is typically controllable using a holding member 112 that inhibits (e.g., prevents) the locking member from locking, such as by inhibiting movement of locking bar 164. As described hereinabove, each control rod 86, used to push prosthetic valve support 42 toward the annulus of valve 10, is reversibly coupled at a distal end thereof to a respective locking member 110, such that the pushing is typically performed by pushing with control rod 86 and locking member 110. For some applications, and as shown in FIGS. 4A-C, holding member 112 comprises and/or is defined by control rod 86. For such applications, control rod 86 defines one or more slits 168 in a lateral wall thereof (e.g., two slits 168 on opposite sides of the lateral wall of the control rod). Typically, slits 168 are L-shaped, thereby providing (1) a holding region 170 that is generally orthogonal to the proximal-distal (e.g., longitudinal) axis of control rod 86, and (2) a release region 172 that is generally parallel with the proximal-distal axis of the control rod, and that is open to the distal end of the control rod. Locking bar 164 is configured such that ends thereof extend at least into (e.g., through) slits 168.

In the unlocked state in which locking member 110 is advanced over guide member 56 toward upstream support portion 43 and the annulus of the native valve, the ends of locking bar 164 are disposed in holding region 170 of each slit 168, and the locking bar is thereby inhibited from moving distally and locking the locking member (FIG. 4A). In order to lock the locking member, control rod 86 is rotated with respect to locking member 110, such that the ends of locking bar 164 move into release region 172 of each slit 168. In this position, spring 166 is thereby able to move locking bar toward the distal end of release region 172, thereby locking the locking member (FIG. 4B).

As described hereinabove, tubular member 100 is typically withdrawn from locking member 110 before the locking member is locked, and the locking member is locked to longitudinal member 102, e.g., by locking bar 164 sandwiching longitudinal member 102 against the inner surface of the channel of the locking member (e.g., effectively narrowing the channel at the site of the locking bar). Movement of the ends of locking bar 164 into and through release region 172 also decouples control rod 86 from the locking member, allowing the control rod to be removed from the body of the subject (typically along with tubular member 100)(FIG. 4C). For some applications, longitudinal member 102 comprises suture. For some applications, long member 102 comprises a polymer, such as polyester. For some applications, longitudinal member 102 comprises a metal. For example, the longitudinal member may comprise one or more wires, such as a plurality of wires twisted or braided into a cable. It is hypothesized that for some applications, a metallic composition reduces compressibility of longitudinal member 102 and/or facilitates locking of locking member 110 to the longitudinal member.

It is to be noted that locking member 110 thereby (1) when unlocked, facilitates sliding therethrough of a relatively wide element, tubular member 100, and (2) when locked, locks to a relatively narrow element, longitudinal member 102. To facilitate this, between the locked and unlocked states, locking bar 164 thereby moves a sufficient distance across the channel defined by locking member 110. That is, locking bar 164 moves a larger distance than would be necessary to lock a similar locking member that does not facilitate, in the unlocked state thereof, sliding therethrough of a tubular member that is wider than the longitudinal element.

Reference is again made to FIGS. 1D and 4A-C. It is to be noted that locking member 110 is typically configured to lock to longitudinal member 102 independently of (e.g., in the absence of) a complementary element, such as teeth, on the longitudinal member. For some applications, locking member 110 is configured to be coupled to any part of longitudinal member 102.

Reference is made to FIG. 5, which is a schematic illustration of steps in the delivery of tissue anchors 48 to ventricle 8, and anchoring of the anchors in the ventricle, in accordance with some applications of the invention. For some applications, the steps shown in FIG. 5 (and/or states A-D thereof) can be used in place of the steps shown in FIG. 1B (and/or states A/D thereof), mutatis mutandis (e.g., after the steps shown in FIG. 1A and/or before the steps shown in FIG. 1C). FIG. 1B shows one delivery catheter 50 being used to deliver both anchors 48, and when delivering second tissue anchor 48b, anchor-delivery tube 52 fitting alongside first guide member 56a within catheter 50. As stated hereinabove, for some applications, a separate catheter is used for each anchor. FIG. 5 shows one such application.

Typically, first anchor 48a is delivered and anchored as described hereinabove with reference to FIG. 1A, wherein catheter 50 in FIG. 1A comprises a first catheter 50a. Subsequently, and as shown in FIG. 5, a second catheter 50b is advanced through sheath 46, such that second catheter 50b is disposed alongside first guide member 56a within sheath 46. It is to be noted that, in both FIG. 1B and FIG. 5, two anchors 48 are anchored at respective ventricular sites, and two respective guide members 56, extend from the anchors, through atrium 6, and typically out of the body of the subject.

Figure 6:
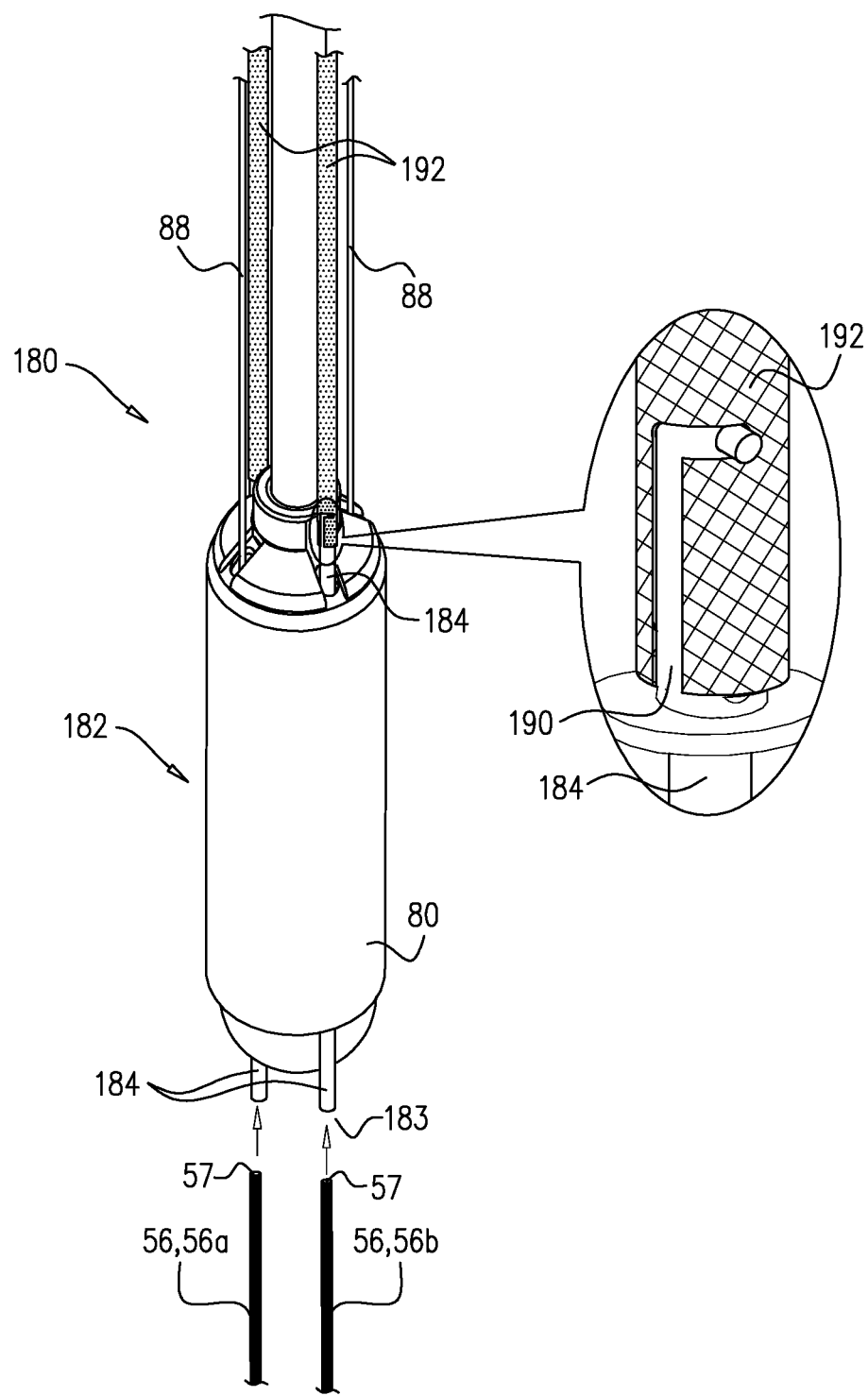
FIG. 6 is a schematic illustration of a system for use with a prosthetic valve support, in accordance with some applications of the invention.

Reference is made to FIG. 6, which is a schematic illustration of a system 180 for use with prosthetic valve support 42, in accordance with some applications of the invention. For such applications of the invention, prosthetic valve support 42 is slidable toward native valve 10 over guide members 56, including while the prosthetic valve support is compressed within delivery tube 80. Following coupling of anchors 48 to the ventricular sites, guide members 56 extend from the anchors to outside of the body of the subject, and have respective free proximal ends 57. Before introduction of support 42 within tube 80 into the body of the subject (e.g., into sheath 46), guide members 56 are threaded through holes 82 in upstream support portion 43 of prosthetic valve 42, and through delivery tube 80, e.g., by the operating physician.

FIGS. 3A-C and the descriptions thereof describe prosthetic valve support 42 being provided as a unit 140 comprising introducer tubes 144, which are removed subsequently to advancement of guide members 56 through upstream support portion 43 and prior to introduction of the unit into the body of the subject. FIG. 6 shows system 180, in which prosthetic valve support is provided within delivery tube 80, e.g., as a unit 182, coupled to a distal end of controller 142, described hereinabove.

Unit 182 comprises (e.g., is provided having) one or more introducer tubes 184, each introducer tube being shaped to define a lumen therethrough, and having an open distal end 183. Distal end 183 of each tube is disposed outside a distal end of support 42 and/or tube 80, and each introducer tube 184 extends out of a proximal end of the support and/or tube 80. Similarly to unit 140 described with reference to FIGS. 3A-C, each introducer tube 144 of system 180 passes from the distal end thereof, through a respective hole in upstream support portion 43 from the downstream surface of the support portion (which defines an outer surface of the support portion in the compressed state thereof) to an upstream surface of the support portion (which defines an inner surface of the support portion in the compressed state thereof). In contrast to unit 140, introducer tubes 184 extend from a proximal end of delivery tube 80 to a proximal end portion of the apparatus. In further contrast to unit 140, tubes 184 remain in place as unit 182 is advanced transluminally over guide members 56. Tubes 184 are typically flexible to facilitate transluminal advancement thereof.

A locking member 190 is disposed over each introducer tube 184, such that the introduction of guide member 56 through the introducer tube also introduces the guide member through the locking member. Locking member 190 is slidable over guide member 56 (e.g., over tubular member 100 thereof), and is configured to lock to longitudinal member 102. Typically, locking member 190 is identical to locking member 110, described hereinabove, except that locking member 190 is configured (e.g., dimensioned) to be slidable also over introducer tube 184. Each locking member 190 is disposed at the distal end of a respective tubular control rod 192, which is typically identical to control rod 86, described hereinabove, except that control rod 192 is configured (e.g., dimensioned) to be slidable also over introducer tube 184.

The use of system 180, including introducer tubes 184, advantageously (1) removes the requirement for two separate introductions of proximal end 57 of guide member 56 (i.e., through an introducer tube and subsequently through a locking member and control rod); and (2) facilitates control rods 192 (and locking members 190) being present in the atrium of the subject during expansion of prosthetic valve support 42, thereby reducing an interval between the expansion of the prosthetic valve support and pressing of the prosthetic valve support against the annulus of the native valve.

Reference is made to FIGS. 7A-C, which are schematic illustrations of a system 200 for facilitating transluminal delivery of a prosthetic valve assembly 202, in accordance with some applications of the invention. FIG. 7A shows prosthetic valve assembly 202 in an expanded state thereof. Prosthetic valve assembly comprises (1) a prosthetic valve body 204, which comprises a first frame 206 (e.g., a wire frame), and is shaped to define a lumen 208 therethrough, (2) an annular upstream support 210, which comprises a second frame 212 (e.g., a wire frame), is shaped to define an opening through the upstream support, and is configured to be placed against an upstream surface (e.g., an atrial surface) of native valve 10 (e.g., of an annulus thereof), and (3) a flexible sheet 214 that couples the first frame to the second frame. In the expanded state of assembly 202 (and thereby of body 204), frame 206 of body 204 is generally cylindrical, and has a diameter d1. In the expanded state of assembly 202 (and thereby of upstream support 210), frame 212 of support 210 is typically generally annular, and has an outer perimeter 213 that has a diameter d2, which is greater than diameter d1.

Sheet 214 may be a fabric, a film, and/or another sheet-like structure, and may comprise a natural material, a polymer, a biomaterial, and/or any other suitable material. Typically, sheet 214 comprises polyester, PTFE, and/or pericardial tissue.

For some applications, and as shown in FIG. 7A, in the expanded state of assembly 202, and in the absence of external forces (e.g., if the assembly were resting on a table surface), sheet 214 is generally annular and flat, and an upstream end 218 of frame 206 is disposed generally on a plane defined by support 210. For such applications, an inner perimeter 211 of frame 212 defines an opening that has a diameter d3 that is greater than diameter d1.

For some applications, in such an expanded and unconstrained state, sheet 214 is generally frustoconical or funnel-shaped, and upstream end 218 of frame 206 is disposed below the plane defined by support 210. (For some such frustoconical or funnel-shaped arrangements, the sheet may also be considered to be annular.)

For some applications, in such an expanded and unconstrained state, sheet 214 is generally tubular, upstream end 218 of frame 206 is disposed below the plane defined by support 210. For such applications, diameter d3 is typically generally equal to diameter d1.

Typically, one or both of frames 206 and 212 is covered on at least one side by a covering 220. For some applications, sheet 214 comprises a portion of covering 220, e.g., the sheet is defined by a portion of the covering that is disposed between frames 206 and 212. For some applications, and as shown in FIG. 7A, covering 220 is disposed (1) on a tissue-facing side of frame 212 (e.g., defines a tissue-contacting surface of support 210), and (2) on an inner surface of frame 206 (i.e., lines the frame, and defines lumen 208).

A valve member 205 (e.g., comprising one or more prosthetic leaflets; shown in FIGS. 8D-G) is coupled to frame 206, is disposed within lumen 208, and provides valve (e.g., one-way) functionality to assembly 202. Valve member 205 may alternatively or additionally comprise a different valve member, such as a mechanical valve member.

At least two eyelets 222 are disposed on an outer surface of body 204 (i.e., protrude radially outward from body 204). Typically, eyelets 222 are pivotably coupled to body 204, e.g., such that the eyelets can pivot (e.g., rotate) in both directions by at least 5 degrees (e.g., more than 5 degrees and/or less than 90 degrees, such as between 5 and 90 degrees, e.g., between 5 and 60 degrees, such as between 5 and 45 degrees). For some applications, the eyelets can pivot in a plane parallel to a plane defined by a tangent of the valve body at the site to which the eyelet is coupled, as shown in the blowup box. Alternatively or additionally, the eyelets can pivot in a plane that is orthogonal to the plane defined by the tangent, e.g., such that the eyelets can point toward and/or away from the valve body. For some applications, eyelets 222 are sutured to body 204. Eyelets 222 are arranged in at least one pair; each eyelet of the pair being disposed on the opposite side of body 206 from the other eyelet of the pair.

FIG. 7B shows system 200 in a delivery configuration thereof. System 200 comprises a delivery tool 230, which comprises a first housing 232 (e.g., a proximal housing) and a second housing 234 (e.g., a distal housing), which are articulatably coupled to each other via a flexible control rod assembly 240 disposed through the housings.

In the delivery configuration of system 200, assembly 202 is in a compressed state thereof, in which prosthetic valve body 204 (in a compressed state thereof) is generally cylindrical, and upstream support 210 (in a compressed state thereof) is also generally cylindrical. Typically, in the delivery configuration of system 200, sheet 214 is also generally cylindrical. Assembly 202, in the compressed configuration thereof, (1) has a central longitudinal axis, at one zone (e.g., at one end) of which body 204 is disposed, and at another zone (e.g., the other end) of which support 210 is disposed, and (2) defines an articulation zone 236 in which (a) at least part of sheet 214 is disposed, and (b) neither frame 206 of body 204 nor frame 212 of support 210 is disposed, and about which body 204 and support 210 are articulatable with respect to each other.

In the delivery configuration of system 200, at least part of support 210 is disposed within housing 232 (which maintains the at least part of the support in the compressed state thereof), and at least part of body 204 is disposed within housing 234 (which maintains the at least part of the support in the compressed state thereof). Housing 232 defines an orifice 233 through which support 210 is introducible into the housing, and removable from the housing. Housing 234 defines an orifice 235 that faces orifice 233, and through which body 204 is introducible into the housing, and removable from the housing. In the delivery configuration, eyelets 222 protrude radially outward beyond the surface of delivery tool 230 (e.g., beyond a lateral wall of housing 234). Typically, housing 234 (e.g., the lateral wall thereof) is shaped to define a respective slit 237 for each eyelet, through which the eyelet protrudes beyond the surface of the housing. Each slit 237 is continuous with (i.e., is in communication with) orifice 235 such that, as described hereinbelow, during deployment of valve body 204, eyelet 222 can slide out of the slit at the orifice.

In the delivery configuration of system 200, tool 230 is in a contracted state, in which housing 232 is disposed at a distance d4 from housing 234 (e.g., orifice 233 is disposed at distance d4 from orifice 235). Distance d4 is typically greater than 1.5 mm and/or less than 30 mm, such as between 1.5 mm and 30 mm (e.g., between 10 and 15 mm). In this state, at least part of sheet 214 is exposed between the housings. The at least part of sheet 214 (and thereby of articulation zone 236) that is exposed between housings 232 and 234 facilitates articulation of housing 234 containing body 204 with respect to housing 232 containing support 210, and thereby defines an articulation zone 238 of system 200 in the delivery configuration thereof. Typically at least part of control rod assembly 240 is flexible, so as to facilitate articulation at articulation zone 238. For example, although assembly 240 as a whole is typically sufficiently flexible so as to facilitate its transluminal delivery to the heart, control rods 244 and 246 may be more flexible than control rod 240 (e.g., more flexible than required for transluminal delivery to the heart alone), so as to facilitate articulation at articulation zone 238. For some such applications, respective portions of control rods 244 and 246 that are disposed within articulation zone 238 when tool 230 is in the contracted state (FIG. 7C) are more flexible than adjacent portions of the control rods (e.g., portions disposed within housings 232 and 234 when tool 230 is in the contracted state). For example, and as shown, a portion 245 of control rod 244 may be narrower than adjacent portions of the control rod.

Control rod assembly 240 comprises (1) a first housing-control rod 242, coupled to first housing 232, (2) a second housing-control rod 244, coupled to second housing 234, and (3) a prosthesis-control rod 246, coupled to a mount 248 that is reversibly couplable to valve assembly 202, e.g., via a plurality of recesses 250 in the mount which receive respective portions of assembly 202. Typically, assembly 202 is couplable to mount 248 by valve body 204 being coupled to the mount, and further typically by a plurality of protrusions 252 of frame 206 being disposed within respective recesses 250. Housing 234 retains this coupling by inhibiting body 204 from expanding radially away from mount 248.

Typically, at least part of second housing-control rod 244 is disposed within and slidable through prosthesis-control rod 246, and at least part of the prosthesis-control rod is disposed within and slidable through first housing-control rod 242 (e.g., coaxially).

System 200 (e.g., tool 230 thereof) further comprises at least two flexible reference-force tubes 260, which extend, (a) from a proximal end of the system (e.g., from an extracorporeal portion of the system, such as from a handle of tool 230), (b) through a proximal end of housing 232, (c) through a lumen 254 defined by support 210 in the compressed state thereof, (d) through sheet 214, (e) along the outside of at least part of body 204, and typically (f) until a distal portion of body 204. A locking member 262 is disposed between each eyelet 222 and a respective tube 260. Typically, locking members 262 are not directly coupled to body 204, but are instead each held in position between eyelet 222 and tube 260 by a guide member 256 being disposed through the eyelet, the tube, and the locking member. For some applications, locking member 262 is integral with eyelet 222 (e.g., eyelet 222 is configured to and/or shaped to define locking member 262).

For some applications, guide members 256 are identical to guide members 56, described hereinabove. Guide members 256 are described in more detail hereinbelow.

Reference is now made to FIGS. 8A-H, which are schematic illustrations of a technique for use with system 200, to transluminally implant prosthetic valve assembly 202, in accordance with some applications of the invention. Typically, sheath 46 is advanced transluminally (e.g., transfemorally) to right atrium 12 of heart 4, through the fossa ovalis, and into left atrium 6 using standard transseptal techniques, as described hereinabove with reference to FIGS. 1A-B. Subsequently, first tissue anchor 48a and second tissue anchor 48b are anchored at respective ventricular sites, e.g., as described with reference to FIGS. 1A-B and/or 5, mutatis mutandis.

A guide member 256 is coupled to each tissue anchor (e.g., the tissue anchors are provided pre-coupled to the guide members), such that after anchoring of the tissue anchors, each guide member extends from the anchor, out of the body of the subject, e.g., as described hereinabove with respect to guide member 56, mutatis mutandis. A proximal end of each guide member 256 is introduced through a respective eyelet 222, locking member 262, and reference-force tube 260, such that system 200 appears as shown in FIG. 7B. As described hereinabove, each guide member 256 typically holds each locking member 262 in place between its respective eyelet 222 and reference-force tube 260.

Figure 8A:
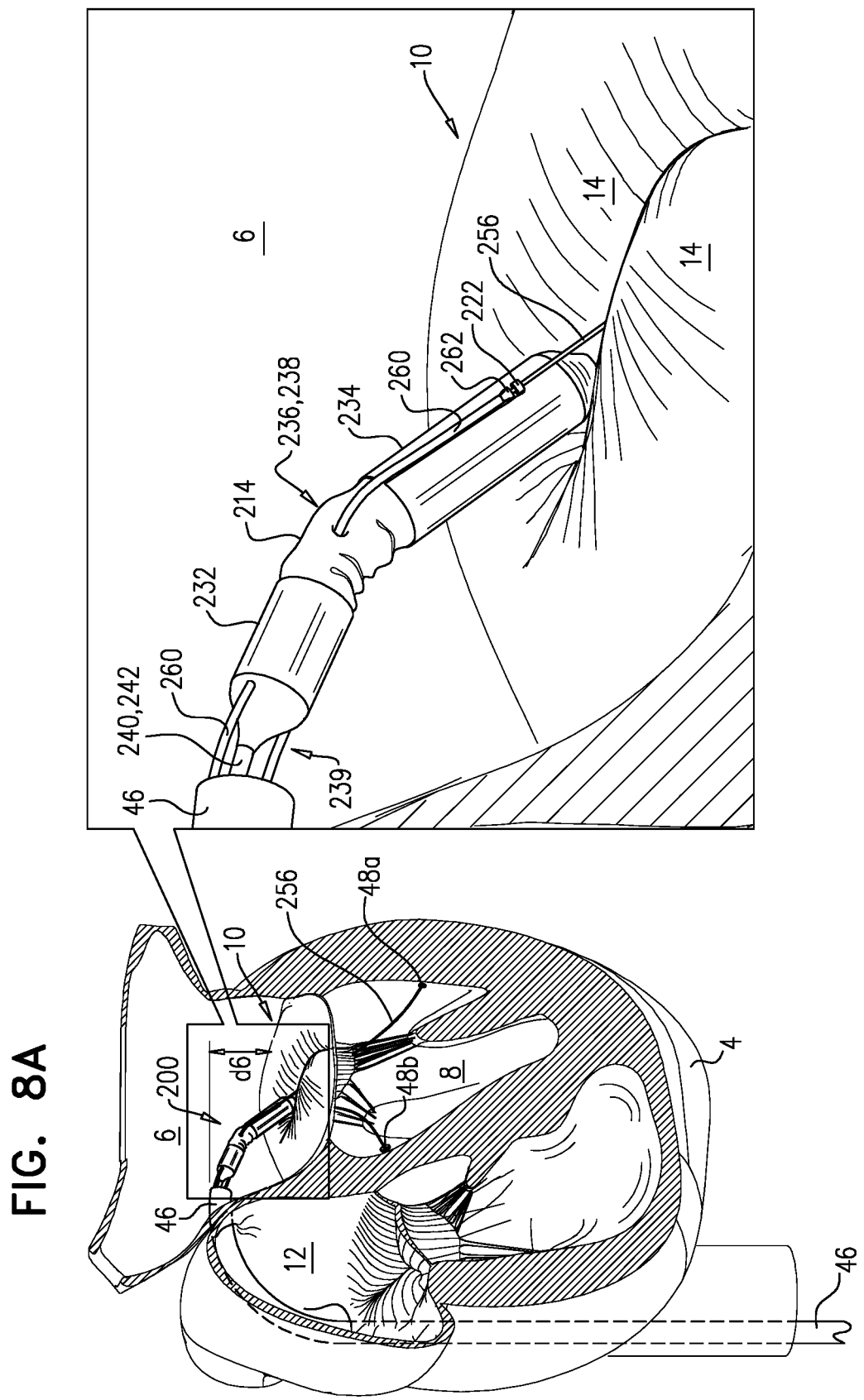

System 200 (e.g., assembly 202 within delivery tool 230) is subsequently advanced along guide members 256 and via sheath 46 to left atrium 6 (FIG. 8A). Once exposed outside of the distal end of sheath 46, system 200 is guided by guide members 256 generally toward the ventricular sites at which anchors 48 are anchored. Articulation of system 200 (e.g., at articulation zone 238, and/or at another articulation zone 239 proximal to housing 232) facilitates transluminal advancement of the system past curves in the vasculature. The articulation also facilitates movement of system 200 from the distal end of sheath 46 and between leaflets 14 of valve 10, e.g., by facilitating steering of the system along a path defined by guide members 256. This steering is typically further facilitated by (1) the position of eyelets 222 at a distal portion of system 200 (e.g., at a distal portion of housing 234), which turns the housing in response to encountering a turn in members 256, and/or (2) the pivotable coupling of eyelets 222 to body 204, described hereinabove; pivoting of eyelet 222 reduces a likelihood of the eyelet snagging on guide member 256 when encountering a turn in the guide member. For some applications, eyelets 222 are internally coated with a material having a low coefficient of friction, such as polytetrafluoroethylene, to further facilitate sliding of the eyelet over guide member 256.

It is to be noted that, due to the described articulation, a distance d5 between a proximal end of housing 232 and a distal end of housing 234 may be greater than for a similar system that does not articulate. For example, distance d5 may be greater than a distance d6 along an atrioventricular axis between (a) a height on the atrioventricular axis of the upstream surface of native valve 10, and (b) a height on the atrioventricular axis of the transseptal entry point into left atrium 6 (e.g., the fossa ovalis). For some applications, distance d5 may be greater than the overall height of left atrium 6. Distance d5 is typically greater than 25 mm and/or less than 100 mm, such as between 25 mm and 100 mm (e.g., 35-60 mm, such as 40-50 mm).

Reference is made to FIG. 8B. System 200 is advanced such that distal housing 234, containing valve body 204 in the compressed state thereof, passes between leaflets 14 of native valve 10. Valve body 204 is withdrawn out of orifice 235 of housing 234 by moving control rod 244 with respect to control rod 246. For example, and as shown in FIGS. 8B-C, control rod 244 (and thereby housing 234) may be moved distally into ventricle 8, while control rod 246 (and thereby mount 248 and valve body 204) remains stationary, thereby increasing the distance between housing 232 and housing 234.

When protrusions 252 of frame 206 become withdrawn from housing 234, the portion of valve body 204 coupled to the mount expands (e.g., automatically), thereby disengaging the protrusions from recesses 250 of mount 248, and decoupling the valve body from the mount (FIG. 8C). For clarity, FIGS. 8C-D show the distal portion of valve body 204 expanding before the proximal portion of the valve body. It is to be noted, however, that portions of the valve body typically expand as they become exposed from housing 234, and therefore the proximal portion of the valve body typically expands while the distal portion of the valve body is still disposed within housing 234.

FIG. 8D shows valve body 204 having been completely removed from housing 234, and support 210 having been removed from proximal housing 232 by control rod 242 (and thereby housing 232) being withdrawn proximally, thereby further increasing the distance between housing 232 and housing 234. Typically, an opposing reference force is provided by reference-force tubes 260, so as to hold assembly 202 in place at the native valve while housing 232 is withdrawn.

During the withdrawal of valve body 204 from housing 234, eyelets 222 typically slide through slits 237, and out of the slits at orifice 235.

For some applications, support 210 is deployed from housing 232 before valve body 204 is deployed from housing 234.

Subsequently, tension is applied to guide members 256 while an opposing reference force is provided to assembly 202 by tubes 260, thereby reducing a length of each guide member 256 that is disposed between eyelet 222 and its respective tissue anchor 48 (FIG. 8E). That is, each guide member 256 is slid proximally with respect to its respective reference-force tube 260. Typically, the reference-force is provided to assembly 202 by a distal end of each reference-force tube 260 abutting a respective locking member; the reference force being transferred via the locking member (and typically further via eyelet 222 to valve body 204).

For some applications this tensioning moves valve body 204 at least slightly distally into ventricle 8, such that sheet 214 becomes at least slightly frustoconical (e.g., as shown in FIG. 8E). For some applications this tensioning deforms support 210 and/or deflects the support with respect to body 204, e.g., such that the support becomes less flat (e.g., less planar). For example, before tensioning, support 210 may be flat annular (as shown in FIG. 8D), and after tensioning the support may be frustoconical (as shown in FIG. 8E). Alternatively, and as described in more detail with reference to FIGS. 14A-B, mutatis mutandis, the prosthetic valve assembly may be configured such that the upstream support is frustoconical before tensioning, and the tensioning changes a slant of the frustoconical shape. For example, before tensioning, the upstream support may be frustoconical with the larger base of the frustum closer to a ventricular end of an atrioventricular axis than is the smaller base of the frustum, and after tensioning the support may become flatter, or may even invert, such that it becomes frustoconical with the smaller base closer to the ventricular end of the atrioventricular axis (e.g., the conformation shown in FIG. 8E, mutatis mutandis).

For some applications, tensioning is performed before deployment of support 210 from housing 232.

Each guide member 256 typically comprises a tether 282 (e.g., a longitudinal member), a pull-wire 284, and a tubular member 280 in which the pull-wire and the tether are disposed. A distal portion of pull-wire 284 is reversibly coupled to a proximal portion of tether 282, and tubular member 280 fits snugly over at least the distal portion of the pull-wire and the proximal portion of the tether so as to inhibit the pull-wire from becoming decoupled from the tether (e.g., to maintain a state of coupling therebetween). For some applications, and as shown, the reversible coupling is provided by pull-wire 284 and tether 282 defining respective mating surfaces. For some applications, the reversible coupling is provided as described hereinabove for guide member 56.

When each guide member 256 (e.g., the tether 282 thereof) is tensioned, the guide member is withdrawn proximally until at least part of tether 282 (within tubular member 280) is disposed within locking member 262 (e.g., at least until the proximal portion of the tether has passed through the locking member; FIG. 8E state B).

Reference is now made to FIG. 8F. Once a desired tension is obtained, the tension is fixed. Tubular member 280 is withdrawn proximally with respect to tether 282, pull-wire 284 and locking member 262 (FIG. 8F). State A of FIG. 8F shows tubular member 280 having been withdrawn until eyelet 222. State B of FIG. 8F shows tubular member 280 having been withdrawn until a distal end of the tubular member is disposed proximal to locking member 262, thereby exposing tether 282 to the locking member.

Typically, locking member 262 is biased (e.g., shape-set) to assume a locked state, and while tubular member 280 is disposed within the locking member, the tubular member inhibits locking of the locking member to tether 282 (or to pull-wire 284), and the removal of the tubular member from within the locking member facilitates automatic locking of the locking member to the tether (i.e., transitioning of the locking member into a locked state). Tubular member 280 is slidable through locking member 262 despite such biasing of the locking member, e.g., due to (a) the tubular member having a smooth surface, and/or (b) the tubular member retaining locking elements 263 of the locking member at an angle alpha_1 with respect to the tubular member, which is shallower than an angle alpha_2 with respect to tether 282 that the locking elements assume when the tubular element is withdrawn (compare FIG. 8F state A to state B).

Typically, tether 282 defines a plurality of nodules 286, which facilitate locking of locking member 262 to the tether. For some applications, locking elements 263 and nodules 286 function as a ratchet. For some such applications, subsequently to transitioning of locking member 262 into the locked state thereof, one-way movement of tether 282 through the locking member is possible, thereby facilitating further increase, but not reduction, of tension.

Reference is now made to FIG. 8G. Tubular member 280 and pull-wire 284 are decoupled from tether 282 and prosthetic valve assembly 202, and delivery tool 230 is withdrawn proximally (e.g., into sheath 46, and out of the body of the subject). Typically, housing 234 and mount 248 are withdrawn via the lumen of valve body 204 (e.g., between the prosthetic leaflets disposed therein). For some applications, housing 234, rods 244 and 246, and mount 248 are withdrawn prior to the tensioning step (e.g., prior to withdrawal of reference-force tubes 260, such as between the step shown in FIG. 8D and the step shown in FIG. 8E, mutatis mutandis).

Typically, tubular member 280 and pull-wire 284 are decoupled from tether 282 by withdrawing the tubular member further proximally, such that the distal portion of pull-wire 284 and the proximal portion of tether 282 are exposed from the tubular member (state A of FIG. 8G). Reference force for this withdrawal is provided by the anchored tether 282, and optionally also by reference-force tubes 260. Tubular member 280, pull-wire 284, and reference-force tube 260 are then withdrawn (state B of FIG. 8H).

Figure 8H:
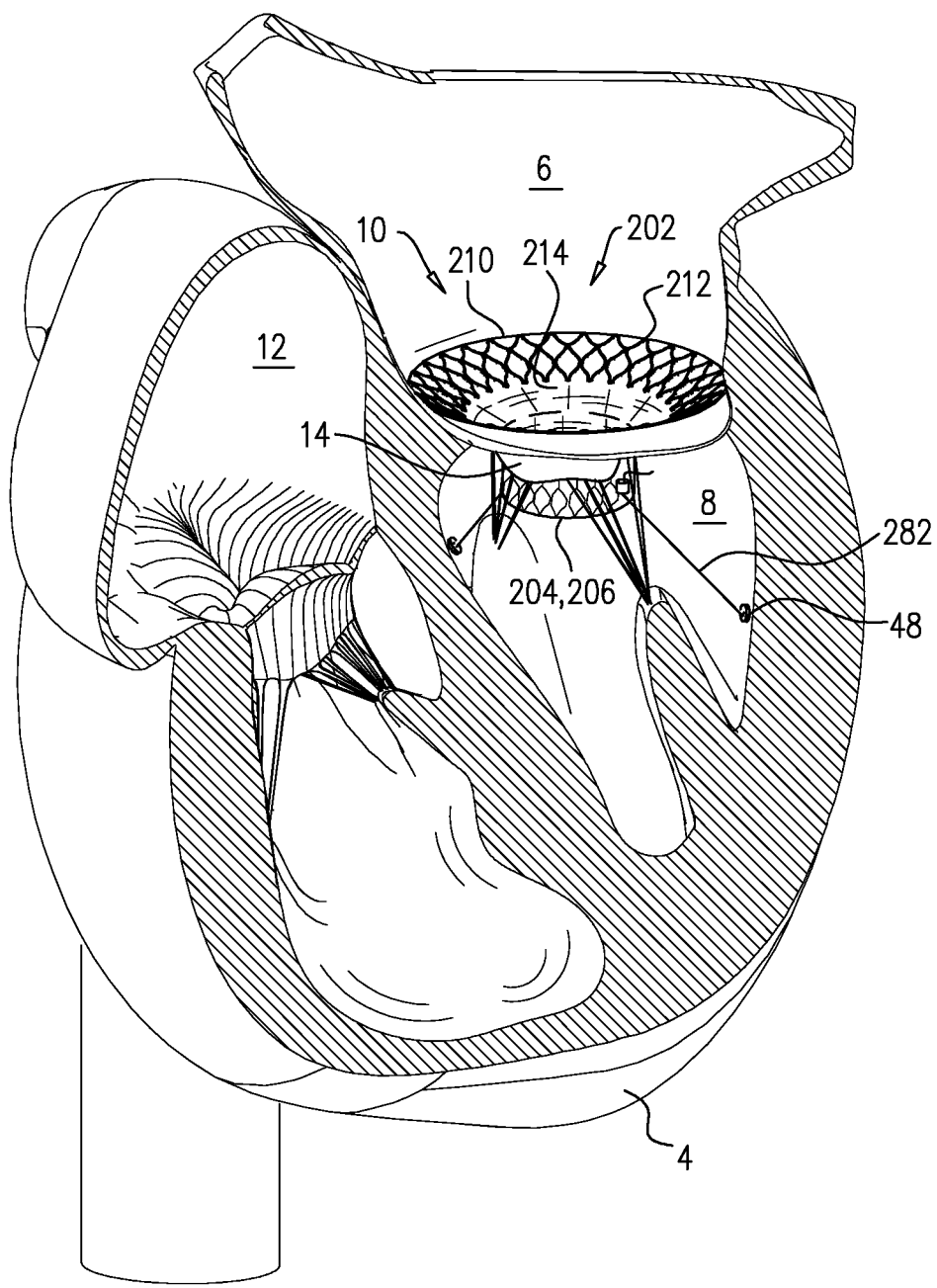

FIG. 8H is a schematic illustration of prosthetic valve assembly 202 following implantation at native valve 10 of heart 4. Assembly 202 provides replacement one-way valve functionality in which blood flows from atrium 6, through the opening defined by upstream support 210, past sheet 214, through lumen 208 of valve body 204, and into atrium 8. Sheet 214 thereby defines and/or serves as a conduit that provides fluid communication between the opening defined by upstream support 210 (e.g., by frame 212 thereof) and lumen 208 of valve body 204. Further typically, this conduit is uninterrupted except for holes (not shown) that may remain where reference-force tubes 260 originally extended through the sheet.

Regurgitation through these holes is typically minimal or absent due to their small size. The holes may be slit-like (rather than punched holes), such that in the absence of reference-force tubes 260 the holes become generally closed. Additionally, coaptation of leaflets 14 and tissue growth over the holes may further facilitate sealing. Alternatively or additionally, the holes may be defined by tubular protrusions 215 that extend from sheet 214 (shown in the "optional" box, FIG. 7B). Tubular protrusions 215 may comprise the same material as sheet 214, or may comprise a different material. Tubular protrusions 215 may be flexible or rigid. The tubular protrusions are configured to provide a channel through which tubes 260 may pass, but which, in the absence of tubes 260, inhibit movement of fluid therethrough. For example, tubes 215 may inhibit fluid flow due to the ratio between their length and lumen diameter, and/or may act as duckbill valves. Therefore, sheet 214 typically provides a generally sealed conduit between upstream support 210 and valve body 204.

The positioning of prosthetic valve assembly 202 at the native valve typically results in leaflets 14 of the native valve coapting around valve body 204, thereby providing sealing that inhibits (e.g., prevents) perivalvular leakage.

The positioning of prosthetic valve assembly typically also places sheet 214 in contact with the annulus and/or leaflets of the native valve. In general, a prosthetic valve implanted at a native valve encounters forces due to beating of the heart and/or the resulting flow of blood. Small movements (e.g., oscillations) resulting from these forces may inhibit tissue growth (e.g., fibrosis) that would otherwise facilitate sealing between the prosthetic valve and the native valve. For some applications, such movements are reduced (e.g., dampened) at sites at which the contact between assembly 202 and the surrounding tissue is provided by sheet 214, e.g., due to flexibility of the sheet. Thereby sheet 214 typically provides stabilized (e.g., more constant) contact with tissue than would a less flexible structure in the same position; this is hypothesized to improve tissue growth and thereby sealing. Furthermore, sheet 214 itself may be configured to promote tissue growth thereon, e.g., due to surface treatments and/or impregnation, and/or structure, such as weave and/or porosity, thereby further facilitating sealing.

Reference is made to FIGS. 9A-14B, which are schematic illustrations of prosthetic valve assemblies, in accordance with some applications of the invention. Each prosthetic valve assembly shown in FIGS. 9A-14B comprises a valve body, an upstream support, and a sheet, which are typically identical, mutatis mutandis, to valve body 204, upstream support 210 and sheet 214 described hereinabove, except for where noted.

Figure 9A:
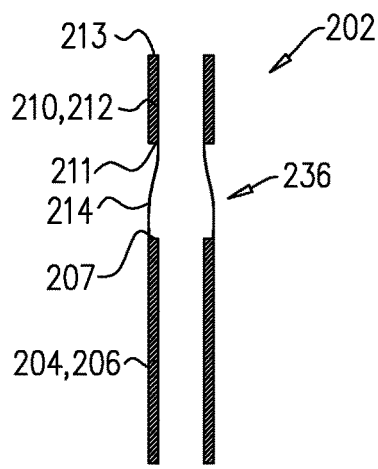
Figure 9B:
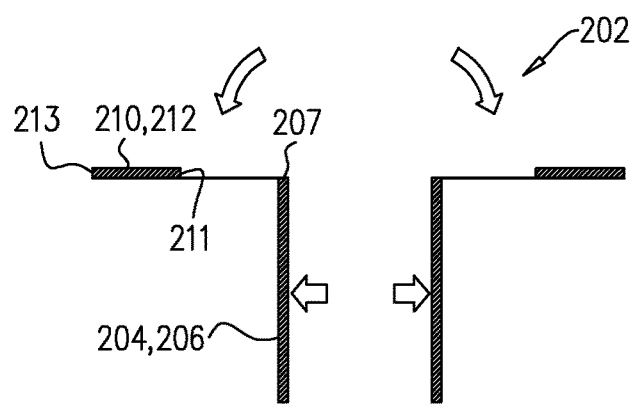

FIGS. 9A-B show, prosthetic valve assembly 202 described hereinabove, in a simplified (e.g., two-dimensional) schematic manner that illustrates the arrangement of valve body 204, upstream support 210 and sheet 214, in the compressed state (FIG. 9A) and the expanded (e.g., implanted) state (FIG. 9B). FIGS. 9A-B are included at least in part in order to facilitate interpretation of the simplified schematic illustrations of the prosthetic valve assemblies of FIGS. 10A-14B. FIG. 9A, like FIGS. 10A, 11A, 12A and 13A, shows the prosthetic valve assembly in the compressed state as if it were contained in the delivery tool thereof (e.g., tool 230), but for clarity does not show the delivery tool. Typically, sheet 214 is attached at least to inner perimeter 211 of upstream support 210, and to an upstream end 207 of frame 206 of valve body 204.

Figure 10A:
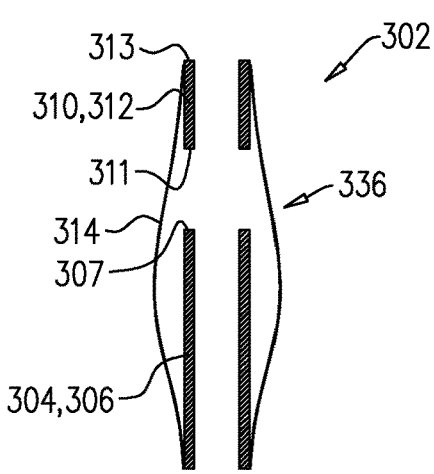
Figure 10B:
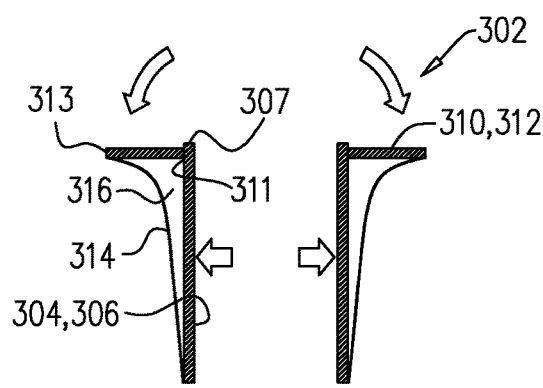

FIGS. 10A-B show a prosthetic valve assembly 302, which comprises a valve body 304 comprising a first frame 306, an upstream support 310 comprising a second frame 312, and a flexible sheet 314. In the expanded state of support 310 (FIG. 10B), frame 312 defines an outer perimeter 313 and an inner perimeter 311 that defines an opening through the support. During implantation, support 310 is placed against the upstream surface of the native valve, and valve body 304 is subsequently intracorporeally coupled (e.g., directly coupled) to the support by being expanded within the opening of the support, e.g., as described hereinabove with reference to FIG. 1F, mutatis mutandis.

Sheet 314 is not attached to inner perimeter 311 of frame 312, but rather is circumferentially attached to frame 312 at a radius that is greater than that of the inner perimeter. For example, sheet 314 may be attached to frame 312 at outer perimeter 313. Sheet 314 is also not attached to an upstream end 307 of valve body 304. Thereby a pocket region 316 is defined between sheet 314 and at least inner perimeter 311, in which sheet 314 is not attached to frame 312 or frame 306.

In the compressed state (FIG. 10A), sheet 314 is disposed alongside and outside at least part of frame 312 and at least part of frame 306. Frame 312 is configured such that when the frame is in the compressed state, inner perimeter 311 defines a downstream end of the frame (e.g., of the cylindrical shape of the frame), and outer perimeter 313 defines an upstream end. Therefore, when frame 312 expands, the upstream end of the frame expands radially outward more than does the downstream end of the frame.

Figure 11A:
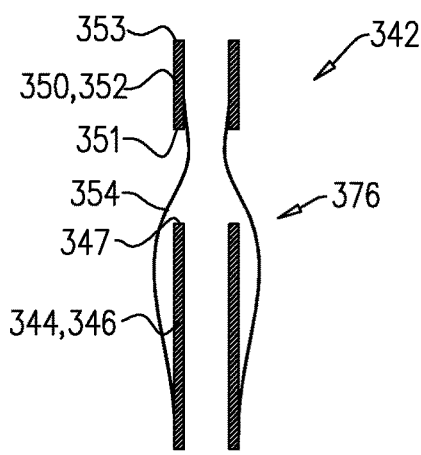
Figure 11B:
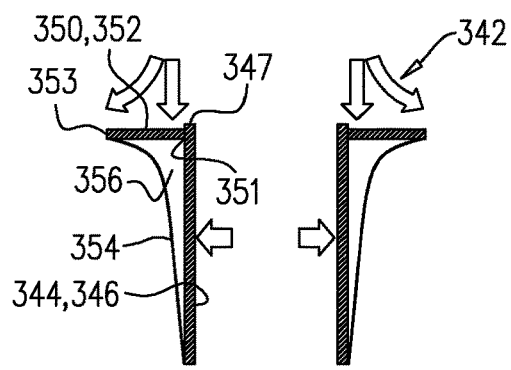

FIGS. 11A-B show a prosthetic valve assembly 342, which comprises a valve body 344 comprising a first frame 346, an upstream support 350 comprising a second frame 352, and a flexible sheet 354. In the expanded state of support 350 (FIG. 11B), frame 352 defines an outer perimeter 353 and an inner perimeter 351 that defines an opening through the support. During implantation, support 350 is placed against the upstream surface of the native valve, and valve body 344 is subsequently intracorporeally coupled (e.g., directly coupled) to the support by being expanded within the opening of the support, e.g., as described hereinabove with reference to FIG. 1F, mutatis mutandis.

Sheet 354 is not attached to inner perimeter 351 of frame 352, but rather is circumferentially attached to frame 352 at a radius that is greater than that of the inner perimeter. For example, sheet 354 may be attached to frame 352 at outer perimeter 353. Sheet 354 is also not attached to an upstream end 347 of valve body 344. Thereby a pocket region 356 is defined between sheet 354 and at least inner perimeter 351, in which sheet 354 is not attached to frame 352 or frame 346.

Frame 352 is configured such that when the frame is in the compressed state, the frame has a generally cylindrical shape that defines a lumen therethrough, inner perimeter 351 defines an upstream end of the frame (e.g., of the cylindrical shape of the frame), and outer perimeter 353 defines a downstream end. Therefore, when frame 352 expands, the downstream end of the frame expands radially outward more than does the upstream end of the frame. In the compressed state (FIG. 11A), sheet 354 is disposed alongside and outside of at least part of frame 346, and through at least part of the lumen defined by frame 352.

FIGS. 12A-B show a prosthetic valve assembly 382, which comprises a valve body 384 comprising a first frame 386, an upstream support 390 comprising a second frame 392, and a flexible sheet 394. In the expanded state of support 390 (FIG. 12B), frame 392 defines an outer perimeter 393 and an inner perimeter 391 that defines an opening through the support. Frame 392 is coupled to frame 386 prior to implantation (e.g., assembly 382 is provided with frame 392 coupled to frame 386). For some applications, frames 392 and 386 are integral, e.g., are defined by respective regions of a single frame. During implantation, valve body 384 is advanced between leaflets of the native valve, and support 390 is placed against the upstream surface of the native valve (e.g., as described with reference to FIGS. 8B-D, mutatis mutandis.

Sheet 394 is not attached to inner perimeter 391 of frame 392, but rather is circumferentially attached to frame 392 at a radius that is greater than that of the inner perimeter. For example, sheet 394 may be attached to frame 392 at outer perimeter 393. Sheet 394 is also not attached to an upstream end 387 of valve body 384. Thereby a pocket region 396 is defined between sheet 394 and at least inner perimeter 391, in which sheet 394 is not attached to frame 392 or frame 386.

Assembly 382 is configured such that, in the compressed state thereof (FIG. 12A), frames 386 and 392 are generally collinear, and form a generally continuous cylinder. Frame 392 is configured such that in the compressed state, outer perimeter 393 defines an upstream end of the frame (and thereby of assembly 382). Therefore, when frame 392 expands, the upstream end of the frame expands radially outward more than does the downstream end of the frame. In the compressed state, sheet 394 is disposed alongside and outside of at least part of frame 386, and at least part of frame 392.

FIGS. 13A-B show a prosthetic valve assembly 402, which comprises a valve body 404 comprising a first frame 406, an upstream support 410 comprising a second frame 412, and a flexible sheet 414. In the expanded state of support 410 (FIG. 13B), frame 412 defines an outer perimeter 413 and an inner perimeter 411 that defines an opening through the support. Frame 412 is coupled to frame 406 prior to implantation (e.g., assembly 402 is provided with frame 412 coupled to frame 406). For some applications, frames 412 and 406 are integral, e.g., are defined by respective regions of a single frame. During implantation, valve body 404 is advanced between leaflets of the native valve, and support 410 is placed against the upstream surface of the native valve (e.g., as described with reference to FIGS. 8B-D, mutatis mutandis.

Sheet 414 is not attached to inner perimeter 411 of frame 412, but rather is circumferentially attached to frame 412 at a radius that is greater than that of the inner perimeter. For example, sheet 414 may be attached to frame 412 at outer perimeter 413. Sheet 414 is also not attached to an upstream end 407 of valve body 404. Thereby a pocket region 416 is defined between sheet 414 and at least inner perimeter 411, in which sheet 414 is not attached to frame 412 or frame 406.

Assembly 402 is configured such that, in the compressed state thereof (FIG. 13A), frame 412 is disposed generally alongside at least a portion of frame 406. Frame 412 is configured such that in the compressed state, outer perimeter 413 defines a downstream end of the frame. Therefore, when frame 412 expands, the downstream end of the frame expands radially outward more than does the upstream end of the frame. In the compressed state, sheet 414 is disposed alongside and outside of at least part of frame 406.

FIGS. 14A-B show a prosthetic valve assembly 422 an expanded state thereof, implanted at native valve 10, in accordance with some applications of the invention. Assembly 422 comprises a valve body 424 comprising a first frame 426, an upstream support 430 comprising a second frame 432, and a sheet 434.

Frame 426 of valve body 424 has an upstream end 427 and a downstream end 429. In the expanded state, in the absence of external forces, an outer perimeter 433 of second frame 432 of upstream support 430 is disposed closer to downstream end 429 than is an inner perimeter 431 of the second frame. For example, upstream support 430 may define a frustum, the larger base of which is disposed closer to downstream end 429 (and closer to a ventricular end of an atrioventricular axis) than is the smaller base of the frustum. For some applications, the assembly is thus configured such that, when placed at the native valve, outer perimeter 433 of the upstream support contacts the upstream surface of the native valve (e.g., the valve annulus), and the inner perimeter of the upstream support does not (FIG. 14A). For some such applications, frame 432 may be flat annular in the absence of external forces, and in the expanded state, sheet 434 retains the second frame in the frustoconical shape by inhibiting expansion of the second frame (e.g., expansion of at least outer perimeter 433 thereof). For some applications, frame 432 curves downward toward the tissue that outer perimeter 433 contacts (configuration not shown).

Sheet 434 is not attached to inner perimeter 431 of frame 432, but rather is circumferentially attached to frame 432 at a radius that is greater than that of the inner perimeter. For example, sheet 434 may be attached to frame 432 at outer perimeter 433. Sheet 434 is also not attached to upstream end 427 of valve body 424. Thereby a pocket region 436 is defined between sheet 434 and at least inner perimeter 431, in which sheet 434 is not attached to frame 432 or frame 426.

For some such applications, such a configuration provides a spring functionality that allows valve body 424 to move along an atrioventricular axis while outer perimeter 433 and/or portions of sheet 434 remain in contact with tissue (FIG. 14B). For example, assembly 422 may be implanted using techniques described with reference to FIGS. 8A-H, mutatis mutandis, and the spring functionality may allow movement of valve body 424 ventricularly during tensioning of tethers 282 while maintaining contact between outer perimeter 433 and the atrial surface. Similarly, such a configuration may allow oscillation of valve body 424 along the atrioventricular axis (e.g., caused by beating of the heart and the resulting blood flow), while maintaining constant contact between outer perimeter 433 and the tissue.

For some applications, a compressed state of assembly 422 is as described for one or more of the prosthetic valve assemblies described with reference to FIGS. 10A-13B, mutatis mutandis. For example, for some applications frame 426 of body 424 is coupled to frame 432 of support 430 prior to implantation (e.g., assembly 422 is provided with frame 426 coupled to frame 432), such as described for assembly 382 and/or assembly 402, mutatis mutandis. Alternatively, frame 426 is intracorporeally coupled to frame 432, e.g., as described for assembly 302 and/or assembly 342, and/or with reference to FIG. 1F, mutatis mutandis.

For some applications, assembly 422 is implanted as described for one or more of the prosthetic valve assemblies described with respect to FIGS. 10A-13B, mutatis mutandis.

Reference is again made to FIGS. 9A-B, 10A-B, and 11A-B. As described hereinabove, in its compressed state, assembly 202 defines an articulation zone in which (a) at least part of sheet 214 is disposed, and (b) neither frame 206 of body 204 nor frame 212 of support 210 is disposed, and about which body 204 and support 210 are articulatable with respect to each other. It is to be noted that in their compressed states, assemblies 302 and 342 also define respective articulation zones 336, 376. For each assembly, at least part of the respective sheet is disposed in the articulation zone, neither the respective frame of the valve body nor the respective frame of the support is disposed in the articulation zone, and the respective valve body and support are articulatable with respect to each other, about the articulation zone.

Reference is again made to FIGS. 10A-B, 11A-B, 12A-B, 13A-B, and 14A-B. As described hereinabove, assemblies 302, 342, 382, 402 and 422 each define a respective pocket region between the respective sheet and at least the inner perimeter of the frame of the upstream support. As also described hereinabove, (e.g., with reference to assembly 202), placement of the flexible sheet of the prosthetic valve assembly in contact with tissue provides stabilized contact with the tissue, and thereby improves tissue growth and sealing. Provision of a pocket region such as those described hereinabove is hypothesized to further improve sealing (e.g., by further facilitating tissue growth). For example, such configurations (1) may provide a greater surface area of the flexible sheet and/or a greater tissue-contact area of the sheet (e.g., due to an angle of the sheet), and/or (2) may hold the flexible sheet under less tension (e.g., compared to assembly 202), such that the sheet is freer to move with movement of the valve assembly and/or tissue, thereby dampening movements that may otherwise inhibit tissue growth and/or sealing. This is illustrated in FIGS. 14A-B, which show an example of the contact between flexible sheet 434 and tissue (e.g., leaflets 14). For some applications, the sheet is elastic, so as to further facilitate maintenance of contact despite movement of the frames of the prosthetic valve assembly with respect to the native valve.

As described hereinabove, the respective pocket region of each assembly 302, 342, 382, 402 and 422 is defined by the manner in which the sheet of the assembly is coupled to the frames of the assembly. When the assembly is in the expanded state thereof, the sheet is typically frustoconical and/or funnel-shaped. This shape is defined by a lateral wall (i.e., the sheet itself), and first and second apertures (at either end of the shape), the first aperture being larger than the second aperture. A portion of the sheet that defines the first aperture is circumferentially attached to the frame of the upstream support at a radius that is greater than a radius of the inner perimeter of the support. A portion of the sheet that defines the second aperture is circumferentially attached to the frame of the valve body at a longitudinal site that is closer to a downstream end of the valve body than is the longitudinal site at which the upstream support is coupled to the valve body.

For some applications, the sheet extends radially past the radius at which it is coupled to the upstream support. As described hereinabove, for some applications the sheet is coupled to the upstream support at an outer perimeter of the upstream support. For some applications, the sheet extends radially past the outer perimeter of the upstream support.

Reference is made to FIGS. 15A-C, which are schematic illustrations of a tool 460 for facilitating application of force between prosthetic valve assembly 202 and guide members 256 (e.g., tethers 282 thereof), in accordance with some applications of the invention. For some applications, tool 460 serves as a tension-detector tool. For some applications, tool 460 alternatively or additionally serves as a tension-applicator tool.

The boxes on the right-hand side of FIGS. 15A-C shows assembly 202 being implanted at native valve 10, as described hereinabove. The box of FIG. 15A shows assembly 202 having been deployed (e.g., delivered and expanded) at the native valve, e.g., as described with reference to FIG. 8D. The box of FIG. 15B shows tethers 282 of guide members 256 having been tensioned with respect to assembly 202, e.g., as described with reference to FIG. 8E. The box of FIG. 15C shows tubular member 280 of each guide member 256 having been withdrawn proximally so as to (1) facilitate locking of the respective locking member 262 to its respective tether 282, e.g., as described with reference to FIG. 8F, and (2) decouple pull-wire 284 from tether 282, e.g., as described with reference to FIG. 8G.

The left-hand side of FIGS. 15A-C shows (1) a proximal end of system 200 (e.g., a proximal end of delivery tool 230 thereof, e.g., including a handle 231 thereof), including a proximal portion of pull-wire 284, a proximal portion of tubular member 280, and a proximal portion of reference-force tube 260, and (2) tool 460 coupled to the proximal portion of pull-wire 284 and the proximal portion of reference-force tube 260. The left-hand side of FIGS. 15A-C shows one tool 460 being used with one pull-wire 284, tubular member 280, tube 260 and tool 460 (and one handle 231). However it is to be noted that tool 460 is typically used with each guide member (e.g., each tether 282), either sequentially, or by providing more than one tool 460 for use at generally the same time.

Tool 460 comprises a pull-wire-coupling element 462, configured to be coupled to the proximal portion of pull-wire 284 (e.g., to a grip 464 of the pull-wire), and a reference-force-tube-coupling element 466, configured to be coupled to the proximal portion of reference-force tube 260 (e.g., to a grip 468 of the tubular member). Coupling elements 462 and 466 are coupled to each other via an adjustment member 470 that facilitates adjustment of a distance between the coupling elements. Adjustment member 470 may comprise screw threads, a ratchet mechanism, or any other suitable adjustment mechanism.

Pull-wire-coupling element 462 is coupled to the proximal portion of pull-wire 284 (e.g., to a grip 464 of the pull-wire), and reference-force-tube-coupling element 466 is coupled to the proximal portion of reference-force tube 260 (e.g., to a grip 468 of the tubular member), typically subsequently to delivery of prosthetic valve assembly 202 to the native valve (FIG. 15A). A distance d7 exists between coupling elements 462 and 466.

Subsequently, adjustment member 470 is used (e.g., actuated) so as to change (e.g., increase) the distance between coupling elements 462 and 466 (FIG. 15B; distance d8). This reduces the length of tether 282 that is disposed distal to the distal end of reference-force tube 282, (and thereby the length of the tether that is disposed between eyelet 222 and anchor 48), thereby applying tension to the tether). Typically, a length indicator 471 (e.g., a rule) is provided on tool 460 that indicates the change in length that has been made. Further typically, tool 460 comprises a force detector 472 that detects and displays a force differential (e.g., a linear force differential) between coupling elements 462 and 466, and thereby provides an indication of the tensile state of tether 282.

When a desired tensile state of tether 282 has been achieved (e.g., an absolute value and/or a value relative to other detected forces, such as the tensile state of the other tether 282), the tension is fixed, and pull-wire 284 is decoupled from tether 282 (FIG. 15C). As described with reference to FIG. 8F, this is achieved by withdrawing tubular member 280 proximally with respect to tether 282, pull-wire 284 and locking member 262. FIG. 15C shows a proximal portion of tubular member 280 (e.g., a grip 474 thereof) being withdrawn proximally with respect to (1) pull-wire 284 (and therefore with respect to tether 282 to which the pull-wire is coupled), and (2) reference-force tube 260 (and therefore with respect to locking member 262 which the distal end of the reference-force tube abuts). This is illustrated by a distance d10 between grips 468 and 474 in FIG. 15C, which is greater than a distance d9 between grips 468 and 474 in FIG. 15B. This thereby facilitates (1) locking of locking member 262 to tether 282, and (2) subsequently (i.e., after further proximal withdrawal of the tubular member), decoupling of pull-wire 284 from the tether.

For some applications, this is performed by one continuous movement of tubular member 280. For some applications, visual and/or tactile indicators allow the operating physician to lock locking member 262 to tether 282 without decoupling pull-wire 284 from the tether. This may advantageously allow the physician to further increase the tension on the tether (e.g., by using the ratchet functionality described with reference to FIG. 8F) before decoupling the pull-wire from the tether.

Although tool 460 is described hereinabove for facilitating implantation of assembly 202, the tool may also be used, mutatis mutandis, in combination with other systems described herein, such as system 40 described hereinabove and/or assembly 552 described hereinbelow (e.g., for tensioning tethers 582 thereof).

Reference is now made to FIG. 16, which is a schematic illustration of a system 480 comprising a prosthetic valve assembly 482 and one or more springs 484 via which the prosthetic valve assembly is elastically coupled to one or more tissue anchors 48, in accordance with some applications of the invention. For illustrative purposes, system 480 is shown as comprising system 200 (e.g., comprising prosthetic valve assembly 202), described hereinabove, with the addition of springs 484. However it is to be noted that the techniques described with reference to FIG. 16 may alternatively or additionally be used to facilitate implantation of other prosthetic valves and/or prosthetic valve assemblies described herein, mutatis mutandis (e.g., springs 484 may be added to other prosthetic valves and/or prosthetic valve assemblies described herein).

Each spring 484 is disposed outside of valve body 204, typically laterally outside the valve body, and further typically between eyelet 222 and locking member 262 (e.g., coupling the eyelet to the locking member). For example, and as shown, spring 484 may have a longitudinal axis that is generally parallel with lumen 208 of the valve body. When reference-force tube 260 provides the reference force to locking member 262 during tensioning of guide member 256 (e.g., tether 282 thereof), the reference force is transferred via spring 484. Typically spring 484 serves as a compression spring, such that increasing tension on guide member 256 (e.g., the tether 282 thereof) compresses the spring.

For some applications, spring 484 provides an indication of a state of the spring that is observable and recognizable using imaging techniques (e.g., fluoroscopy). That is, spring 484 is configured to change shape in response to a force applied to it, in a manner that is observable and recognizable using fluoroscopy. This functionality therefore provides intracorporeal measurement of tension on tether 282 (in a manner that is itself observable extracorporeally). It is hypothesized that for some applications, this intracorporeal measurement advantageously detects the tension with reduced interference (e.g., noise) that may be present in extracorporeal measurement techniques. For example, for some applications, extracorporeal measurement of the tension by extracorporeally measuring tension on pull-wire 284 (e.g., tension with respect to reference-force tube 280) may be inhibited by interference by inherent elasticity of the pull-wire and other elements of the system, and by friction between elements of the system.

For some applications, the shape of spring 484 alone provides the tension indication. For such applications, spring 484 may be coated with a radiopaque material such as tantalum. For some applications, spring 484 has (e.g., comprises and/or is coupled to) one or more radiopaque markers 486, and the juxtaposition of the markers facilitates extracorporeal detection of the shape of the spring. For example, when spring 484 serves as a compression spring, a reduction of a distance d11 (compare d11 to d11') between adjacent markers 486 indicates an increase in tension on tether 282.

For some applications, an intracorporeal reference (e.g., a scale) 488 is provided, to facilitate identification of shape change of spring 484 (e.g., to facilitate quantification of the shape change by (1) comparing the position of markers 486 to reference 488, and/or (2) comparing the juxtaposition of markers 486 to the juxtaposition of elements of the scale. For example, and as shown in FIG. 16, scale 488 may itself also comprise a plurality of radiopaque markers 490 disposed on valve body 204 (e.g., coupled to frame 206) at known (e.g., regular) intervals, and distance d11 (observed using fluoroscopy) is compared to a distance d12 between adjacent markers 490 (observed using fluoroscopy) in order to determine the actual change in distance d11. That is, an observed relative change between d11 and d12 is used to determine an actual absolute change in d11.

For some applications, spring 484 also alters the relationship between (a) changes in the length of tether 282 disposed between eyelet 222 and anchor 48 and (b) tension on the tether. For example, for system 200 described hereinabove (i.e., in the absence of spring 484), starting with slack on tether 282 between the eyelet and the anchor, as the length of the tether between the eyelet and the anchor is reduced, tension on tether 282 may remain constant and low despite the reduction in the length of the tether, until the tether encounters resistance provided by tissue anchor 48, at which point tension increases relatively quickly for every unit reduction in length. For system 480 (i.e., using spring 484), the relationship between (a) the length of tether 282 disposed between the eyelet and the anchor, and (b) the tension on the tether, is smoother (e.g., the transition between before and after resistance from the anchor is encountered is smoother). That is, spring 484 absorbs some of the applied tensile force and in exchange provides additional length to the tether. This is hypothesized to advantageously provide more flexibility to the operating physician to adjust the length of tether 282 disposed between the eyelet and the anchor, with reduced changes to tension on the tether.

For some applications, spring 484 is configured so as to provide a desired tension (e.g., a desired resistance) over a range of lengths of tether 282 (e.g., over a range of compression states of the spring). That is, the spring constant of the spring is sufficiently low that a change in resistance is minimized per unit length change. For example, the spring constant may be less than 50 g/mm.

For some applications, the desired tension is above 300 g force and/or below 700 g force, e.g., above 400 g force, and/or below 600 g force, such as between 400 g force and 600 g force, e.g., about 500 g force. For example, a desired target tether tension may be 500 g force, and spring 484 may be configured to provide, over a range of compression states of the spring, resistance that results in a tether tension that is within a margin tension (e.g., within 200 g force, such as within 100 g force) of the target force.

For some applications, spring 484 is configured to provide a distinct indication, observable using fluoroscopy, when the spring experiences a force that is within a margin force (i.e., a force that corresponds to being within the margin tension). For example, spring 484 may undergo (e.g., suddenly undergo) a more obvious shape change when such a force is experienced.

For some applications, spring 484 is configured to act as a constant-force spring or similar, so as to facilitate the behavior described above. For some applications, spring 484 is pre-loaded (e.g., pre-tensioned or pre-compressed).

Reference is made to FIG. 17, which is a schematic illustration of a system 500 comprising a prosthetic valve assembly 502 and one or more springs 504 via which the prosthetic valve assembly is elastically coupled to one or more tissue anchors 48, in accordance with some applications of the invention. For illustrative purposes, system 500 is shown as comprising system 200 (e.g., comprising prosthetic valve assembly 202), described hereinabove, with the addition of springs 504. However it is to be noted that the techniques described with reference to FIG. 17 may alternatively or additionally be used to facilitate implantation of other prosthetic valves and/or prosthetic valve assemblies described herein, mutatis mutandis (e.g., springs 504 may be added to other prosthetic valves and/or prosthetic valve assemblies described herein).

Each spring 504 is disposed outside of valve body 204, typically laterally outside the valve body, and further typically is disposed functionally between locking member 262 and anchor 48 (e.g., between locking member 262 and eyelet 222, or between eyelet 222 and anchor 48. For some applications, and as shown, spring 504 is a cantilever spring, and may be defined by a protrusion of frame 206 that extends away (e.g., laterally away) from valve body 204. That is, spring 504 may comprise an elastically-deformable appendage. For some applications, the protrusion is shaped to define a loop 506 that provides spring 504 with constant-force-spring functionality.

Typically, spring 504 provides similar functionality to spring 484, described hereinabove, mutatis mutandis. For example, for some applications, spring 504 provides an indication of a state of the spring that is observable and recognizable using fluoroscopy. That is, spring 504 is configured to change shape in response to a force applied to it, in a manner that is detectable and recognizable using fluoroscopy. For some applications, spring 504 also alters the relationship between (a) the length of tether 282 disposed between eyelet 222 and anchor 48 and (b) tension on the tether, e.g., as described hereinabove with reference to spring 484, mutatis mutandis.

Reference is made to FIGS. 18A-B, which are schematic illustrations of springs coupled to tether 282 so as to elastically couple tissue anchor 48 (e.g., a tissue-engaging element 49 thereof) to prosthetic valve assembly 202 (e.g., to valve body 204 thereof), in accordance with some applications of the invention. FIG. 18A shows a spring 520 disposed partway along tether 282. FIG. 18B shows a spring 530, one end of which is coupled to anchor 48 (e.g., to an anchor head 47 thereof) and the other end of which is coupled to tether 282. Springs 520 and 530 are typically tension springs. For some applications, spring 530 is rigidly coupled to anchor head 47.

For illustrative purposes, springs 520 and 530 are shown being used with system 200 (e.g., with prosthetic valve assembly 202), described hereinabove. However it is to be noted that the techniques described with reference to FIGS. 18A-B may alternatively or additionally be used to facilitate implantation of other prosthetic valves and/or prosthetic valve assemblies described herein, mutatis mutandis.

Typically, springs 520 and 530 provide similar functionality to springs 484 and 504, described hereinabove, mutatis mutandis. For example, for some applications, springs 520 and 530 provide an indication of a state of the spring that is observable and recognizable using fluoroscopy. That is, the springs are configured to change shape in response to a force applied to them, in a manner that is detectable and recognizable using fluoroscopy. For some applications, springs 520 and 530 also alter the relationship between (a) the length of tether 282 disposed between eyelet 222 and anchor 48 and (b) tension on the tether, e.g., as described hereinabove with reference to springs 484 and 504, mutatis mutandis.

Reference is again made to FIGS. 16, and 18A-B. Springs 484, 520 and 530 are shown as helical springs. However it is to be noted that each of these springs may have a shapes other than a helix. For example, each of these springs may have a zigzag shape. For some applications, the use of a spring that defines a repeating (e.g., oscillating) pattern such as a helix or a zigzag facilitates fluoroscopic identification of the state of the spring. For example, whereas a linear elastically-stretchable member (e.g., a strip of elastic rubber) remains linear when stretched, the shape of a helical or zigzag spring changes as force increases.

Figure 19A:
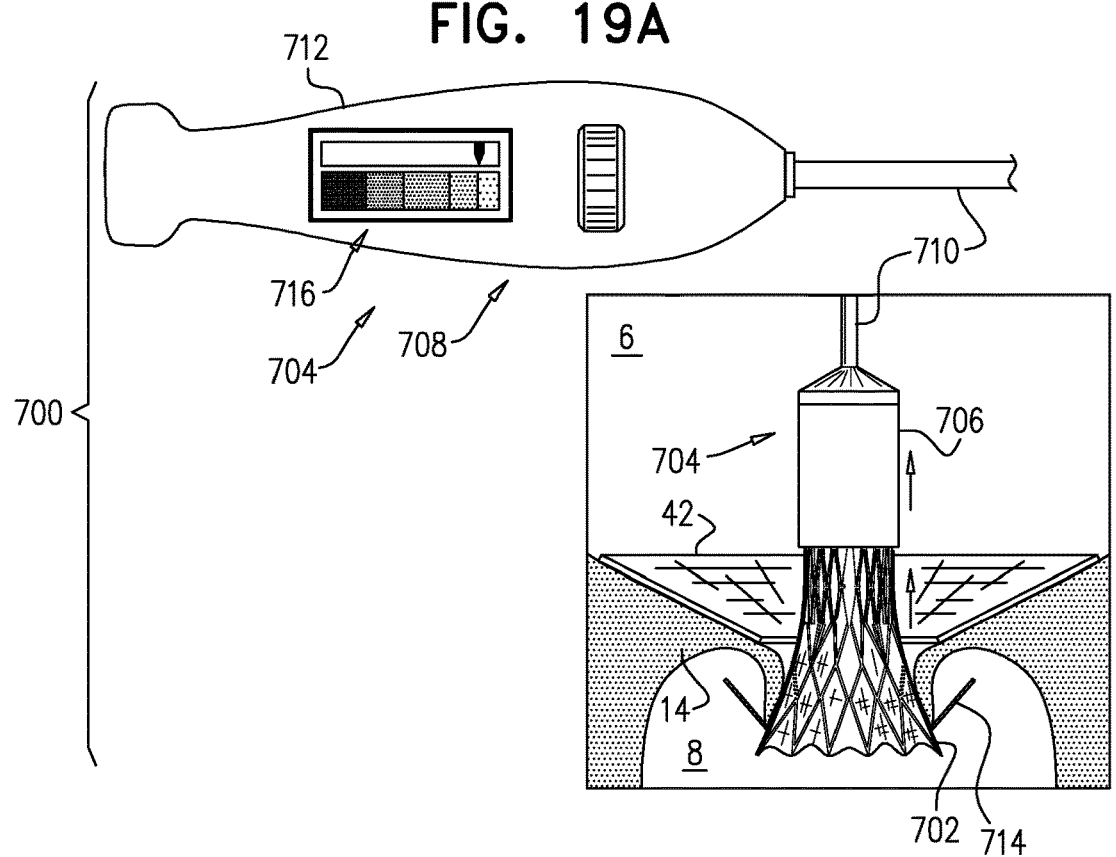
FIGS. 19A-B are schematic illustrations of a system for facilitating delivery of a prosthetic valve body, in accordance with some applications of the invention.
Figure 19B:
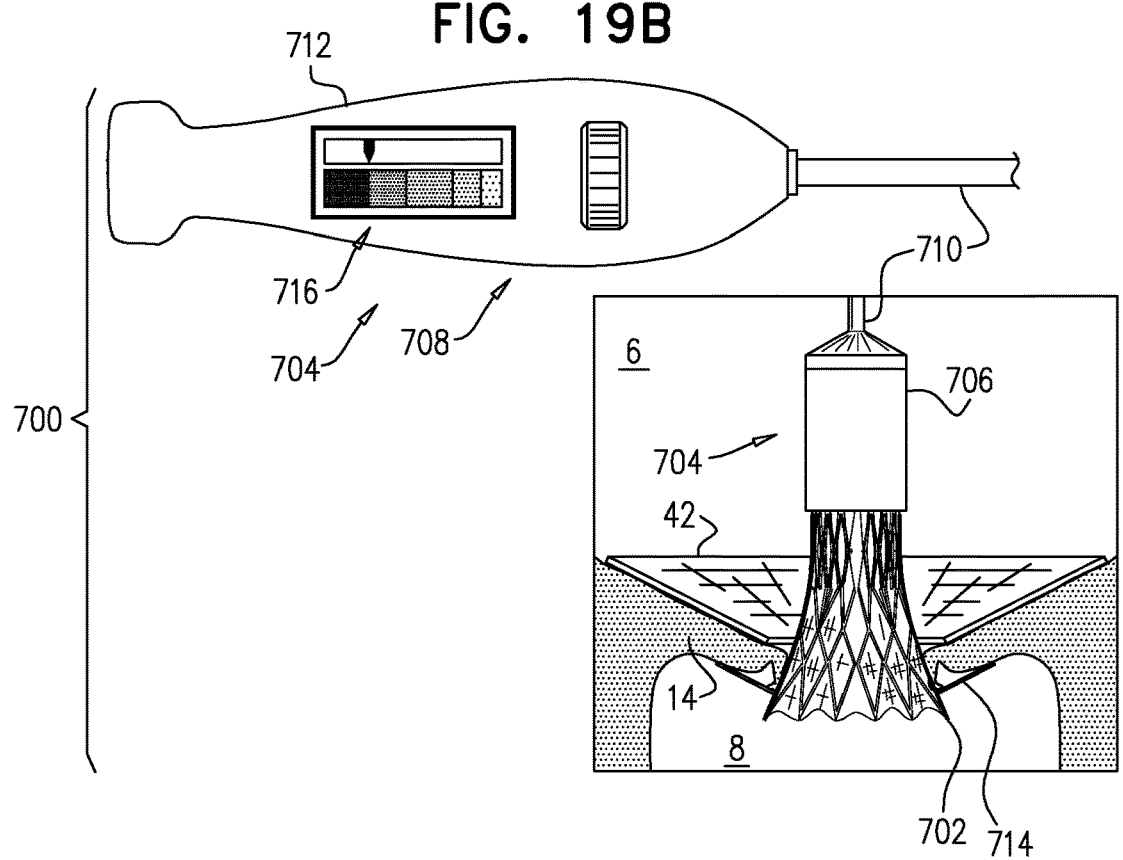

Reference is made to FIGS. 19A-B, which are schematic illustrations of a system 700 for facilitating delivery of a prosthetic valve body 702, in accordance with some applications of the invention. System 700 comprises a delivery tool 704 that comprises a distal housing 706, configured to house valve body 702 in a compressed state thereof, a proximal portion 708, and a flexible longitudinal portion 710 (e.g., a catheter) therebetween. Proximal portion 708 typically comprises a handle 712. Housing 706 is configured to be transluminally advanced to the heart of the subject (e.g., as described herein, mutatis mutandis, while proximal portion 708 remains outside the body of the subject. Proximal portion 708 (e.g., handle 712 thereof) comprises a force detector 716 that detects a force between (a) the proximal portion, and (b) housing 706 and/or valve body 702 coupled thereto. Typically, force detector 716 detects tension. That is, the force detector detects resistance of valve body 702 to a proximally-directed force applied by tool 704 (e.g., when tool 704 is moved proximally).

Housing 706 is advanced through native valve 10 and into ventricle 8, and valve body 702 is partly advanced out of the housing, and automatically expands toward an expanded state (FIG. 19A). Valve body 702 is coupled to a plurality of tissue-engaging elements (e.g., tissue-engaging legs) 714 that protrude radially out from the valve body when exposed from housing 706. Tissue-engaging elements 714 are configured to engage leaflets 14 of the native valve, thereby facilitating anchoring of the valve body.

Typically system 700 is used for implantation of valve body 702 at a native valve at which a prosthetic valve support (e.g., an upstream support) has already been delivered, and to which the valve body is intracorporeally coupled (e.g., as described elsewhere herein). For example, and as shown in FIGS. 19A-B, system 700 may be used to implant valve body at native valve 10 after implantation of support 42 at the native valve. As described with reference to FIGS. 1A-D, support 42 is secured against the upstream surface of native valve 10 by being anchored, via tethers (e.g., longitudinal members 102), to ventricular muscle tissue. (The tethers are not visible in FIGS. 19A-B.)

Pulling housing 706 and valve body 702 proximally (i.e., atrially) while tissue-engaging elements 714 are protruding pushes the tissue-engaging elements against leaflets 14, reducing a height of a gap between the tissue-engaging elements and support 42, and sandwiching the leaflets against the support (FIG. 19B). Resistance to proximal movement of valve body 702 (e.g., due to support 42 and leaflets 14) is detected and displayed by force detector 716. The operating physician is thereby able to couple valve body 702 to support 42 (e.g., by fully deploying the valve body within the opening defined by the support) while a desired degree of tension is observed. The coupling of the valve body to the support fixes the degree of tension, such that leaflets 14 remain sandwiched, and the valve body remains secured to the native valve.

For some applications, alternatively or additionally to using extracorporeal force detector 716, the force encountered by tissue-engaging elements 714 is observed using fluoroscopy (e.g., by observing a shape and/or position of the tissue-engaging elements). For such applications, the tissue-engaging elements are typically configured to facilitate such observation, as described herein for various springs. For some applications, elements 714 are configured (e.g., shaped) to define a loop, e.g., as described hereinabove for springs 504, mutatis mutandis.

For some applications, valve body 702 is coupled via tethers to tissue anchors that are anchored to ventricular muscle tissue, as described elsewhere herein. For some such applications, a spring couples the valve body to each tissue anchor (e.g., as described with reference to FIGS. 16-18B, mutatis mutandis). For some applications in which a spring couples the valve body to each tissue anchor, reducing the height of the gap automatically (and typically immediately) alters a force on the spring (e.g., when the valve body is locked to the tether before reducing the height of the gap). For some applications in which a spring couples the valve body to each tissue anchor, reducing the height of the gap does not necessarily alter the force on the spring (e.g., when the valve body is slidably couplable to the tether until after the height is reduced, and is subsequently locked to the tether. For example, tool 230 and/or tool 460 may be used, mutatis mutandis, to measure and control tension and length of the tether until the valve body is locked to the tether.

It is to be noted that the above technique may be used for prosthetic valve assemblies in which the valve body is pre-coupled to the upstream support, mutatis mutandis. For such applications, the proximal pulling force is not a sandwiching force, but rather is a testing force, typically used in combination with another testing force, e.g., as described hereinbelow, e.g., with reference to FIG. 20.

Reference is made to FIG. 20, which is a schematic illustration showing examples in which force measurements described herein may be combined to facilitate implantation of a prosthetic valve, in accordance with some applications of the invention. Each apparatus and technique described herein for measuring force (e.g., tension) is described in a particular context (e.g., with reference to a particular prosthetic valve assembly, prosthetic valve body, and/or support) for the purpose of clarity. It is to be understood that the apparatus and techniques described in one context may be used to measure force in another context (e.g., to facilitate controlled implantation of a different prosthetic valve assembly, prosthetic valve body, and/or support), and may be combined with one or more of the other apparatus and/or techniques.

FIG. 20 shows examples of combinations of apparatus and techniques described herein, which include:

(1) Extracorporeal detection of tension on tethers (box 722). This is described, for example, with reference to force detector 472 of tool 460 of FIGS. 15A-C.

(2) Extracorporeal detection of atrially-directed force of valve-mounted tissue-engaging elements against tissue (e.g., leaflets or annulus) of the native valve (box 742). This is described, for example, with reference to FIGS. 19A-B.

(3) Extracorporeal detection of sandwiching force (box 720). That is, extracorporeal detection of the force of tissue-engaging elements coupled to the valve body against the native valve tissue and/or the upstream support. This is described, for example, (a) with reference to FIGS. 19A-B, and (b) with reference to force detector 472 of tool 460 (FIGS. 15A-C) being used to augment the apparatus and facilitate the techniques described with reference to FIGS. 21A-B.

(4) Intracorporeal detection (observed using imaging) of tension on tethers (724). This is described, for example, with reference to the springs described with reference to FIGS. 16, 17, and 18A-B.

(5) Intracorporeal detection (observed using imaging) of atrially-directed force of valve-mounted tissue-engaging elements against tissue (e.g., leaflets or annulus) of the native valve (box 744). This is described, for example, with reference to FIGS. 19A-B.

(6) Intracorporeal detection (observed using imaging) of sandwiching force (box 726). This is described, for example, with reference to one or more of the springs described with reference to FIGS. 16, 17, and 18A-B being used to augment the apparatus and facilitate the techniques described with reference to FIGS. 21A-B.

(7) Intracorporeal detection (observed using imaging) of ventricularly-directed force of the upstream support against the native annulus (box 728). For some applications, this is achieved by using imaging (e.g., fluoroscopy) to extracorporeally observe intracorporeal changes in the shape of the upstream support (e.g., changes described with reference to FIGS. 8D-E, 14A-B, and/or 15A-B), in a similar manner to that described for extracorporeally observing changes in the shape of springs (e.g., described with reference to FIGS. 16, 17, and 18A-B), mutatis mutandis.

It is hypothesized that combining two or more of the force-measurement techniques described herein may provide synergistic benefits when implanting an implant (e.g., a prosthetic valve assembly, prosthetic valve body, and/or prosthetic valve support), so as to facilitate controlled implantation (box 730). The ability to control various forces that secure the implant allows, inter alia, the forces to be spread as desired by the operating physician. For example, it may be desirable:

that tension is equally (or otherwise) distributed between the tethers, that tension on a given tether is optimized (discussed hereinbelow), that, during operation of the valve, resistance to a force that pushes the valve body in an atrial direction (e.g., during ventricular systole) is optimally balanced between the various anchoring elements, such as between (a) tissue anchors 48 and tethers coupled thereto and (b) other tissue-engaging elements (e.g., tissue-engaging elements 714 (FIGS. 19A-B) or tissue-engaging elements 580 (FIGS. 21A-B), thereby balancing the anchoring forces between different tissue sites, and/or that sandwiching forces are greater than, equal to, or less than the tensile force provided by the tethers.

It is to be noted that the example combinations provided hereinabove are intended to be illustrative, and not limiting.

As described hereinabove, it may be desirable to that tension on a given tether is optimized. For example, it may be desirable that tension on the given tether to be maximized within a tension range that is known to be supported by (1) the tissue anchor to which the tether is coupled, and (2) the tissue to which the tissue anchor is anchored. For some applications, subsequently to anchoring the tissue anchor, the operating physician applies a testing pulling force to the tissue anchor. The testing pulling force is used to confirm that the anchored tissue anchor is capable of supporting an overload tension that is greater than an expected tension that it is expected that the anchor will encounter during operation. The expected tension may be determined at least in part based on possible ventricular blood pressure and the cross-sectional area of the lumen of the valve body.

For some applications, the testing pulling force is applied (e.g., via the tether or via the anchor manipulator), and movement of the tissue anchor is observed using imaging, e.g., as described with reference to FIGS. 1A-B). For some applications, the testing pulling force is applied while measuring tension using an extracorporeal force detector such as detector 472 (FIGS. 15A-C), mutatis mutandis.

For some applications, the testing pulling force is applied by applying tension to the tether, and the tension is measured using intracorporeal springs and fluoroscopy, as described hereinabove, mutatis mutandis. It is to be noted that, for such applications, the same technique is used (1) to confirm that the anchored tissue anchor is capable of supporting the overload tension, and (2) to facilitate the application of the tension (e.g., the anchoring tension) that will be fixed when the locking member is locked to the tether.

As described hereinabove, it may be desirable that, during operation of the valve, resistance to a force that pushes the valve body in an atrial direction (e.g., during ventricular systole) is optimally balanced between the various anchoring elements. For some applications, the following technique is used:

(1) Anchor at least one tissue anchor coupled to a respective at least one tether (e.g., within guide members).

(2) Advance a valve body that comprises at least one tissue-engaging element (e.g., a tissue-engaging leg) over at least part of the tether (e.g., by advancing over a guide member), such that a length of the tether is disposed between the valve body and the tissue anchor. Examples of such tissue-engaging elements are described with reference to FIGS. 19A-B and 21A-B. The valve body may or may not be pre-coupled to an upstream support.

(3) Apply a first tension to the tether (measured intracorporeally or extracorporeally).

(4) Apply proximal pulling force to the valve body such that the tissue-engaging element applies force against tissue of the native valve, such as leaflets and/or annulus. This pulling typically automatically increases the tension on the tether.

(5) While applying the proximal pulling force, intracorporeally and/or extracorporeally measure (a) force of tissue-engaging element against tissue, and (b) tension on the tether (e.g., the change in tension on the tether caused by the proximal pulling.

(6) At least in part based on measurements (a) and (b) of step 5, adjust the length of the tether disposed between the valve body and the tissue anchor, and/or lock the valve body to the tether (i.e., fix the length of the tether disposed between the valve body and the tissue anchor).

It is hypothesized that the above technique provides a prediction of the force distribution between the various anchoring elements that will exist during operation of the prosthetic valve assembly (e.g., during the lifetime thereof). For example, the technique provides a prediction of force distribution between the ventricular anchors and the valve-mounted tissue-engaging elements if/when atrially-directed force increases (e.g., as will be encountered during ventricular systole and/or increases in systemic blood pressure). Based on this indication, the technique facilitates adjustment of this distribution, via adjustment of the length of tethers disposed between the valve body and the tissue anchors.

Figure 21A:
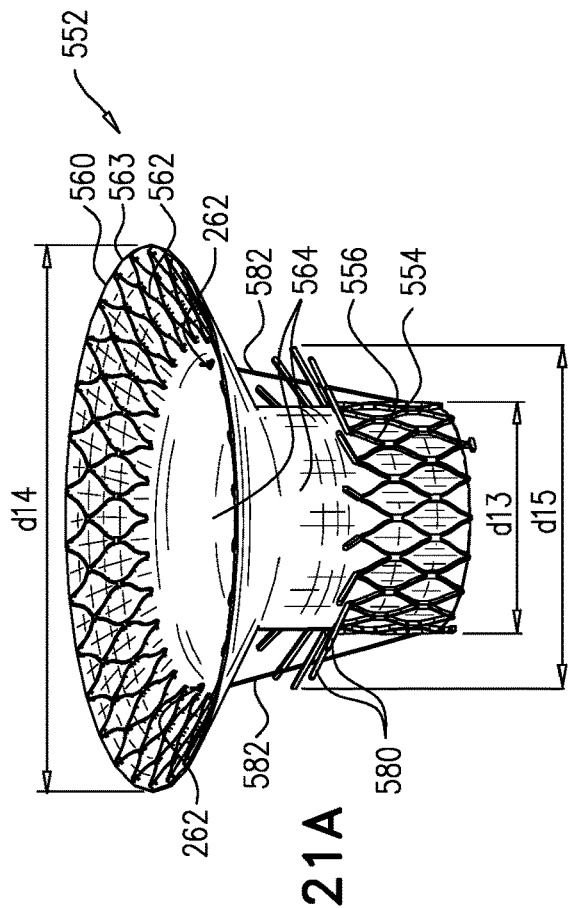
FIGS. 21A-B are schematic illustrations of a prosthetic valve assembly, in accordance with some applications of the invention.
Figure 21B:
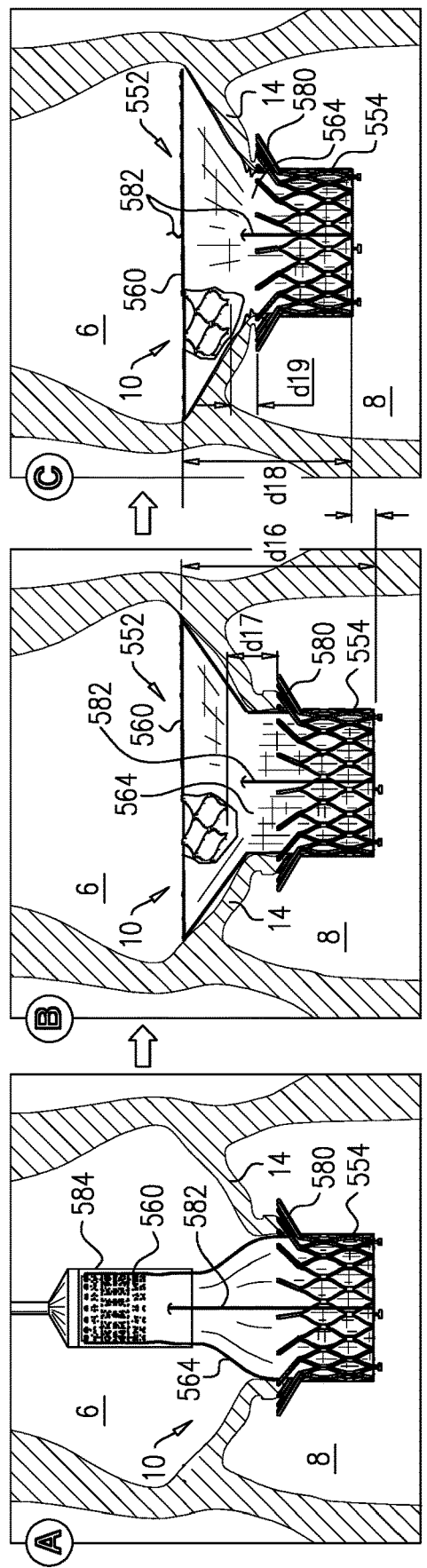

Reference is made to FIGS. 21A-B, which are schematic illustrations of a prosthetic valve assembly 552, in accordance with some applications of the invention. Prosthetic valve assembly 552 comprises (1) a prosthetic valve body 554, which comprises a first frame 556 (e.g., a wire frame), and is shaped to define a lumen therethrough, (2) an annular upstream support 560, which comprises a second frame 562 (e.g., a wire frame), is shaped to define an opening through the upstream support, and is configured to be placed against an upstream surface (e.g., an atrial surface) of native valve 10 (e.g., of an annulus thereof), and (3) a flexible sheet 564 that couples the first frame to the second frame. FIG. 21A shows assembly 552 in an expanded state thereof (e.g., in the absence of external forces, such as if the assembly were resting on a table surface). In the expanded state of assembly 552 (and thereby of body 554), frame 556 of body 554 is generally cylindrical, and has a diameter d13. In the expanded state of assembly 552 (and thereby of upstream support 560), frame 562 of support 560 is typically generally annular, and has an outer perimeter 563 that has a diameter d14, which is greater than diameter d13.

Assembly 552 comprises one or more tissue-engaging elements 580 (e.g., legs) that protrude radially outward from valve body 554 so as to define a diameter d15, which is greater than diameter d13. Typically, and as shown in FIGS. 21A-B, frame 556 of body 554 is shaped to define tissue-engaging elements 580. Assembly 552 further comprises one or more tensioning elements (e.g., contraction wires) such as one or more tethers 582, a first portion (e.g., a distal end) of each tether being coupled to valve body 554, and a second portion of each tether being coupled (e.g., slidably coupled) to a portion of assembly 552 that is configured to be placed upstream of valve body 554. For example, and as shown, the second portion of each tether 582 may be slidably coupled to an upstream region of sheet 564. Alternatively or additionally, the second portion of each tether 582 may be slidably coupled to frame 562 of support 560. For some applications, this is facilitated by frame 562 being shaped to define one or more respective protrusions that protrude radially inward from the annular shape of the frame, to the site at which each tether 582 is shown in FIG. 21A passing through the sheet.

For some applications, except for (1) the presence of tissue-engaging elements 580 and tethers 582, and (2) the absence of eyelets 222, assembly 552 is identical to (e.g., comprises the same components as, and/or has identical functionality to) assembly 202, described hereinabove. Identically-named components of system 202 and system 552 are typically identical in structure and/or function.

For some applications, assembly 202 comprises tissue-engaging elements 580 and/or tethers 582. For some applications, assembly 552 comprises eyelets 222 and/or locking members 262 for sliding over and locking to guide members.

Both support 560 of assembly 552 and support 210 of assembly 202 may be flat annular (e.g., as shown for support 210) or frustoconical (as shown for support 560).

FIG. 21B shows assembly 552 being implanted. Following translumenal delivery to native heart valve 10, valve body 554 is typically deployed first (i.e., before support 560), as shown in state A of FIG. 21B. For some applications, valve body is deployed sufficiently far into the ventricle that tissue-engaging elements 580 can expand freely without interfering with leaflets 14 of the native valve, and valve assembly is subsequently moved atrially into the position shown in state A of FIG. 21B.

Subsequently, upstream support 560 is deployed, e.g., by a delivery housing 584 thereof being retracted (state B of FIG. 21B). Support 560 becomes placed against the upstream (e.g., atrial) surface of native valve 10, such as against the annulus of the valve and/or against the upstream surface of native leaflets 14. Typically, immediately subsequently to deployment of body 554 and support 560, assembly 552 has a total height d16 from a proximal end of support 560 to a distal end of body 554 (e.g., a height along an atrioventricular axis), and a distance d17 (e.g., a gap) measured along the height exists between a distal end of frame 562 and a proximal-most part of frame 554 (e.g., tissue-engaging elements 580 defined by the frame).

Subsequently, tethers 582 are tensioned so as to draw support 560 and body 554 closer to each other, thereby reducing the total height of assembly 552 to height d18, and reducing the distance between the distal end of frame 562 and the proximal-most part of frame 554 to a distance d19 (state C of FIG. 21B). This moves body 554 and tissue-engaging elements 580 closer to leaflets 14, thereby sandwiching the leaflets between the tissue-engaging elements and support 560, and thereby anchoring assembly 552 at the native valve. Sheet 564 maintains fluid communication (e.g., sealed fluid communication) through assembly 252, while also allowing the described contraction of the assembly. Typically, this characteristic is due to sheet 564 having tensile strength, but not compressive strength, and therefore rumpling when tethers 582 are tensioned.

Tensioning of tethers 582 may be accomplished by any suitable technique. For some applications, the tensioning is performed using control rods 86 and locking members 110, e.g., as described with reference to FIGS. 1C-D, mutatis mutandis. For some applications, the tensioning is performed using reference-force tubes and locking members, e.g., as described with reference to FIGS. 7B-8H, mutatis mutandis. For some applications, support 560 comprises a ratchet mechanism that facilitates the tensioning by allowing only one-way movement of tether 582 through the support. For some applications, assembly 552 comprises a spool mechanism for each tether, and tensioning is performed by rotating the spool mechanism.

For some applications, assembly 552 has a compressed state (e.g., for transluminal delivery) in which the assembly defines an articulation zone between frames 556 and 562, e.g., as described hereinabove for assembly 202, mutatis mutandis.

For some application, one or more of the techniques described hereinabove may be used to (1) control applied to tethers 582, and/or (2) facilitate intracorporeal measurement of tension on the tethers (and optionally fluoroscopic detection of that measurement). For example, assembly 552 may comprise a tension spring midway along each tether 582, and/or may comprise a compression spring at the coupling point of support 560 and the tether (e.g., between the support and a locking member 262 configured to lock a respective tether to the support). Alternatively or additionally, for applications in which the tensioning is performed using reference-force tubes and locking members (e.g., as described with reference to FIGS. 7B-8H), tool 460 may be used, mutatis mutandis, to extracorporeally detect the tension applied to tethers 582.

Reference is made to FIGS. 22A-B, which are schematic illustrations of a prosthetic valve assembly 602, comprising a prosthetic valve 603 having a tubular valve body 604 that comprises an upstream portion 606, a downstream portion 608, and an elastic portion 610 disposed between the upstream portion and the downstream portion, in accordance with some applications of the invention. Prosthetic valve 603 (e.g., valve body 604 thereof) is shaped to define a continuous lumen through portions 606, 610, and 608. Prosthetic valve 603 is configured to be implanted at native valve 10 such that upstream portion 606 is disposed in atrium 6 of the heart of the subject, and such that downstream portion 608 is disposed in ventricle 8 of the heart of the subject. For example, prosthetic valve 603 may be coupled to a prosthetic valve support 612 that has been previously placed against (e.g., coupled to) the native valve, and that defines an opening. Support 612 may comprise (1) a support described elsewhere herein (e.g., support 42 described with reference to FIGS. 1A-F and 19A-B, support 310 described with reference to FIGS. 10A-B, and/or support 350, described with reference to FIGS. 11A-B, and/or (2) a support described in U.S. Provisional Patent application 61/756,034 to HaCohen et al., from which the present application claims priority, and which is incorporated herein by reference.

For some applications, and as shown in FIG. 22B, prosthetic valve support 612 comprises one or more tissue-engaging elements 618, an annular upstream support portion 620, and a flexible stabilizing member 622, such as a stabilizing band, coupled to the tissue-engaging elements, and configured to form a ring that is shaped to define an opening therethrough. Tissue-engaging elements 618 may comprise, as shown in FIGS. 22A-B, clips configured to be coupled to leaflets 14 of the native valve.

Tubular valve body 604 typically comprises a frame 614, such as a stent-like wire frame. As shown in FIG. 22A, prosthetic valve 603 typically further comprises a covering 616, disposed over (e.g., covering) an inner surface of frame 614, thereby providing a sealed lumen from an upstream end to a downstream end of the tubular valve body. Typically, an excess of covering 616 is provided in the vicinity of elastic portion 610, so as to facilitate elastic stretching of the elastic portion.

Typically, prosthetic valve 603 comprises an expandable prosthetic valve, and is deployed such that it (1) expands within the opening defined by upstream support portion 620 and/or the opening defined by stabilizing member 622, (2) applies a radially-expansive force against the upstream support portion and/or the stabilizing member, and (3) thereby becomes coupled thereto. Typically, and as shown in FIG. 22B, downstream portion 608 is expanded and coupled to stabilizing member 622 before upstream portion 606 is expanded and coupled to upstream support portion 620. While downstream portion 608 is coupled to member 622, and before upstream portion 606 is coupled to portion 620, elastic portion 610 may be stretched and compressed e.g., such as by moving upstream portion 606 further upstream and downstream. Such stretching and compressing changes a length of prosthetic valve 603, and for some applications, facilitates the coupling of a pre-determined portion of the prosthetic valve (e.g., of upstream portion 606) to upstream support portion 620, irrespective, to some degree, of (a) a distance between tissue-engaging elements 618 and upstream support portion 620, and/or (b) a dimension of native valve 10 (e.g., a length of leaflets 14). For some applications, such stretching and compressing adjusts a degree of tension of elastic portion 610, and may alternatively or additionally facilitate "tightening" of leaflets 14 against the implanted apparatus, such as drawing of the leaflets toward upstream support portion 620.

For some applications, prosthetic valve 603 may be used in combination with other apparatus and techniques described herein. For example, valve body 604 may be substituted for another valve body described herein, mutatis mutandis, including valve bodies that are described herein as being intracorporeally coupled to an upstream support, and valve bodies that are described herein as being provided pre-coupled to an upstream support (either directly, or via a flexible sheet).

Reference is again made to FIGS. 22A-B, which are schematic illustrations of apparatus 680 comprising an implant 682 for replacing the native valve. Implant 682 comprises frame 614 which is expandable and which is shaped to define a continuous lumen 615 through the frame. Frame 614 is shaped so as to define at least one upstream row 684 of upstream cells. Frame 614 is also shaped so as to define at least two downstream rows 686 of downstream cells, comprising an upstream row 687 of downstream cells and a downstream row 689 of downstream cells. An upstream portion 690 of each cell is shaped by ascending struts 691 and descending struts 693 that form a respective peak 695 that points in an upstream direction. At least one valve member is disposed within lumen 615 and is configured to facilitate unidirectional flow of blood of the subject from an upstream end 617 of frame 614 to a downstream end 619 of frame 614.

As described hereinabove, prosthetic valve 603 typically comprises a covering 616. Covering 616 has (i) a first portion 700 that entirely covers an outer surface of the downstream row 689 of downstream cells, and (ii) a second portion 702 that partially covers an outer surface of the upstream row 687 of downstream cells such that outer surfaces of the peaks 695 of the upstream row 687 of downstream cells are disposed upstream of an upstream end 704 of second portion 702 of covering 616.

For some applications, frame 614 is shaped to define exactly four rows of cells 1R, 2R, 3R, and 4R.

As shown, each cell defines a window 706, and each row of cells defines respective junctions 708 between adjacent cells. Upstream end 704 of second portion 702 of covering 616 spans a respective window 706a of each cell of the upstream row 687 of downstream cells at a longitudinal level 710 of frame 614 that is at junctions 708 between the adjacent cells, such that for each window 706 of each cell of the upstream row 687 of downstream cells:
  a downstream portion 705 of the window 706 is covered at the outer surface 720 of the upstream row 687 of downstream cells, and
  an upstream portion 707 of the window 706 is uncovered at the outer surface 720 of the upstream row 687 of downstream cells.

Typically, covering 616 extends in the upstream direction, from a downstream perimeter 722 of the frame. A third portion 730 of covering 616 lines an inner surface 732 of frame 614 and extends around the downstream end 619 of frame 614 to meet the first portion 700 of covering 616. The upstream row 684 of upstream cells defines respective spaces 734 between respective junctions 708 of the ascending struts 691 and descending struts 693 at peaks 695 of upstream row 684 of upstream cells. An upstream end 736 of third portion 730 of covering 616 spans the respective spaces 734 between the respective junctions 708 of the ascending struts 691 and descending struts 693 at the peaks 695 of the upstream row 684 of upstream cells.

As shown in FIG. 22B, for some applications of the present invention, implant 682 comprises a first tissue-engaging element 740 configured to engage a first leaflet of the native valve, and a second tissue-engaging element 742 configured to engage a second leaflet of the native valve.

Figure 24:
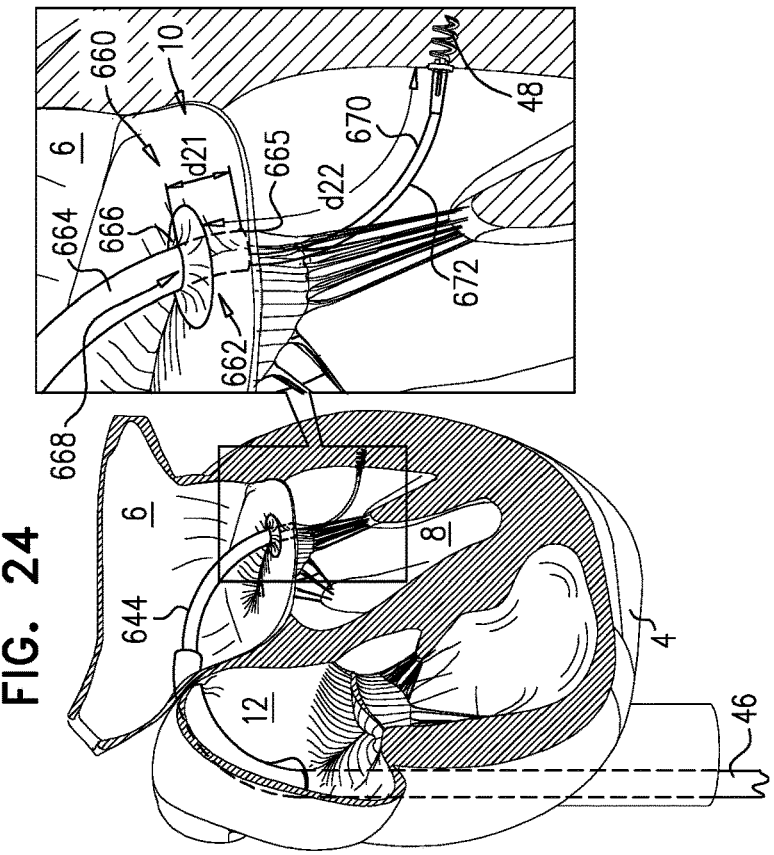
FIGS. 23-24 are schematic illustrations of systems for facilitating anchoring of a tissue anchor in the heart of a subject, in accordance with some applications of the invention.
Figure 23:
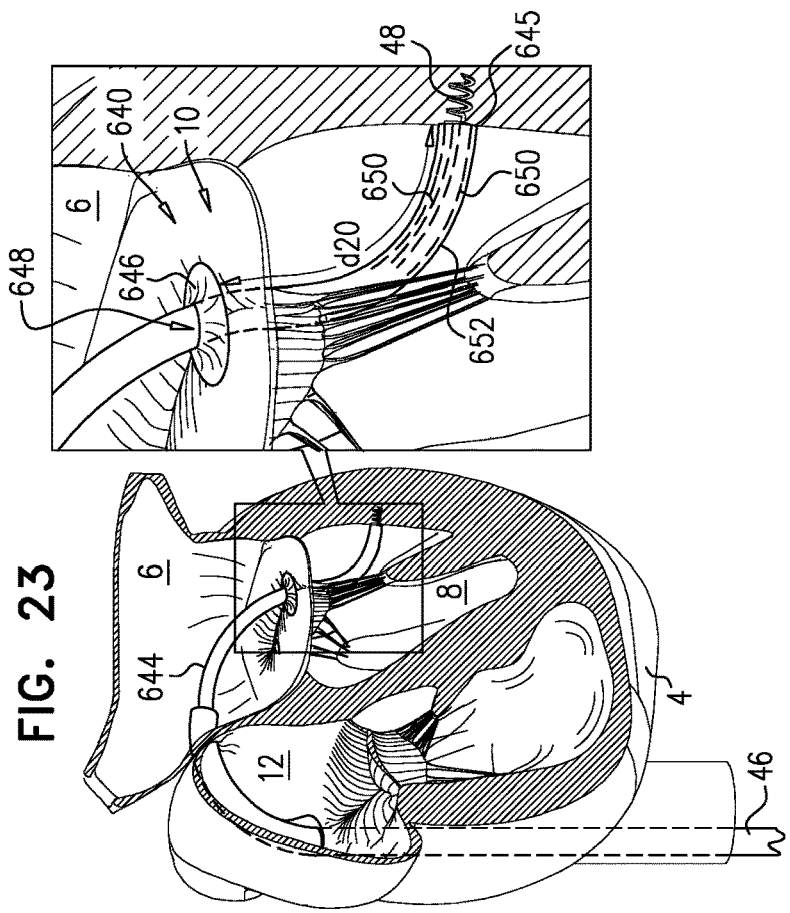

Reference is made to FIGS. 23-24, which are schematic illustrations of respective systems for facilitating anchoring of a tissue anchor in the heart of a subject, in accordance with some applications of the invention. Each system comprises a delivery tool that comprises (1) a steerable catheter configured to be transluminally advanced to the heart of the subject (e.g., via sheath 46), and (2) an obstructing element disposed at a longitudinal site of the catheter, and configured to extend laterally (e.g., radially) outward from the catheter so as to inhibit movement of at least the longitudinal site of the catheter through the heart valve by abutting tissue of the heart valve.

FIG. 23 shows a system 640, comprising a delivery tool 642 that comprises a catheter 644 and an obstructing element 646. Obstructing element 646 is typically collapsible for transluminal delivery (e.g., via sheath 46), and expandable in atrium 6 of the heart. For some applications, element 646 is configured to expand automatically upon becoming exposed from the distal end of sheath 46. Obstructing element 646 is disposed at a longitudinal site 648 of catheter 644, and is dimensioned, when in the expanded state thereof, to not pass through native valve 10 (i.e., between leaflets 14 of the native valve). When a distal end 645 of the catheter is extended through native valve 10, obstructing element 646 abuts the atrial surface of the native valve (e.g., one or more leaflets, or the annulus), and thereby inhibits movement of at least longitudinal site 648 of the catheter from passing through the valve. Therefore a known length d20 of catheter 644 (i.e., the length between longitudinal site 648 and distal end 645) is disposed downstream of the atrial surface of valve 10. Distal end 645 is thereby placeable against ventricular tissue at ventricular sites that are disposed at a distance from the atrial surface (e.g., from a portion of the atrial surface that element 646 abuts) that is generally equal to d20. A distal portion 652 of catheter 644, disposed distal to longitudinal site 648, is typically steerable, so as to facilitate placement of distal end 645 against many (e.g., any) ventricular site that is disposed at that distance from the atrial surface.

A tissue anchor 48 is advanced through catheter 644 using an anchor manipulator 650, and anchored to tissue at the ventricular site at which distal end 645 is disposed. Typically, little or none of anchor 48 or manipulator 650 becomes exposed from distal end 645 during anchoring.

FIG. 24 shows a system 660, comprising a delivery tool 662 that comprises a catheter 664 and an obstructing element 666. Obstructing element 666 is typically collapsible for transluminal delivery (e.g., via sheath 46), and expandable in atrium 6 of the heart, and may be identical to obstructing element 646, described hereinabove. For some applications, element 666 is configured to expand automatically upon becoming exposed from the distal end of sheath 46. Obstructing element 666 is disposed at a longitudinal site 668 of catheter 664, and is dimensioned, when in the expanded state thereof, to not pass through native valve 10 (i.e., between leaflets 14 of the native valve). When a distal end 665 of the catheter is extended through native valve 10, obstructing element 666 abuts the atrial surface of the native valve (e.g., one or more leaflets, or the annulus), and thereby inhibits movement of at least longitudinal site 668 of the catheter from passing through the valve. Therefore a known length d21 of catheter 664 (i.e., the length between longitudinal site 668 and distal end 665) is disposed downstream of the atrial surface of valve 10.

Length d21 of system 660 is typically shorter than length d20 of system 640, and in contrast to system 640, for system 660, catheter 664 is not configured for distal end 665 to be placed against ventricular tissue. Rather, an anchor manipulator 670 advances tissue anchor 48 through catheter 664, out of the distal end 665, and toward a ventricular site at which it anchors the tissue anchor. Typically, anchor manipulator 670 is slidably coupled to catheter 664 such that a distal end of the anchor manipulator is slidable distally no more than a pre-determined distance d22 from longitudinal site 668 (and thereby no more than a pre-determined distance from distal end 665 of catheter 664). Anchor manipulator 670 is thereby used to anchor anchor 48 at a ventricular site that is disposed at a distance from the atrial surface (e.g., from a portion of the atrial surface that element 666 abuts) that is generally equal to d22. Typically, anchor manipulator 670 (or at least a distal portion 672 thereof that is exposable from distal end 665 of catheter 664) is steerable independently of catheter 664.

It is to be noted that, for systems 640 and 660, the distance from the atrial surface at which anchor 48 is anchored is generally equal, but not necessarily exactly equal, to d20 or d22. For example, anchor 48 may be anchored at a site that is closer to another portion of the atrial surface than to the portion of the atrial surface that the obstructing element abuts. Alternatively or additionally, curvature of the catheter and/or the anchor manipulator may result in a direct distance between the atrial surface and the tissue anchor being smaller than d20 or d22.

Typically, anchor 48 is coupled to a tether, guide member, and/or other longitudinal member (e.g., as described hereinabove with reference to other systems). When the anchor driver is decoupled from the anchor and withdrawn proximally, the tether extends proximally from the anchor (e.g., out of the body of the subject) so that an implant, such as a prosthetic valve, prosthetic valve support, and/or a prosthetic valve assembly (e.g., those described hereinabove) may be advanced therealong and/or locked thereto, e.g., as described hereinabove for other systems, mutatis mutandis. Because the distance between the tissue anchor and the atrial surface is known, for some applications the tether coupled to the tissue anchor may comprise fewer locking sites for locking to the implant, a relatively shorter locking site, and/or only one locking site. It is hypothesized that this may provide the possibility of using simpler, smaller and/or more effective mechanisms to lock the implant to the tether.

Reference is again made to FIGS. 7A-C, 8A-H, 9A-B, 15A-C, 16, 17, 18A-B, and 21A-B. The flexible sheets described hereinabove typically have tensile strength but very low compressive strength along the longitudinal axis of assembly 202. Due to this characteristic, inter alia, implant-control rod 246 is coupled (via mount 248) to assembly 202 by being coupled to valve body 204, such that when the valve body is pushed distally, the valve body pulls upstream support 210 via sheet 214. (It is hypothesized that it would be less effective for the implant-control rod to be coupled to the support, because in such a case sheet 214 may rumple and the support may move toward the valve body, possibly reducing articulation at the articulation zone. Nevertheless, for applications in which such reduced articulation is in any case sufficient, the implant-control rod may be coupled to the support) This characteristic of the flexible sheet also facilitates the height-adjustment of assembly 552 and its sandwiching of the native leaflets by tensioning tethers 582.

Although each of the prosthetic valve assemblies is shown implanted in a generally symmetrical state, it is to be noted that for some applications this characteristic of the sheet facilitates asymmetrical implantation. For example, the assembly may better conform to the native anatomy, and/or one tether of assembly 552 may be tensioned more than another so as to alter the anchoring, sealing, and/or flow characteristics of the assembly, e.g., in response to the native anatomy.

For some applications it may be advantageous for the valve body to be disposed at a particular rotational orientation within ventricle 8, and for the upstream support to be disposed at a particular rotational orientation within atrium 6. For example, for prosthetic valve assemblies such as assembly 202 that are tethered to ventricular anchors, it may be advantageous for each eyelet to be aligned with a respective anchor, and for the point at which each guide members passes through the upstream support to be aligned with a respective commissure. Alternatively or additionally, the upstream support may be geometrically asymmetric, and a particular rotational orientation with respect to atrial tissue may be advantageous. (Examples of such upstream supports are described in PCT patent application publication WO/2013/021374 to Gross et. al, which is incorporated herein by reference.) Alternatively or additionally, the upstream support may be asymmetric with respect to rigidity (i.e., some regions of the support may be more rigid than others). Alternatively or additionally, it may be advantageous to place the holes in sheet 214 through which tubes 260 pass in a particular rotational orientation with respect to the native valve.

For some applications, the sheet facilitates implantation of the upstream support in a different rotational position to its valve body, e.g., by twisting. For example, the upstream support may be implanted at more than 5 degrees (e.g., more than 10 degrees, such as more than 20 degrees) rotational offset with respect to the valve body.

Reference is again made to FIGS. 7A-14B, 16-18B, and 21A-B. For some applications the first frame of the valve body is coupled to the second frame of the upstream support by the sheet (e.g., generally only by the sheet) in the compressed state (e.g., assemblies 202, 302, 342 and 552) and/or in the expanded state (e.g., assemblies 202 and 552). As used in the present application, including in the claims, (a) the first and second frames being "coupled by the sheet", and/or (b) the sheet "coupling the first frame to the second frame", do not include applications in which the frames are primarily and/or independently coupled to each other by a different means, and the covering extends over both frames. For example, the first and second frames are not "coupled to each other by the sheet" (1) in assemblies 382, 402 and 422, in which the frames are provided pre-coupled directly to each other, or (2) in the expanded state of assemblies 302 and 342, in which the frames are intracorporeally coupled directly to each other.

For applications in which the first frame of the valve body is coupled to the second frame of the upstream support by the sheet, a gap typically exists between the first frame and the second frame. For some such applications, no metallic structure is disposed within the gap.

For some applications (including some applications in which the first and second frames are coupled independently of the sheet), the flexible sheet comprises, in addition to the sheet-like structure, one or more flexible longitudinal members, such as metallic or polymer wires (e.g., embedded within or attached to a surface of the sheet-like structure). These flexible longitudinal members may provide a small amount of rigidity to the sheet without detracting from the general nature of the sheet. For example, the flexible longitudinal members may facilitate opening of the sheet during deployment of the prosthetic valve assembly.

It is to be noted that for applications in which the first and second frames are coupled by the sheet, even when the sheet comprises flexible longitudinal members that are metallic wires, the frame of the valve body and the frame of the upstream support are typically distinct from each other, and can be considered to be coupled to each other by the sheet (e.g., generally only by the sheet).

For some applications, within the total height of the prosthetic valve assembly, a distance exists within which no rigid and/or metallic structure is disposed. For example, for assembly 552, typically no rigid and/or metallic structure is disposed within distance d17 and/or distance d19. It is to be noted that a similar distance exists for assembly 202 between frames 210 and 206 (e.g., when implanted; see FIGS. 8F-G). For some applications, for assembly 552, only sheet 564 and tethers 582 are disposed within distances d17 and d19. However, for some applications, tissue-engaging elements 580 extend proximally toward frame 562 such that the distance in which no rigid and/or metallic structure is disposed is reduced and/or absent (e.g., when tethers 582 are tensioned).

Reference is again made to FIGS. 1A-F, 3A-C, 6 and 7A-8H. For some applications of the invention, tissue anchor 48 and/or the guide member coupled thereto (e.g., guide member 56, guide member 256, and/or the components thereof) are included as components of the provided apparatus. That is, they are typically provided with the prosthetic valve assembly. For some applications of the invention, the tissue anchor and/or the guide member coupled thereto are not included as components of the provided apparatus (e.g., they are obtained separately).

It will be understood that, although the terms "first, "second," etc. may be used in the present application (including the specification and the claims) to describe various elements and/or directions, these terms should not be limiting. These terms are only used to distinguish one element and/or direction from another. Thus, a "first" element described herein could also be termed a "second" element without departing from the teachings of the present disclosure.

As used in the present application, including in the claims, a "central longitudinal axis" of a structure (e.g., an elongate structure) is the set of all centroids of transverse cross-sectional sections of the structure along the structure. Thus the cross-sectional sections are locally perpendicular to the central longitudinal axis, which runs along the structure. (If the structure is circular in cross-section, the centroids correspond with the centers of the circular cross-sectional sections.)

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus, for use at a native valve of a heart of a subject, the apparatus comprising an implant for replacing the native valve, the implant comprising:
    an expandable frame shaped to define a continuous lumen through the frame, the frame being shaped so as to define:
        (a) at least one upstream row of upstream cells, and
        (b) at least two downstream rows of downstream cells defined by an upstream row of downstream cells and a downstream row of downstream cells,
        an upstream portion of each cell being shaped by ascending and descending struts that form a respective peak that points in an upstream direction;
    at least one valve member, disposed within the lumen, and configured to facilitate unidirectional flow of blood of the subject from an upstream end of the frame to a downstream end of the frame; and
    a covering that has (i) a first portion that entirely covers an outer surface of the downstream row of downstream cells, and (ii) a second portion that partially covers an outer surface of the upstream row of downstream cells such that outer surfaces of the peaks of the upstream row of downstream cells are disposed upstream of an upstream end of the second portion of the covering.

2. The apparatus according to claim 1, wherein the covering comprises a fabric covering.

3. The apparatus according to claim 1, wherein the expandable frame is shaped to define exactly four rows of cells.

4. The apparatus according to claim 1, wherein:
    each cell defines a window,
    each row of cells defines respective junctions between adjacent cells, and
    the upstream end of the second portion of the covering spans a respective window of each cell of the upstream row of downstream cells at a longitudinal level of the frame that is at the junctions between the adjacent cells, such that for each window of each cell of the upstream row of downstream cells:
        a downstream portion of the window is covered at the outer surface of the upstream row of downstream cells, and
        an upstream portion of the window is uncovered at the outer surface of the upstream row of downstream cells.

5. The apparatus according to claim 1, wherein the upstream end of the second portion of the covering surrounds the frame at a generally constant height above the downstream end of the frame.

6. The apparatus according to claim 1, wherein the covering extends in the upstream direction, from a downstream perimeter of the frame.

7. The apparatus according to claim 1, wherein a third portion of the covering lines an inner surface of the frame and extends around the downstream end of the frame to meet the first portion of the covering.

8. The apparatus according to claim 7, wherein:
    the upstream row of upstream cells defines respective spaces between respective junctions of the ascending and descending struts at the peaks of the upstream row of upstream cells, and
    an upstream end of the third portion of the covering spans the respective spaces between the respective junctions of the ascending and descending struts at the peaks of the upstream row of upstream cells.

9. The apparatus according to claim 7, wherein:
    the upstream row of upstream cells defines respective spaces between respective junctions of the ascending and descending struts at the peaks of the upstream row of upstream cells, and
    an upstream end of the third portion of the covering surrounds the frame at the upstream row of upstream cells at a generally constant height above the downstream end of the frame.

10. The apparatus according to claim 1, wherein the implant further comprises:
    a first tissue-engaging element configured to engage a first leaflet of the native valve, and
    a second tissue-engaging element configured to engage a second leaflet of the native valve.

11. The apparatus according to claim 10, wherein the implant is implantable such that:
    the first and second tissue-engaging elements are coupled to the leaflets,
    subsequently, the two downstream rows of downstream cells of the frame expand and are disposed at least in part within a ventricle of the heart, and
    subsequently, the upstream row of upstream cells of the frame expands and is disposed at least in part within an atrium of the heart.

12. Apparatus, for use at a native valve of a heart of a subject, the apparatus comprising an implant for replacing the native valve, the implant comprising:
- an expandable frame shaped to define a continuous lumen through the frame, the frame being shaped so as to define:
  - (a) a downstream row of downstream cells, and
  - (b) an upstream row of cells upstream of the downstream row of downstream cells,
  - an upstream portion of each cell being shaped by ascending and descending struts that form a respective peak that points in an upstream direction;
- at least one valve member, disposed within the lumen, and configured to facilitate unidirectional flow of blood of the subject from an upstream end of the frame to a downstream end of the frame; and
- a covering that has (i) a first portion that entirely covers an outer surface of the downstream row of downstream cells, and (ii) a second portion that partially covers an outer surface of the upstream row of cells such that outer surfaces of the peaks of the upstream row of cells are disposed upstream of an upstream end of the second portion of the covering.

13. The apparatus according to claim 12, wherein the covering comprises a fabric covering.

14. The apparatus according to claim 12, wherein the expandable frame is shaped to define exactly four rows of cells.

15. The apparatus according to claim 12, wherein:
- each cell defines a window,
- each row of cells defines respective junctions between adjacent cells, and
- the upstream end of the second portion of the covering spans a respective window of each cell of the upstream row of cells at a longitudinal level of the frame that is at the junctions between the adjacent cells, such that for each window of each cell of the upstream row of cells:
  - a downstream portion of the window is covered at the outer surface of the upstream row of cells, and
  - an upstream portion of the window is uncovered at the outer surface of the upstream row of cells.

16. The apparatus according to claim 12, wherein the upstream end of the second portion of the covering surrounds the frame at a generally constant height above the downstream end of the frame.

17. The apparatus according to claim 12, wherein the covering extends in the upstream direction, from a downstream perimeter of the frame.

18. The apparatus according to claim 12, wherein a third portion of the covering lines an inner surface of the frame and extends around the downstream end of the frame to meet the first portion of the covering.

19. The apparatus according to claim 12, wherein the implant further comprises:
- a first tissue-engaging element configured engage a first leaflet of the native valve, and
- a second tissue-engaging element configured to engage a second leaflet of the native valve.

20. The apparatus according to claim 19, wherein the implant is implantable such that:
- the first and second tissue-engaging elements are coupled to the leaflets, and
- subsequently, the downstream row of downstream cells of the frame expands and is disposed at least in part within a ventricle of the heart.

21. The apparatus according to claim 20, wherein the implant is implantable such that, subsequently to the expanding of the downstream row of downstream cells of the frame, the upstream row of cells upstream of the downstream row of downstream cells of the frame expands.

* * * * *